(12) United States Patent
Konnai et al.

(10) Patent No.: US 11,697,686 B2
(45) Date of Patent: Jul. 11, 2023

(54) ANTI-PD-L1 ANTIBODY FOR DETECTING PD-L1

(71) Applicants: National University Corporation Hokkaido University, Hokkaido (JP); Fuso Pharmaceutical Industries, Ltd., Osaka (JP)

(72) Inventors: Satoru Konnai, Hokkaido (JP); Kazuhiko Ohashi, Hokkaido (JP); Shiro Murata, Hokkaido (JP); Tomohiro Okagawa, Hokkaido (JP); Asami Nishimori, Hokkaido (JP); Naoya Maekawa, Hokkaido (JP); Satoshi Takagi, Hokkaido (JP); Yumiko Kagawa, Hokkaido (JP); Yasuhiko Suzuki, Hokkaido (JP); Chie Nakajima, Hokkaido (JP)

(73) Assignees: NATIONAL UNIVERSITY CORPORATION HOKKAIDO UNIVERSITY, Hokkaido (JP); FUSO PHARMACEUTICAL INDUSTRIES, LTD., Osaka (JP)

( * ) Notice: Subject to any disclaimer, the term of this patent is extended or adjusted under 35 U.S.C. 154(b) by 38 days.

(21) Appl. No.: 16/949,415

(22) Filed: Oct. 28, 2020

(65) Prior Publication Data

US 2021/0079095 A1 Mar. 18, 2021

Related U.S. Application Data

(63) Continuation of application No. 16/491,145, filed as application No. PCT/JP2018/011895 on Mar. 23, 2018, now Pat. No. 10,865,246.

(30) Foreign Application Priority Data

Mar. 27, 2017 (JP) ................. 2017-061389

(51) Int. Cl.
| | |
|---|---|
| C07K 16/28 | (2006.01) |
| C12N 15/85 | (2006.01) |
| G01N 33/569 | (2006.01) |
| G01N 33/574 | (2006.01) |

(52) U.S. Cl.
CPC .......... C07K 16/2827 (2013.01); C12N 15/85 (2013.01); G01N 33/5695 (2013.01); G01N 33/57492 (2013.01); *C07K 2317/52* (2013.01); *C07K 2317/565* (2013.01); *G01N 2800/26* (2013.01)

(58) Field of Classification Search
CPC ......... C07K 2317/565; G01N 33/5695; G01N 33/57492
See application file for complete search history.

(56) References Cited

U.S. PATENT DOCUMENTS

| | | | |
|---|---|---|---|
| 10,865,246 B2* | 12/2020 | Konnai | ............ G01N 33/57492 |
| 2011/0076284 A1 | 3/2011 | Corbin et al. | |
| 2020/0031932 A1 | 1/2020 | Konnai et al. | |

FOREIGN PATENT DOCUMENTS

| | | |
|---|---|---|
| RU | 2478400 C2 | 4/2013 |
| WO | WO-2016006241 A1 | 1/2016 |
| WO | WO-2016050721 A1 | 4/2016 |

OTHER PUBLICATIONS

"Russian Application Serial No. 2019130661, Office Action and Search Report dated Apr. 1, 2021", w/ English Translation, (Apr. 1, 2021), 5 pgs.
"European Application Serial No. 18774959.2, Extended European Search Report dated Nov. 24, 2020", (Nov. 24, 2020), 6 pgs.
Nishimori, Asami, et al., "In vitro and in vivo antivirus activity of an anti-programmed death-ligand 1 (PD-L1) rat-bovine chimeric antibody against bovine leukemia virus infection", PLoS One 12.4, (Apr. 26, 2017), 18 pgs.
"International Application Serial No. PCT/JP2018/011895 International Preliminary Report on Patentability dated Oct. 3, 2019", 7 pgs.
"International Application Serial No. PCT/JP2018/011895, International Search Report dated Jun. 19, 2018", w/ English Translation, (Jun. 19, 2018), 6 pgs.
"International Application Serial No. PCT/JP2018/011895, Written Opinion dated Jun. 19, 2018", (Jun. 19, 2018), 6 pgs.
Ikebuchi, Ryoyo, et al. "Influence of PD-L 1 cross-linking on cell death in PD-L 1-expressing cell lines and bovine lymphocytes", Immunology 142.4, (2014), 551-561.
Koenig, A., et al., "Expression of S100a, vimentin, NSE, and Melan A/MART-1 in seven canine melanoma cell lines and twenty-nine retrospective cases of canine melanoma", Veterinary pathology 38.4, (2001), 427-435.
Maekawa, Naoya, et al., "Expression of PD-L1 on canine tumor cells and enhancement of IFN-? production from tumor-infiltrating cells by PD-L1 blockade", PLoS One 9.6, (2014), e98415.

(Continued)

*Primary Examiner* — Brian Gangle
*Assistant Examiner* — Lakia J Jackson-Tongue
(74) *Attorney, Agent, or Firm* — Wenderoth, Lind & Ponack, L.L.P.

(57) ABSTRACT

The present invention provides an anti-PD-L1 antibody capable of staining tumor cells such as melanoma cells.
An anti-PD-L1 antibody comprising (a) a light chain comprising CDR1 having the amino acid sequence of KSISKY (SEQ ID NO: 1), CDR2 having the amino acid sequence of SGS and CDR3 having the amino acid sequence of QQH-NEYPLT (SEQ ID NO: 2) and (b) a heavy chain comprising CDR1 having the amino acid sequence of GYTFTDYI (SEQ ID NO: 3), CDR2 having the amino acid sequence of INPDSGGN (SEQ ID NO: 4) and CDR3 having the amino acid sequence of ARGITMMVVISHWKFDP (SEQ ID NO: 5). A composition for detecting PD-L1, comprising the above antibody as an active ingredient. A method for preparing the above antibody is also provided.

13 Claims, 17 Drawing Sheets
Specification includes a Sequence Listing.

(56) References Cited

OTHER PUBLICATIONS

Okagawa, Tomohiro, et al., "Bovine immunoinhibitory receptors contribute to suppression of *Mycobacterium avium* subsp. *paratuberculosis*-specific T-cell responses", Infection and immunity 84.1, (2016), 77-89.
Ramos-Vara, J.A., et al., "Retrospective study of 338 canine oral melanomas with clinical, histologic, and immunohistochemical review of 129 cases", Veterinary Pathology 37.6, (2000), 597-608.
Todoroff, R. J., et al., "Oral and pharyngeal neoplasia in the dog: a retrospective survey of 361 cases", Journal of the American Veterinary Medical Association 175.6, (1979), 567-571.
Ganbaatar, Otgontuya et al., "Programmed death-ligand 1 expression in swine chronic infections and enhancement of interleukin-2 production via programmed death-1/programmed death ligand 1 blockade", Immunity, Inflammation and Disease, 2021, vol. 9., pp. 1573-1583.
Ganbaatar, Otgontuya et al., "PD-L1 expression in equine malignant melanoma and functional effects of PD-L1 blockade", PLOS ONE 15(11), Nov. 2020, 17 pages.
Goto, Shinya et al., "Upregulation of PD-L1 Expression by Prostaglandin $E_2$ and the Enhancement of IFN-γ by Anti-PD-L1 Antibody Combined With a COX-2 Inhibitor in *Mycoplasma bovis* Infection", Frontiers in Veterinary Science, Feb. 2020, vol. 7, Article 12, 14 pages.
Sajiki, Yamato et al., "Prostaglandin $E_2$-Induced Immune Exhaustion and Enhancement of Antiviral Effects by Anti-PD-L1 Antibody Combined with COX-2 Inhibitor in Bovine Leukemia Virus Infection", The Journal of Immunology, 2019, vol. 203, pp. 1313-1324.

\* cited by examiner

Fig. 2

CDR1
CDR2
CDR3

Light chain variable region
MRVQIQFWGLLLLLWTSGIQCDVQMTQSPSNLAASPGESVSINCKASKSISKYLAWYQ
QKPGKANKLLIYSGSTLQSGTPSRFSGSGSGTDFTLTIRNLEPEDFGLYYCQQHNEY
PLTFGSGTKLEIK Heavy chain variable region
MGWICIIFLVAIATGAHSQVKLLQSGAALVKPGDSVKMSCKASGYTFTDYIIHWVKQ
SHGKSLEWIGYINPDSGGNNYNEKFKSKATLTVDKSSSTAYMEFSRLTSEDSAIYYC
ARGITMMVVISHWKFDFWGPGTMVTVSS

Rat Anti-Bovine PD-L1 Antibody
Commercial Antibody (MelanA Antibody)
Fig. 3

Fig. 4 — Case of Canine Melanoma

Fig. 5-1
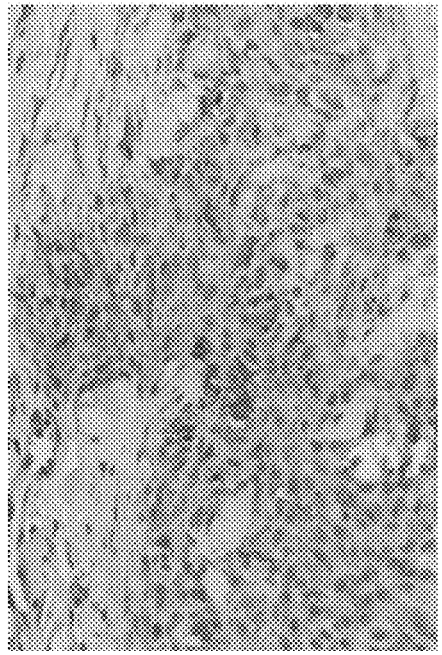
Case of Canine Osteosarcoma
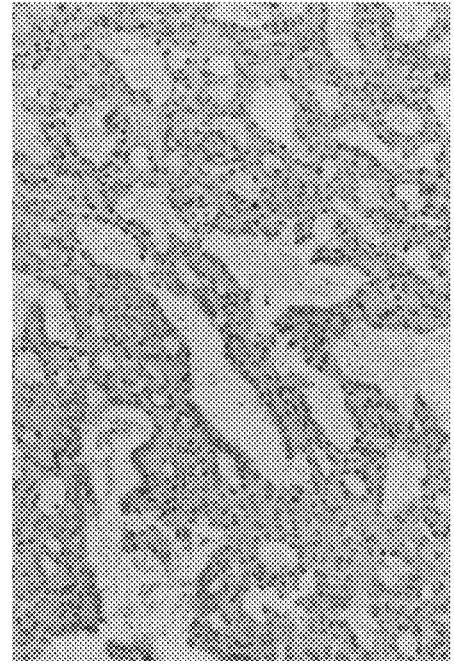
Case 2 of Canine Renal Cell Carcinoma
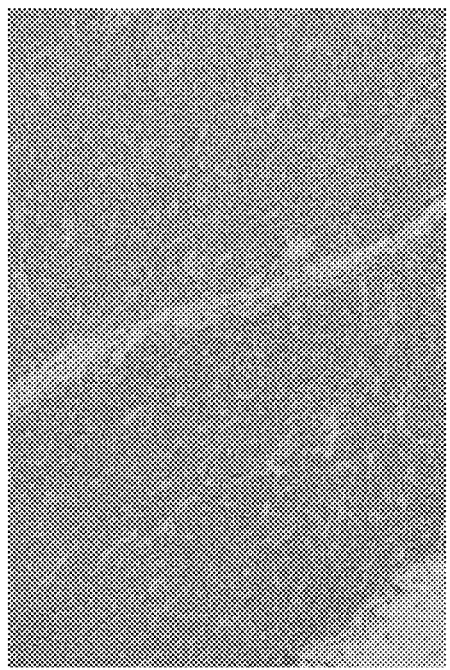
Case of Canine Lymphoma
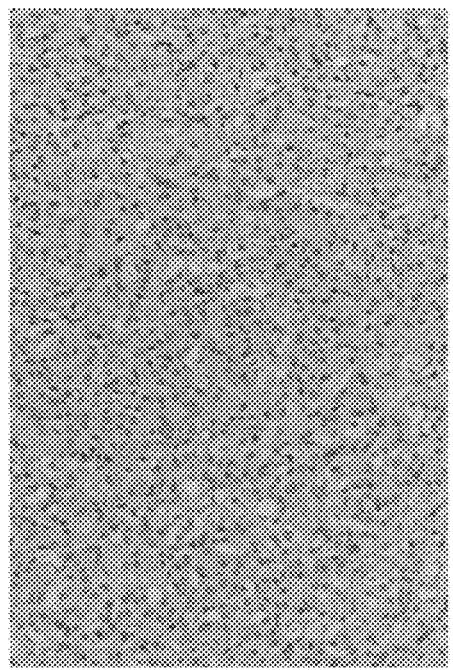
Case 1 of Canine Renal Cell Carcinoma Case of Canine Fibrosarcoma Case of Canine Squamous Cell Carcinoma

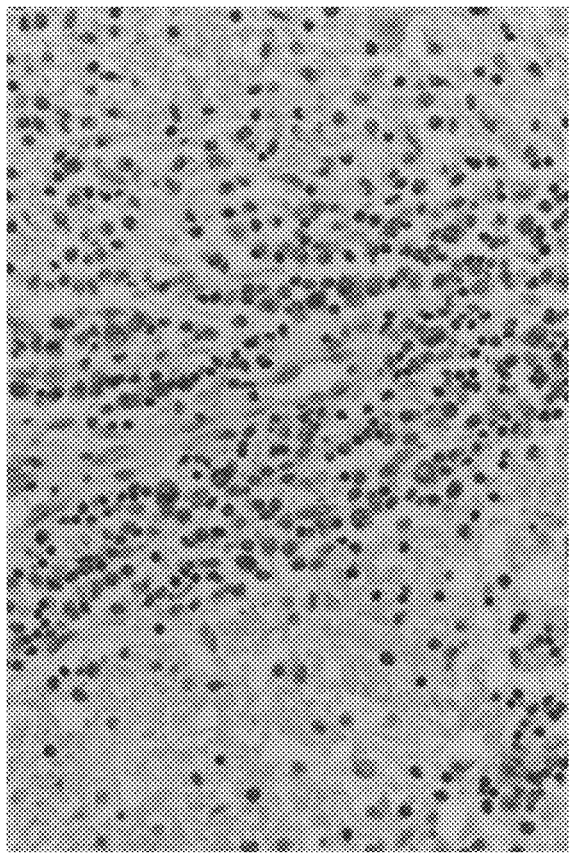
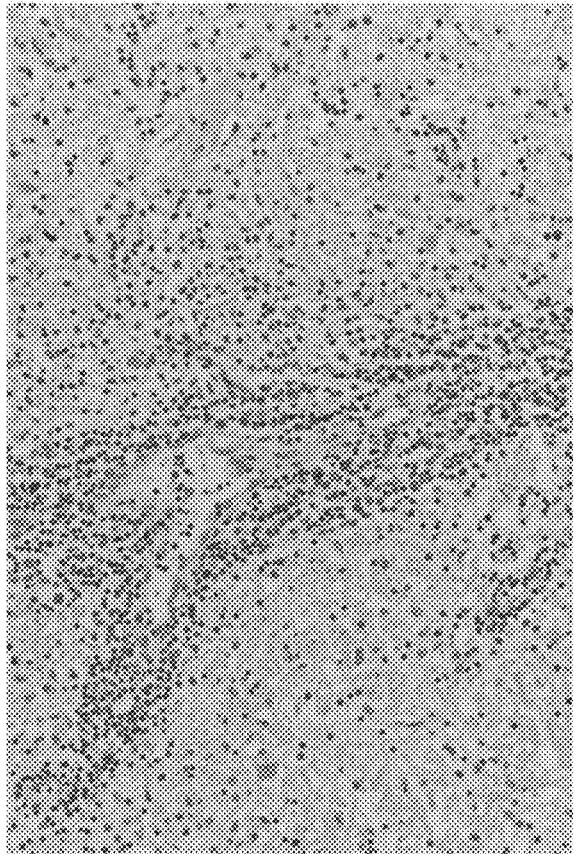
Fig. 6    Case of Ovine Listeriosis    Enlarged Photo of the Left Micrograph Fig. 7
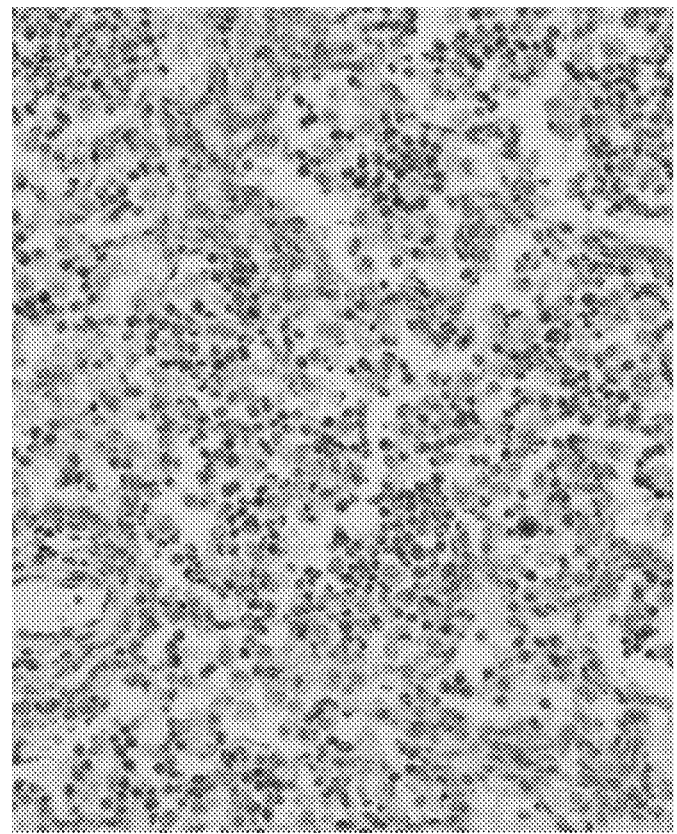
Porcine Mycoplasma Pneumonia
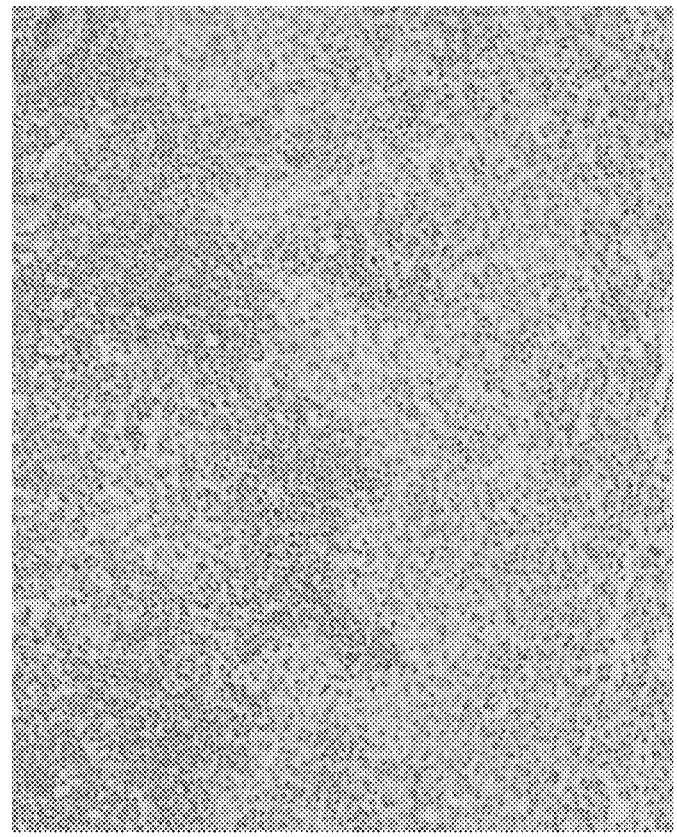
Porcine Circovirus Type 2 Infection

Fig. 9

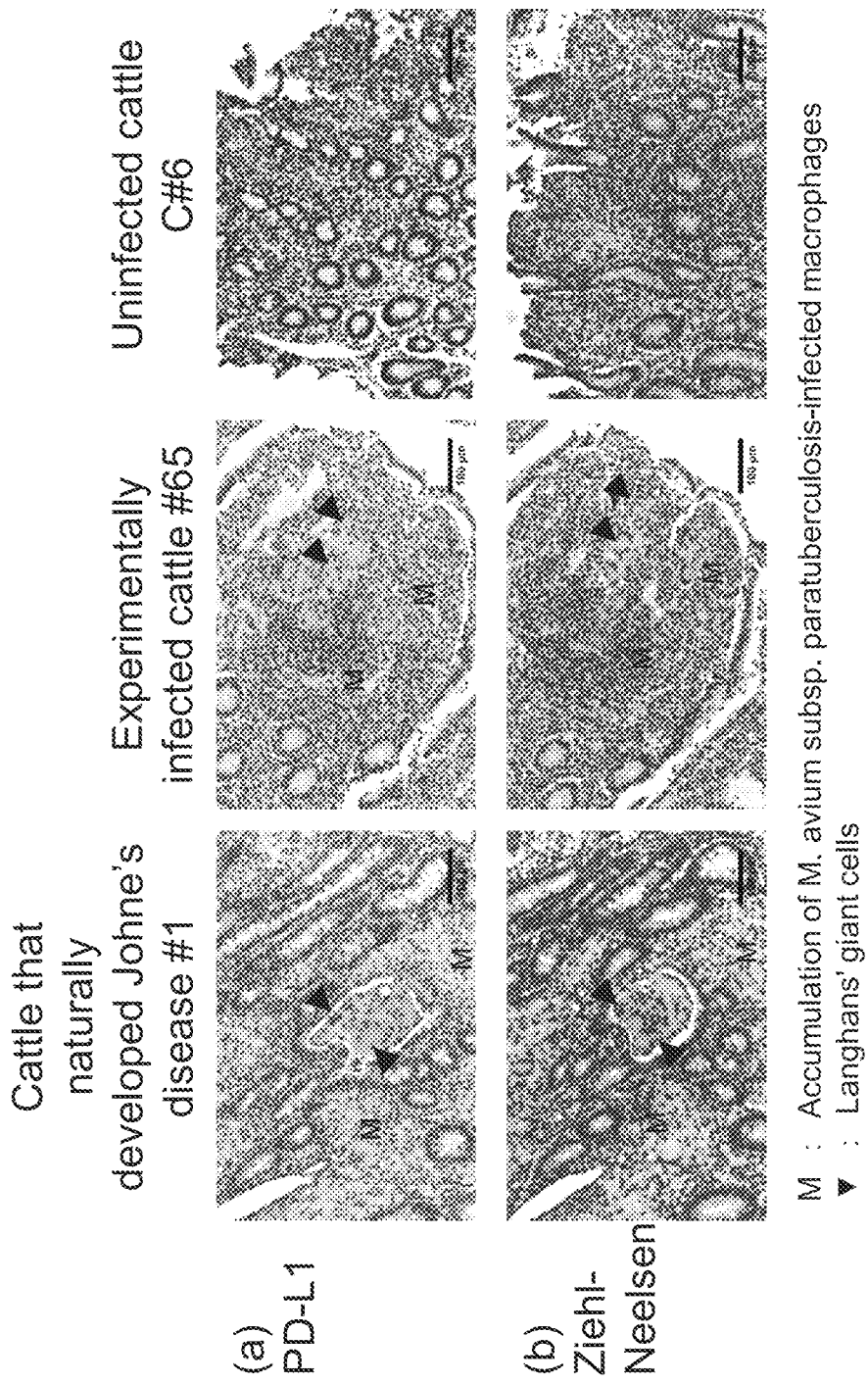

ANTI-PD-L1 ANTIBODY FOR DETECTING PD-L1

CLAIM FOR PRIORITY

This application is a continuation of U.S. application Ser. No. 16/491,145, filed Sep. 4, 2019 which is a U.S. National Stage Filing under 35 U.S.C. 371 from International Application No. PCT/JP2018/011895, filed on Mar. 23, 2018, and published as WO2018/181064 on Oct. 4, 2018, which claims the benefit of priority to Japanese Application No. 2017-061389, filed on Mar. 27, 2017; the benefit of priority of each of which is hereby claimed herein, and which applications and publication are hereby incorporated herein by reference in their entirety.

TECHNICAL FIELD

The present invention relates to an anti-PD-L1 antibody for detecting PD-L1.

BACKGROUND ART

Malignant melanoma originating from melanocytes is one of the most commonly observed malignant tumors in the canine oral cavity (Non-Patent Document No. 1: Todoroff et al., J Am Vet Med Assoc. 1979 Sep. 15; 175(6):567-71). Since this type of melanoma generally tends to be highly invasive and metastatic, early diagnosis and treatment are desired. On the other hand, malignant melanoma has a wide tissue variation, presenting various morphologies such as epithelial-like, round cell-like or fibrosarcoma-like morphology. Thus, malignant melanoma is one of those tumors which involve difficulty in tissue diagnosis. Although confirmation of melanin pigment is important for their diagnosis, a large number of malignant melanomas do not have melanin pigment and, sometimes, diagnosis cannot be made with histological observations alone. This has led to searches for diagnostic markers that can be used in immunohistochemical techniques. Among such markers, Melan A/MART-1, vimentin, S100, neuron-specific enolase and the like have been reported to be useful (Non-Patent Document No. 2: Ramos-Vara et al., Vet Pathol. 2000 November; 37(6):597-608). However, even Melan A/MART-1, the most widely used diagnostic marker, has a positive rate not higher than about 60% which varies among reports (Non-Patent Document No. 3: Koenig et al., Vet Pathol. 2001 July; 38(4):427-35). Because of this sensitivity problem, the utility of Melan A/MART-1 in actual diagnosis is still arguable. Further, Melan A/MART-1 is not stained in amelanotic melanoma (Non-Patent Document No. 3: Koenig et al., Vet Pathol 2001 July 38(4):427-35), so its application to diagnosis is limited. Under these circumstances, it is desired to develop highly sensitive, novel diagnostic markers to malignant melanoma.

PRIOR ART LITERATURE

Non-Patent Documents

Non-Patent Document No. 1: Todoroff et al., J Am Vet Med Assoc. 1979 Sep. 15, 175(6):567-71
Non-Patent Document No. 2: Ramos-Vara et al., Vet Pathol. 2000 November; 37(6):597-608
Non-Patent Document No. 3: Koenig et al., Vet Pathol. 2001 July; 38(4):427-35

DISCLOSURE OF THE INVENTION

Problem for Solution by the Invention

It is an object of the present invention to provide a PD-L1 antibody capable of staining tumor cells such as melanoma cells.

Means to Solve the Problem

The present inventors have established a number of monoclonal antibodies which react with the PD-L1 protein of various animals. It has been revealed that, among those monoclonal antibodies, a rat anti-bovine PD-L1 monoclonal antibody (6C11-A11) is capable of staining melanoma tumor cells very strongly. Currently, this monoclonal antibody is used for selecting candidate dogs for therapy with chimeric antibodies. The subject PD-L1 antibody (6C11-3A11) is also capable of immunohistochemically staining ovine, porcine and bovine PD-L1 proteins. Further, the present inventors have determined the CDRs (complementarity-determining regions) of the variable regions of the subject PD-L1 antibody (6C11-3A11). The present invention has been achieved based on these findings.

A summary of the present invention is as described below.
(1) An anti-PD-L1 antibody comprising (a) a light chain comprising CDR1 having the amino acid sequence of KSISKY (SEQ ID NO: 1), CDR2 having the amino acid sequence of SGS and CDR3 having the amino acid sequence of QQHNEYPLT (SEQ ID NO: 2) and (b) a heavy chain comprising CDR1 having the ammo acid sequence of GYTFTDYI (SEQ ID NO: 3), CDR2 having the ammo arid sequence of INPDSGGN (SEQ ID NO: 4) and CDR3 having the amino acid sequence of ARGITMMVVISHWKFDF (SEQ ID NO: 5).
(2) The antibody of (1) above, which is derived from rat.
(3) The antibody of (2) above, which is a rat anti-bovine PD-L1 antibody.
(4) The antibody of (3) above, wherein the light chain variable region has the amino acid sequence as shown in SEQ ID NO: 6 and the heavy chain variable region has the amino acid sequence as shown m SEQ ID NO: 7.
(5) The antibody of any one of (1) to (4) above, wherein die light chain constant region has the amino acid sequence of the constant region of kappa chain.
(6) The antibody of any one of (1) to (5) above, wherein the heavy chain constant region has the amino acid sequence of the constant region of IgG2a.
(7) The antibody of (5) or (6) above, wherein the light chain constant region has the amino acid sequence as shown in any one of SEQ ID NOS: 8, 10 to 12 and the heavy chain constant region has the amino acid sequence as shown in SEQ ID NO: 9 or 13.
(8) The antibody of any one of (1) to (7) above which has a four-chain structure comprising two light chains and two heavy chains.
(9) A composition for detecting PD-L1, comprising the antibody of any one of (1) to (8) above as an active ingredient.
(10) The composition of (9) above for use in diagnosis of cancers and/or inflammations.
(11) The composition of (10) above, wherein the cancers and/or inflammations are selected from the group consisting of neoplastic diseases, leukemia, Johne's disease, anaplasmosis, bacterial mastitis, mycotic mastitis, mycoplasma infections (such as mycoplasma mastitis, mycoplasma pneumonia or the like), tuberculosis, *Theileria orientalis* infection, cryptosporidiosis, coccidiosis, trypanosomiasis and leishmaniasis.

(12) The composition of (9) above for use in selecting subject animals suitable for therapy with anti-PD-L1 antibodies.
(13) A DNA encoding the anti-PD-L1 antibody of (1) above.
(14) A vector comprising the DNA of (13) above.
(15) A host cell transformed with the vector of (14) above.
(16) A method of preparing an antibody, comprising culturing the host cell of (15) above and collecting an anti-PD-L1 antibody from the resultant culture.
(17) A DNA encoding the light chain of an anti-PD-L1 antibody, said light chain comprising CDR1 having the amino acid sequence of KSISKY (SEQ ID NO: 1), CDR2 having the amino acid sequence of SGS arid CDR3 having the amino acid sequence of QQHNEYPLT (SEQ ID NO. 2).
(18) A DMA encoding the heavy chain of an anti-PD-L1 antibody, said heavy chain comprising CDR1 having the amino acid sequence of GYTFTDYI (SEQ ID NO: 3), CDR2 having the amino acid sequence of INPDSGGN (SEQ ID NO: 4) and CDR3 having the amino acid sequence of ARGITMMVVISHWKFDF (SEQ ID NO: 5).

Effect of the Invention

According to the present invention, a novel anti-PD-L1 anti-body capable of staining tumor cells, such as melanoma cells, has been obtained.

The present specification encompasses the contents disclosed in the specification and/or the drawings of Japanese Patent Application No. 2017-61389 based on which the present patent application claims priority.

BRIEF DESCRIPTION OF THE DRAWINGS

FIG. 3 Comparative immunohistochemical staining images of canine melanoma. Left: stained with a commercial antibody (MelanA antibody). Tumor cells were stained very weakly. Right stained with the PD-L1 antibody 6C11-3A11 established by the present inventors. Tumor cells were stained very strongly.

FIG. 5-1 Immunohistochemical staining images of other tumors. Upper left: case of canine lymphoma. Upper right: case of canine osteosarcoma. Lower left: case 1 of canine renal cell carcinoma. Lower right: case 2 of canine renal cell carcinoma.

FIG. 5-2 Immunohistochemical staining images of other tumors. Left: Case of canine squamous cell carcinoma. Right: case of canine fibrosarcoma.

FIG. 6 Immunohistochemical staining image of a case of ovine listeriosis. Left: PD-L1 staining image of a brain lesion of ovine listeriosia exhibiting neurologic symptoms. Right: enlarged photograph of the left image.

FIG. 7 Immunohistochemical staining images of porcine infections. Left: case of porcine circovirus type 2 infection. Right: case of porcine mycoplasma pneumonia.

FIG. 9 Alignment of amino acid sequences of the constant region of rat IgG2a chain (heavy chain).

FIG. 16 Immunohistochemical staining images of ileal lesions of cattle naturally and experimentally infected with *Mycobacterium avium* subsp. *paratuberculosis*, using (a) 6C11-3A11 and (b) Ziehl-Neelsen staining. 6C11-3A11 detected PD-L1 expression in cells infected with *M. avium* subsp. *paratuberculosis* (positive in Ziehl-Neelsen staining).

BEST MODES FOR CARRYING OUT THE INVENTION

Hereinbelow, the present invention will be described in detail.

The present invention provides an anti-PD-L1 antibody comprising (a) a light chain comprising CDR1 having the amino acid sequence of KSISKY (SEQ ID NO: 1), CDR2 having the amino acid sequence of SGS and CDR3 having the amino acid sequence of QQHNEYPLT (SEQ ID NO: 2) and (b) a heavy chain comprising CDR1 having the amino acid sequence of GYTFTDYI (SEQ ID NO: 3), CDR2 having the amino acid sequence of INPDSGGN (SEQ ID NO: 4) and CDR3 having the amino acid sequence of ARGITMMVVISHWKFDF (SEQ ID NO: 5).

Figure 2:
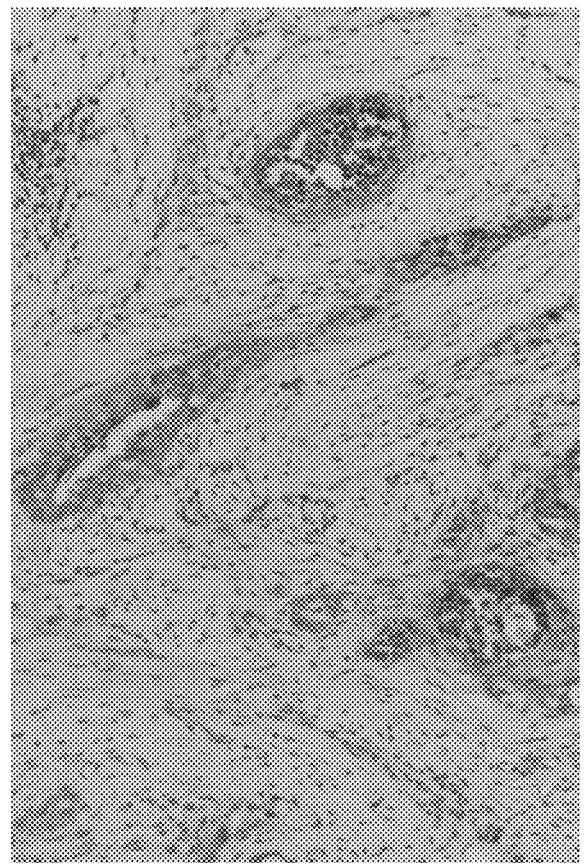
FIG. 2 Predicted CDR regions of rat anti-bovine PD-L1 antibody 6C11-3A11. The regions of CDR1, CDR2 and CDR3 in the light chain variable region and the heavy chain variable region of rat anti-bovine PD-L1 antibody 6C11-3A11 are shown.

CDR1, CDR2 and CDR3 in the light chain variable region (VL) of rat anti-bovine PD-L1 antibody 6C11-3A11 (monoclonal antibody) established by the present inventors are a region consisting of the amino acid sequence of KSISKY (SEQ ID NO: 1), a region consisting of the amino acid sequence of SGS and a region consisting of the amino acid sequence of QQHNEYPLT (SEQ ID NO: 2), respectively (see FIG. 2).

Further, CDR1, CDR2 and CDR3 in the heavy chain variable region (VH) of rat anti-bovine PD-L1 antibody 6C11-3A11 are a region consisting of the amino acid sequence of GYTFTDYI (SEQ ID NO: 3), a region consisting of the amino acid sequence of INPDSGGN (SEQ ID NO: 4) and a region consisting of the amino acid sequence of ARGITMMVVISHWKFDF (SEQ ID NO: 5), respectively (see FIG. 2).

In the ammo acid sequences of KSISKY (SEQ ID NO: 1), SGS and QQHNEYPLT (SEQ ID NO: 2), as well as the amino acid sequences of GYTFTDYI (SEQ ID NO: 3), INPDSGGN (SEQ ID NO: 4) and ARGITMMVVISHWKFDF (SEQ ID NO: 5), one, two, three, four or five amino acids may be deleted, substituted or added. Even when such mutations have been introduced, the resulting amino acid sequences are capable of having the function as CDR of VL or CDR of VH of the PD-L1 antibody.

As used herein, the term "antibody" is a concept encompassing not only full-length antibodies but also antibodies of smaller molecular sizes such as Fab, F(ab)'$_2$, ScFv, Diabody, $V_H$, $V_L$, Sc(Fv)$_2$, Bispecific sc(Fv)$_2$, Minibody, scFv-Fc monomer and scFv-Fc dimer.

The anti-PD-L1 antibody of the present invention may be derived from rat. For example, the anti-PD-L1 antibody may be a rat anti-bovine PD-L1 antibody.

The amino acid sequence of the VL and the amino acid sequence of the VH of rat anti-bovine PD-L1 antibody 6C11-3A11 (monoclonal antibody) are shown in SEQ ID NOS: 6 and 7, respectively. The amino acid sequences as shown in SEQ ID NOS: 6 and 7 may have deletion(s), substitution(s) or addition(s) of one or several (e.g., up to five, about 10 at the most) amino acids. Even when such mutations have been introduced, the resulting amino acid sequences are capable of having the function as VL or VH of the PD-L1 antibody.

There are two types of immunoglobulin light chain, which are called Kappa chain (κ) and Lambda chain (λ). In the anti-PD-L1 antibody of the present invention, the light chain constant region (CL) may have the amino acid sequence of the constant region of either Kappa chain or Lambda chain. However, the relative abundance of Lambda chain is higher in ovine, feline, canine and equine, and that of Kappa chain is higher in mouse, rat, human and porcine. Rat anti-bovine PD-L1 antibody 6C11-3A11 (monoclonal antibody) is a rat-derived IgG2a, and the CL thereof has the amino acid sequence of the constant region of Kappa chain.

The heavy chain constant region (CH) of the anti-PD-L1 antibody of the present invention may have the amino acid sequence of the constant region of rat IgG2a. Immunoglobulin heavy chain is classified into γ chain, μ chain, α chain, δ chain and ε chain depending on the difference in constant region. According to the type of heavy chain present, five classes (isotypes) of immunoglobulin are formed: they are IgG, IgM, IgA, IgD and IgE.

Immunoglobulin G (IgG) accounts for 70-75% of human immunoglobulins and is the most abundantly found monomeric antibody in plasma. IgG has a four-chain structure consisting of two light chains and two heavy chains. Human IgG1, IgG2 and IgG4 have molecular weights of about 146,000, whereas human IgG3 has a long hinge region that connects Fab region and Fc region and has a larger molecular weight of 170,000. Human IgG1 accounts for about 65%, human IgG2 about 25%, human IgG3 about 7%, and human IgG4 about 3% of human IgG. They are uniformly distributed inside and outside of blood vessels. Having a strong affinity for Fc receptors and complement factors on effector cell surfaces, human IgG1 induces antibody-dependent cell cytotoxicity (ADCC) and also activates complements to induce complement-dependent cell cytotoxicity (CDC). Human IgG2 and IgG4 are low at ADCC and CDC activities because their affinity for Fc receptors and complement factors is low.

Immunoglobulin M (IgM), which accounts for about 10% of human immunoglobulins, is a pentameric antibody consisting of five basic four-chain structures joined together. It has a molecular weight of 970,000. Usually occurring only in blood, IgM is produced against infectious microorganisms and takes charge of early stage immunity.

Immunoglobulin A (IgA) accounts for 10-15% of human immunoglobulins. It has a molecular weight of 160,000. Secreted IgA is a dimeric antibody consisting of two IgA molecules joined together. IgA1 is found in serum, nasal discharge, saliva and breast milk. In intestinal juice, IgA2 is found abundantly.

Immunoglobulin D (IgD) is a monomeric antibody accounting for no more than 1% of human immunoglobulins. IgD is found on B cell surfaces and involved in induction of antibody production.

Immunoglobulin E (IgE) is a monomeric antibody that occurs in an extremely small amount, accounting for only 0.001% or less of human immunoglobulins. Immunoglobulin E is considered to be involved in immune response to parasites but in advanced countries where parasites are rare, IgE is largely involved in bronchial asthma and allergy among other things.

With respect to rat, sequences of IgG1, IgG2a, IgG2b and IgG2c have been identified as the heavy chain of IgG. Rat anti-bovine PD-L1 antibody 6C11-3A11 has the amino acid sequence of the CH of IgG2a.

In the antibody of the present invention, it is more preferable that the CL has the amino acid sequence of the constant region of Kappa chain and that the CH has the amino acid sequence of the constant region of IgG2a.

The amino acid sequence and the nucleotide sequence of the VL of rat anti-bovine PD-L1 antibody 6C11-3A11 identified by the present inventors are shown in SEQ ID NOS: 6 and 14, respectively.

The amino acid sequence and the nucleotide sequence of the VH of rat anti-bovine PD-L1 antibody 6C11-3A11 identified by the present inventors are shown in SEQ ID NOS: 7 and 15, respectively.

The amino acid sequence and the nucleotide sequence of the CL (Kappa chain) of rat anti-bovine PD-L1 antibody 6C11-3A11 identified by the present inventors are shown in SEQ 3 ID NOS: 8 and 16, respectively. These sequences are identical with the sequences registered at GenBank (a nucleotide sequence database provided by National Center for Biotechnology Information (NCBI)) under accession numbers #XM_08775358.2, #BC062802.1, #BC088255.1, #L22653.1, #L22655.1 and #M14434.1.

The amino acid sequence and the nucleotide sequence of the CH (IgG2a) of rat anti-bovine PD-L1 antibody 6C11-3A11 identified by the present inventors are shown in SEQ ID NOS: 9 and 17, respectively. These sequences are identical with the sequences registered at GenBank under accession numbers #BC088240.1, #BC091257.1, 1909 BC091272.1, #BC088423.1, #L22652.1 and #L22654.1.

Amino acid sequences and nucleotide sequences of CLs and CHs for rat antibodies other than the above may be obtained from known databases for use in the present invention.

As an amino acid sequence and a nucleotide sequence of rat Ig Kappa chain, the sequence registered at GenBank under accession number #V01241.1 is shown in SEQ ID NOS: 10 and 18.

As an amino acid sequence and a nucleotide sequence of rat Ig Kappa chain, the sequence registered at GenBank under accession number #X16129.1 is shown in SEQ ID NOS: 11 and 19.

As an amino acid sequence and a nucleotide sequence of rat Ig Kappa chain, the sequence registered at GenBank under accession number #DQ402471.1 is shown in SEQ ID NOS: 12 and 20.

As the CH of rat IgG2a, the sequence registered at GenBank under accession number #DQ402472.1 is shown in SEQ ID NOS: 13 and 21.

The anti-PD-L1 antibody of the present invention may be an anti-PD-L1 antibody in which the CL has the amino acid sequence as shown in any one of SEQ ID NOS: 8 and 10 to 12 and the CH has the amino acid sequence as shown in SEQ ID NO: 9 or 13.

The amino acid sequences as shown in SEQ ID NOS: 8 to 13 may have deletion(s), substitution(s) or addition(s) of one or several (e.g., up to five, about 10 at the most) amino acids. Even when such mutations have been introduced, the resulting amino acid sequences are capable of having the function as CL or CH of the PD-L1 antibody.

Figure 8:
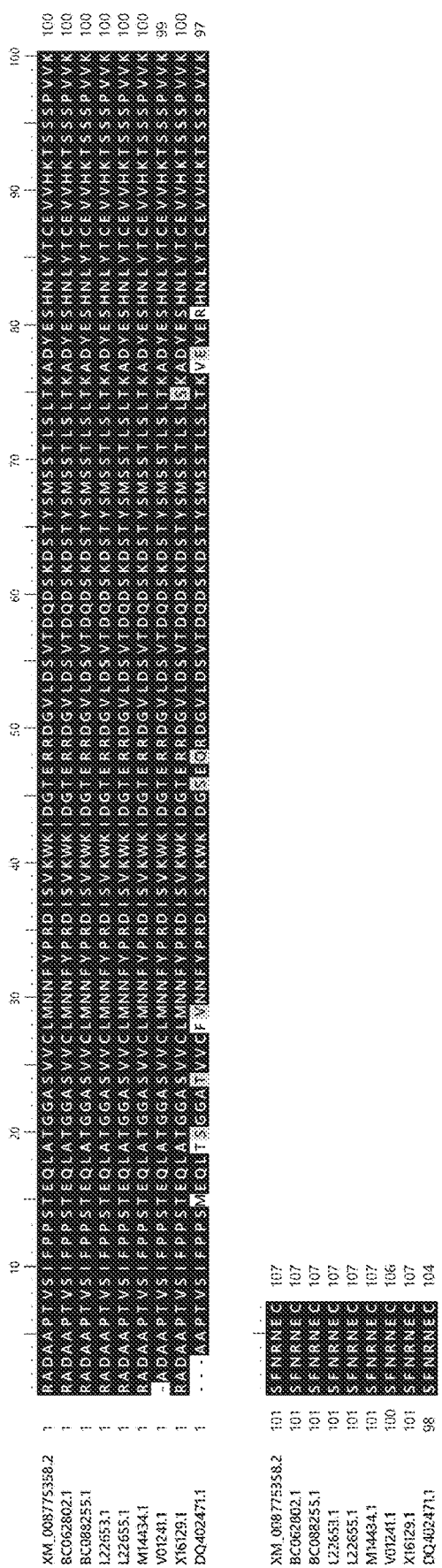
FIG. 8 Alignment of amino acid sequences of the constant region of rat Ig kappa chain (light chain).
Figure 9:
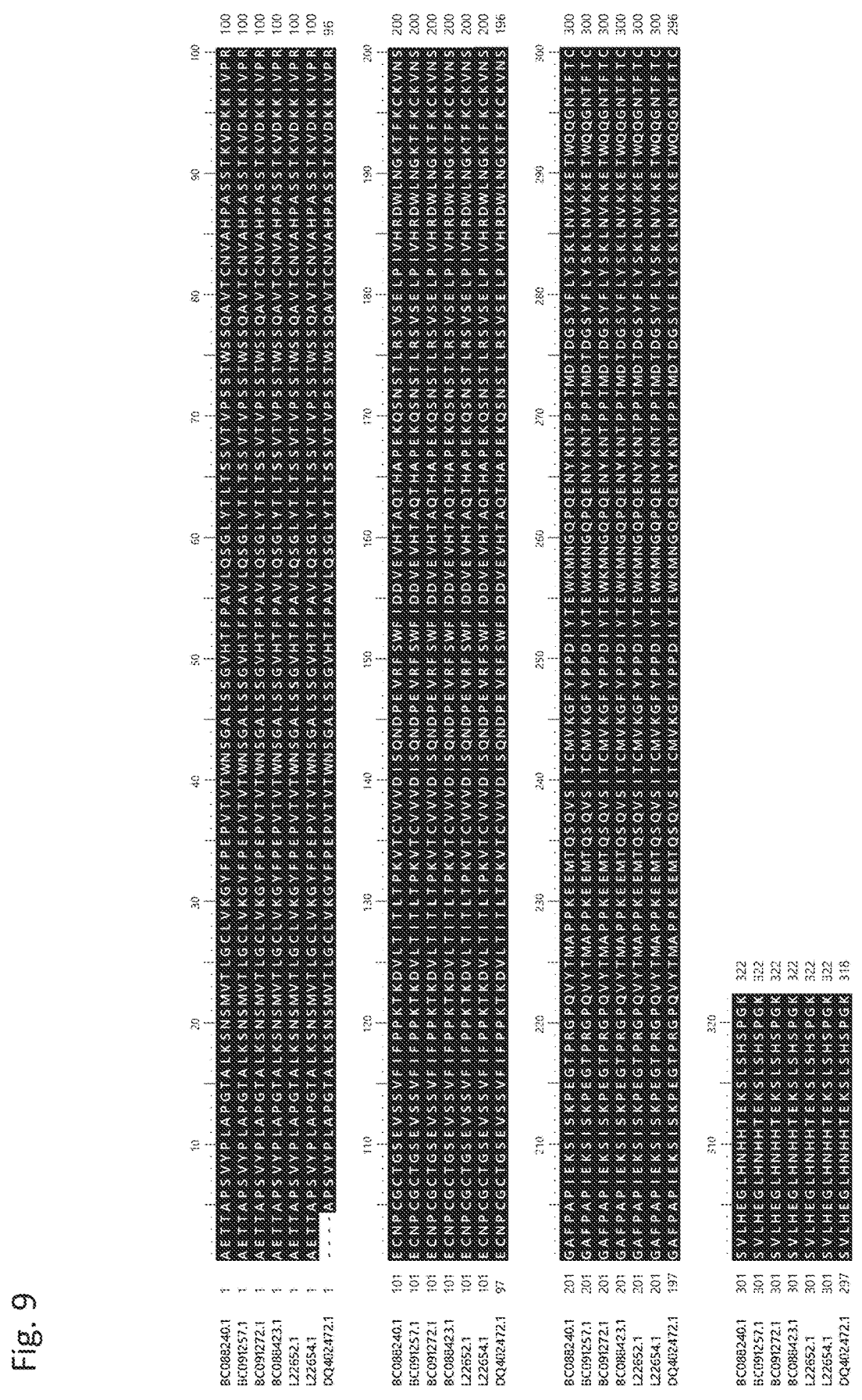

Alignments of amino acid sequences of the CL and the CH of a rat anti-PD-L1 antibody are shown in FIG. 8 and FIG. 9, respectively. The above-described mutations such as deletion, substitution or addition of amino acids may suitably have occurred at the mutation sites as shown in FIGS. 8 and 9 or at the vicinity thereof.

The anti-PD-L1 antibody of the present invention may be a chimeric antibody. The VL and the VH of the antibody may be suitable derived from rat. For example, the VL may be the VL of a rat anti-PD-L1 antibody (e.g., 6C11-3A11); the VH may be the VH of a rat anti-PD-L1 antibody; and the CL and the CH may be derived from an animal other than rat. For example, when a rat antibody a chimerized using the constant regions of a mouse antibody, the resulting chimeric antibody will be useful for testing and diagnosis because various secondary antibodies to mouse antibodies are commercially available. Amino acid sequences and nucleotide sequences of the CLs and the CHs of antibodies of animals other than rat may be obtained from known databases for use in the present invention.

Amino acid sequences and nucleotide sequences of CLs and CHs for human, mouse, bovine, canine, ovine, porcine and water buffalo are summarized in the table below.

TABLE

| Species | Ig Domain | Nucleotide Sequence | Amino Acid Sequence | GenBank Accession No. | IMGT Database | Reference |
|---|---|---|---|---|---|---|
| Human (Scientific Name: *Homo sapiens*) | Human Ig heavy chain constant region (CH1~CH3) | IgG 4 variant 1 | GAGTCCAAATATGGT CCCCCATGCCCATCA TGCCCAGCACCTGA GTTCCTGGGGGAC CATCAGTCTTCCTGT TCCCCCCAAAACCCA AGGACACTCTCATGA TCTCCCGGACCCCTG AGGTCACGTGCGTG GTGGTGGACGTGAG CCAGGAAGACCCCG AGGTCCAGTTCAACT GGTACGTGGATGGC GTGGAGGTGCATAA TGCCAAGACAAAGC CGCGGGAGGAGCAG TTCAACAGCACGTAC CGTGTGGTCAGCGT CCTCACCGTCCTGCA CCAGGACTGGCTGA ACGGCAAGGAGTAC AAGTGCAAGGTCTC CAACAAAGGCCTCC CGTCCTCCATCGAGA AAACCATCTCCAAAG CCAAAGGGCAGCCC CGAGAGCCACAGGT GTACACCCTGCCCCC ATCCCAGGAGGAGA TGACCAAGAACCAG GTCAGCCTGACCTG CCTGGTCAAAGGCTT CTACCCCAGCGACAT CGCCGTGGAGTGGG AGAGCAATGGGCAG CCGGAGAACAACTA CAAGACCACGCCTC CCGTGCTGGACTCC GACGGCTCCTTCTTC CTCTACAGCAGGCTA ACCGTGGACAAGAG CAGGTGGCAGGAGG GGAATGTCTTCTCAT GCTCCGTGATGCAT GAGGCTCTGCACAA CCACTACACACAGAA | ESKYGPPCPSCPAPEFL GGPSVFLFPPKPKDTL MISRTPEVTCVVVDVSQ EDPEVQFNWYVDGVEV HNAKTKPREEQFNSTY RVVSVLTVLHQDWLNG KEYKCKVSNKGLPSSIE KTISKAKGQPREPQVYT LPPSQEEMTKNQVSLT CLVKGFYPSDIAVEWES NGQPENNYKTTPPVLD SDGSFFLYSRLTVDKSR WQEGNVFSCSVMHEAL HNHYTQKSLSLSLGK* (SEQ ID NO: 30) | K01316 | http://www.imgt.org/ IMGT reper toire/ index.php?PMID: section = Locus Genes & reper toire = gene table & species = human & group = IGHC | Ellison J. et al., DNA, 1, 11-18 (1981). 6299662 |

TABLE-continued

| Species | Ig Domain | Nucleotide Sequence | Amino Acid Sequence | GenBank Accession No. | IMGT Database | Reference |
|---|---|---|---|---|---|---|
| | | GAGCCTCTCCCTGTC TCTGGGTAAATGA (SEQ ID NO: 31) | | | | |
| | IgG 4 variant 2 | GAGTCCAAATATGGT CCCCCGTGCCCATCA TGCCCAGCACCTGA GTTCCTGGGGGGAC CATCAGTCTTCCTGT TCCCCCCAAAACCCA AGGACACTCTCATGA TCTCCCGGACCCCTG AGGTCACGTGCGTG GTGGTGGACGTGAG CCAGGAAGACCCCG AGGTCCAGTTCAACT GGTACGTGGATGGC GTGGAGGTGCATAA TGCCAAGACAAAGC CGCGGGAGGAGCAG TTCAACAGCACGTAC CGTGTGGTCAGCGT CCTCACCGTCGTGCA CCAGGACTGGCTGA ACGGCAAGGAGTAC AAGTGCAAGGTCTC CAACAAAGGCCTCC CGTCCTCCATCGAGA AAACCATCTCCAAAG CCAAAGGGCAGCCC CGAGAGCCACAGGT GTACACCCTGCCCCC ATCCCAGGAGGAGA TGACCAAGAACCAG GTCAGCCTGACCTG CCTGGTCAAAGGCTT CTACCCCAGCGACAT CGCCGTGGAGTGGG AGAGCAATGGGCAG CCGGAGAACAACTA CAAGACCACGCCTC CCGTGCTGGACTCC GACGGCTCCTTCTTC CTCTACAGCAGGCTA ACCGTGGACAAGAG CAGGTGGCAGGAGG GGAATGTCTTCTCAT GCTCCGTGATGCAT GAGGCTCTGCACAA CCACTACACGCAGA AGAGCCTCTCCCTGT CTCTGGGTAAATGA (SEQ ID NO: 33) | ESKYGPPCPSCPAPEFL GGPSVFLFPPKPKDTL MISRTPEVTCVVVDSQ EDPEVQFNWYVDGVEV HNAKTKPREEQFNSTY RVVSVLTVVHQDWLNG KEYKCKVSNKGLPSSIE KTISKAKGQPREPQVYT LPPSQEEMTKNQVSLT CLVKGFYPSDIAVEWES NGQPENNYKTTPPVLD SDGSFFLYSRLTVDKSR WQEGNVFSCSVMHEAL HNHYTQKSLSLSLGK* (SEQ ID NO: 32) | AJ001563 | | Brusco A, et al., Eur. J. Immunogen et., 25, 349-355 (1998). PMID: 9805657 |
| | IgG 4 variant 3 | GCACCTGAGTTCCTG GGGGGACCATCAGT CTTCCTGTTCCCCCC AAAACCCAAGGACA CTCTCATGATCTCCC GGACCCCTGAGGTC ACGTGCGTGGTGGT GGACGTGAGCCAGG AAGACCCCGAGGTC CAGTTCAACTGGTAC GTGGATGGCGTGGA GGTGCATAATGCCA AGACAAAGCCGCGG GAGGAGCAGTTCAA CAGCACGTACCGTG TGGTCAGCGTCCTCA CCGTCCTGCACCAG GACTGGCTGAACGG CAAGGAGTACAAGT GCAAGGTCTCCAAC AAAGGCCTCCCGTC | APEFLGGPSVFLFPPKP KDTLMISRTPEVTCVVV DVSQEDPEVQFNWYVD GVEVHNAKTKPREEQF NSTYRVVSVLTVLHQD WLNGKEYKCKVSNKG LPSSIEKTISKAKGQPR EPQVYTLPPSQEEMTK NQVSLTCLVKGFYPSDI AVEWESNGQPENNYKT TPPVLDSDGSFFLYSKL TVDRSRWQEGNVFSCS VMHEALHNHYTQKSLS LSLGK* (SEQ ID NO: 34) | AJ001564 | | |

| Species | Ig Domain | | Nucleotide Sequence | Amino Acid Sequence | GenBank Accession No. | IMGT Database | Reference |
|---|---|---|---|---|---|---|---|
| | | | CTCCATCGAGAAAAC CATCTCCAAAGCCAA AGGGCAGCCCCGAG AGCCACAGGTGTAC ACCCTGCCCCCATCC CAGGAGGAGATGAC CAAGAACCAGGTCA GCCTGACCTGCCTG GTCAAAGGCTTCTAC CCCAGCGACATCGC CGTGGAGTGGGAGA GCAATGGGCAGCCG GAGAACAACTACAA GACCACGCCTCCCG TGCTGGACTCCGAC GGCTCCTTCTTCCTC TACAGCAAGCTCACC GTGGACAAGAGCAG GTGGCAGGAGGGGA ACGTCTTCTCATGCT CCGTGATGCATGAG GCTCTGCACAACCAC TACACGCAGAAGAG CCTCTCCCTGTCTCT GGGTAAATGA (SEQ ID NO: 35) | | | | |
| | Human Ig light chain constant region | Ig kappa (CK) | ACTGTGGCTGCACG ATCTGTCTTCATCTT CCCGCCATCTGATGA GCAGTTGAAATCTG GAACTGCCTCTGTTG TGTGCCTGCTGAATA ACTTCTATCCCAGAG AGGCCAAAGTACAG TGGAAGGTGGATAA CGCCCTCCAATCGG GTAACTCCCAGGAG AGTGTCACAGAGCA GGACAGCAAGGACA GCACCTACAGCCTCA GCAGCACCCTGACG CTGAGCAAAGCAGA CTACGAGAAACACA AAGTCTACGCCTGC GAAGTCACCCATCA GGGCCTGAGCTCGC CCGTCACAAAGAGC TTCAACAGGGGAGA GTGTTAG (SEQ ID NO: 29) | TVAAPSVFIFPPSDEQL KSGTASVVGLLNNFYPR EAKVQWKVDNALQSG NSQESVTEQDSKDSTYS LSSTLTLSKADYEKHKV YACEVTHQGLSSPVTKS FNRGEC* (SEQ ID NO: 28) | X96754 | http:// www. imgt.org/ IMGT reper toire/ index.php? section = Locus Genes & reper toire = gene table & species = human & group = IGKC | |
| Mouse (Scientific Name: Mus musculus) | Mouse Ig heavy chain constant region (CH1~ CH3) | IgG1 variant 1 | GCCAAAACGACACCCCCA TCTGTCTATCCACTGGCC CCTGGATCTGCTGCCCAA ACTAACTCCATGGTGACC CTGGGATGCCTGGTCAAG GGCTATTTCCCTGAGCCA GTGACAGTGACCTGGAAC TCTGGATCCCTGTCCAGC GGTGTGCACACCTTCCCA GCTGTCCTGGAGTCTGAC CTCTACACTCTGAGCAGC TCAGTGACTGTCCCCTCC AGCCCTCGGCCCAGCGA GACCGTCACCTGCAACGT TGCCCACCCGGCCAGCAG CACCAAGGTGGACAAGAA AATTGTGCCCAGGGATTG TGGTTGTAAGCCTTGCAT ATGTACAGTCCCAGAAGT ATCATCTGTCTTCATCTT CCCCCCAAAGCCCAAGGA TGTGCTCACCATTACTCT GACTCCTAAGGTCACGTG | AKTTPPSVYPLAPGSAAQ TNSMVTLGCLVKGYFPE PVTVTWNSGSLSSGVHT FPAVLESDLYTLSSSVTV PSSPRPSETVTCNVAHPA SSTKVDKKIVPRDCGCKP CICTVPEVSSVFIFPPKP KDVLTITLTPKVTCVVVD ISKDDPEVQFSWFVDDVE VHTAQTQPREEQFNSTFR SVSELPIMHQDWLNGKE FRCRVNSAAFPAPIEKTI SKTKGRPKAPQVYTIPPP KEQMAKDKVSLTCMITD FFPEDITVEWQWNGQPA ENYKNTQPIMNTNGSYF VYSKLNVQKSNWEAGNT FTCSVLHEGLHNHHTEK SLSHSPGK (SEQ ID NO: 44) | J00453 AH00530 9 V00793 D78344 | http:// www. imgt.org/ IMGT reper toire/ index.php?PMID: section = 115593 Locus Genes & reper toire = gene table & species = Mus_ musculus & group = IGHC | Honjo T. et al., Cell, 18, 559-568 (1979). Akahori Y. and Kurosawa Y., Geno- mics., 41, 100-104 (1997). PMID: 9126488 |

TABLE-continued

| Species | Ig Domain | Nucleotide Sequence | Amino Acid Sequence | GenBank Accession No. | IMGT Database | Reference |
|---------|-----------|---------------------|---------------------|----------------------|---------------|-----------|
| | | TGTTGTGGTAGACATCAG CAAGGATGATCCCGAGGT CCAGTTCAGCTGGTTTGT AGATGATGTGGAGGTGCA CACAGCTCAGACGCAACC CCGGGAGGAGCAGTTCA ACAGCACTTTCCGCTCAG TCAGTGAACTTCCCATCA TGCACCAGGACTGGCTCA ATGGCAAGGAGTTCAAAT GCAGGGTCAACAGTGCA GCTTTCCCTGCCCCCATC GAGAAAACCATCTCCAAA ACCAAAGGCAGACCGAA GGCTCCACAGGTGTACAC CATTCCACCTCCCAAGGA GCAGATGGCCAAGGATAA AGTCAGTCTGACCTGCAT GATAACAGACTTCTTCCC TGAAGACATTACTGTGGA GTGGCAGTGGAATGGGC AGCCAGCGGAGAACTACA AGAACACTCAGCCCATCA TGAACACGAATGGCTCTT ACTTCGTCTACAGCAAGC TCAATGTGCAGAAGAGCA ACTGGGAGGCAGGAAAT ACTTTCACCTGCTCTGTG TTACATGAGGGCCTGCAC AACCACCATACTGAGAAG AGCCTCTCCCACTCTCCT GGTAAATGA (SEQ ID NO: 45) | | | | |
| | IgG1 variant 2 | GCCAAAACGACACCCCCA TCTGTCTATCCACTGGCC CCTGGATCTGCTGCCCAA ACTAACTCCATGGTGACC CTGGGATGCCTGGTCAAG GGCTATTTCCCTGAGCCA GTGACAGTGACCTGGAAC TCTGGATCCCTGTCCAGC GGTGTGCACACCTTCCCA GCTGTCCTGCAGTCTGAC CTCTACACTCTGAGCAGC TCAGTGACTGTCCCCTCC AGCACCTGGCCCAGCCAG ACCGTCACCTGCAACGTT GCCCACCCGGCCAGCAG CACCAAGGTGGACAAGAA AATTGTGCCCAGGGATTG TGGTTGTAAGCCTTGCAT ATGTACAGTCCCAGAAGT ATCATCTGTCTTCATCTT CCCCCCAAAGCCCAAGGA TGTGCTCACCATTACTCT GACTCCTAAGGTCACGTG TGTTGTGGTAGACATCAG CAAGGATGATCCCGAGGT CCAGTTCAGCTGGTTTGT AGATGATGTGGAGGTGCA CACAGCTCAGACGAAACC CCGGGAGGAGCAGATCA ACAGCACTTTCCGTTCAG TCAGTGAACTTCCCATCA TGCACCAGGACTGGCTGA ATGGCAAGGAGTTCAAAT GCAGGGTCAACAGTGCA GCTTTCCCTGCCCCCATC GAGAAAACCATCTCCAAA ACCAAAGGCAGACCGAA GGCTCCACAGGTGTACAC CATTCCACCTCCCAAGGA GCAGATGGCCAAGGATAA AGTCAGTCTGACCTGCAT | AKTTPPSVYPLAPGSAAQ TNSMVTLGCLVKGYFPE PVTVTWNSGSLSSGVHT FPAVLQSDLYTLSSSVTV PSSTWPSQTVTCNVAHP ASSTKAMKKIVPRDCGCK PCICTVPEVSSVFIFPPKP KDVLTITLTPKVTCVVVD ISKDDPEVQFSWFVDDV EVHTAQTKPREEQINSTF RSVSELPIMHQDWLNGK EFKCRVNSAAFPAPIEKT ISKTKGRPKAPQVYTIPP PKEQMAKDKVSLTCMIT NFFPEDITVEWQWNGQP AENYKNTQPIMDTDGSY FVYSKLNVQKSNWEAGN TFTCSVEHEGLHNHHTE KSLSHSPGK (SEQ ID NO: 46) | L35252 | | Honjo T. et al., Cell, 18, 559-568 (1979). PMID: 115593 |

TABLE-continued

| Species | Ig Domain | Nucleotide Sequence | Amino Acid Sequence | GenBank Accession No. | IMGT Database | Reference |
|---|---|---|---|---|---|---|
| | | GATAACAAACTTCTTCCC TGAAGACATTACTGTGGA GTGGCAGTGGAATGGGC AGCCAGCGGAGAACTACA AGAACACTCAGCCCATCA TGGACACAGATGGCTCTT ACTTCGTCTACAGCAAGC TCAATGTGCAGAAGAGCA ACTGGGAGGCAGGAAAT ACTTTCACCTGCTCTGTG TTACATGAGGGCCTGCAC AACCACCATACTGAGAAG AGCCTCTCCCACTCTCCT GGTAAATGA (SEQ ID NO: 47) | | | | |
| | IgG2a variant 1 | GCCAAAACAACAGCCCCA TCGGTCTATCCACTGGCC CCTGTGTGTGGAGATACA ACTGGCTCCTCCGGTGACT CTAGGATGCCTGGTCAAG GGTTATTTCCCTGAGCCA GTGACCTTGACCTGGAAC TCTGGATCCCTGTCCAGT GGTGTGCACACCTTCCCA GCTGTCCTGCAGTCTGAC CTCTACACCCTCAGCAGC TCAGTGACTGTAACCTCG AGCACCTGGCCCAGCCAG TCCATCACCTGCAATGTG GCCGACCCGGCAAGCAG CACCAAGGTGGACAAGAA AATTGAGCCCAGAGGGGC CACAATCAAGCCCTGTCC TCCATGCAAATGCCCAGC ACCTAACCTCTTGGGTGG ACCATCCGTCTTCATCTT CCCTCCAAAGATCAAGGA TGTACTCATGATCTCCCT GAGCCCCATAGTCACATG TGTGGTGGTGGATGTGAG CGAGGATGACCCAGATGT CGAGATCAGCTGGTTTGT GAACAACGTGGAAGTACA CACAGCTCAGACACAAAC CCATAGAGAGGATTACAA CAGTACTCTCCGGGTGGT CAGTGCCCTCCCCATCCA GCACCAGGACTGGATGA GTGGCAAGGAGTTCAAAT GCAAGGTCAACAACAAAG ACCTCCCAGCGCCCATCG AGAGAACCATCTCAAAAC CCAAAGGGTCAGTAAGAG CTCCACAGGTATATGTCT TGCCTCCACCAGAAGAAG AGATGACTAAGAAACAGG TCACTCTGACCTGCATGG TCACAGACTTCATGCCTG AAGACATTTACGTGGAGT GGACCAACAACGGGAAA ACAGAGCTAAACTACAAG AACACTGAACCAGTCCTG GACTCTGATGGTTCTTAC TTCATGTACAGCAAGCTG AGAGTGGAAAAGAAGAA CTGGGTGGAAAGAAATAG CTACTCCTGTTCAGTGGT CCACGAGGGTCTGCACAA TCACCACACGACTAAGAG CTTCTCCCGGACTCCGGG TAAATGA (SEQ ID NO: 49) | AKTTAPSVYPLAPVCGDT TGSSVTLGCLVKGYFPEP VTLTWNSGSLSSGVHTFP AVLQSDLYTLSSSVTVTS STWPSQSITCNVAHPASS TKVDKKIEPRGPTIKPCP PCKCPAPNLLGGPSVFIF PPKIKDVLMISLSPIVTC VVVDVSEDDPDVQISWFV NNVEVHTAQTQTHREDY NSTLRVVSALPIQHQDW MSGKEFKCKVNNKDLPA PIERTISKPKGSVRAPQV YVLPPPEEEMTKKQVTL TCMVTDFMPEDIYVEWT NNGKTELNYKNTEPVLD SDGSYFMYSKLRVEKKN WVERNSYSCSVVHEGLH NHHTTKSFSRTPGK (SEQ ID NO: 48) | J00470 AH00530 9 V00825 V00766 D78344 | | Yamawaki- Kataoka Y. et al., Nucleic Acids Res., 9, 1365- 1381 (1981). PMID: 6262729 Ollo R. et al., Proc. Natl. Acad. Sci. U.S.A., 78, 2442- 2446 (1981). PMID: 6787604 Sikorav J. L. et al., Nucleic Acids Res., 8, 3143- 3155 (1980). PMID: 6777755 Akahori Y., and Kurosawa Y., Genomics., 41, 100-104 (1997). PMID: 9126488 |

TABLE-continued

| Species | Ig Domain | Nucleotide Sequence | Amino Acid Sequence | GenBank Accession No. | IMGT Database | Reference |
|---|---|---|---|---|---|---|
| | IgG2a variant 2 | GCCAAAACAACAGCCCCA TCGGTCTATCCACTGGCC CCTGTGTGTGGAGATACA ACTGGCTCCTCGGTGACT CTAGGATGCCTGGTCAAG GGTTATTTCCCTGAGCCA GTGACCTTGACCTGGAAC TCTGGATCCCTGTCGAGT GGTGTGCACACCTTCCCA GCTGTCCTGCAGTCTGAC CTCTACACCCTCAGCAGC TCAGTGACTGTAACCTCG AGCACCTGGCCCAGCCAG TCCATCACCTGCAATGTG GCCCACCCGGCAAGCAG CACCAAGGTGGACAAGAA AATTGAGCCCAGAGGGCC CACAATCAAACCCTGTGC TCCATGCAAATGCCCAGC ACCTAACCTCTTGGGTGG ACCATCCGTCTTCATCTT CCCTCCAAAGATCAAGGA TGTACTCATGATCTCCCT GAGTCCCATGGTCACATG TGTGGTGGTGGATGTGAG CGAGGATGACCCAGATGT CCAGATCAGCTGGTTCGT GAACAACGTGGAAGTACT CACAGCTCAGACACAAAC CCATAGAGAGGATTACAA CAGTACTCTCCGGGTGGT CAGTGCCCTCCCCATCCA GCACCAGGACTGGATGA GTGGCAAGGAGTTCAAAT GCAAGGTCAACAACAAAG CCCTCCCAGCGCCCATCG AGAGAACCATCTCAAAAC CCAAAGGGTCAGTAAGAG CTCCACAGGTATATGTCT TGCCTCCACCAGAAGAAG AGATGACTAAGAAACAGG TCACTCTGACCTGCATGG TCACAGACTTCATGCCTG AAGACATTTACGTGGAGT GGACCAACAACGGGAAA ACAGAGCTAAACTACAAG AACACTGAACCAGTCCTG GACTCTGATGGTTCTTAC TTCATGTACAGCAAGCTG AGAGTGGAAAAGAAGAA CTGGGTGGAAAGAAATAG CTACTCCTGTTCAGTGGT CCACGAGGGTCTGCACAA TCACCACACGACTAAGAG CTTCTCCCGGACTCCGGG TAAATGA (SEQ ID NO: 51) | AKTTAPSYYPLAPVCGDT TGSSVTLGCLVKGYFPEP VTLTWNSGSLSSGVHTFP AVLQSDLYTLSSSVTVTS STWPSQSITCNVAHPASS TKVDKKIEPRGPTIKPCP PCKCPAPNLLGGPSVFIF PPKIKDVLMISLSPMVTC VVVDVSEDDPDVQISWF VNNVEVLTAQTQTHRED YNSTLRVVSALPIQHQD WMSGKEFKCKVNNKAL PAPIERTLSKPKGSVRAP QVYVLPPPEEEMTKKQV TLTCMVTDFMPEDIYVE WTNNGKTELNYKNTEPV LDSDGSYFMYSKLRVEK KNWVERNSYSCSVVHEG LHNHHTTKSFSRITGK (SEQ ID NO: 50) | X16997 | | Morgado M. G. et al., EMBO J., 8, 3245- 3251 (1989). PMID: 2510996 |
| | IgG2b variant 1 | GCCAAAACAACACCCCCA TCAGTCTATCCACTGGCC CCTGGGTGTGGAGATACA ACTGGTTCCTCCGGTGACT CTGGTTCCTCCGGTGACT CTGGGATGCCTGGTCAAG GGCTACTTCCCTGAGTCA GTGACTGTGACTTGGAAC TCTGGATCCCTGTCCAGC AGTGTGCACACCTTCCCA GCTCTCCTGCAGTCTGGA CTCTACACTATGAGCAGC TCAGTGACTGTCCCCTCC AGCACTTGGCCAAGTCAG ACCGTCACCTGCAGCGTT GCTCACCCAGCCAGCAGC ACCACGGTGGACAAAAAA CTTGAGCCCAGCGGGCCC | AKTTPPSVYPLAPGCGDT TGSSVTLGCLVKGYFPES VTVTWNSGSLSSSVHTFP ALLQSGLYTMSSSVTVPS STWPSQTVTCSVAHPASS TTVDKKLEPSGPISTINP CPPCKECHKCPAPNLEG GPSVFIFPPNIKDVLMIS LTPKVTCVVVDVSEDDPD VQISWFVNNVEVHTAQT QTHREDYNSTIRVVSTLP IQHQDWMSGKEFKCKV NNKDLPSPIERTISKIKG LVRAPQVYILPPPAEQLS RKDVSLTCLVVGFNPGDI SVEWTSNGHTEENYKDTA PVLDSDGSYFIYSKLNMK | J00461 AH00530 9 V00801 D78344 | | Yamawak i- Kataoka Y. et al., Nature, 283, 786-789 (1980). PMID: 6766534 Ollo R. and Rougeon F., Nature, 296, |

TABLE-continued

| Species | Ig Domain | Nucleotide Sequence | Amino Acid Sequence | GenBank Accession No. | IMGT Database | Reference |
|---|---|---|---|---|---|---|
| | | ATTTCAACAATCAACCCC TGTCCTCCATGCAAGGAG TGTCACAAATGCCCAGCT CCTAACCTCGAGGGTGGA CCATCCGTCTTCATCTTC CCTCCAAATATCAAGGAT GTACTCATGATCTCCCTG ACACCCAAGGTCACGTGT GTGGTGGTGGATGTGAG CGAGGATGACCCAGACGT CCAGATCAGCTGGTTTGT GAACAACGTGGAAGTACA CACAGCTCAGACACAAAC CCATAGAGAGGATTACAA CAGTACTATCCGGGTGGT CAGCACCCTCCCCATCCA GCACCAGGACTGGATGA GTGGCAAGGAGTTCAAAT GCAAGGTCAACAACAAAG ACCTCCGATCACCGATCG AGAGAACCATCTCAAAAA TTAAAGGGCTAGTCAGAG CTCCACAAGTATACATCT TGCCGCCACCAGCAGAGC AGTTGTCCAGGAAAGATG TCAGTCTCACTTGCCTGG TCGTGGGCTTCAACCCTG GAGACATCAGTGTGGAGT GGACCAGCAATGGGCATA CAGAGGAGAACTACAAG GACACCGCACCAGTCCTA GACTCTGACGGTTCTTAC TTCATATATAGCAAGCTC AATATGAAAACAAGCAAG TGGGAGAAAACAGATTCC TTCTCATGCAACGTGAGA CACGAGGGTCTGAAAAAT TACTACCTGAAGAAGACC ATCTCCCGGTCTCCGGGT AAATGA (SEQ ID NO: 53) | TSKWEKTDSFSCNVRHE GLKNYYLKKTISRSPGK (SEQ ID NO: 52) | | | 761-763 (1982). PMID: 6803173 Akahori Y. and Kurosawa Y., Genomics., 41, 100-104 (1997). PMID: 9126488 |
| | IgG2b variant 2 | GCCAAAACAACACCCCCA TCAGTCTATCCACTGGCC CCTGGGTGTGGAGATACA ACTGGTTCCTCCGTGACC TCTGGGTGCCTGGTCAAG GGGTACTTCCCTGAGCCA GTGACTGTGACTTGGAAC TCTGGATCCCTGTCCAGC AGTGTGCACACCTTCCCA GCTCTCCTGCAGTCTGGA CTCTACACTATGAGCAGC TCAGTGACTGTCCCCTCC AGCACCTGGCCAAGTCAG ACCGTCACCTGCAGCGTT GCTCACCCAGCCAGCAGC ACCACGGTGGACAAAAAA CTTGAGCCCAGCGGGCCC ATTTCAACAATCAACCCC TGTCCTCCATGCAAGGAG TGTCACAAATGCCCAGCT CCTAACCTCGAGGGTGGA CCATCCGTCTTCATCTTC CCTCCAAATATCAAGGAT GTACTCATGATCTCCCTG ACACCCAAGGTCACGTGT GTGGTGGTGGATGTGAG CGAGGATGACCCAGACGT CCAGATCAGCTGGTTTGT GAACAACGTGGAAGTACA CACAGCTCAGACACAAAC CCATAGAGAGGATTACAA CAGTACTATCCGGGTGGT CAGCACCCTCCCCATCCA | AKTTPPSVYPLAPGCGDT TGSSVTSGCLVKGYFPEP VTVTWNSGSLSSSVHTFP ALLQSGLYTMSSSVTVPS STWPSQTVTCSVAHPASS TTVDKKLEPSGPISTINP CPPCKECHKCPAPNLEG GPSVFIFPPNIKDVLMIS LTPKVTCVVVDVSEDDPD VQISWFVNNVEVHTAQT QTHREDYNSTIRVVSTLP IQHQDWMSGKEFKCKV NNKDLPSPIERTISKIKG LVRAPQVYTLPPPAEQLS RKDVSLTCLVVGFNPGDI SVEWTSNGHTEENYKDTA PVLDSDGSYFIYSKLNMK TSKWEKTDSFSCNVRHE GLKNYYLKKTISRSPGK (SEQ ID NO: 54) | V00763 | | Tucker P. W. et al., Science., 206, 1303-1306 (1979). PMID: 117549 |

TABLE-continued

| Species | Ig Domain | Nucleotide Sequence | Amino Acid Sequence | GenBank Accession No. | IMGT Database | Reference |
|---|---|---|---|---|---|---|
| | | GCACCAGGACTGGATGA<br>GTGGCAAGGAGTTCAAAT<br>GCAAGGTGAACAACAAAG<br>ACCTCCCATCACCCATCG<br>AGAGAACCATCTCAAAAA<br>TTAAAGGGCTAGTCAGAG<br>CTCCACAAGTATACACTT<br>TGCCGCCACCAGCAGAGC<br>AGTTGTCCAGGAAAGATG<br>TCAGTCTCACTTGCCTGG<br>TCGTGGGCTTCAACCCTG<br>GAGACATCAGTGTGGAGT<br>GGACCAGCAATGGGCATA<br>CAGAGGAGAACTACAAG<br>GACACCGCACCAGTTCTT<br>GACTCTGACGGTTCTTAC<br>TTCATATATAGCAAGCTC<br>AATATGAAAACAAGCAAG<br>TGGGAGAAAACAGATTCC<br>TTCTCATGCAACGTGAGA<br>CACGAGGGTCTGAAAAAT<br>TACTACCTGAAGAAGACC<br>ATCTCCCGGTCTCCGGGT<br>AAATGA<br>(SEQ ID NO: 55) | | | | |
| | IgG2c variant 1 | GCCAAAACAACAGCCCCA<br>TCGGTCTATCCACTGGCC<br>CCTGTGTGTGGAGGTACA<br>ACTGGCTCCTCGGTGACT<br>CTAGGATGCCTGGTCAAG<br>GGTTATTTCCCTGAGCCA<br>GTGACCTTGACCTGGAAC<br>TCTGGATCCCTGTCCAGT<br>GGTGTGCACACCTTCCCA<br>GCTCTCCTGCAGTCTGGC<br>CTCTACACCCTCAGCAGC<br>TCAGTGACTGTAACCTCG<br>AACACCTGGCCCAGCCAG<br>ACCATCACCTGCAATGTG<br>GCCCACCCGGCAAGCAG<br>CACCAAAGTGGACAAGAA<br>AATTGAGCCCAGAGTGCC<br>CATAACACAGAACCCCTG<br>TCCTCCACTCAAAGAGTG<br>TCCCCCATGCGCAGCTCC<br>AGACCTCTTGGGTGGACC<br>ATCCGTCTTCATCTTCCC<br>TCCAAAGATCAAGGATGT<br>ACTCATGATCTCCCTGAG<br>CCCCATGGTCACATGTGT<br>GGTGGTGGATGTGAGCG<br>AGGATGACCCAGACGTCC<br>AGATCAGCTGGTTTGTGA<br>ACAACGTGGAAGTACACA<br>CAGCTCAGACACAAACCC<br>ATAGAGAGGATTACAACA<br>GTACTCTCCGGGTGGTCA<br>GTGCCCTCCCCATCCAGC<br>ACCAGGACTGGATGAGTG<br>GCAAGGAGTTCAAATGCA<br>AGGTCAACAACAGAGCCC<br>TCCCATCCCCCATCGAGA<br>AAACCATCTCAAACCCA<br>GAGGGCCAGTAAGAGCT<br>CCACAGGTATATGTCTTG<br>CCTCCACCAGCAGAAGAG<br>ATGACTAAGAAAGAGTTC<br>AGTCTGACCTGCATGATC<br>ACAGGCTTCTTACCTGCC<br>GAAATTGCTGTGGACTGG<br>ACCAGCAATGGGCGTACA<br>GAGCAAAACTACAAGAAC<br>ACCGCAACAGTCCTGGAC<br>TCTGATGGTTCTTACTTC | AKTTAPSVYPLAPVCGGT<br>TGSSVTLGCLVKGYFPEP<br>VTLTWNSGSLSSGVHTFP<br>ALLQSGLYTLSSSVTVTS<br>NTWPSQTITCNVAHPASS<br>TKVDKKIEPRVPITQNPC<br>PPLKECPPCAAPDLLGGP<br>SVFIFPPKIKDVLMISLS<br>PMVTCVVVDVSEDDPDVQ<br>ISWFVNNVEVHTAQTQT<br>HREDYNSTLRVVSALPIQ<br>HQDWMSGKEFKCKVNN<br>RALPSPIEKTISKPRGPV<br>RAPQVYVLPPPAEEMTKK<br>EFSLTCMITGFLPAEIAV<br>DWTSNGRTEQNYKNTAT<br>VLDSDGSYFMYSKLRVQ<br>KSTWERGSLFACSVVHE<br>VLHNHLTTKTISRSLGK<br>(SEQ ID NO: 56) | J00479 | | Ollo R. and Rougeon F., Cell, 32, 515-523 (1983). PMID: 6297797 |

TABLE-continued

| Species | Ig Domain | Nucleotide Sequence | Amino Acid Sequence | GenBank Accession No. | IMGT Database | Reference |
|---|---|---|---|---|---|---|
| | | ATGTACAGCAAGCTCAGA GTACAAAAGAGCACTTGG GAAAGAGGAAGTCTTTTC GCCTGCTCAGTGGTCCAC GAGGTGCTGCACAATCAC CTTACGACTAAGACCATC TCCCGGTCTCTGGGTAAA TGA (SEQ ID NO: 57) | | | | |
| | IgG2c variant 2 | GCCAAAAGAACAGCCCCA TCGGTCTATCCACTGGCC CCTGTGTGTGGAGGTACA ACTGGCTCCTCGGTGACT CTAGGATGCCTGGTCAAG GGTTATTTCCCTGAGCCA GTGACCTTGACCTGGAAC TCTGGATCCCTGTCCAGT GGTGTGCACACCTTCCCA GCTCTCCTGCAGTCTGGC CTCTACACCCTCAGCAGC TCAGTGACTGTAACCTCG AACACCTGGCCCAGCCAG ACCATCACCTGCAATGTG GCCCACCCGGCAAGCAG CACCAAAGTGGACAAGAA AATTGAATCCAGAAGGCC CATACCACCCAACTCCTG TCCTCCATGCAAAGAGTG TTCCATATTCCCAGCTCC TGACCTCTTGGGTGGACC ATCCGTCTTCATCTTCCC TCCAAAGATCAAGGATGT ACTCATGATCTCCCTGAG CCCCATAGTCACATGTGT GGTGGTGGATGTGAGCG AGGATGACCCAGATGTCC AGATCAGCTGGTTTGTGA ACAACGTGGAAGTACACA CAGCTCAGACACAAACCC ATAGAGAGGATTACAACA GTACTCTCCGGGTGGTCA GTGCCCTCCCCATCCAGC ACCAGGACTGGATGAGTG GCAAGGAGTTCAAATGCA AGGTCAACAACAGAGCCC TCCCATCCCCCATCGAGA AAACCATCTCAAAACCCA GAGGGCCAGTAAGAGCT CCACAGGTATATGTCTTG CCTCCACCAGCAGAAGAG ATGACTAAGAAAGAGTTC AGTCTGACCTGCATGATC ACAGACTTCTTACCTGCC GAAATTGCTGTGGACTGG ACCAGCAATGGGCATAAA GAGCTGAACTACAAGAAC ACCGCACCAGTCCTGGAC ACTGATGGTTCTTACTTC ATGTACAGCAAGCTCAGA GTGCAAAAGAGCACTTGG GAAAAGGAAGTCTTTTC GCCTGCTCAGTGGTCCAC GAGGGTCTGCACAATCAC CATACGACTAAGACCATC TCCCGGTCTCTGGGTAAA TGA (SEQ ID NO: 59) | AKTTAPSVYPLAPVCGGT TGSSVTLGCLVKGYFPEP VTLTWNSGSLSSGVHTFP ALLQSGLYTLSSSVTVTS NTWPSQTITCNVAHPASS TKVDKKIESRRPIPPNSC PPCKECSIFPAPDLLGGP SVFIFPPKIKDVLMISLS PIVTCVVVDVSEDDPDVQ ISWFVNNVEVHTAQTQTH REDYNSTLRVVSALPIQH QDWMSGKEFKCKVNNR ALPSPIEKTISKPRGPVR APQVYVLPPPAEEMTKKE FSLTCMITDFLPAEIAVD WTSNGHKELNYKNTAPV LDTDGSYFMYSKLRVQK STWEKGSLFACSVVHEG LHNHHTTKTISRSLGK (SEQ ID NO: 58) | X16998 | | Morgado M. G. et al., EMBO J., 8, 3245- 3251 (1989). PMID: 2510996 |
| | IgG2c variant 3 | GCCAAAACAACAGCCCCA TCGGTCTATCCACTGGCC CCTGTGTGTGGAGGTACA ACTGGCTCCTCGGTGACT CTAGGATGCCTGGTCAAG GGTTATTTCCCTGAGCCA | AKTTAPSVYPLAPVCGGT TGSSVTLGCLVKGYFPEP VTLTWNSGSLSSGVHTFP ALLQSGLYTLSSSVTVTS NTWPSQTITCNVAHPASS TKVDKKIEPRVPITQNPC | Y10606 | | Martin R. M. et al., Immuno- gene- tics, |

TABLE-continued

| Species | Ig Domain | Nucleotide Sequence | Amino Acid Sequence | GenBank Accession No. | IMGT Database | Reference |
|---|---|---|---|---|---|---|
| | | GTGACCTTGACCTGGAAC TCTGGATCCCTGTCCAGT GGTGTGCACACCTTCCCA GCTCTCCTGCAGTCTGGC CTCTACACCCTCAGCAGC TCAGTGACTGTAACCTCG AACACCTGGCCCAGCCAG ACCATCACCTGCAATGTG GCCCACCCGGCAAGCAG CACCAAAGTGGACAAGAA AATTGAGCCCAGAGTGCC CATAACACAGAACCCCTG TCCTCCACTCAAAGAGTG TCCCCCATGCGCAGCTCC AGACCTCTTGGTGGACC ATCCGTCTTCATCTTCCC TCCAAAGATCAAGGATGT ACTCATGATCTCCCTGAG CCCCATGGTCACATGTGT GGTGGTGGATGTGAGCG AGGATGACCCAGACGTCC AGATCAGCTGGTTTGTGA ACAACGTGGAAGTACACA CAGCTCAGACACAAACCC ATAGAGAGGATTACAACA GTACTCTCCGGGTGGTCA GTGCCCTCCCCATCCAGC ACCAGGACTGGATGAGTG GCAAGGAGTTCAAATGCA AGGTGAACAACAGAGCCC TCCCATCCCCCATCGAGA AAACCATCTCAAAACCCA GAGGGCCAGTAAGAGCT CCACAGGTATATGTCTTG CCTCCACCAGCAGAAGAG ATGACTAAGAAAGAGTTC AGTCTGACCTGCATGATC ACAGGCTTCTTACCTGCC GAAATTGCTGTGGACTGG ACCAGCAATGGGCGTACA GAGCAAAACTACAAGAAC ACCGCAACAGTCCTGGAC TCTGATGGTTCTTACTTC ATGTACAGCAAGCTCAGA GTACAAAAGAGCACTTGG GAAAGAGGAAGTCTTTTC GCCTGCTCAGTGGTCCAC GAGGGTCTGCACAATCAC CTTACGACTAAGACCATC TCCCGGTCTCTGGGTAAA TGA (SEQ ID NO: 61) | PPLKECPPCAAPDLLGGP SVFIFPPKIKDVLMISLS PMVTCVVVDVSEDDPDVQ ISWFVNNVEVHTAQTQT HREDYNSTLRVVSALPIQ HQDWMSGKEFKCKVNN RALPSPIEKTISKPRGPV RAPQVYVLPPPAEEMTKK EFSLTCMITGFLPAEIAV DWTSNGRTEQNYKNTAT VLDSDGSYFMYSKLRVQ KSTWERGSLFACSVVHE GLHNHLTTKTISRSLGK (SEQ ID NO: 60) | | | 46, 167-168 (1997). PMID: 9162106 |
| | IgG3 | GCTACAACAACAGCCCCA TCTGTCTATCCCTTGGTC CCTGGCTGCAGTGACACA TCTGGATCCTCGGTGACA CTGGGATGCCTTGTCAAA GGCTACTTCCCTGAGCCG GTAACTGTAAAATGGAAC TATGGAGCCCTGTCCAGC GGTGTGCGCACAGTCTCA TCTGTCCTGCAGTCTGGG TTCTATTCCCTCAGCAGC TTGGTGACTGTACCCTCC AGCACCTGGCCCAGCCAG ACTGTCATCTGCAACGTA GCCCACCGAGCCAGCAAG ACTGAGTTGATCAAGAGA ATCGAGCCTAGAATACCC AAGCCCAGTACCCCCCCA GGTTCTTCATGCCCACCT GGTAACATCTTGGGTGGA CCATCCGTCTTCATCTTC CCCCCAAAGCCCAAGGAT | ATTTAPSVYPLVPGCSDT SGSSVTLGCLVKGYFPEP VTVKWNYGALSSGVRTV SSVLQSGFYSLSSLVTVP SSTWPSQTVICNVAHPAS KTELIKRIEPRIPKPSTP PGSSCPPGNILGGPSVFI FPPKPKDALMISLTPKVT CVVVDVSEDDPDVHVSWF VDNKEVHTAWTQPREAYN NSTFRVVSALPIQHDW MRGKEFKCKVNNKALPA PIERTISKPKGRAQTPQV YTIPPPREQMSKKKVSLT CLVTNFFSEAISVEWERN GELEQDYKNTPPILDSDG TYFLYSKLTVDTDSWLQ GEIFTCSVVHEALHNHH TQKNLSRSPGK (SEQ ID NO: 62) | J00451 AH00530 9 X00915 D78343 | | Stanton L. W. and Marcu K. B., Nucleic Acids Res., 10, 5993-6006 (1982). PMID: 6292864 Wels J. A. et al., EMBO J., 3, 2041-2046 (1984). |

| Species | Ig Domain | Nucleotide Sequence | Amino Acid Sequence | GenBank Accession No. | IMGT Database | Reference |
|---|---|---|---|---|---|---|
| | | GCACTCATGATCTCCCTA<br>ACCCCCAAGGTTACGTGT<br>GTGGTGGTGGATGTGAG<br>CGAGGATGACCCAGATGT<br>CCATGTCAGCTGGTTTGT<br>GGACAACAAAGAAGTACA<br>CACAGCCTGGACACAGCC<br>CCGTGAAGCTCAGTACAA<br>CAGTACCTTCCGAGTGGT<br>CAGTGCCCTCCCCATCCA<br>GCACCAGGACTGGATGA<br>GGGGCAAGGAGTTCAAAT<br>GCAAGGTCAACAACAAAG<br>CCCTCCCAGCCCCCATCG<br>AGAGAACCATCTCAAAAC<br>CCAAAGGAAGAGCCCAG<br>ACACCTCAAGTATACACC<br>ATACCCCCACCTCGTGAA<br>CAAATGTCCAAGAAGAAG<br>GTTAGTCTGACCTGCCTG<br>GTCACCAACTTCTTCTCT<br>GAAGCCATCAGTGTGGAG<br>TGGGAAAGGAACGGAGA<br>ACTGGAGCAGGATTACAA<br>GAACACTCCACCCATCCT<br>GGACTCAGATGGGACCTA<br>CTTCCTCTAGAGCAAGCT<br>CACTGTGGATACAGACAG<br>TTGGTTGCAAGGAGAAAT<br>TTTTACCTGCTCCGTGGT<br>GCATGAGGCTCTCCATAA<br>CCACCACACACAGAAGAA<br>CCTGTCTCGCTCCCCTGG<br>TAAATGA<br>(SEQ ID NO: 63) | | | | PMID:<br>6092053<br>Akahori<br>Y. and<br>Kurosawa<br>Y.,<br>Geno-<br>mics.,<br>41,<br>100-104<br>(1997).<br>PMID:<br>9126488 |
| Mouse<br>Ig<br>light<br>chain<br>con-<br>stant<br>re-<br>gion | Ig<br>kappa<br>(CK) | GCTGATGCTGCACCAACT<br>GTATCCATCTTCCCACCA<br>TCCAGTGAGCAGTTAACA<br>TCTGGAGGTGCCTCAGTC<br>GTGTGCTTCTTGAACAAC<br>TTCTACCCCAAAGACATC<br>AATGTCAAGTGGAAGATT<br>GATGGCAGTGAACGACAA<br>AATGGCGTCCTGAACAGT<br>TGGACTGATCAGGACAGC<br>AAAGACAGCACCTACAGC<br>ATGAGCAGCACCCTCACG<br>TTGACCAAGGACGAGTAT<br>GAACGACATAACAGCTAT<br>ACCTGTGAGGCCACTCAC<br>AAGACATCAACTTCACCC<br>ATTGTCAAGAGCTTCAAC<br>AGGAATGAGTGTTAG<br>(SEQ ID NO: 37) | ADAAPTVSIFPPSSEQLT<br>SGGASVVCFLNNFYPKDI<br>NVKWKIDGSERQNGVLN<br>SWTDQDSKDSTYSMSST<br>LTLTKDEYERHNSYTCE<br>ATHKTSTSPIVKSFNRN<br>EC<br>(SEQ ID NO: 36) | V00807<br>V00777<br>V01569<br>V00806<br>X67002<br>X67003<br>X67004<br>X67005<br>X67006<br>X67007<br>X67008<br>X67009<br>X67010<br>X67011<br>X67012 | http://<br>www.<br>imgt.org/<br>IMGT<br>reper<br>toire/<br>index.php?<br>section =<br>Locus<br>Genes &<br>reper<br>toire =<br>gene<br>table &<br>species =<br>Mus_<br>musculus<br>group =<br>IGKC | Hieter<br>P. A.<br>et al.,<br>Cell,<br>22,<br>197-207<br>(1980).<br>PMID:<br>6775818<br>Max<br>E. E.<br>et al.,<br>J. Biol.<br>Chem.,<br>256,<br>5116-<br>5120<br>(1981).<br>PMID:<br>6262318<br>Seidman<br>J. G.,<br>et al.,<br>Nature,<br>280,<br>370-375<br>(1979).<br>PMID:<br>111146<br>Solin<br>M. L.<br>and<br>Kaarti-<br>nen<br>Immuno-<br>gene-<br>tics,<br>37,<br>401-407 |

| Species | Ig Domain | Nucleotide Sequence | Amino Acid Sequence | GenBank Accession No. | IMGT Database | Reference |
|---|---|---|---|---|---|---|
| | | | | | | (1993). PMID: 8436414 |
| | Ig lambda 1 (CL) | GGCCAGCCCAAGTCTTCG CCATCAGTCACCCTGTTT CCACCTTCCTCTGAAGAG CTCGAGACTAACAAGGCC ACACTGGTGTGTACGATC ACTGATTTCTACCCAGGT GTGGTGACAGTGGACTG GAAGGTAGATGGTACCCC TGTCACTCAGGGTATGGA GACAACCCAGCCTTCCAA ACAGAGCAACAACAAGTA CATGGCTAGCAGCTACCT GACCCTGACAGCAAGAGC ATGGGAAAGGCATAGCA GTTACAGCTGCCAGGTCA CTCATGAAGGTCACACTG TGGAGAAGAGTTTGTCCC GTGCTGACTGTTCCTAG (SEQ ID NO: 39) | GQPKSSPSVTLFPPSSEE LETNKATLVCTITDFYPG VVTVDWKVDGTPVTQG METTQPSKQSNNKYMAS SYLTLTARAWERHSSYSC QVTHEGHTVEKSLSRAD CS (SEQ ID NO: 38) | J00587 AH00531 1 X58411 V00814 | http://www.imgt.org/IMGT reper toire/index.php?section = Locus Genes & reper toire = gene table & species = Mus_musculus & group = IGLC | Selsing E. et al., Proc. Natl. Acad. Sci. USA, 79, 4681- 4685 (1982). PMID: 6812053 Weiss S. and Wu GE, EMBO J., 6, 927-937 (1987). PMID: 3109891 Bernard O. et al., Cell, 15, 1133- 1144 (1978). PMID: 103630 |
| | Ig lambda 2 (CL) | GGTCAGCCCAAGTCCACT CCCACTCTCACCGTGTTT CCACCTTCCTCTGAGGAG CTCAAGGAAAACAAAGCC ACACTGGTGTGTCTGATT TCCAACTTTTCCCCGAGT GGTGTGACAGTGGCCTG GAAGGCAAATGGTACACC TATCACCCAGGGTGTGGA CACTTCAAATCCCACCAA AGAGGGCAACAAGTTCAT GGCCAGCAGCTTCCTACA TTTGACATCGGACCAGTG GAGATCTCACAACAGTTT TACCTGTCAAGTTACACA TGAAGGGGACACTGTGG AGAAGAGTCTGTCTCCTG CAGAATGTCTCTAA (SEQ ID NO: 41) | GQPKSTPTLTVFPPSSEE LKENKATLVCLISNFSPS GVTVAWKANGTPITQGV DTSNPTKEGNKFMASSF LHLTSDQWRSHNSFTCQ VTHEGDTVEKSLSPAECL (SEQ ID NO: 40) | J00595 AH00196 8 J00592 AH00196 7 X58414 | | Selsing E. et al., Proc. Natl. Acad. Sci. USA, 79, 4681- 4685 (1982). PMID: 6812053 Wu G. et al., Cell, 33, 77-83 (1983). PMID: 6432336 Weiss S. and Wu GE, EMBO J., 6, 927-937 (1987). PMID: 3109891 |
| | Ig lambda 3 (CL) | GGTCAGCCCAAGTCCACT CCCACACTCACCATGTTT CCACCTTCCCCTGAGGAG CTCCAGGAAAACAAAGCC ACACTCGTGTGTCTGATT TCCAATTTTTCCCCAAGT GGTGTGACAGTGGCCTG | GQPKSTPTLTMFPPSPEE LQENKATLVCLISNFSPS GVTVAWKANGTPITQGV DTSNPTREDNKYMASSF LHLTSDQWRSHNSFTCQ VTHEGDTVEKSLSPAECL (SEQ ID NO: 42) | J00585 AH00531 1 X58415 X58411 | | Selsing E. et al., Proc. Natl. Acad. Sci. |

| Species | Ig Domain | | Nucleotide Sequence | Amino Acid Sequence | GenBank Accession No. | IMGT Database | Reference |
|---|---|---|---|---|---|---|---|
| | | | GAAGGCAAATGGTACACC TATCACCCAGGGTGTGGA CACTTCAAATCCCACCAA AGAGGACAACAAGTACAT GGCCAGCAGCTTCTTACA TTTGACATCGGACCAGTG GAGATCTCACAACAGTTT TACCTGCCAAGTTACACA TGAAGGGGACACTGTGG AGAAGAGTCTGTCTCCTG CAGAATGTCTCTAA (SEQ ID NO: 43) | | | | USA, 79, 4681-4685 (1982). PMID: 6812053 Weiss S. and Wu GE, EMBO J., 6, 927-937 (1987). PMID: 3109891 |
| Bovine (Scientific Name: *Bos taurus*) | Bovine Ig heavy chain constant region (CH1~ CH3) | IgG1 variant 1 | GCCTCCACCACAGCCCCG AAAGTCTACCCTCTGAGTT CTTGCTGCGGGACAAGT CCAGCTCCACCGTGACCC TGGGCTGCCTGGTCTCCA GCTACATGCCCGAGCCGG TGACCGTGACCTGGAACT CGGGTGCCCTGAAGAGCG GCGTGCACACCTTCCCGG CTGTCCTTCAGTCCTCCGG GCTGTACTCTCTCAGCAG CATGGTGACCGTGCCCGG CAGCACCTCAGGACAGAC CTTCACCTGCAACGTAGC CCACCCGGCCAGCAGCAC CAAGGTGGACAAGGCTGT TGATCCCACATGCAAACC ATCACCCTGTGACTGTTGC CCACCCCCTGAGCTCCCC GGAGGACCCTCTGTCTTC ATCTTCCCACGAAACCCA AGGACACCCTCACAATCT CGGGAACGCCCGAGGTCA CGTGTGTGGTGGTGGACG TGGGCCACGATGACCCCG AGGTGAAGTTCTCCTGGT TCGTGGACGACGTGGAGG TAAACACAGCCACGACGA AGCCGAGAGGAGCAGT TCAACAGCACCTACCGCG TGGTCAGCGCCCTGCGCA TCCAGCACCAGGACTGGA CTGGAGGAAAGGAGTTCA AGTGCAAGGTCCACAACG AAGGCCTCCCGGCCCCCA TCGTGAGGACCATCTCCA GGACCAAAGGGCCGGCCC GGGAGCCGCAGGTGTATG TCCTGGCCCCACCCCAGG AAGAGCTCAGCAAAAGCA CGGTCAGCCTCACCTGCA TGGTCACCAGCTTCTACCC AGACTACATCGCCGTGGA GTGGCAGAGAAACGGGCA GCCTGAGTCGGAGGACAA GTACGGCACGACCCCGCC CCAGCTGGACGCCGACAG CTCCTACTTCCTGTAGAGC AAGCTCAGGGTGGACAGG AACAGCTGGCAGGAAGGA GACACCTACACGTGTGTG GTGATGCACGAGGCCCTG CACAATCACTACACGCAG AAGTCCACCTCTAAGTCTG CGGGTAAATGA (SEQ ID NO: 67) | ASTTAPKVYPLSSCCGDKSSST VTLGCLVSSYMPEPVTVTWNS GALKSGVHTFPAVLQSSGLYSL SSMVTVPGSTSGQTFTCNVAHP ASSTKVDKAVDPTCKPSPCDCC PPPELPGGPSVFIFPPKPKDTLT ISGTPEVTCVVVDVGHDDPEVK FSWFVDDVEVNTATTKPREEQ FNSTYRVVSALRIQHQDWTGG KEFKCKVHNEGLPAPIVRTISR TKGPAREPQVYYLAPPQEELSK STVSLTCMVTSFYPDYIAVEWQ RNGQPESEDKYGTTPPQLDAD SSYFLYSKLRVDRNSWQEGDT YTCVVMHEALHNHYTQKSTSK SAGE* (SEQ ID NO: 66) | X62916 | http:// www. imgt.org/ IMGT reper toire/ index.php? section = Locus Genes & reper toire = gene table & species = bovine & group = IGHC | Symons D. B. et al., J. Immuno-genet., 14, 273-283 (1987). PMID: 3141517 Symons D. B. et al., Mol. Immun-ol., 26, 841-850 (1989). PMID: 2513487 Kacsko-vics I. and Butler J. E., Mol. Immun-ol., 33, 189-195 (1996). PMID: 8649440 Rabbani H. et al., Immuno-gene-tics, 46, 326-331 (1997). PMID: 9218535 Saini S. S. et al., Scand. J. Immunol. 65, 32-8 (2007). PMID: 17212764 |

TABLE-continued

| Species | Ig Domain | Nucleotide Sequence | Amino Acid Sequence | GenBank Accession No. | IMGT Database | Reference |
|---|---|---|---|---|---|---|
| | IgG1 variant 2 | GCCTCGACCACAGCCCCG AAAGTCTACCCTCTGAGTT CTTGCTGCGGGGACAAGT CCAGCTCCACCGTGACCC TGGGCTGCCTGGTCTCCA GCTACATGCCCGAGCCGG TGACCGTGACCTGGAACT CGGGTGCCCTGAAGAGCG GCGTGCACACCTTCCCGG CCGTCCTTCAGTCCTCCG GGCTGTACTCTCTCAGCA GCATGGTGACCGTGCCCG GCAGCACCTCAGGACAGA CCTTCACCTGCAACGTAG CCCACCCGGCCAGCAGCA CCAAGGTGGACAAGGCTG TTGATCCCACATGCAAACC ATCACCCTGTGACTGTTGC CCACCCCCTGAGCTCCCC GGAGGACCCTCTGTCTTC ATCTTCCCACCGAAACCCA AGGACACCCTCACAATCT CGGGAACGCCCGAGGTCA CGTGTGTGGTGGTGGACG TGGGCCACGATGACCCCG AGGTGAAGTTCTCCTGGT TCGTGGACGACGTGGAGG TAAACACAGCCACGACGA AGCCGAGAGAGGAGCAGT TCAACAGCACCTACCGCG TGGTCAGCGCCCTGCGCA TCCAGCACCAGGACTGGA CTGGAGGAAAGGAGTTCA AGTGCAAGGTCCACAACG AAGGCCTCCCGGCCCCCA TCGTGAGGACCATCTCCA GGACCAAAGGGCCGGCCC GGGAGCCGCAGGTGTATG TCCTGGCCCCACCCCAGG AAGAGCTCAGCAAAAGCA CGGTCAGCCTCACCTGCA TGGTCACCAGCTTCTACCC AGACTACATCGCCGTGGA GTGGCAGAGAAACGGGCA GCCTGAGTCGGAGGACAA GTACGGCACGACCCCGCC CCAGCTGGACGCCGACAG CTCCTACTTCCTGTACAGC AAGCTCAGGGTGGACAGG AACAGCTGGCAGGAAGGA GACACCTACACGTGTGTG GTGATGCACGAGGCCCTG CACAATCACTACACGCAG AAGTCCACCTCTAAGTCTG CGGGTAAATGA (SEQ ID NO: 69) | ASTTAPKVYPLSSCCGDKSSST VTLGCLVSSYMPEPVTVTWNS GALKSGVHTFPAVLQSSGLYSL SSMVTVPGSTSGQTFTCNVAHP ASSTKVDKAVDPTCKPSPCDCC PPPELPGGPSVFIFPPKPKDTLT ISGTPEVTCVVVDVGHDDPEVK FSWFVDDVEVNTATTKPREEQ FNSTYRVVSALRIQHQDWTGG KEFKCKVHNEGLPAPIVRTISR TKGPAREPQVYVLAPPQEELSK STVSLTCMVTSFYPDYIAVEWQ RNGQPESEDKYGTTPPQLDAD SSYFLYSKLRVDRNSWQEGDT YTCVVMHEALHNHYTQKSTSK SAGK* (SEQ ID NO: 68) | X16701 (M25278) | | |
| | IgG1 variant 3 | GCCTCCACCACAGCCCCG AAAGTCTACCCTCTGAGTT CTTGCTGCGGGGACAAGT CCAGCTCCACCGTGACCC TGGGCTGCCTGGTCTCCA GCTACATGCCCGAGCCGG TGACCGTGACCTGGAACT CGGGTGCCCTGAAGAGCG GCGTGCACACCTTCCCGG CCGTCCTTCAGTCCTCCG GGCTCTACTCTCTCAGCA GCATGGTGACCGTGCCCG GCAGCACCTCAGGAACCC AGACCTTCACCTGCAACG TAGCCCACCCGGCCAGCA GCACCAAGGTGGACAAGG CTGTTGATCCCAGATGCA | ASTTAPKVYPLSSCCGDKSSST VTLGCLVSSYMPEPVTVTWNS GALKSGVHTFPAVLQSSGLYSL SSMVTVPGSTSGTQTFTCNVAH PASSTKYDKAVDPRCKTTCDCC PPPELPGGPSVFIFPPKPKDTLT ISGTPEVTCVVVDVGHDDPEVK FSWFVDDVEVNTATTKPREEQ FNSTYRVVSALRIQHQDWTGG KEFKCKVHNEGLPAPIVRTISR TKGPAREPQVYVLAPPQEELSK STVSLTCMVTSFYPDYIAVEWQ RNGQPESEDKYGTTPPQLDAD GSYFLYSRLRVDRNSWQEGDT YTCVVMHEALHNHYTQKSTSK SAGK* (SEQ ID NO: 70) | S82409 | | |

TABLE-continued

| Species | Ig Domain | Nucleotide Sequence | Amino Acid Sequence | GenBank Accession No. | IMGT Database | Reference |
|---|---|---|---|---|---|---|
| | | AAACAACCTGTGACTGTT GCCCACCGCCTGAGCTCC CTGGAGGACCCTCTGTCT TCATCTTCCCACCGAAACC CAAGGACACCCTCACAAT CTCGGGAACGCCCGAGGT CACGTGTGTGGTGGTGGA CGTGGGCCACGATGACCC CGAGGTGAAGTTCTCCTG GTTCGTGGACGACGTGGA GGTAAACACAGCCACGAC GAAGCCGAGAGAGGAGCA GTTCAACAGCACCTACCG CGTGGTCAGCGCCCTGCG CATCCAGCACCAGGACTG GACTGGAGGAAAGGAGTT CAAGTGCAAGGTCCACAA CGAAGGCCTCCCAGCCCC CATCGTGAGGACCATCTC CAGGACCAAAGGGCCGGC CCGGGAGCCGCAGGTGTA TGTCCTGGCCCCACCCCA GGAAGAGCTCAGCAAAAG CACGGTCAGCCTCACCTG CATGGTCACCAGCTTCTAC CCAGACTACATCGCCGTG GAGTGGCAGAGAAATGGG CAGCCTGAGTCAGAGGAC AAGTACGGCACGACCCCT CCCCAGCTGGACGCCGAC GGCTCCTACTTCCTGTACA GCAGGCTCAGGGTGGACA GGAACAGCTGGCAGGAAG GAGACACCTACACGTGTG TGGTGATGCACGAGGCCC TGCACAATCACTACACGC AGAAGTCCACCTCTAAGT CTGCGGGTAAATGA (SEQ ID NO: 71) | | | | |
| | IgG2 variant 1 | GCCTCCACCACAGCCCCG AAAGTCTACCCTCTGGCAT CCAGCTGCGGAGACACAT CCAGCTCCACCGTGACCC TGGGCTGCCTGGTGTCCA GCTACATGCCCGAGCCGG TGACCGTGACCTGGAACT CGGGTGCCCTGAAGAGCG GCGTGCACACCTTCCCGG CTGTCCTTCAGTCCTCCGG GCTCTACTCTCTCAGCAGC ATGGTGACCGTGCCCGCC AGCAGCTCAGGACAGACC TTCACCTGCAACGTAGCC CACCCGGCCAGCAGCACC AAGGTGGACAAGGCTGTT GGGGTCTCCATTGACTGC TCCAAGTGTCATAACCAG CCTTGCGTGAGGGAACCA TCTGTCTTCATCTTCCCAC CGAAACCCAAAGACACCC TGATGATCACAGGAACGC CCGAGGTCACGTGTGTGG TGGTGAACGTGGCCACG ATAACCCCGAGGTGCAGT TCTCCTGGTTCGTGGATG ACGTGGAGGTGCACACGG CCAGGTCGAAGCCAAGAG AGGAGCAGTTCAACAGCA CGTACCGCGTGGTCAGCG CCCTGCCCATCCAGCACC AGGACTGGACTGGAGGAA AGGAGTTCAAGTGCAAGG TCAACAACAAAGGCCTCT CGGCCCCCATCGTGAGGA | ASTTAPKVYPLASSCGDTSSST VTLGCLVSSYMPEPVTVTWNS GALKSGVHTFPAVLQSSGLYSL SSMVTVPASSSGQTFTCNVAHP ASSTKVDKAVGVSIDCSKCHNQ PCVREPSVFIFPPKPKDTLMITG TPEVTCVVVNVGHDNPEVQFS WFVDDVEVHTARSKPREEQFN STYRVVSALPIQHQDWTGGKE FKCKVNNKGLSAPIVRIISRSKG PAREPQVYVLDPPKEELSKSTL SVTCMVTGFYPEDVAVEWQRN RQTESEDKYRTTPPQLDTDRSY FLYSKLRVDRNSWQEGDAYTC VVMHEALHNHYMQKSTSKSA GK* (SEQ ID NO: 72) | S82407 | | |

TABLE-continued

| Species | Ig Domain | Nucleotide Sequence | Amino Acid Sequence | GenBank Accession No. | IMGT Database | Reference |
|---|---|---|---|---|---|---|
| | | TCATCTCCAGGAGCAAAG GGCCGGCCCGGGAGCCGC AGGTGTATGTCCTGGACC CACCCAAGGAAGAGCTCA GCAAAAGCACGCTCAGCG TCACCTGCATGGTCACCG GCTTCTACCCAGAAGATG TAGCCGTGGAGTGGCAGA GAAACCGGCAGACTGAGT CGGAGGACAAGTACCGCA CGACCCCGCCCCAGCTGG ACACCGACCGCTCCTACTT CCTGTACAGCAAGCTCAG GGTGGACAGGAACAGCTG GCAGGAAGGAGACGCCTA CACGTGTGTGGTGATGCA CGAGGCCCTGCACAATCA CTACATGCAGAAGTCCAC CTCTAAGTCTGCGGGTAA ATGA (SEQ ID NO: 73) | | | | |
| | IgG2 variant 2 | GCCTCCACCAGAGCCCCG AAAGTCTACCCTCTGAGTT CTTGCTGCGGGGACAAGT CCAGCTCCACCGTGACCC TGGGCTGCCTGGTGTCCA GCTACATGCCCGAGCCGG TGACCGTGACCTGGAACT CGGGTGCCCTGAAGAGCG GCGTGCACACCTTCCCGG CCGTCCTTCAGTCCTCCG GGCTCTACTCTCTCAGCA GCATGGTGACCGTGCCCG GCAGCACCTCAGGACAGA CCTTCACCTGCAACGTAG CCCACCCGGCCAGCAGCA CCAAGGTGGACAAGGCTG TTGGGGTCTCCAGTGACT GCTCCAAGCCTAATAACC AGCATTGCGTGAGGGAAC CATCTGTCTTCATCTTCCC ACCGAAACCCAAAGACAC CCTGATGATCACAGGAAC GCCCGAGGTCACGTGTGT GGTGGTGAACGTGGGCCA CGATAACCCCGAGGTGCA GTTCTCCTGGTTCGTGGA CGACGTGGAGGTGCACAC GGCCAGGACGAAGCCGAG AGAGGAGCAGTTCAACAG CACGTACCGCGTGGTCAG CGCCCTGCCCATCCAGCA CCAGGACTGGACTGGAGG AAAGGAGTTCAAGTGCAA GGTCAACATCAAAGGCCT CTCGGCCTCCATCGTGAG GATCATCTCCAGGAGCAA AGGGCCGGCCCGGGAGCC GCAGGTGTATGTCCTGGA CCCACCCAAGGAAGAGCT CAGCAAAAGCACGGTCAG CGTGAGCTGCATGGTCAT CGGCTTCTACCCAGAAGA TGTAGACGTGGAGTGGCA GAGAGACCGGCAGACTGA GTCGGAGGACAAGTACCG CACGACCCCGCCCCAGCT GGACGCCGACCGCTCCTA CTTCCTGTACAGCAAGCTC AGGGTGGACAGGAACAGC TGGCAGAGAGGAGACACC TACACGTGTGTGGTGATG CACGAGGCCCTGCACAAT | ASTTAPKVYPLSSCCGDKSSST VTLGCLVSSYMPEPVTVTWNS GALKSGVHTFPAVLQSSGLYSL SSMVTVPGSTSGQTFTCNVAHP ASSTKVDKAVGVSSDCSKPNN QHCVREPSVFIFPPKPKDTLMI TGTPEVTCVVVNVGHDNPEVQ FSWFVDDVEVHTARTKPREEQ FNSTYRVVSALPIQHQDWTGG KEFKCKVNIKGLSASIVRIISRS KGPAREPQVYVLDPPKEELSKS TVSVTCMVIGFYPEDVDVEWQ RDRQTESEDKYRTTPPQLDAD RSYFLYSKLRVDRNSWQRGDT YTCVVMHEALHNHYMQKSTS KSAGK* (SEQ ID NO: 74) | M36946 (X06703) | | |

| Species | Ig Domain | Nucleotide Sequence | Amino Acid Sequence | GenBank Accession No. | IMGT Database | Reference |
|---|---|---|---|---|---|---|
| | | CACTACATGCAGAAGTCC ACCTCTAAGTCTGCGGGT AAATGA (SEQ ID NO: 75) | | | | |
| | IgG2 variant 3 | GCCTCCACCACAGCCCCG AAAGTCTACCCTCTGAGTT CTTGCTGCGGGGACAAGT CCAGCTCGGGGGTGACCC TGGGCTGCCTGGTCTCCA GCTACATGCCCGAGCCGG TGACCGTGACCTGGAACT CGGGTGCCCTGAAGAGCG GCGTGCACACCTTCCCGG CCGTCCTTCAGTCCTCCG GGCTCTACTCTCTCAGCA GCATGGTGACCGTGCCCG CCAGCAGCTCAGGAACCC AGACCTTCACCTGCAACG TAGCCCACCCGGCCAGCA GCACCAAGGTGGACAAGG CTGTTGGGGTCTCCAGTG ACTGCTCCAAGCCTAATAA CCAGCATTGCGTGAGGGA ACCATCTGTCTTCATCTTC CCACCGAAACCCAAAGAC ACCCTGATGATCACAGGA ACGCCCGAGGTCACGTGT GTGGTGGTGAACGTGGGC CACGATAACCCCGAGGTG CAGTTCTCCTGGTTCGTG GACGACGTGGAGGTGCAC ACGGCCAGGACGAAGCCG AGAGAGGAGCAGTTCAAC AGCACGTACCGCGTGGTC AGCGCCCTGCCCATCCAG CACCAGGACTGGACTGGA GGAAAGGAGTTCAAGTGC AAGGTCAACATCAAAGGC CTCTCGGCCTCCATCGTG AGGATCATCTCCAGGAGC AAAGGGCCGGCCCGGGAG CCGCAGGTGTATGTCCTG GACCCACCCAAGGAAGAG CTCAGCAAAAGCACGGTC AGCCTCACCTGCATGGTC ATCGGCTTCTACCCAGAA GATGTAGACGTGGAGTGG CAGAGAGACCGGCAGACT GAGTCGGAGGACAAGTAC CGCACGACCCCGCCCCAG CTGGACGCCGACCGCTCC TACTTCCTGTACAGCAAGC TCAGGGTGGACAGGAACA GCTGGCAGAGAGGAGACA CCTACACGTGTGTGGTGA TGCACGAGGCCCTGCACA ATCACTACATGCAGAAGT CCACCTCTAAGTCTGCGG GTAAATGA (SEQ ID NO: 77) | ASTTAPKVYPLSSCCGDKSSSG VTLGCLVSSYMPEPVTVTWNS GALKSGVHTFPAVLQSSGLYSL SSMVTVPASSSGTQTFTCNVAH PASSTRVDKAVGVSSDCSKPNN QHCVREPSVFIFPPKPKDTLMI TGTPEVTCVVVNVGHDNPEVQ FSWFVDDVEVHTARTKPREEQ FNSTYRVVSALPIQHQDWTGG KEFKCKVNIKGLSASIVRIISRS KGPAREPQVYVLDPPKEELSKS TVSLTCMVIGFYPEDVDVEWQ RDRQTESEDKYRTTPPQLDAD RSYFLYSKLRVDRNSWQRGDT YTCVVMHEALHNHYMQKSTS KSAGK* (SEQ ID NO: 76) | X16702 (M25279) | | |
| | IgG3 variant 1 | GCCTCCACCACAGCCCCG AAAGTCTACCCTCTGGCAT CCAGCTGCGGAGACACAT CCAGCTCCACCGTGACCC TGGGCTGCCTGGTCTCCA GCTACATGCCCGAGCCGG TGACCGTGACCTGGAACT CGGGTGCCCTGAAGAGCG GCGTGCACACCTTCCCGG CCGTCCGGCAGTCCTCTG GGCTGTACTCTCTCAGCA GCATGGTGACTGTGCCCG CCAGCAGCTCAGAAACCC | ASTTAPKVYPLASSCGDTSSST VTLGCLVSSYMPEPVTVTWNS GALKSGVHTFPAVRQSSGLYSL SSMVTVPASSSETQTFTCNVAH PASSTKVDKAVTARRPVPTTPK TTIPPGKPTTPKSEVEKTPCQC SKCPEPLGGLSVFIFPPKPKDT LTISGTPEVFCVVVDVGQDDPE VQFSWFVDDVEVHTARTKPRE EQFNSTYRVVSALRIQHQDWL QGKEFKCKVNNKGLPAPIVRTI SRTKGQAREPQVYVLAPPREEL SKSTLSLTCLITGFYPEEIDVEW | U63638 | | |

| Species | Ig Domain | Nucleotide Sequence | Amino Acid Sequence | GenBank Accession No. | IMGT Database | Reference |
|---------|-----------|---------------------|---------------------|-----------------------|---------------|-----------|
| | | AGACCTTCACCTGCAACG<br>TAGCCCACCCGGCCAGCA<br>GCACCAAGGTGGACAAGG<br>CTGTCACTGCAAGGCGTC<br>CAGTCCCGACGACGCCAA<br>AGACAACTATCCCTCCTG<br>GAAAACCCACAACCCCAA<br>AGTCTGAAGTTGAAAAGA<br>CACCCTGCCAGTGTTCCA<br>AATGCCCAGAACCTCTGG<br>GAGGACTGTCTGTCTTCAT<br>CTTCCCACCGAAACCCAA<br>GGACACCCTCACAATCTC<br>GGGAACGCCCGAGGTCAC<br>GTGTGTGGTGGTGGACGT<br>GGGCCAGGATGACCCCGA<br>GGTGCAGTTCTCCTGGTT<br>CGTGGACGACGTGGAGGT<br>GCACACGGCCAGGACGAA<br>GCCGAGAGAGGAGCAGTT<br>CAACAGCACCTACCGCGT<br>GGTCAGCGCCCTGCGCAT<br>CCAGCACCAGGACTGGCT<br>GCAGGGAAAGGAGTTCAA<br>GTGCAAGGTCAACAACAA<br>AGGCCTCCCGGCCCCCAT<br>TGTGAGGACCATCTCCAG<br>GACCAAAGGGCAGGCCCG<br>GGAGCCGCAGGTGTATGT<br>CCTGGCCCCACCCCGGGA<br>AGAGCTCAGCAAAAGCAC<br>GCTCAGCCTCACCTGCCT<br>GATCACCGGTTTCTACCCA<br>GAAGAGATAGACGTGGAG<br>TGGCAGAGAAATGGGCAG<br>CCTGAGTCGGAGGACAAG<br>TACCACACGACCGCACCC<br>CAGCTGGATGCTGACGGC<br>TCCTACTTCCTGTACAGCA<br>AGCTCAGGGTGAACAAGA<br>GCAGCTGGCAGGAAGGAG<br>ACCACTACACGTGTGCAG<br>TGATGCACGAAGCTTTAC<br>GGAATCACTACAAAGAGA<br>AGTCCATCTCGAGGTCTC<br>CGGGTAAATGA<br>(SEQ ID NO: 79) | QRNGQPESEDKYHTTAPQLDA<br>DGSYFLYSKLRVNKSSWQEGD<br>HYTCAVMHEALRNHYKEKSIS<br>RSPGK*<br>(SEQ ID NO: 78) | | | |
| | IgG3 variant 2 | GCCTCCACCACAGCCCCG<br>AAAGTCTACCCTCTGGCAT<br>CCCGCTGCCGAGACACAT<br>CCAGCTCCACCGTGACCC<br>TGGGCTGCCTGGTCTCCA<br>GCTACATGCCCGAGCCGG<br>TGACCGTGACCTGGAACT<br>CGGGTGCCCTGAAGAGTG<br>GCGTGCACACCTTCCCGG<br>CCGTCCTTCAGTCCTCCG<br>GGCTGTACTCTCTCAGCA<br>GCATGGTGACCGTGCCCG<br>CCAGCACCTCAGAAACCC<br>AGACCTTCACCTGCAACG<br>TAGCCCACCCGGCCAGCA<br>GCACCAAGGTGGACAAGG<br>CTGTCACTGCAAGGCGTC<br>CAGTCCCGACGACGCCAA<br>AGACAACCATCCCTCCTG<br>GAAAACCCACAACCCAGG<br>AGTCTGAAGTTGAAAAGA<br>CACCCTGCCAGTGTTCCA<br>AATGCCCAGAACCTCTGG<br>GAGGACTGTCTGTCTTCAT<br>CTTCCCACCGAAACCCAA<br>GGACACCCTCACAATCTC<br>GGGAACGCCCGAGGTCAC | ASTTAPKVYPLASRCGDTSSST<br>VTLGCLVSSYMPEPVTVTWNS<br>GALKSGVHTFPAVLQSSGLYSL<br>SSMVTVPASTSETQTFTCNVAH<br>PASSTKVDKAVTARRPVTTPK<br>TTIPPGKPTTQESEVEKTPCQC<br>SKCPEPLGGLSVFIFPPKPKDT<br>LTISGTPEVTCVVVDVGQDDPE<br>VQFSWFVDDVEVHTARTKPRE<br>EQFNSTYRVVSALRIQHQDWL<br>QGKEFKCKVNNKGLPAPIVRTI<br>SRTKGQAREPQVYVLAPPREEL<br>SKSTLSLTCLITGFYPEEIDVEW<br>QRNGQPESEDKYHTTAPQLDA<br>DGSYFLYSRLRVNKSSWQEGD<br>HYTCAVMHEALRNHYKEKSIS<br>RSPGK*<br>(SEQ ID NO: 80) | U63639 | | |

TABLE-continued

| Species | Ig Domain | Nucleotide Sequence | Amino Acid Sequence | GenBank Accession No. | IMGT Database | Reference |
|---|---|---|---|---|---|---|
| | | GTGTGTGGTGGTGGACGT GGGCCAGGATGACCCCGA GGTGCAGTTCTCCTGGTT CGTGGACGACGTGGAGGT GCACACGGCCAGGACGAA GCCGAGAGAGGAGCAGTT CAACAGCACCTACCGCGT GGTCAGCGCCCTGCGCAT CCAGCACCAGGACTGGCT GCAGGGAAAGGAGTTCAA GTGCAAGGTCAACAACAA AGGCCTCCCGGCCCCCAT TGTGAGGACCATCTCCAG GACCAAAGGGCAGGCCCG GGAGCCGCAGGTGTATGT CCTGGCCCCACCCCGGGA AGAGCTCAGCAAAAGCAC GCTCAGCCTCACCTGCCT GATCACCGGTTTCTACCCA GAAGAGATAGACGTGGAG TGGCAGAGAAATGGGCAG CCTGAGTCGGAGGACAAG TACCACACGACCGCACCC CAGCTGGATGCTGACGGC TCCTACTTCCTGTACAGCA GGCTCAGGGTGAACAAGA GCAGCTGGCAGGAAGGAG ACCACTACACGTGTGCAG TGATGCATGAAGCTTTAC GGAATCACTACAAAGAGA AGTCCATCTCGAGGTCTC CGGGTAAATGA (SEQ ID NO: 81) | | | | |
| | Bovine Ig light chain constant region (CL) | CAGCCCAAGTCCCCACCC Ig lambda TCGGTCACCCTGTTCCCG CCCTCCACGGAGGAGCTC AACGGCAACAAGGCCACC CTGGTGTGTCTCATCAGC GACTTCTACCCGGGTAGC GTGACCGTGGTCTGGAAG GCAGACGGCAGCACCATC ACCCGCAACGTGGAGACC ACCCGGGCCTCCAAACAG AGCAACAGCAAGTACGCG GCCAGCAGCTACCTGAGC CTGACGAGCAGCGACTGG AAATCGAAAGGCAGTTAC AGCTGCGAGGTCACGCAC GAGGGGAGCACCGTGACG AAGACAGTGAAGCCCTCA GAGTGTTCTTAG (SEQ ID NO: 65) | QPKSPPSVTLFPPSTEELNGNK ATLVCLISDFYPGSVTVVWKAD GSTITRNVETTRASKQSNSKYA ASSYLSLTSSDWKSKGSYSCEV THEGSTVTKTVKPSECS* (SEQ ID NO: 64) | X62917 | Not registered | Chen L. et al., Vet. Immunol. Immunopathol., 124, 284-294 (2008). PMID: 18538861 |
| Canine (Scientific Name: Canis lupus familiaris) | Canine Ig heavy chain constant region (CH1~ CH3) | IgG-D GCCTCCACCACGGCCCCCTCG GTTTTCCCACTGGCCCCCAGC TGCGGGTCCACTTCCGGCTCC ACGGTGGCCTGCCTGGTCT GGTGTCAGGCTACTTCCCGA GCCTGTAACTGTGTCCTGAA TTCCGGCTCCTTGACCAGCGG TGTGCACACCTTCCCGTCCGT CCTGCAGTCCTCAGGGCTCTA CTCCCTCAGCAGCACGGTGAC AGTGCCCTCCAGCAGGTGGC CCAGCGAGACCTTCACCTGCA ACGTGGTCCACCCGGCCAGC AACACTAAAGTAGACAAGCCA GTGCCCAAAGAGTCCACCTGC AAGTGTATATCCCCATGCCCA GTCCCTGAATCACTGGGAGG GCCTTCGGTCTTCATCTTTCC CCCGAAACCCAAGGACATCCT CAGGATTACCCGAACACCGA GATCACCTGTGTGGTGTTAGA | ASTTAPSVFPLAPSCGSTS VSTVALACLVSGYFPEPVT VSWNSGSLTSGVHTFPSVL QSSGLYSLSSTVTVPSSRW PSETFTCNVVHPASNTKVD KPVPKESTCKCISPCPVPE SLGGPSVFIFPPKPKDILRI TRTPEITCVVLDLGREDPE VQISWFVDGKEVHTAKTQ PREQQFNSTYRVVSVLPIE HQDWLTGKEFKCRVNHIG LPSPIERTISKARGQAHQPS VYVLPPSPKELSSSDTVTL TCLIKDFFPPEIDVEWQSN GQPEPESKYHTTAPQLDE DGSTFLYSKLSVDKSRWQ GQDTFTCAVMHEALQNHY TDLSLSHSPGK* (SEQ ID NO: 84) | AF35426 7 | http:// www. imgt.org/ IMGT reper toire/ index.php?80 section = (3-4), Locus Genes & reper toire gene = gene table & species = dog & group = IGHC | Tang L. et al., Vet. Immuno- pathol. 124, 259-270 (2001). PMID: 1145747 9 |

| Species | Ig Domain | | Nucleotide Sequence | Amino Acid Sequence | GenBank Accession No. | IMGT Database | Reference |
|---|---|---|---|---|---|---|---|
| | | | TCTGGGCCGTGAGGACCCTG<br>AGGTGCAGATCAGCTGGTTCG<br>TGGATGGTAAGGAGGTGCAC<br>ACAGCCAAGACGCAGCCTCGT<br>GAGCAGCAGTTCAACAGCACC<br>TACCGTGTGGTCAGCGTCCTC<br>CCCATTGAGCACCAGGACTGG<br>CTCACCGGAAAGGAGTTCAAG<br>TGCAGAGTCAACCACATAGGC<br>CTCCCGTCCCCCATCGAGAGG<br>ACTATCTCCAAAGCCAGAGGG<br>CAAGCCCATCAGCCCAGTGTG<br>TATGTCCTGCCACCATCCCCA<br>AAGGAGTTGTCATCCAGTGAC<br>ACGGTCACCCTGACCTGCCTG<br>ATCAAAGACTTCTTCCCACCT<br>GAGATTGATGTGGAGTGGCA<br>GAGCAATGGACAGCCGGAGC<br>CCGAGAGCAAGTACCACACG<br>ACTGCGCCCAGCTGGACGA<br>GGACGGGTCCTACTTCCTGTA<br>CAGCAAGCTCTCTGTGGACAA<br>GAGCCGCTGGCAGCAGGGAG<br>ACACCTTCACATGTGCGGTGA<br>TGCATGAAGCTCTACAGAACC<br>ACTACACAGATCTATCCCTCT<br>CCCATTCTCCGGGTAAATGA<br>(SEQ ID NO: 85) | | | | |
| | Canine Ig light chain constant region | Ig lambda (CL) | CAGCCCAAGGCCTCCCCCTCG<br>GTCACACTCTTCCCGCCCTCC<br>TCTGAGGAGCTCGGCGCCAA<br>CAAGGCCACCCTGGTGTGCCT<br>CATCAGCGACTTCTACCCCAG<br>CGGCGTGACGGTGGCCTGGA<br>AGGCAAGCGGCAGCCCCGTC<br>ACCCAGGGCGTGGAGACCAC<br>CAAGCCCTCCAAGCAGAGCAA<br>CAACAAGTACGCGGCCAGCA<br>GCTACCTGAGCCTGACGCCTG<br>ACAAGTGGAAATCTCACAGCA<br>GCTTCAGCTGCCTGGTCACGC<br>ACGAGGGGAGCACCGTGGAG<br>AAGAAGGTGGCCCCCGCAGA<br>GTGCTCTTAG<br>(SEQ ID NO: 84) | QPKASPSVTLFPPSSEELG<br>ANKATLVCLISDFYPSGVT<br>VAWKASGSPVTQGVETTK<br>PSKQSNNKYAASSYLSLTP<br>DKWKSHSSFSCLVTHEGS<br>TVEKKVAPAECS*<br>(SEQ ID NO: 82) | E02824 | Not registered | None |
| Ovine (Scientific Name: *Ovis aries*) | Ovine Ig heavy chain constant region (CH1~CH3) | IgG1 | GCCTCAACAACACCCCGAAA<br>GTCTACCCTCTGACTTCTTGC<br>TGCGGGACACGTCCAGCTC<br>CATCGTGACCCTGGGCTGCCT<br>GGTCTCCAGCTATATGCCCGA<br>GCCGGTGACCGTGACCTGGA<br>ACTCTGGTGCCCTGACCAGCG<br>GCGTGCACACCTTCCCGGCCA<br>TCCTGCAGTCCTCCGGGCTCT<br>ACTCTCTCAGCAGCGTGGTGA<br>CCGTGCCGGCCAGCACCTCA<br>GGAGCCCAGACCTTCATCTGC<br>AACGTAGCCCACCCGGCCAG<br>CAGCACCAAGGTGGACAAGC<br>GTGTTGAGCCCGGATGCCCG<br>GACCCATGCAAACATTGCCGA<br>TGCCCACCCCTGAGCTCCC<br>GGAGGACCGTCTGTCTTCATC<br>TTCCCACCGAAACCCAAGGAC<br>ACCCTTACAATCTCTGGAACG<br>CCCGAGGTCACGTGTGTGGT<br>GGTGGACGTGGGCCAGGATG<br>ACCCCGAGGTGCAGTTCTCCT<br>GGTTCGTGGACAACGTGGAG<br>GTGCGCACGGCCAGGACAAA<br>GCCGAGAGAGGAGCAGTTCA<br>ACAGCACCTTCCGCGTGGTCA<br>GCGCCCTGCCCATCCAGCACC | ASTTPPKVYPLTSCCGDTS<br>SSIVTLGCLVSSYMPEPVT<br>VTWNSGALTSGVHTFPAIL<br>QSSGLYSLSSVVTVPASTS<br>GAQTFICNVAHPASSTKVD<br>KRVEPGCPDPCKHCRCPP<br>PELPGGPSVFIFPPKPKDT<br>LTISGTPEVTCVVVDVGQD<br>DPEVQFSWFVDNVEVRTA<br>RTKPREEQFNSTFRVVSAL<br>PIQHQDWTGGKEFKCKVH<br>NEALPAPIVRTISRTKGQA<br>REPQVYVLAPPQEELSKST<br>LSVTCLVTGFYPDYIAVEW<br>QKNGQPESEDKYGTTTSQ<br>LDADGSYFLYSRLVDKNS<br>WQEGDTYACVVMHEALH<br>NHYTQKSISKPPGK*<br>(SEQ ID NO: 90) | X69797 | http://<br>www.<br>imgt.org/<br>IMGT<br>repertoire/<br>index.php?<br>section =<br>Locus<br>Genes &<br>repertoire =<br>gene<br>table &<br>species =<br>sheep &<br>group =<br>IGHC | Dufour V. et al., J. Immunol., 156, 2163-2170 (1996). PMID: 8690905 |

TABLE-continued

| Species | Ig Domain | Nucleotide Sequence | Amino Acid Sequence | GenBank Accession No. | IMGT Database | Reference |
|---|---|---|---|---|---|---|
| | | AAGACTGGACTGGAGGAAAG GAGTTCAAGTGCAAGGTCCAC AACGAAGCCCTCCCGGCCCCC ATCGTGAGGACCATCTCCAGG ACCAAAGGGCAGGCCCGGGA GCCGCAGGTGTACGTCCTGG CCCCACCCCAGGAAGAGCTCA GCAAAAGCACGCTCAGCGTCA CCTGCCTGGTCACCGGCTTCT ACCCAGACTACATCGCCGTGG AGTGGCAGAAAAATGGGCAG CCTGAGTCGGAGGACAAGTA CGGCACGACCACATCCCAGCT GGACGCCGACGGCTCCTACTT CCTGTACAGCAGGCTCAGGGT GGACAAGAACAGCTGGCAAG AAGGAGACACCTACGCGTGT GTGGTGATGCACGAGGCTCT GCACAACCACTACACACAGAA GTCGATCTCTAAGCCTCCGGG TAAATGA (SEQ ID NO: 91) | | | | |
| | IgG2 | GCCTCCACCACAGCCCCGAAA GTCTACCCTCTGACTTCTTGC TGCGGGGACACGTCCAGCTC CAGCTCCATCGTGACCCTGGG CTGCCTGGTCTCCAGCTATAT GCCCGAGCCGGTGACCGTGA CCTGGAACTCTGGTGCCCTGA CCAGCGGCGTGCACACCTTCC CGGCCATCCTGCAGTCCTCCG GGCTCTACTCTCTCAGCAGCG TGGTGACCGTGCCGGCCAGC ACCTCAGGAGCCCAGACCTTC ATCTGCAACGTAGCCCACCCG GCCAGCAGCGCCAAGGTGGA CAAGCGTGTTGGGATCTCCAG TGACTACTCCAAGTGTTCTAA ACCGCCTTGCGTGAGCCGACC GTCTGTCTTCATCTTCCCCCC GAAACCCAAGGACAGCCTCAT GATCACAGGAACGCCCCGAGG TCACGTGTGTGGTGGTGGAC GTGGGCCAGGGTGACCCCGA GGTGCAGTTCTCCTGGTTCGT GGACAACGTGGAGGTGCGCA CGGCCAGGACAAAGCCGAGA GAGGAGCAGTTCAACAGCAC CTTCCGCGTGGTCAGCGCCCT GCCCATCCAGCACGACCACTG GACTGGAGGAAAGGAGTTCA AGTGCAAGGTCCACAGCAAA GGCCTCCCGGCCCCCATCGTG AGGACCATCTCCAGGGCCAAA GGGCAGGCCCGGGAGCCGCA GGTGTACGTCCTGGCCCCACC CCAGGAAGAGCTCAGCAAAA GCACGCTCAGCGTCACCTGCC TGGTCACCGGCTTCTACCCAG ACTACATCGCCGTGGAGTGGC AGAGAGCGCGGCAGCCTGAG TCGGAGGACAAGTACGGCAC GACCACATCCCAGCTGGACGC CGACGGCTCCTACTTCCTGTA CAGCAGGCTCAGGGTGGACA AGAGCAGCTGGCAAAGAGGA GACACCTACGCGTGTGTGGTG ATGCACGAGGCTCTGCACAAC CACTACACACAGAAGTCGATC TCTAAGCCTCCGGGTAAATGA (SEQ ID NO: 93) | ASTTAPKVYPLTSCCGDTS SSSSIVTLGCLVSSYMPEPV TVTWNSGALTSGVHTFPAI LQSSGLYSLSSVVTVPASTS GAQTFICNVAHPASSAKVD KRVGISSDYSKCSKPPCVS RPSVFIFPPKPKDSLMITGT PEVTCVVVDVGQGDPEVQ FSWFVDNVEVRTARTKPR EEQFNSTFRVVSALPIQHD HWTGGKEFKCKVHSKGLP APIVRTISRAKGQAREPQV YVLAPPQEELSKSTLSVTC LVTGFYPDYIAVEWQRARQ PESEDKYGTTTSQLDADGS YFLYSRLRVDKSSWQRGD TYACVVMHEALHNHYTQK SISKPPGK* (SEQ ID NO: 92) | X70983 | | Clarkson C. A. et al., Mol. Immunol., 30, 1195-1204 (1993). PMID: 8413324 |

TABLE-continued

| Species | Ig Domain | Nucleotide Sequence | Amino Acid Sequence | GenBank Accession No. | IMGT Database | Reference |
|---|---|---|---|---|---|---|
| | Ovine Ig light chain constant region | Ig kappa (CK) | CCATCCGTCTTCCTCTTCAAA CCATCTGAGGAACAGCTGAG GACCGGAACTGTCTCTGTCGT GTGCTTGGTGAATGATTTCTA CCCCAAAGATATCAATGTCAA GGTGAAAGTGGATGGGGTTA CCCAGAACAGCAACTTCCAGA ACAGCTTCACAGACCAGGACA GCAAGAAAAGCACCTACAGCC TCAGCAGCACCCTGACACTGT CCAGCTCAGAGTACCAGAGCC ATAACGCTATGCGTGTGAGG TCAGCCACAAGAGCCTGCCCA CCGCCCTCGTCAAGAGCTTCA ATAAGAATGAATGTTAG (SEQ ID NO: 87) | PSVFLFKPSEEQLRTGTVS VVCLVNDFYPKDINVKVK VDGVTQNSNFQNSFTDQD SKKSTYSLSSTLTLSSSEYQ SHNAYACEVSHKSLPTALV KSFNKNEC* (SEQ ID NO: 86) | X54110 | Not registered | Jenne C. N. et al., Dev. Comp. Immunol. 30 (1-2), 165-174 (2006). PMID: 16083958 |
| | | Ig lambda (CL) | GGTCAGCCCAAGTCCGCACCC TCGGTCACCCTGTTCCCGCCT TCCACGGAGGAGCTCAGTACC AACAAGGCCACCGTGGTGTGT CTCATCAACGACTTCTACCCG GGTAGCGTGAACGTGGTCTG GAAGGCAGATGGCAGCACCA TCAATCAGAACGTGAAGACCA CCCAGGCCTCCAAACAGAGCA ACAGCAAGTACGCGGCCAGC AGCTACCTGACCCTGACGGGC AGCGAGTGGAAGTCTAAGAG CAGTTACACCTGCGAGGTCAC GCACGAGGGGAGCACCGTGA CGAAGACAGTGAAGCCCTCA GAGTGTTCTTAG (SEQ ID NO: 89) | GQPKSAPSVTLFPPSTEEL STNKATVVCLINDFYPGSV NVVWKADGSTINQNVKTT QASKQSNSKYAASSYLTLT GSEWKSKSSYTCEVTHEG STVTKTVKPSECS* (SEQ ID NO: 88) | AY734681 | | |
| Porcine (Scientific Name: *Sus scrofa*) | Porcine Ig heavy chain constant region (CH1~CH3) | IgG1ᵃ | GCCCCCAAGACGGCCCCCATC GGTCTACCCTCTGGCCCCCT GCGGCAGGGACACGTCTGG CCCTAACGTGGCCTTGGGCT GCCTGGCCTCAAGCTACTTC CCCGAGCCAGTGACCATGAC CTGGAACTCGGGCGCCCTGA CCAGTGGCGTGCATACCTTC CCATCCGTCCTGCAGCCGTC AGGGCTCTACTCCCTCAGCA GCATGGTGACCGTGCCGGCC AGCAGCCTGTCCAGCAAGAG CTACACCTGCAATGTCAACC ACCCGGCCACCACCAAG GTGGACAAGCGTGTTGGAAC AAAGACCAAACCACCATGTC CCATATGCCCAGGCTGTGAA GTGGCCGGGCCCTCGGTCTT CATCTTCCCTCCAAAACCCA AGGACACCCTCATGATCTCC CAGACCCCGAGGTCACGTG CGTGGTGGTGGACGTCAGCA AGGAGCACGCCGAGGTCCA GTTCTCCTGGTACGTGGACG GCGTAGAGGTGCACACGGC CGAGACGAGACCAAAGGAG GAGCAGTTCAACAGCACCTA CCGTGTGGTCAGCGTCCTGC CCATCCAGCACCAGGACTGG CTGAAGGGGAAGGAGTTCAA GTGCAAGGTCAACAACGTAG ACCTCCCAGCCCCCATCACG AGGACCATCTCCAAGGCTAT AGGGCAGAGCCGGGAGCCG CAGGTGTACACCCTGCCCCC ACCCGCCGAGGAGCTGTCCA GGAGCAAAGTCACCGTAACC TGCCTGGTCATTGGCTTCTA CCCACCCTGACATCCATGTTG AGTGGAAGAGCAACGGACA | APKTAPSVYPLAPCGRDTS GPNVALGCLASSYFPEPVT MTWNSGALTSGVHTFPSV LQPSGLYSLSSMVTVPASS LSSKSYTCNVNHPATTTKV DKRVGTKTKPPCPICPGCE VAGPSVFIFPPKPKDTLMIS QTPEVTCVVVDVSKEHAE VQFSWYVDGVEVHTAETR PKEEQFNSTYRVVSVLPIQ HQDWLKGKEFKCKVNNV DLPAPITRTISKAIGQSREP QVYTLPPPAEELSRSKVTV TCLVIGFYPPDIHVEWKSN GQPEPEGNYRTTPPQQDV DGTFFLYSKLAVDKARWD HGETFECAVMHEALHNHY TQKSISKTQGK* (SEQ ID NO: 94) | U03781 | http:// www. imgt.org/ IMGT reper toire/ index.php? section = Locus Genes & reper toire = gene table & species = Pig & group = IGHC | Butler J. E. et al., Immunogenetics 61(3): 209-230 (2009). PMID: 19048248 Kacskovics I. et al., J. Immunol. 153(8): 3565-3573 (1994). PMID: 7930579 |

| Species | Ig Domain | Nucleotide Sequence | Amino Acid Sequence | GenBank Accession No. | IMGT Database | Reference |
|---|---|---|---|---|---|---|
| | | GCCGGAGCCAGAGGGCAAT<br>TACCGCACCACCCCGCCCCA<br>GCAGGACGTGGACGGGACC<br>TTCTTCCTGTACAGCAAGCT<br>CGCGGTGGACAAGGCAAGA<br>TGGGACCATGGAGAAACATT<br>TGAGTGTGCGGTGATGCACG<br>AGGCTCTGCACAACCACTAC<br>ACCCAGAAGTCCATCTCCAA<br>GACTCAGGGTAAATGA<br>(SEQ ID NO: 95) | | | | |
| | IgG1[b] | GCCCCCAAGACGGCCCCATC<br>GGTCTACCCTCTGGCCCCCT<br>GCGGCAGGGACGTGTCTGG<br>CCCTAACGTGGCCTTGGGCT<br>GCCTGGCCTCAAGCTACTTC<br>CCCGAGCCAGTGACCGTGAC<br>CTGGAACTCGGGCGCCCTGA<br>CCAGTGGCGTGCACACCTTC<br>CCATCCGTCCTGCAGCCGTC<br>AGGGCTCTACTCCCTCAGCA<br>GCATGGTGACCGTGCCGGCC<br>AGCAGCCTGTCCAGCAAGAG<br>CTACACCTGCAATGTCAACC<br>ACCCGGCCACCACCACCAAG<br>GTGGACAAGCGTGTTGGAAT<br>ACACCAGCCGCAAACATGTC<br>CCATATGCCCAGGCTGTGAA<br>GTGGCCGGGCCCTCGGTCTT<br>CATCTTCCCTCCAAAACCCA<br>AGGACACCCTCATGATCTCC<br>CAGACCCCCGAGGTCACGTG<br>CGTGGTGGTGGACGTCAGCA<br>AGGAGCACGCCGAGGTCCA<br>GTTCTCCTGGTACGTGGACG<br>GCGTAGAGGTGCACACGGC<br>CGAGACGAGACCAAAGGAG<br>GAGCAGTTCAACAGCACCTA<br>CCGTGTGGTCAGCGTCCTGC<br>CCATCCAGCACCAGGACTGG<br>CTGAAGGGGAAGGAGTTCAA<br>GTGCAAGGTCAACAACGTAG<br>ACCTCCCAGCCCCCATCACG<br>AGGACCATCTCCAAGGCTAT<br>AGGGCAGAGCCGGGAGCCG<br>CAGGTGTACACCCTGCCCCC<br>ACCCGCCGAGGAGCTGTCCA<br>GGAGCAAAGTCACGCTAACC<br>TGCCTGGTCATTGGCTTCTA<br>CCCACCTGACATCCATGTTG<br>AGTGGAAGAGCAACGGACA<br>GCCGGAGCCAGAGAACACAT<br>ACCGCACCACCCCGCCCCAG<br>CAGGACGTGGACGGGACCTT<br>CTTCCTGTACAGGAAACTCG<br>CGGTGGACAAGGCAAGATG<br>GGACCATGGAGACAAATTTG<br>AGTGTGCGGTGATGCACGAG<br>GCTCTGCACAACCACTACAC<br>CCAGAAGTCCATCTCCAAGA<br>CTCAGGGTAAATGA<br>(SEQ ID NO: 97) | APKTAPSVYPLAPCGRDVS<br>GPNVALGCLASSYFPEPVT<br>VTWNSGALTSGVHTFPSVL<br>QPSGLYSLSSMVTVPASSL<br>SSKSYTCNVNHPATTTKVD<br>KRVGIHQPQTCPICPGCEV<br>AGPSVFIFPPKPKDTLMIS<br>QTPEVTCVVVDVSKEHAE<br>VQFSWYVDGVEVHTAETR<br>PKEEQFNSTYRVVSVLPIQ<br>HQDWLKGKEFKCKVNNV<br>DLPAPITRTISKAIGQSREP<br>QVYTLPPPAEELSRSKVTL<br>TCLVIGFYPPDIHVEWKSN<br>GQPEPENTYRTTPPQQDV<br>DGTFFLYSKLAVDKARWD<br>HGDKFECAVMHEALHNH<br>YTQKSISKTQGK*<br>(SEQ ID NO: 96) | U03778 | | |
| | IgG2[a] | GCCCCCAAGACGGCCCCATC<br>GGTCTACCCTCTGGCCCCCT<br>GCAGGAGGGACACGTCTGG<br>CCCTAACGTGGCCTTGGGCT<br>GCCTGGCCTCAAGCTACTTC<br>CCCGAGCCAGTGACCGTGAC<br>CTGGAACTCGGGCGCCCTGT<br>CCAGTGGCGTGCATACTTC<br>CCATCCGTCCTGCAGCCGTC<br>AGGGCTCTACTCCCTCAGCA<br>GCATGGTGACCGTGCCGGCC | APKTAPSVYPLAPCSRDTS<br>GPNVALGCLASSYFPEPVT<br>VTWNSGALSSGVHTFPSVL<br>QPSGLYSLSSMVTVPASSL<br>SSKSYTCNVNHPATTTKVD<br>KRVGTKTKPPCPICPACES<br>PGPSVFIFPPKPKDTLMISR<br>TPQVTCVVVDVSQENPEV<br>QFSWYVDGVEVHTAQTRP<br>KEEQFNSTYRVVSVLPIQH<br>QDWLNGKEFKCKVNNKD | U03779 | | |

| Species | Ig Domain | Nucleotide Sequence | Amino Acid Sequence | GenBank Accession No. | IMGT Database | Reference |
|---|---|---|---|---|---|---|
| | | AGCAGCCTGTCCAGCAAGAG CTACACCTGCAATGTCAACC ACCCGGCCACCACCACGAAG GTGGACAAGCGTGTTGGAAC AAAGACCAAACCACCATGTC CCATATGCCCAGCCTGTGAA TCACCAGGGCCCTCGGTCTT CATCTTCCCTCCAAAACCCA AGGACACCCTCATGATCTCC CGGACACCCCAGGTCACGTG CGTGGTGGTTGATGTGAGCC AGGAGAACCCGGAGGTCCA GTTCTCCTGGTACGTGGACG GCGTAGAGGTGCACACGGC CCAGACGAGGCCAAAGGAG GAGCAGTTCAACAGCACCTA CCGCGTGGTCAGCGTCCTAC CCATCCAGCACCAGGACTGG CTGAACGGGAAGGAGTTCAA GTGCAAGGTCAACAACAAAG ACCTCCCAGCCCCCATCACA AGGATCATCTCCAAGGCCAA AGGGCAGACCCGGGAGCCG CAGGTGTACACCCTGCCCCC ACACGCCGAGGAGCTGTCCA GGAGCAAAGTCAGCATAACC TGCCTGGTCATTGGCTTCTA CCCACCTGACATCGATGTCG AGTGGCAAAGAAACGGACA GCCGGAGCCAGAGGGCAAT TACCGCACCACCCCGCCCCA GCAGGACGTGGACGGGACC TACTTCCTGTACAGCAAGTT CTCGGTGGACAAGGCCAGCT GGCAGGGTGGAGGCATATTC CAGTGTGCGGTGATGCACGA GGCTCTGCACAACCACTACA CCCAGAAGTCTATCTCCAAG ACTCCGGGTAAATGA (SEQ ID NO: 99) | LPAPITRIISKAKGQTREPQ VYTLPPHAEELSRSKVSIT CLVIGFYPPDIDVEWQRNG QPEPEGNYRTTPPQQDVD GTYFLYSKFSVDKASWQG GGIFQCAVMHEALHNHYT QKSISKTPGK* (SEQ ID NO: 98) | | | |
| | IgG2*b* | GCCCCCAAGACGGCCCCATT GGTCTACCCTCTGGCCCCCT GCGGCAGGGACACGTCTGG CCCTAACGTGGCCTTGGGCT GCCTGGCCTCAAGCTACTTC CCCGAGCCAGTGACCGTGAC CTGGAACTCGGGCGCCCTGA CCAGTGGCGTGCATACCTTC CCATCCGTCCTGCAGCCGTC AGGGCTCTACTCCCTCAGCA GCATGGTGACCGTGCCGGCC AGCAGCCTGTCCAGCAAGAG CTACACCTGCAATGTCAACC ACCCGGCCACCACCACCAAG GTGGACAAGCGTGTTGGAAC AAAGACCAAACCACCATGTC CCATATGCCCAGCCTGTGAA TCGCCAGGGCCCTCGGTCTT CATCTTCCCTCCAAAACCCA AGGACACCCTCATGATCTCC CGGACACCCCAGGTCACGTG CGTGGTAGTTGATGTGAGCC AGGAGAACCCGGAGGTCCA GTTCTCCTGGTACGTGGACG GCGTAGAGGTGCACACGGC CCAGACGAGGCCAAAGGAG GAGCAGTTCAACAGCACCTA CCGCGTGGTCAGCGTCCTGC CCATCCAGCACCAGGACTGG CTGAACGGGAAGGAGTTCAA GTGCAAGGTCAACAACAAAG ACCTCCCAGCCCCCATCACA AGGATCATCTCCAAGGCCAA AGGGCAGACCCGGGAGCCG | APKTAPLVYPLAPCGRDTS GPNVALGCLASSYFPEPVT VTWNSGALTSGVHTFPSVL QPSGLYSLSSMVTVPASSL SSKSYTCNVNHPATTTKVD KRVGTKTKPPCPICPACES PGPSVFIFPPKPKDTLMISR TPQVTCVVVDVSQENPEV QFSWYVDGVEVHTAQTRP KEEQFNSTYRVVSVLPIQH QDWLNGKEFKCKVNNKD LPAPITRIISKAKGQTREPQ VYTLPPHAEELSRSKVSIT CLVIGFYPPDIDVEWQRNG QPEPEGNYRTTPPQQDVD GTYFLYSKFSVDKASWQG GGIFQCAVMHEALHNHYT QKSISKTPGK* (SEQ ID NO: 100) | U03780 | | |

TABLE-continued

| Species | Ig Domain | Nucleotide Sequence | Amino Acid Sequence | GenBank Accession No. | IMGT Database | Reference |
|---|---|---|---|---|---|---|
| | | CAGGTGTACACCCTGCCCCC<br>ACACGCCGAGGAGCTGTCCA<br>GGAGCAAAGTCAGCATAACC<br>TGCCTGGTCATTGGCTTCTA<br>CCCCACCTGACATCGATGTCG<br>AGTGGCAAAGAAACGGACA<br>GCCGGAGCCAGAGGGCAAT<br>TACCGCACCACCCCGCCCCA<br>GCAGGACGTGGACGGGACC<br>TACTTCCTGTACAGCAAGTT<br>CTCGGTGGACAAGGCCAGCT<br>GGCAGGGTGGAGGCATATTC<br>CAGTGTGCGGTGATGCACGA<br>GGCTCTGCACAACCACTACA<br>CCCAGAAGTCTATCTCCAAG<br>ACTCCGGGTAAATGA<br>(SEQ ID NO: 01) | | | | |
| | IgG3 | GCCTACAACACAGCTCCATC<br>GGTCTACCCTCTGGCCCCCT<br>GTGGCAGGGACGTGTCTGAT<br>CATAACGTGGCCTTGGGCTG<br>CCTTGTCTCAAGCTACTTCC<br>CCGAGCCAGTGACCGTGACC<br>TGGAACTCGGGTGCCCTGTC<br>CAGAGTCGTGCATACCTTCC<br>CATCCGTCCTGCAGCCGTCA<br>GGGCTCTACTCCCTCAGCAG<br>CATGGTGATCGTGGCGGCCA<br>GCAGCCTGTCCACCCTGAGC<br>TACACGTGCAACGTCTACCA<br>CCCGGCCACCAACACCAAGG<br>TGGACAAGCGTGTTGACATC<br>GAACCCCCCACACCCATCTG<br>TCCCGAAATTTGCTCATGCC<br>CAGCTGCAGAGGTCCTGGGA<br>GCACCGTCGGTCTTCCTCTT<br>CCCTCCAAAACCCAAGGACA<br>TCCTCATGATCTCCCGGACA<br>CCCAAGGTCACGTGCGTGGT<br>GGTGGACGTGAGCCAGGAG<br>GAGGCTGAAGTCCAGTTCTC<br>CTGGTACGTGGACGGCGTAC<br>AGTTGTACACGGCCCAGACG<br>AGGCCAATGGAGGAGCAGTT<br>CAACAGCACCTACCGCGTGG<br>TCAGCGTCCTGCCCATCCAG<br>CACCAGGACTGGCTGAAGG<br>GGAAGGAGTTCAAGTGCAAG<br>GTCAACAACAAAGACCTCCT<br>TTCCCCCATCACGAGGACCA<br>TCTCCAAGGCTACAGGGCCG<br>AGCCGGGTGCCGCAGGTGT<br>ACACCCTGCCCCCAGCCTGG<br>GAAGAGCTGTCCAAGAGCAA<br>AGTCAGCATAACCTGCCTGG<br>TCACTGGCTTCTACCCACCT<br>GACATCGATGTCGAGTGGCA<br>GAGCAACGGACAACAAGAG<br>CCAGAGGGCAATTACCGCAC<br>CACCCCGCCCCAGCAGGACG<br>TGGATGGGACCTACTTCCTG<br>TACAGCAAGCTCGCGGTGGA<br>CAAGGTCAGGTGGCAGCGT<br>GGAGACCTATTCCAGTGTGC<br>GGTGATGCACGAGGCTCTGC<br>ACAACCACTACACCCAGAAG<br>TCCATCTCCAAGACTCAGGG<br>TAAATGA<br>(SEQ ID NO: 103) | AYNTAPSVYPLAPCGRDVS<br>DHNVALGCLVSSYFPEPVT<br>VTWNSGALSRVVHTFPSVL<br>QPSGLYSLSSMVIVAASSLS<br>TLSYTCNVYHPATNTKVD<br>KRVDIEPPTPICPEICSCPA<br>AEVLGAPSVFLFPPKPRDI<br>LMISRTPKVTCVVVDVSQE<br>EAEVQFSWYVDGVQLYTA<br>QTRPMEEQFNSTYRVVSV<br>LPIQHQDWLKGKEFKCKV<br>NNKDLLSPITRTISKATGPS<br>RVPQVYTLPPAWEELSKSK<br>VSITCLVTGFYPPDIDVEW<br>QSNGQQEPEGNYRTTPPQ<br>QDVDGTYFLYSKLAVDKV<br>RWQRGDLFQCAVMHEAL<br>HNHYTQKSISKTQGK<br>(SEQ ID NO: 102) | EU372658 | | |
| | IgG4a | ACCTTCCCATCCGTCCTGCA<br>GCCGTCAGGGCTCTACTCCC<br>TCAGCAGGATGGTGACCGTG<br>CCGGCCAGCAGCCTGTCCAG | TFPSVLQPSGLYSLSSMVT<br>VPASSLSSKSYTCNVNHPA<br>TTTKVDKRVGTKTKPPCPI<br>CPACEGPGPSAFIFPPKPK | U03782 | | |

TABLE-continued

| Species | Ig Domain | Nucleotide Sequence | Amino Acid Sequence | GenBank Accession No. | IMGT Database | Reference |
|---|---|---|---|---|---|---|
| | | CAAGAGCTACACCTGCAATG TCAACCACCCGGCCACCACC ACCAAGGTGGACAAGCGTGT TGGAACAAAGACCAAACCAC CATGTCCCATATGCCCAGCC TGTGAAGGGCCCGGGCCCTC GGCCTTCATCTTCCCTCCAA AACCCAAGGACACCCTCATG ATCTCCCCGGACCCCCAAGGT CACGTGCGTGGTGGTAGATG TGAGCCAGGAGAACCCGGA GGTCCAGTTCTCCTGGTACG TGGACGGCGTAGAGGTGCA CACGGCCCAGACGAGGCCA AAGGAGGAGCAGTTCAACAG CACCTACCGCGTGGTCAGCG TCCTGCCCATCCAGCACCAG GACTGGCTGAACGGGAAGG AGTTCAAGTGCAAGGTCAAC AACAAAGACCTCCCAGCCCC CATCACAAGGATCATCTCCA AGGCCAAAGGGCAGACCCG GGAGCCGCAGGTGTACACCC TGCCCCCACCCACCGAGGAG CTGTCCAGGAGCAAAGTCAC GCTAACCTGCCTGGTCACTG GCTTCTACCCACCTGACATC GATGTCGAGTGGCAAAGAAA CGGACAGCCGGAGCCAGAG GGCAATTACCGCACCACCCC GCCCCAGCAGGACGTGGAC GGGACCTACTTCCTGTACAG CAAGCTCGCGGTGGACAAG GCCAGCTGGCAGCGTGGAG ACACATTCCAGTGTGCGGTG ATGCACGAGGCTCTGCACAA CCACTACACCCAGAAGTCCA TCTTGAAGACTCCGGGTAAA TGA (SEQ ID NO: 105) | DTLMISRTPKVTCVVVDVS QENPEVQFSWYVDGVEVH TAQTRPKEEQFNSTYRVVS VLPIQHQDWLNGKEFKCK VNNKDLPAPITRIISKAKG QTREPQVYTLPPPTEELSR SKVTLTCLVTGFYPPDIDV EWQRNGQPEPEGNYRTTP PQQDVDGTYFLYSKLAVD KASWQRGDTFQCAVMHE ALHNHYTQKSIFKTGK* (SEQ ID NO: 104) | | | |
| | IgG4b | GCCCCCAAGACGGCCCCATC GGTCTACCCTCTGGCCCCCT GCGGCAGGGACGTGTCTGG CCCTAACGTGGCCTTGGGCT GCCTGGCCTCAAGCTACTTC CCCGAGCCAGTGACCGTGAC CTGGAACTCGGGCGCCCTGA CCAGTGGCGTGCACACCTTC CCATCCGTCCTGCAGCCGTC AGGGCTCTACTCCCTGAGCA GCATGGTGACCGTGCCGGCC AGCAGCCTGTCCAGCAAGAG CTACACCTGCAATGTCAACC ACCCGGCCACCACCACCAAG GTGGACAAGCGTGTTGGAAT ACACCAGCCGCAAACATGTC CCATATGCCCAGCCTGTGAA GGGCCCGGGCCCTCGGCCTT CATCTTCCCTCCAAAACCCA AGGACACCCTCATGATCTCC CGGACCCCCAAGGTCACGTG CGTGGTGGTTGATGTGAGCC AGGAGAACCCGGAGGTCCA GTTCTCCTGGTACGTGGACG GCGTAGAGGTGCACACGGC CCAGACGAGGCCAAAGGAG GAGCAGTTCAACAGCACCTA CCGCGTGGTCAGCGTCCTGC TCATCCAGCACCAGGACTGG CTGAACGGGAAGGAGTTCAA GTGCAAGGTCAACAACAAAG ACCTCCCAGCCCCCATCACA AGGATCATCTCCAAGGCCAA AGGGCAGACCCGGGAGCCG | APKTAPSVYPLAPCGRDVS GPNVALGCLASSYFPEPVT VTWNSGALTSGVHTFPSVL QPSGLYSLSSMVTVPASSL SSKSYTCNVNHPATTTKVD KRVGIHQPQTCPICPACEG PGPSAFIFPPKPKDTLMISR TPKVTCVVVDVSQENPEV QFSWYVDGVEVHTAQTRP KEEQFNSTYRVVSVLLIQH QDWLNGKEFECKVNNKD LPAPITRIISKAKGQTREPQ VYTLPPPTEELSRSLVTLT CLVTGFYPPDIDVEWQRN GQPEPEGNYRTTPPQQDV DGTYFLYSKLAVDKASWQ RGDTFQCAVMHEALHNHY T (SEQ ID NO: 106) | EU372654 | | |

| Species | Ig Domain | Nucleotide Sequence | Amino Acid Sequence | GenBank Accession No. | IMGT Database | Reference |
|---|---|---|---|---|---|---|
| | | CAGGTGTACACCCTGCCCCC<br>ACCCACCGAGGAGCTGTCCA<br>GGAGCAAAGTCACGCTAACC<br>TGCCTGGTCACTGGCTTCTA<br>CCCACCTGACATCGATGTCG<br>AGTGGCAAAGAAACGGACA<br>GCCGGAGCCAGAGGGCAAT<br>TACCGCACCACCCCGCCCCA<br>GCAGGACGTGGACGGGACC<br>TACTTCCTGTACAGCAAGCT<br>CGCGGTGGACAAGGCCAGC<br>TGGCAGCGTGGAGACACATT<br>CCAGTGTGCGGTGATGCACG<br>AGGCTCTGCACAACCACTAC<br>ACCC<br>(SEQ ID NO: 107) | | | | |
| | IgG5a | GCCCCAAGACGGCCCCATC<br>GGTCTACCCTCTGGCCCCCT<br>GCAGCAGGGACACGTCTGG<br>CCCTAACGTGGCCTTGGGCT<br>GCCTGGTCTCAAGCTACTTC<br>CCCGAGCCAGTGACCGTGAC<br>CTGGAACTCGGGCGCCCTGA<br>CCAGTGGCGTGCACACCTTC<br>CCATCCGTCCTGCAGCCGTC<br>AGGGCTCTACTCCCTCAGCA<br>GCATGGTGACCGTGCCGGCC<br>CACAGCTTGTCCAGCAAGCG<br>CTATACGTGCAATGTCAACC<br>ACCCAGCCACCAAAACCAAG<br>GTGGACCTGTGTGTTGGACG<br>ACCATGTCCCATATGCCCAG<br>GCTGTGAAGTGGCCGGGCC<br>CTCGGTCTTCATCTTCCCTC<br>CAAAACCCAAGGACATCCTC<br>ATGATCTCCCGGACCCCCGA<br>GGTCACGTGCGTGGTGGTG<br>GACGTCAGCAAGGAGCACG<br>CCGAGGTCCAGTTCTCCTGG<br>TACGTGGACGGCGAAGAGG<br>TGCACACGGCCGAGACGAG<br>GCCAAAGGAGGAGCAGTTCA<br>ACAGCACCTACCGCGTGGTC<br>AGCGTCCTGCCCATCCAGCA<br>CGAGGACTGGCTGAAGGGG<br>AAGGAGTTCGAGTGCAAGGT<br>CAACAACGAAGACCTCCCAG<br>GCCCCATCACGAGGACCATC<br>TCCAAGGCCAAAGGGGTGGT<br>ACGGAGCCCGGAGGTGTAC<br>ACCCTGCCCCCACCCGCCGA<br>GGAGCTGTCCAAGAGCATAG<br>TCACGCTAACCTGCCTGGTC<br>AAAAGCATCTTCCCGNCTTT<br>CATCCATGTTGAGTGGAAAA<br>TCAACGGAAAACCAGAGCCA<br>GAGAACGCATATCGCACCAC<br>CCCGCCTCAGGAGGACGAG<br>GACAGGACCTACTTCCTGTA<br>CAGCAAGCTCGCGGTGGACA<br>AGGCAAGATGGGACCATGG<br>AGAAACATTTGAGTGTGCGG<br>TGATGCACGAGGCTCTGCAC<br>AACCACTACACCCAGAAGTC<br>CATCTCCAAGACTCAGGGTA<br>AATGA<br>(SEQ ID NO: 109) | APKTAPSVYPLAPCSRDTS<br>GPNVALGCLVSSYFPEPVT<br>VTWNSGALTSGVHTFPSVL<br>QPSGLYSLSSMVTVPAHSL<br>SSKRYTCNVNHPATKTKV<br>DLCVGRPCPICPGCEVAGP<br>SVFIFPPKPKDILMISRTPE<br>VTCVVVDVSKEHAEVQFS<br>WYVDGEEVHTAETRPKEE<br>QFNSTYRVVSVLPIQHEDW<br>LKGKEFECKVNNEDLPGP<br>ITRTISKAKGVVRSPEVYTL<br>PPPAEELSKSIVTLTCLVKS<br>IFP?FIHVEWKINGKPEPE<br>NAYRTTPPQEDEDRTYFLY<br>SKLAVDKARWDHGETFEC<br>AVMHEALHNHYTQKSISK<br>TQGK*<br>(SEQ ID NO: 108) | EU372657 | | |
| | IgG5b | GCCTACAACACAGCTCCATC<br>GGTCTACCCTCTGGCCCCCT<br>GTGGCAGGGACGTGTCTGAT<br>CATAACGTGGCCTTGGGCTG<br>CCTGGTCTCAAGCTACTTCC<br>CCGAGCCAGTGACCGTGACC | AYNTAPSVYPLAPCGRDVS<br>DHNVALGCLVSSYFPEPVT<br>VTWNWGAQTSGVHTFPSV<br>LQPSGLYSLSSTVTVPAHS<br>ISSKCFTCNVNHPATTTKV<br>DLCVGKKTKPRCPICPGCE | EU372656 | | |

TABLE-continued

| Species | Ig Domain | Nucleotide Sequence | Amino Acid Sequence | GenBank Accession No. | IMGT Database | Reference |
|---------|-----------|---------------------|---------------------|----------------------|---------------|-----------|
| | | TGGAACTGGGGCGCCCAGA CCAGTGGCGTGCACACCTTC CCATCCGTCCTGCAGCCGTC AGGGCTCTACTCCCTCAGCA GCACGGTGACCGTGCCGGC CCACAGCTTGTCCAGCAAGT GCTTCACGTGCAATGTCAAC CACCCGGCCACCACCACCAA GGTGGACCTGTGTGTTGGAA AAAAGACCAAGCCTCGATGT CCCATATGCCCAGGCTGTGA AGTGGCCGGGCCCTCGGTCT TCATCTTCCCTCCAAAACCC AAGGACATCCTCATGATCTC CCGGACCCCCGAGGTCACGT GCGTGGTGGTGGACGTCAG CAAGGAGCACGCCGAGGTC CAGTTCTCCTGGTACGTGGA CGGCGAAGAGGTGCACACG GCCGAGACGAGACCAAGG AGGAGCAGTTCAACAGCACT TACCGCGTGGTCAGCGTCCT GCCCATCCAGCACGAGGACT GGCTGAAGGGGAAGGAGTT CGAGTGCAAGGTCAACAACG AAGACCTCCCAGGCCCCATC ACGAGGACCATCTCCAAGGC CAAAGGGGTGGTACGGAGC CCGGAGGTGTACACCCTGCC CCCACCCGCCGAGGAGCTGT CCAAGAGCATAGTCACGCTA ACCTGCCTGGTCAAAAGCTT CTTCCCGCCTTTCATCCATG TTGAGTGGAAAATCAACGGA AAACCAGAGCCAGAGAACGC ATACCGCACCACCCCGCCCC AGGAGGACGAGGACGGGAC CTACTTCCTGTACAGCAAGT TCTCGGTGGAAAAGTTCAGG TGGCACAGTGGAGGCATCCA CTGTGCGGTGATGCACGAGG CTCTGCACAACCACTACACC C (SEQ ID NO: 111) | VAGPSVFIFPPKPKDILMIS RTPEVTCVVVDVSKEHAE VQFSWYVDGEEVHTAETR PKEEQFNSTYRVVSVLPIQ HEDWLKGKEFECKVNNE DLPGPITRTISKAKGVVRSP EVYTLPPPAEELSKSIVTLT CLVKSFPPPFIHVEWKING KPEPENAYRTTPPQEDED GTYFLYSKFSVEKFRWHS GGIHCAVMHEALHNHYT (SEQ ID NO: 110) | | | |
| | IgG6a | GCCCCCAAGACGGCCCCCATC GGTCTACCCTCTGGCCCCCT GCGGCAGGGACACGTCTGG CCCTAACGTGGCCTTGGGCT GCCTGGCCTCAAGCTACTTC CCCGAGCCAGTGACCCTGAC CTGGAACTCGGGCGCCCTGA CCAGTGGCGTGCATACCTTC CCATCCGTCCTGCAGCCGTC AGGGCTCTACTCCCTCAGCA GCATGGTGACCGTGCCGGCC AGCAGCCTGTCCAGCAAGAG CTACACCTGCAATGTCAACC ACCCGGCCACCACCACCAAG GTGGACCTGTGTGTTGGACG ACCATGTCCCATATGCCCAG CCTGTGAAGGGCCCGGGCC CTCGGTCTTCATCTTCCCTC CAAAACCCAAGGACACCCTC ATGATCTCCCGGACACCCCA GGTCACGTGCGTGGTGGTAG ATGTGAGCCAGGAAAACCCG GAGGTCCAGTTCTCCTGGTA TGTGGACGGTGTAGAGGTGC ACACGGCCCAGACGAGGCC AAAGGAGGCGCAGTTCAACA GCACCTACCGTGTGGTCAGC GTCCTGCCCATCCAGCACGA GGACTGGCTGAAGGGGAAG GAGTTCGAGTGCAAGGTCAA CAACAAAGACCTCCCAGCCC | APKTAPSVYPLAPCGRDTS GPNVALGCLASSYFPEPVT LTWNSGALTSGVHTFPSVL QPSGLYSLSSMVTVPASSL SSKSYTCNVNHPATTTKVD LCVGRPCPICPACEGPGPS VFIFPPKPKDTLMISRTPQ VTCVVVDVSQENPEVQFS WYVDGVEVHTAQTRPKEA QFNSTYRVVSVLPIQHEDW LKGKEFECKVNNKDLPAP ITRIISKAKGPSREPQVYTL SPSAEELSRSKVSITCLVTG FYPPDIDVEWKSNGQPEP EGNYRTTPPQQDVDGTYF LYSKLAVDKASWQRGDPF QCAVMHEALHNHYT (SEQ ID NO: 112) | EU37265 5 | | |

TABLE-continued

| Species | Ig Domain | Nucleotide Sequence | Amino Acid Sequence | GenBank Accession No. | IMGT Database | Reference |
|---|---|---|---|---|---|---|
| | | CCATCACAAGGATCATCTCC<br>AAGGCCAAAGGGCCGAGCC<br>GGGAGCCGCAGGTGTACAC<br>CCTGTCCCCATCCGCCGAGG<br>AGCTGTCCAGGAGCAAAGTC<br>AGCATAACCTGCCTGGTCAC<br>TGGCTTCTACCCACCTGACA<br>TCGATGTCGAGTGGAAGAGC<br>AACGGACAGCCGGAGCCAG<br>AGGGCAATTACCGCACCACC<br>CCGCCCCAGCAGGACGTGG<br>ACGGGACCTACTTCCTGTAC<br>AGCAAGCTCGCGGTGGACAA<br>GGCCAGCTGGCAGCGTGGA<br>GACCCATTCCAGTGTGCGGT<br>GATGCACGAGGCTCTGCACA<br>ACCACTACACCC<br>(SEQ ID NO: 113) | | | | |
| | IgG6b | GCCCCCAAGACGGCCCCATC<br>GGTCTACCCTCTGGCCCCCT<br>GCGGCAGGGACACGTCTGG<br>CCCTAACGTGGCCTTGGGCT<br>GCCTGGCCTCAAGCTACTTC<br>CCCGAGCCAGTGACCGTGAC<br>CTGGAACTCGGGCGCCCTGA<br>CCAGTGGCGTGCACACCTTC<br>CCATCCGTCCTGCAGCCGTC<br>AGGGCTCTACTCCCTCAGCA<br>GCACGGTGACCGTGCCGGC<br>CAGGAGCTCGTCCAGAAAGT<br>GCTTCACGTGCAATGTCAAC<br>CACCCGGCCACCACCACCAA<br>GGTGGACCTGTGTGTTGGAC<br>GACCATGTCCCATATGCCCA<br>GCCTGTGAAGGGAACGGGC<br>CCTCGGTCTTCATCTTCCCT<br>CCAAAACCCAAGGACACCCT<br>CATGATCTCCCGGACCCCCG<br>AGGTCACGTGCGTGGTGGTA<br>GATGTGAGCCAGGAAAACCC<br>GGAGGTCCAGTTCTCCTGGT<br>ACGTGGACGGCGAAGAGGT<br>GCACACGGCCGAGACGAGG<br>CCAAAGGAGGAGCAGTTCAA<br>CAGCACCTACCGTGTGGTCA<br>GCGTCCTGCCCATCCAGCAC<br>CAGGACTGGCTGAAGGGAA<br>AGGAGTTCGAGTGCAAGGTC<br>AACAACAAAGACCTCCCAGC<br>CCCCATCACAAGGATCATCT<br>CCAAGGCCAAAGGGCCGAG<br>CCGGGAGCCGCAGGTGTAC<br>ACCCTGTCCCCATCCGCCGA<br>GGAGCTGTCCAGGAGCAAA<br>GTCAGCATAACCTGCCTGGT<br>CACTGGCTTCTACCCACCTG<br>ACATCGATGTCGAGTGGAAG<br>AGCAACGGACAGCCGGAGC<br>CAGAGGGCAATTACCGCTCC<br>ACCCCGCCCCAGGAGGACG<br>AGGACGGGACCTACTTCCTG<br>TACAGCAAACTCGCGGTGGA<br>CAAGGCGAGGTTGCAGAGT<br>GGAGGCATCCACTGTGCGGT<br>GATGCACGAGGCTCTGCACA<br>ACCACTACACCCAGAAGTCC<br>ATCTCCAAGACT<br>(SEQ ID NO: 115) | APKTAPSVYPLAPCGRDTS<br>GPNVALGCLASSYFPEPVT<br>VTWNSGALTSGVHTFPSVL<br>QPSGLYSLSSTVTVPARSSS<br>RKCFTCNVNHPATTTKVD<br>LCVGRPCPICPACEGNGPS<br>VFIFPPKPKDTLMISRTPEV<br>TCVVVDVSQENPEVQFSW<br>YVDGEEVHTAETRPKEEQ<br>FNSTYRVVSVLPIQHDWL<br>KGKEFECKVNNKDLPAPI<br>TRIISKAKGPSREPQVYTLS<br>PSAEELSRSKVSITCLVTGF<br>YPPDIDVEWKSNGQPEPE<br>GNYRSTPPQEDEDGTYFLY<br>SKLAVDKARLQSGGIHCAV<br>MHEALHNHYTQKSISKT<br>(SEQ ID NO: 114) | EU37265<br>3 | | |
| Porcine Ig light chain con- | Ig kappa (CK) vari- ant 1 | | | FP31289<br>8 | http://<br>www.<br>imgt.org/<br>IMGT<br>reper | Schwartz<br>J. C. et<br>al.,<br>Immuno-<br>gene- |

TABLE-continued

| Species | Ig Domain | Nucleotide Sequence | Amino Acid Sequence | GenBank Accession No. | IMGT Database | Reference |
|---|---|---|---|---|---|---|
| | stant region | | | | toire/ index.php?64, section = Locus Genes & reper toire = gene table & species = Pig & group = IGLC | tics, 303-311 (2012). PMID: 22109540 |
| | Ig kappa (CK) variant 2 | | | CU694848 | | 11 |
| | Ig lambda (CL) variant 1 | | | CU467669 | http:// www. imgt.org/ IMGT reper toire/ index.php? section = Locus Genes & reper toire = gene table & species = Pig & group = IGKC | |
| | Ig lambda (CK) variant 2 | | | CU467599 | | |
| Water buffalo (Scientific Name: *Bubalus bubalis* | Water buffalo Ig heavy chain constant region (CH1~CH3) | IgG1? GAGCGGCGTGCACACCTTCCC GGCCGTCCTTCAGTCCTCCGG GCTCTACTCTCTCAGCAGCAC GGTGACCGCGCCCGCCAGCG CCACAAAAGCCAGACCTTCA CCTGCAACGTAGCCCACCCGG CCAGCAGCACCAAGGTGGAC AAGGCTGTTGTTCCCCCATGC AGACCGAAACCCTGTGATTGC TGCCCACCCCTGAGCTCCCC GGAGGACCCTCTGTCTTCATC TTCCCACCAAAACCCAAGGAC ACCCTCACAATCTCTGGAACT CCTGAGGTCACGTGTGTGGTG GTGGACGTGGGCCACGATGA CCCCGAGGTGAAGTTCTCCTG GTTCGTGGACGATGTGGAGG TAAACACAGCCAGGACGAAG CCAAGAGAGGAGCAGTTCAA CAGCACCTACCGCGTGGTCAG CGCCCTGCCCATCCAGCACAA CGACTGGACTGGAGGAAAGG AGTTCAAGTGCAAGGTCTACA ATGAAGGCCTCCCAGCCCCCA TCGTGAGGACCATCTCCAGGA CCAAAGGGCAGGCCCGGGAG CCGCAGGTGTACGTCCTGGCC CCACCCCAGGACGAGCTCAG CAAAAGCACGGTCAGCATCAC TTGCATGGTCACTGGCTTCTA | SGVHTFPAVLQSSGLYSLS STVTAPASATKSQTFTCNV AHPASSTKVDKAVVPPCRP KPCDCCPPPELPGGPSVFI FPPKPKDTLTISGTPEVTC VVVDVGHDDPEVKFSWFV DDVEVNTARTKPREEQFN STYRVVSALPIQHNDWTG GKEFKCKVYNEGLPAPIVR TISRTKGQAREPQVYVLAP PQDELSKSTVSITCMVGF YPDYIAVEWQKDGQPESE DKYGTTPPQLDSDGSYFLY SRLRVNKNSWQEGGAYTC VVMHE (SEQ ID NO: 118) | NW_005 690903 | Not registered | None |

| Species | Ig Domain | Nucleotide Sequence | Amino Acid Sequence | GenBank Accession No. | IMGT Database | Reference |
|---|---|---|---|---|---|---|
| | | CCCAGACTACATCGCCGTAGA GTGGCAGAAAGATGGGCAGC CTGAGTCAGAGGACAAATATG GCACGACCCCGCCCCAGCTG GACAGCGATGGCTCCTACTTC CTGTACAGCAGGCTCAGGGT GAACAAGAACAGCTGGCAAG AAGGAGGCGCCTACACGTGT GTAGTGATGCATGAGGC (SEQ ID NO: 119) | | | | |
| | IgG2? | GCCTCCATCACAGCCCCGAAA GTCTACCCTCTGACTTCTTGC CGCGGGGAAACGTCCAGCTC CACCGTGACCCTGGGCTGCCT GGTCTCCAGCTACATGCCCGA GCCGGTGACCGTGACCTGGA ACTCGGGTGCCCTGAAGAGC GGCGTGCACACCTTCCCGGCC GTCCTTCAGTCCTCTGGGCTC TACTCTCTCAGCAGCACGGTG ACCGCGCCCGCCAGCGCCAC AAAAAGCCAGACCTTCACCTG CAACGTAGCCCACCCGGCCA GCACCAAGGTGGACACG GCTGTTGGGTTCTCCAGTGAC TGCTGCAAGTTTCCTAAGCCT TGTGTGAGGGGACCATCTGTC TTCATCTTCCCGCCGAAACCC AAAGACACCCTGATGATCACA GGAAATCCCGAGGTCACATGT GTGGTGGTGGACGTGGGCCG GGATAACCCCGAGGTGCAGTT CTCCTGGTTCGTGGGTGATGT GGAGGTGCACACGGGCAGGT CGAAGCCGAGAGAGGAGCAG TTCAACAGCACCTACCGCGTG GTCAGCACCCTGCCCATCCAG CACAATGACTGGACTGGAGG AAAGGAGTTCAAGTGCAAGGT CAACAACAAAGGCCTCCCAGC CCCCATCGTGAGGACCATCTC CAGGACCAAAGGGCAGGCCC GGGAGCCGCAGGTGTACGTC CTGGCCCCACCCCAGGAAGA GCTCAGCAAAAGCACGGTCA GCGTCACTTGCATGGTCACTG GCTTCTACCCAGACTACATCG CCGTAGAGTGGCATAGAGAC CGGCAGGCTGAGTCGGAGGA CAAGTACCGCACGACCCCGCC CCAGCTGGACAGCGATGGCT CCTACTTCCTGTACAGCAGGC TCAAGGTGAACAAGAACAGCT GGCAAGAAGGAGGCGCCTAC ACGTGTGTAGTGATGCATGAG GC (SEQ ID NO: 121) | ASITAPKVYPLTSCRGETSS STVTLGCLVSSYMPEPVTV TWNSGALKSGVHTFPAVL QSSGLYSLSSTVTAPASAT KSQTFTCNVAHPASSTKVD TAVGFSSDCCKFPKPCVRG PSVFIFPPKPKDTLMITGN PEVTCVVVDVGRDNPEVQ FSWFVGDVEVHTGRSKPR EEQFNSTYRVVSTLPIQHN DWTGGKEFKCKVNNKGL PAPIVRTISRTKGQAREPQ VYVLAPPQEELSKSTVSVT CMVTGFYPDYIAVEWHRD RQAESEDKYRTTPPQLDSD GSYFLYSRLKVNKNSWQE GGAYTCVVMHE (SEQ ID NO: 120) | NW_005 766143 | | |
| | IgG3? | GCCTCCACCACAGCCCCGAAA GTCTACCCTCTGGCATCCAGC TGCGGGGACACGTCCAGCTC CACCGTGACCCTGGGCTGCCT GGTCTCCAGCTACATGCCCGA GCCGGTGACCGTGACCTGGA ACTCGGGTGCCCTGAAGAAC GGCGTGCACACCTTCCCGGCC GTCCGGCAGTCCTCCGGGCTC TACTCTCTCAGCAGCATGGTG ACCATGCCCACCAGCACCGCA GGAACCCAGACCTTCACCTGC AACGTAGCCCACCCGGCCAG CACCAAGGTGGACACGG CTGTCACTGCAAGGCATCCGG TCCCGAAGACACCAGAGACAC CTATCCATCCTGTAAAACCCC | ASTTAPKVYPLASSCGDTS SSTVTLGCLVSSYMPEPVT VTWNSGALKNGVHTFPAV RQSSGLYSLSSMVTMPTST AGTQTFTCNVAHPASSTKV DTAVTARHPVPKTPETPIH PVKPPTQEPRDEKTPCQCP KCPEPLGGLSVFIFPPKPK DTLTISGTPEVTCVVVDVG QDDPEVQFSWFVDDVEVH TARMKPREEQFNSTYRVV SALPIQHQDWLREKEFKC KVNNKGLPAPIVRTISRTK GQAREPQVYVLAPPREELS KSTLSLTCLITGFYPEEVD VEWQRNGQPESEDKYHTT PPQLDADGSYFLYSRLRVN | NW_005 784206 | | |

| Species | Ig Domain | Nucleotide Sequence | Amino Acid Sequence | GenBank Accession No. | IMGT Database | Reference |
|---|---|---|---|---|---|---|
| | | CAACCCAGGAGCCCAGAGAT<br>GAAAAGACACCCTGCCAGTGT<br>CCCAAATGCCCAGAACCTCTG<br>GGAGGACTGTCTGTCTTCATC<br>TTCCCACCGAAACCCAAGGAC<br>ACCCTCACAATCTCTGGAACG<br>CCCGAGGTCACGTGTGTGGT<br>GGTCGACGTGGGCCAGGATG<br>ACCCCGAAGTGCAGTTCTCCT<br>GGTTCGTGGATGACGTGGAG<br>GTGCACAGAGCCAGGATGAA<br>GCCAAGAGAGGAGCAGTTCA<br>ACAGCACCTACCGCGTGGTCA<br>GCGCCCTGCCCATCCAGCACC<br>AGGACTGGCTGCGGGAAAAG<br>GAGTTCAAGTGCAAGGTCAAC<br>AACAAAGGCCTCCCGGCCCCC<br>ATCGTGAGGACCATCTCCAGG<br>ACCAAAGGGCAGGCCCGGGA<br>GCCACAGGTGTATGTCCTGGC<br>CCCACCCCGGGAAGAGCTCA<br>GCAAAAGCACGCTCAGCCTCA<br>CCTGCCTAATCACCGGCTTCT<br>ACCCAGAAGAGGTAGACGTG<br>GAGTGGCAGAGAAATGGGCA<br>GCCTGAGTCAGAGGACAAGT<br>ACCACACGACCCCACCCCAGC<br>TGGACGCTGACGGCTCCTACT<br>TCCTGTACAGCAGGCTCAGGG<br>TGAACAGGAGCAGCTGGCAG<br>GAAGGAGACCACTACACGTGT<br>GCAGTGATGCATGAAGCTTTA<br>CGGAATCACTACAAAGAGAAG<br>CCCATCTCGAGGTCTCCGGGT<br>AAATGA<br>(SEQ ID NO: 123) | RSSWQEGDHYTCAVMHEA<br>LRNHYKEKPISRSPGK*<br>(SEQ ID NO: 122) | | | |
| Water buffalo Ig light chain constant region (CL) | Ig lambda? | CAGCCCAAGTCCGCACCCTCA<br>GTCACCCTGTTCCCACCCTCC<br>ACGGAGGAGCTCAGCGCCAA<br>CAAGGCCACCCTGGTGTGTCT<br>CATCAGCGACTTCTACCCGGG<br>TAGCATGACCGTGGCCAGGA<br>AGGCAGACGGCAGCACCATC<br>ACCCGGAACGTGGAGACCAC<br>CCGGGCCTCCAAACAGAGCA<br>ACAGCAAGTACGCGGCCAGC<br>AGCTACCTGAGCCTGACGGG<br>CAGCGAGTGGAAATCGAAAG<br>GCAGTTACAGCTGCGAGGTCA<br>CGCACGAGGGGAGCACCGTG<br>ACAAAGACAGTGAAGCCCTCA<br>GAGTGTTCTTAG<br>(SEQ ID NO: 117) | QPKSAPSVTLFPPSTEELS<br>ANKATLVCLISDFYPGSMT<br>VARKADGSTITRNVETTRA<br>SKQSNSKYAASSYLSLTGS<br>EWKSKGSYSCEVTHEGST<br>VTKTVKPSECS*<br>(SEQ ID NO: 116) | NW_005<br>690786 | Not registered | None |

The amino acid sequences as shown in SEQ ID NOS: 8 to 13, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120 and 122 may have deletion(s), substitution(s) or addition(s) of one or several (e.g., up to five, about 10 at the most) amino acids. Even when such mutations have been introduced, the resulting amino acid sequences are capable of having the function as the constant region of Ig heavy chain or light chain.

The anti-PD-L1 antibody of the present invention may have a four-chain structure comprising two light chains and two heavy chains.

The anti-PD-L1 antibody of the present invention may be prepared as described below. Briefly, an artificial gene is synthesized which comprises the light chain sequence (variable region sequence and constant region sequence) and the heavy chain sequence (variable region sequence and constant region sequence) of the anti-PD-L1 antibody of the present invention. The resultant gene is inserted into a vector (e.g., plasmid), which is then introduced into a host cell (e.g., mammal cell such as CHO cell). The host cell is cultured, and the antibody of interest is collected from the resultant culture. In the synthesis of the artificial gene, codons of the nucleotide sequence may be optimized.

The present invention provides a DNA encoding an anti-PD-L1 antibody comprising: (a) a light chain comprising CDR1 having the amino acid sequence of KSISKY (SEQ ID NO: 1), CDR2 having the amino acid sequence of SGS and CDR3 having the amino acid sequence of QQH- NEYPLT (SEQ ID NO: 2) and (b) a heavy chain comprising CDR1 having the amino acid sequence of GYTFTDYI (SEQ ID NO: 3). CDR2 having the amino acid sequence of INPDSGGN (SEQ ID NO: 4) and CDR3 having the amino acid sequence of ARGITMMVVISHWKFDF (SEQ ID NO: 5). The present invention also provides a DNA encoding a light chain of an anti-PD-L1 antibody comprising CDR1 having the amino acid sequence of KSISKY (SEQ ID NO: 1), CDR2 having the amino acid sequence of SGS and CDR3 having the amino acid sequence of QQHNEYPLT (SEQ ID NO: 2) (the DNA of (a')). Further, the present invention provides a DNA encoding a heavy chain of an anti-PD-L1 antibody comprising CDR1 having the amino acid sequence of GYTFTDYI (SEQ ID NO: 3), CDR2 having the amino acid sequence of INPDSGGN (SEQ ID NO: 4) and CDR3 having the amino acid sequence of ARGITMMVVISHWKFDF (SEQ ID NO: 5) (the DNA of (b)).

For (a) a light chain comprising CDR1 having the amino acid sequence of KSISKY (SEQ ID NO: 1), CDR2 having the amino acid sequence of SGS and CDR3 having the amino acid sequence of QQHNEYPLT (SEQ ID NO: 2) and (b) a heavy chain comprising CDR1 having the amino acid sequence of GYTFTDYI (SEQ ID NO: 3), CDR2 having the amino acid sequence of INPDSGGN (SEQ ID NO: 4) and CDR3 having the amino acid sequence of ARGITMMV-VISHWKFDF (SEQ ID NO: 5), reference should be had to the foregoing description. A DNA comprising the DNA of (a') and the DNA of ('b) may be synthesized on commercial synthesizer. Restriction enzyme recognition sites, KOZAK sequences, poly-A addition signal sequences, promoter sequences, intron sequences or the like may be added to this DNA.

The present invention also provides a vector comprising the above-mentioned DNA encoding an anti-PD-L1 antibody.

As the vector, *Escherichia coli*-derived plasmids (e.g., pBR322, pBR325, pUC12 or pUC13); *Bacillus subtilis*-derived plasmids (e.g., pUB110, pTP5 or pC194), yeast-derived plasmids (e.g., pSH19 or pSH15); bacteriophages such as λ phage; animal viruses such as retrovirus or vaccinia virus; or insect pathogen viruses such as baculovirus may be used. In the Examples described later, pDC6 (Japanese Patent No. 5704753, U.S. Pat. No. 9,096,878, EU Patent 2385115, Hong Kong (China) patent HK1163739 and Australia Patent 2009331326) is used.

The vector may also comprise promoters, enhancers, splicing signals, poly-A addition signals, intron sequences, selection markers, SV40 replication origins, and so forth.

The present invention also provides a host cell transformed by the above vector. It is possible to prepare the anti-PD-L1 antibody of the invention by culturing the host cell and collecting the antibody of interest from the resultant culture. Therefore, the present invention also provides a method of preparing an antibody, comprising culturing the above-described host cell and collecting the anti-PD-L1 antibody of the invention from the culture. In the method of the present invention for preparing an antibody, a vector incorporating a DNA comprising a DNA encoding the light chain and a DNA encoding the heavy chain may be transfected into a host cell. Alternatively, a vector incorporating a DNA encoding the light chain and a vector incorporating a DNA encoding the heavy chain may be co-transfected into a host cell.

Examples of the host cell include, but are not limited to, bacterial cells (such as *Escherichia bacteria, Bacillus bacteria* or *Bacillus subtilis*), fungal cells (such as yeast or *Aspergillus*), insect cells (such as S2 cells or Sf cells), animal cells (such as CHO cells, COS cells, HeLa cells, C127 cells, 3T3 cells, BHK cells or HEK 293 cells) and plant cells. Among these, CHO-DG44 cell (CHO-DG44 (dfhr$^{-/-}$)) which is a dihydrofolate reductase deficient cell is preferable.

Introduction of a recombinant vector into a host cell may be performed by the methods disclosed in Molecular Cloning 2nd Edition, J. Sambrook et al., Cold Spring Harbor Lab. Press, 1989 (e.g., the calcium phosphate method, the DEAE-dextran method, transfection, microinjection, lipofection, electroporation, transduction, scrape loading, the shotgun method, etc.) or by infection.

The resultant transformant may be cultured in a medium, followed by collection of the anti-PD-L1 antibody of the present invention from the culture. When the antibody is secreted into the medium, the medium may be recovered, followed by isolation and purification of the antibody from the medium. When the antibody is produced within the transformed cells, the cells may be lysed, followed by isolation and purification of the antibody from the cell lysate.

Examples of the medium include, but are not limited to, OptiCHO medium, Dynamis medium, CD CHO medium, ActiCHO medium, FortiCHO medium, Ex-Cell CD CHO medium, BalanCD CHO medium, ProCHO 5 medium and Cellvento CHO-100 medium.

The pH of the medium varies depending on the cell to be cultured. Generally, a pH range from 6.8 to 7.6 is used; mostly, a pH range from 7.0 to 7.4 is appropriate.

When the cell to be cultured is CHO cells, culture may be performed by methods known to those skilled in the art. For example, it is usually possible to perform culturing in a gas-phase atmosphere having a $CO_2$ concentration of 0-40%, preferably 2-10%, at 30-39° C., preferably around 37° C.

The appropriate period of culture is usually from one day to three months, preferably from one day to three weeks.

Isolation and purification of the antibody may be performed by known methods. Known isolation/purification methods which may be used in the present invention include, but are not limited to, methods using difference in solubility (such as salting-out or solvent precipitation); methods using difference in molecular weight (such as dialysis, ultrafiltration, gel filtration or SDS-polyacrylamide gel electrophoresis); methods using difference in electric charge (such as ion exchange chromatography); methods using specific affinity (such as affinity chromatography), methods using difference in hydrophobicity (such as reversed phase high performance liquid chromatography); and methods using difference in isoelectric point (such as isoelectric focusing).

It is also possible to prepare the anti-PD-L1 antibody of the present invention by culturing a hybridoma which may be prepared by the method disclosed in the literature (Ikebuchi R, Konnai S, Okagavva T, Yokoyama K, Nakajima C, Suzuki Y, Murata S, Ohashi K, Immunology. 2014 August: 142(4):551-61). A hybridoma producing anti-PD-L1 antibody 6C11-3A11 is stored at the laboratory of the present inventor's (Laboratory of Infectious Diseases, Department of Disease Control, Faculty of Veterinary Medicine, Hokkaido University).

The PD-L1 antibody of the present invention may be used for detecting PD-L1. Therefore, the present invention provides a composition for detecting PD-L1, comprising the PD-L1 antibody as an active ingredient.

Detection of PD-L1 may be performed by such methods including, but are not limited to, immunohistochemical staining, immunocytochemical staining, flow cytometry, enzyme linked immunosorbent assay (ELISA) and Western blotting.

Analytes for detection may be exemplified by samples such as tissues or body fluids taken from organisms (e.g., blood (whole blood, plasma, serum, or specific cell such as erythrocyte, leukocyte or lymphocyte), urine, saliva, etc.); cell culture; and cultured cells (established cell lines, primary cultured cells, subcultured cells, etc.). The source of such analytes is not particularly limited. Examples include rat, canine, ovine, goat, porcine, feline, human, equine, bovine, water buffalo, yak, rabbit, mouse, hamster, and guinea pig.

The PD-L1 antibody of the present invention may be labeled with radioisotopes, enzymes, luminescent substances, fluorescent substances, biotin, or the like. If reaction with a primary antibody (the anti-PD-L1 antibody of the present invention) which specifically binds to a target molecule (PD-L1) is followed by reaction with a secondary antibody which binds to the primary antibody so as to detect the target molecule, it is suitable to label the secondary antibody.

Since PD-L1 is strongly expressed in cancer cells and virus-infected cells, the composition of the present invention may be used for diagnosis of cancers and/or infections. Usually, the amount (concentration) of PD-L1 in an analyte is determined based on the amount (concentration) of the complex of PD-L1 and anti-PD-L1 antibody. When the amount (concentration) of PD-L1 in the analyte is high compared to negative control (e.g., healthy surrounding tissue (connecting tissue, blood vessels, etc.)), the analyte may be diagnosed as suffering cancer and/or infection. Alternatively, if PD-L1 is detected in the analyte, the analyte may be diagnosed as suffering cancer and/or infection.

Examples of cancers and/or infections include, but are not limited to, neoplastic diseases (e.g., malignant melanoma, lung cancer, gastric cancer, renal cancer, breast cancer, bladder cancer, esophageal cancer, ovarian cancer and the like), leukemia, Johne's disease, anaplasmosis, bacterial mastitis, mycotic mastitis, mycoplasma infections (such as mycoplasma mastitis, mycoplasma pneumonia or the like), tuberculosis, *Theileria orientalis* infection, cryptosporidiosis, coccidiosis, trypanosomiasis and leishmaniasis.

The composition of the present invention can be used to select subject animals suitable for therapy using an anti-PD-L1 antibody. For example, animals satisfying the following two points may be considered as candidate animals.
1. A case diagnosed as suffering cancer (such as melanoma) or infection in pathological examination
2. A case found positive for anti-PD-L1 antibody Negative control may be healthy surrounding tissue (connecting tissue, blood vessels, etc.), and positive control may be a case of cancer (such as melanoma) or infection. Basically, animals with a tumor which is positive in immunohistochemical staining of almost all regions may be subjected to clinical trial.

Subject animals are not particularly limited and may include rat, canine, ovine, goat, porcine, feline, human, equine, bovine, water buffalo, yak, rabbit, mouse, hamster, and guinea pig.

The composition of the present invention may further comprise reagents for detecting labels, diluents, lavage fluids, written instructions describing criteria for diagnosis/selection, and so on.

EXAMPLES

Hereinbelow, the present invention will be described in more detail with reference to the following Examples. However, the present invention is not limited to these Examples.

Example 1

1. Introduction

Programmed cell death 1 (PD-1), an immunoinhibitory receptor, and its ligand programmed cell death ligand 1 (PD-L1) are molecules identified by Prof. Tasuku Honjo et al., Kyoto University, as factors which inhibit excessive immune response and are deeply involved in immunotolerance. Recently, it has been elucidated that these molecules are also involved in immunosuppression in infections and tumors in various animals. In the subject Example, an anti-bovine PD-L1 monoclonal antibody was prepared by immunizing rats, and then a clone (6C11-3A11) capable of detecting canine PD-L1 was selected. Further, the present inventors performed immunohistochemical staining to examine whether or not this anti-bovine PD-L1 antibody 6C11-3A11 would be useful for detecting PD-L1 in canine malignant tumors (such as melanoma) and porcine/ovine infections.

2. Materials and Methods 2.1 Rat Anti-Bovine PD-L1 Monoclonal Antibody Producing Cells The nucleotide sequence of bovine PD-L1 was identified (Ikebuchi R, Konnai S, Shirai T, Sunden Y, Murata S, Onuma M, Ohashi K, Vet Res. 2011 September 26:42:103). Based on the sequence information, a recombinant bovine PD-L1 was prepared. Rat was immunized in the footpad with this recombinant protein, and hybridomas were established by the iliac lymph node method. As a result, a plurality of hybridomas producing rat anti-bovine PD-L1 monoclonal antibodies were obtained (Ikebuchi R, Konnai S, Okagawa T, Yokoyama K, Nakajima C, Suzuki Y, Murata S, Ohashi K, Immunology 2014 August; 142(4):551-561). Rat anti-bovine PD-L1 antibody 6C11-3A11 is one of the monoclonal antibodies established from the above-described immunized rat.

2.2 Identification of Full-Length Canine PD-L1 Gene

To determine the full length of canine PD-L1 cDNA, PCR primers were first designed based on the putative nucleotide sequence of canine PD-L1 already registered at The National Center for Biotechnology Information (NCBI) (GenBank accession number; XM_541302). Briefly, primers to amplify the inner sequence of the open reading frame (ORF) of this gene were designed (cPD-1 inner F and R), and PCR was performed. For the amplified products, nucleotide sequences were determined with a capillary sequencer according to conventional methods. Further, to determine the nucleotide sequence of full-length PD-L1 cDNA, primers (cPD-L1 5' GSP and 3' GSP) were designed based on the canine PD-L1 cDNA sequences determined above. 5'-RACE and 3'-RACE were then performed using, respectively, the 5'-RACE system for rapid amplification of cDNA ends and 3'-RACE system for rapid amplification of cDNA ends (Invitrogen). The resultant gene fragments of interest were sequenced as described above (Maekawa N, Konnai S, Ikebuchi R, Okagawa T, Adachi M, Takagi S, Kagavva Y, Nakajima C, Suzuki Y, Murata S, Ohashi K. PLoS One. 2014 June 10;9(6):e98415).

```
Primer (cPD-L1 inner F):
ATGAGAATGTTTAGTGTCTT           (SEQ ID NO: 22)

Primer (cPD-L1 inner R):
TTATGTCTCTTCAAATTGTATATC       (SEQ ID NO: 23)

Primer (cPD-L1 5'GSP):
TTTTAGACAGAAAGTGA              (SEQ ID NO: 24)

Primer (cPD-L1 3'GSP):
GACCAGCTCTTCTTGGGGAA           (SEQ ID NO: 25)
```

2.3 Preparation of Canine PD-L1 Expressing COS-7 Cells

For preparing a canine PD-L1-EGFP expression plasmid, PCR was performed using a synthesized beagle PBMC-derived cDNA as a template and primers designed by adding BglII and EcoRI recognition sites on the 5' side (cPD-L1-EGFP F and R). The resultant PCR products were digested with BglII (New England Biolabs) and EcoRI (Takara), and then purified with FastGene Gel/PCR Extraction Kit (NIPPON Genetics), followed by cloning into pEGFP-N2 vector (Clontech) similarly treated with restriction enzymes. The resultant expression plasmid of interest was extracted with QIAGEN Plasmid Midi kit (Qiagen) and stored at −30° C. until use in experiments. Hereinafter, the thus prepared expression plasmid is designated as pEGFP-N2-cPD-L1.

```
Primer (cPD-L1-EGFP F):
GAAGATCTATGAGAATGTTTAGTGTC     (SEQ ID NO: 26)

Primer (cPD-L1-EGFP R):
GGAATTCTGTCTCTTCAAATTGTATATC   (SEQ ID NO: 27)
```

COS-7 cells were subcultured at a density of $5 \times 10^4$ cells/cm$^2$ in 6-well plates, and then cultured overnight in RPMI 1640 medium containing 10% inactivated fetal bovine serum and 0.01% L-glutamine at 37° C. in the presence of 5% CO$_2$. The pEGFP-N2-cPD-L1 or pEGFP-N2 (negative control) was introduced into COS-7 cells at 0.4 μg/cm$^2$ using Lipofectamine 2000 (Invitrogen). The cells were cultured for 48 hours (canine cPD-L1-EGFP expressing cell and EGFP expressing cell). In order to confirm the expression of PD-L1 in the thus prepared expressing cells, intracellular localization of enhanced green fluorescent protein (EGFP) was visualized with an inverted confocal laser microscope LSM700 (ZEISS) (Maekawa N, Konnai S, Ikebuchi R, Okagawa T, Adachi M, Takagi S, Kagawa Y, Nakajima C, Suzuki Y, Murata S, Ohashi K. PLoS One. 2014 June 10;9(6):e98415).

2.4 Cross-Reactivity of Rat Anti-Bovine PD-L1 Antibody 6C11-3A11 with Canine PD-L1

Figure 1:
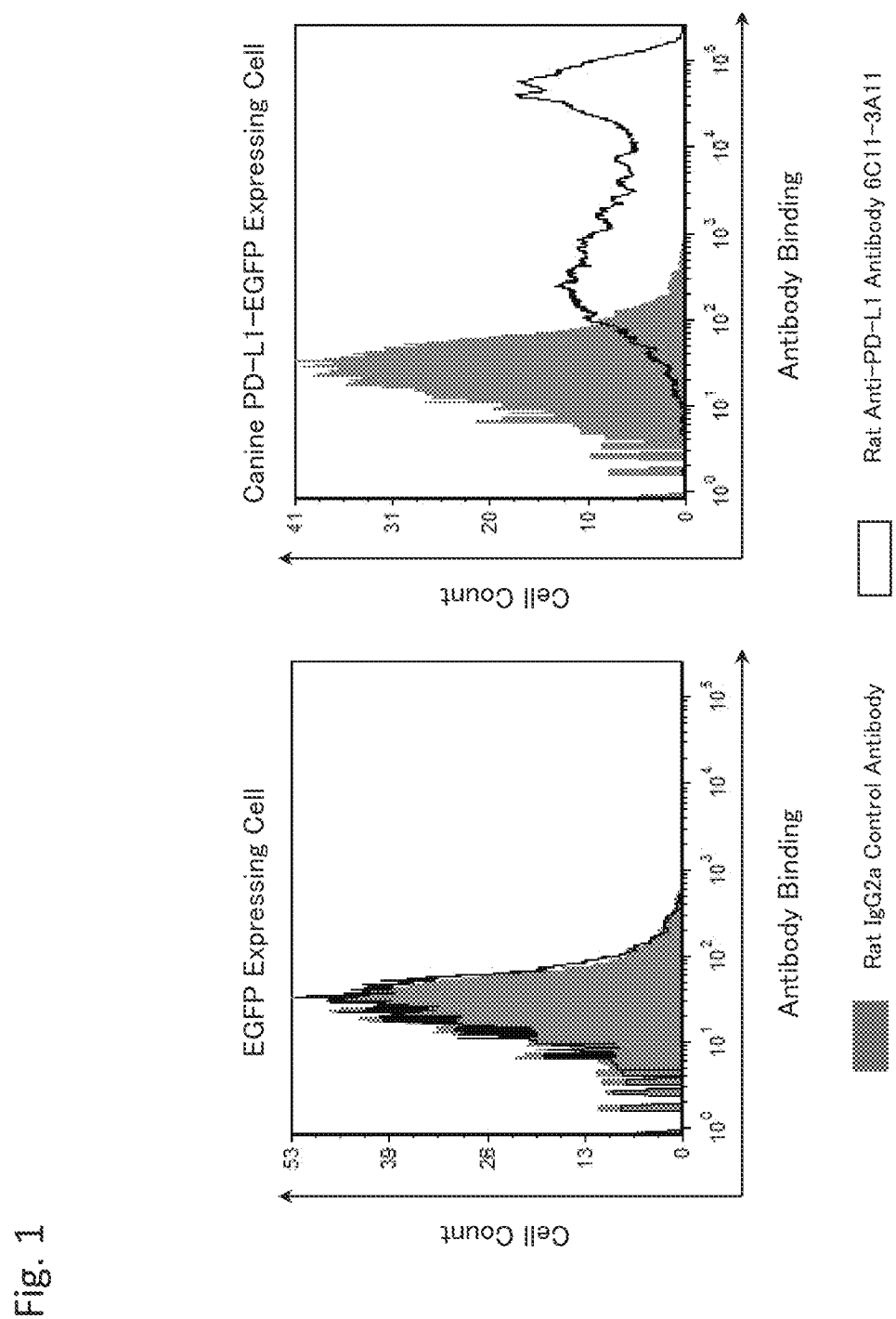
FIG. 1 Binding specificity of rat anti-bovine PD-L1 antibody 6C11-3A11. Rat anti-bovine PD-L1 antibody 6C11-3A11 did not bind to EGFP expressing cells, but specifically bound to canine PD-L1-EGFP expressing cells.
Figure 4:
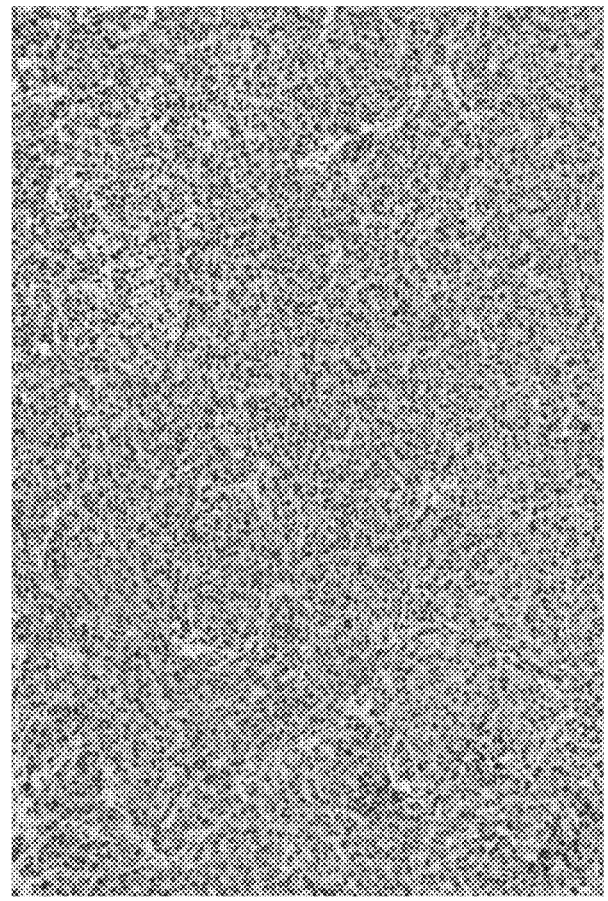
FIG. 4 Immunohistochemical staining image of canine melanoma.
Figure 5:
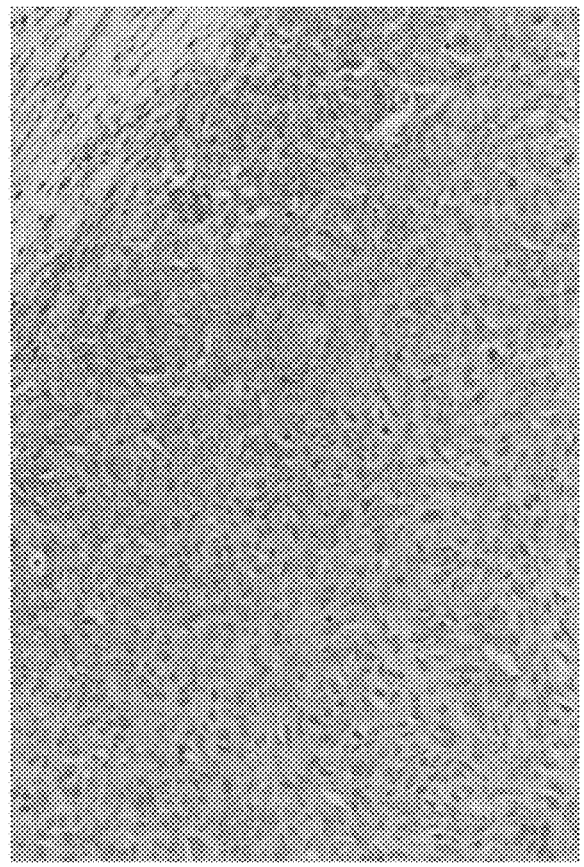

In order to confirm that rat anti-bovine PD-L1 antibody 6C11-3A11 specifically binds to canine PD-L1, flow cytometry was performed using the canine cPD-L1-EGFP expressing cell or the EGFP expressing cell prepared in 2.3 above. To $2 \times 10^5$–$1 \times 10^6$ cells, 10 μg/ml of anti-bovine PD-L1 antibody 6C11-3A11 was added and reacted for 30 min at room temperature. After washing, the antibody binding to cell surfaces was detected with Altophycocyanine-labeled goat anti-rat Ig antibody (Beckman Coulter). For the analysis, FACS Verse (Becton, Dickinson and Company) was used. As a negative control antibody, rat IgG2a (κ) isotype control (BD Bioscience) was used. For every washing operation and dilution of antibodies, 10% inactivated goat serum-supplemented PBS was used. The results are shown in FIG. 1.

2.5 CDR Analysis of Rat Anti-Bovine PD-L1 Antibody 6C11-3A11

The heavy chain and the light chain genes of rat anti-bovine PD-L1 antibody 6C11-3A11 were identified from a hybridoma producing the antibody by RACE method. The complementarity-determining regions (CDRs) of rat anti-bovine PD-L1 antibody 6C11-3A11 were determined using NCBI IGBLAST (www.ncbi.nlm.nih.gov/igblast/). The results are shown in FIG. 2.

2.6 Immunohistochemical Staining of Canine Tumor Tissues and Ovine/Porcine Infected Tissues In order to confirm that rat anti-bovine PD-L1 antibody 6C11-3A11 is applicable to PD-L1 immunohistochemical staining of canine tumors, formalin-fixed and paraffin-embedded canine tumor samples were immunohistochemically stained. According to conventional methods, the resultant samples were deparaffinized and then subjected to microwave treatment (5 min, twice) in citrate buffer. Subsequently, the samples were reacted with PD-L1 antibody 6C11-3A11 (400-fold dilution) for 30 min and then with Simple Stain Mouse MAX-PO (Rat) (Nichirei Bioscience) for 30 min. For coloring, diaminobenzidine (DAB) was reacted for 10 min.

The results are shown in FIGS. 3,4, 5-1, 5-2, 6 and 7.

Anti-MelanA antibody, the only commercially available antibody specific to melanoma stained tumor cells very weakly (FIG. 3, left). On the other hand, the PD-L1 antibody (6C11-3A11) established by the present inventors stained tumor cells very strongly (FIG. 3, Right). The PD-L1 antibody (6C11-3A11) was capable of staining almost all cases of melanoma.

In canine melanoma tumor cells were found diffusely positive for the PD-L1 antibody (6C11-3A11). (Positive number/tested number=12/12; positive rate 100%)

In canine lymphoma, tumor cells were found diffusely positive for the PD-L1 antibody (6C11-3A11). In canine osteosarcoma, some tumor cells were stained intracellularly. In canine renal cell carcinoma, tumor cells were found diffusely positive in various tissue types.

In a case of ovine listeriosis, a PD-L1 staining image of a brain lesion of ovine listeriosis showing neurologic symptoms is shown in FIG. 6, left panel. In an enlarged photograph of this image, expression of PD-L1 was observed in macrophages infiltrating into brain lesions (FIG. 6, Right).

In a case of porcine circovirus type 2 infection, PD-L1 was stained with lymphoid follicles, and virus was stained in these cells (FIG. 7, Left).

In a case of porcine mycoplasma pneumonia a great number of macrophages infiltrated pulmonary lesions, and PD-L1 was stained in these infiltrating cells (FIG. 7, Right).

As described so far, anti-bovine PD-L1 antibody 6C11-3A11 may be used for detecting PD-L1 in various canine tumors (such as malignant melanoma) and ovine/porcine infections by immunohistochemical staining. This suggests the possibility of using anti-bovine PD-L1 antibody 6C11-3A11 for diagnosis in a multiple-animal and a multiple-disease manner.

Example 2

1. Introduction

Monoclonal antibodies may be produced by culturing hybridomas and purifying antibodies from the resultant culture supernatants. Alternatively, when the nucleotide sequence of an antibody of interest has been identified, a cell expressing the antibody may be prepared by transfecting cultured cells with a vector for expressing the nucleotide sequence; the thus prepared antibody expressing cell may be used as a substitute for hybridoma. In the subject Example, a method will be illustrated below in which an antibody is produced by a protein expression system using an expression vector and a mammalian cell.

2. Materials and Methods 2.1 Preparation of Rat Anti-Bovine PD-L1 Antibody 6C11-3A11 Expression Vector Based on the nucleotide sequence of rat anti-bovine PD-L1 antibody 6C11-3A11 identified in 2.5 of Example 1 above, gene synthesis is performed so that NotI restriction enzyme recognition site, KOZAK sequence, antibody's light chain sequence, poly-A addition signal sequence (PABGH), promoter sequence (PCMV), SacI restriction enzyme recognition site, intron sequence (INRBG), KOZAK sequence, antibody's heavy chain sequence and XbaI restriction enzyme recognition site will be located in this order. In this case, codons of the antibody gene may have been optimized in advance depending on the type of the cell that is to express the gene. The synthesized gene strand is incorporated into an expression vector pDC6 (kindly provided by Prof. S. Suzuki, Research Center for Zoonosis Control. Hokkaido University) at the cloning site (NotI and XbaI restriction enzyme recognition sequences located downstream of PCMV and between INRBG and PABGH) using restriction enzyme recognition sequences so that the above-listed sequences will be located in the above-mentioned order to thereby construct a rat anti-bovine PD-L1 antibody expressing vector pDC6.

2.2 Expression of Rat Anti-Bovine PD-L1 Antibody 6C11-3A11

The rat anti-bovine PD-L1 antibody expressing vector pDC6 as prepared in 2.1 above is transfected into CHO-DG44 cells (CHO-DG44(dfhr$^{-/-}$)) which are dihydrofolate reductase deficient cells, and high expression clones are selected by dot blotting. For increased expression, gene amplification treatment may be performed by adding load on cells in a medium containing 60 nM, 250 nM or 1000 nM methotrexate (Mtx). The thus prepared cells stably expressing rat anti-bovine PD-L1 antibody 6C11-3A11 are transferred to Mtx-free Opti-CHO medium. By culturing those cells under shaking for 14 days (125 rpm, 37° C., 5% $CO_2$), a culture supernatant containing the antibody of interest can be obtained. The antibody in the culture supernatant may be purified by known methods such as affinity chromatography or ion exchange chromatography for use in various experiments.

Example 3

1. Introduction

For the purpose of establishing a novel diagnosis method for tumor diseases, a rat-human chimeric anti-PD-L1 antibody is obtained in the subject Example by culturing Chinese hamster ovary cells (CHO cells) that will express a chimeric antibody gene in which the variable region gene of rat anti-bovine PD-L1 antibody 6C11-3A11 is combined with the constant region gene of human immunoglobulin (IgG4).

Figure 10:
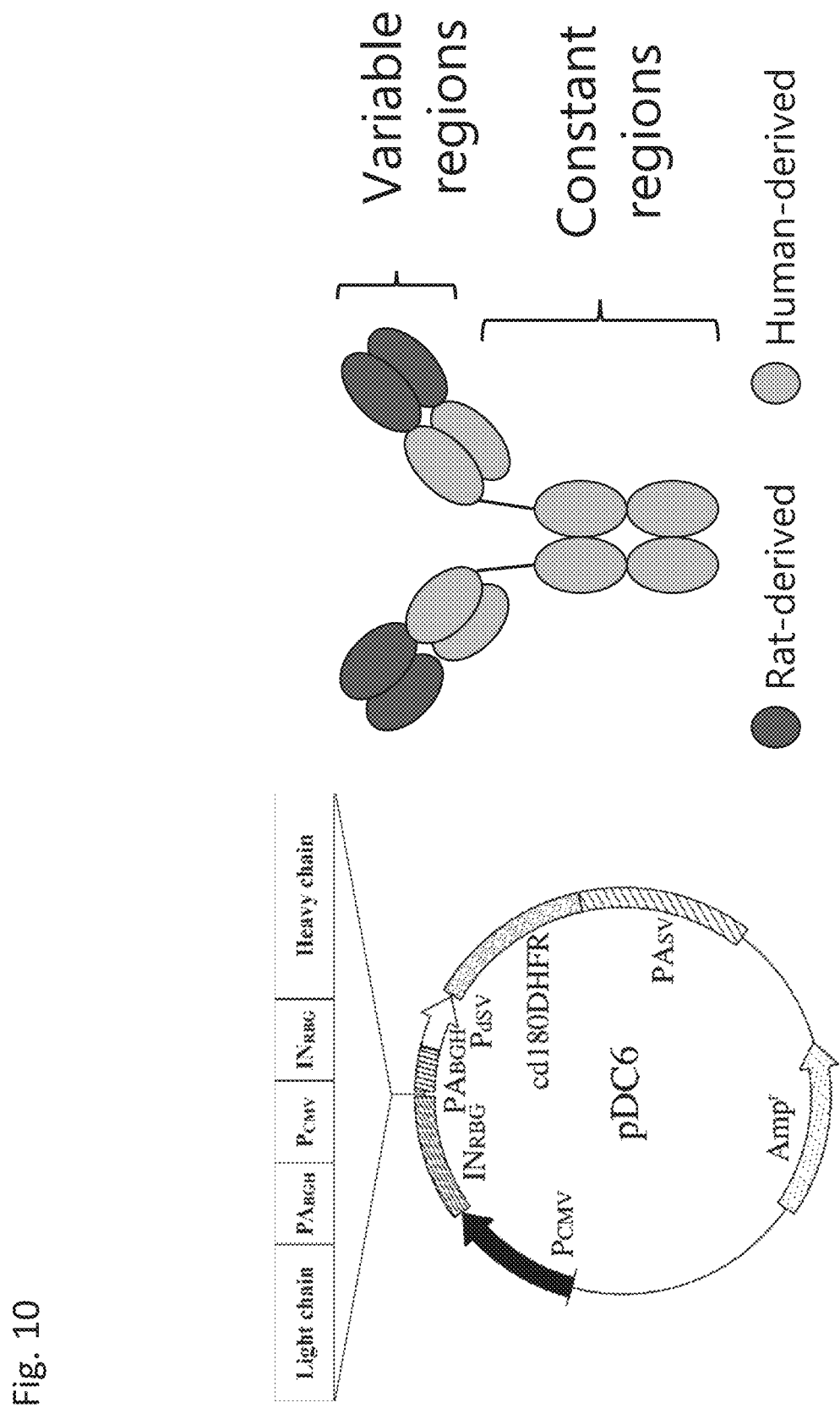
FIG. 10 Schematic drawing of pDC6 vector and a rat-human chimeric anti-PD-L1 antibody.

2. Materials and Methods 2.1 Preparation of Rat-Human Chimeric Anti-PD-L1 Expression Vector (FIG. 10)

Hereinbelow, a rat-human chimeric anti-PD-L1 antibody is established using rat anti-bovine PD-L1 monoclonal antibody 6C11-3A11 as its variable region.

Briefly, heavy chain and light chain variable region genes were identified from a hybridoma producing the rat anti-bovine PD-L1 antibody 6C11-3A11. Further, a nucleotide sequence was prepared by linking the heavy chain and light chain variable region genes of the above rat antibody to the constant region of heavy chain IgG4 and the constant region of light chain Kappa of a known human antibody, respectively. After codon optimization, gene synthesis is performed so that NotI restriction enzyme recognition site, KOZAK sequence, chimeric antibody's light chain sequence, poly-A addition signal sequence (PABGH), promoter sequence (PCMV), SacI restriction enzyme recognition site, intron sequence (INRBG), KOZAK sequence, chimeric antibody's heavy chain sequence and XbaI restriction enzyme recognition site will be located in this order. The synthesized gene strand is incorporated into the expression vector pDC6 (kindly provided by Prof. S. Suzuki, Research Center for Zoonosis Control, Hokkaido University) at the cloning site (NotI and XbaI restriction enzyme recognition sequences located downstream of PCMV and between INRBG and PABGH) using restriction enzyme recognition sequences so that the above-listed sequences will be located in the above-mentioned order (FIG. 10). Thus, a rat-human chimeric anti-PD-L1 antibody expressing vector is constructed. This expression vector is transfected into CHO-DG44 cells (CHO-DG44(dfhr$^{-/-}$)) which are dihydrofolate reductase deficient cells, and high expression clones are selected by dot blotting. For increased expression, gene amplification treatment may be performed by adding load on cells in a medium containing 60 nM, 250 nM or 1000 nM methotrexate (Mtx). The thus prepared cells stably expressing rat-human chimeric anti-PD-L1 antibody 6C11-3A11 are transferred to Mtx-free Opti-CHO medium. By culturing those cells under shaking for 14 days (125 rpm, 37° C., 5% $CO_2$), a culture supernatant containing the antibody of interest can be obtained. The antibody in the culture supernatant may be purified by known methods such as affinity chromatography or ion exchange chromatography for use in various experiments.

Example 4

1. Introduction

With respect to PD-L1 in canine tumors, a detection method by immunohistochemical staining with rat anti-bovine PD-L1 antibody 6G7-E1 was previously established, and the expression profiles in various tumors have been reported (Maekawa N, Konnai S, Okagawa T, Ikebuchi R, Izumi Y, Takagi S, Kagavva Y, Nakajima C, Suzuki Y, Kato Y, Murata S, Ohashi K. PLoS One. 2016 June 11(6): e0157176). In the subject Example, in order to examine whether rat anti-bovine PD-L1 antibody 6C11-3A11 is more useful than existing anti-PD-L1 antibody 6G7-E1 in expression analysis of PD-L1 in canine tumors, immunohistochemical staining of various canine tumors was performed to thereby directly compare the PD-L1 detection sensitivities of 6G7-E1 and 6C11-3A11.

2. Materials and Methods 2.1 Comparison by Flow Cytometry Using Canine PD-L1-EGFP Stably Expressing CHO-DG44 Cells (FIG. 11)

First, in order to prepare canine PD-L1 membrane expressing cells, 2.5 µg of canine PD-L1-EGFP expression plasmid (pEGFP-N2-cPD-L1) prepared in 2.3 of Example 1 or pEGFP-N2 (negative control) was introduced into 4×10$^6$ CHO-DG44 cells using Lipofectamine LTX (Invitrogen). Forty-eight hours later, the medium was exchanged with CD DG44 medium (Life Technologies) containing G418 (Enzo Life Science) 800 µg/ml, GlutaMAX supplement (Life Technologies) 20 ml/L, and 10% Pluronic F-68 (Life Technologies) 18 ml/L, followed by selection of stably expressing cells and cloning by limiting dilution. The thus prepared canine PD-L1 membrane expressing cell or EGFP expressing cell was reacted with rat anti-bovine PD-L1 antibody 6C11-3A11 or 6G7-E1 at room temperature for 30 min. After washing, antibodies binding to cell surfaces were detected with Allophycocyanine-labeled goat anti-rat Ig antibody (Beckman Coulter). For analysis, FACS Verse (Becton, Dickinson and Company) was used. As a negative control, rat IgG2a (κ) or IgM (κ) isotype control (BD Bioscience) was used. For every washing operation and dilution of antibodies, 10% inactivated goat serum-supplemented PBS was used.

Figure 11:
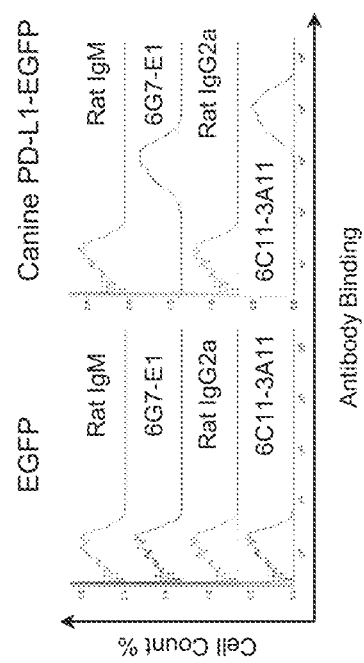
FIG. 11 Binding of rat anti-bovine PD-L1 antibodies 6C11-3A11 and 6G7-E1 to canine PD-L1-EGFP expressing cells. 6C11-3A11 specifically bound to canine PD-L1-EGFP expressing cells.

The results are shown in FIG. 11. Rat anti-bovine PD-L1 antibodies 6C11-3A11 and 6G7-E1 bound specifically to canine PD-L1 membrane expressing cells. The resultant fluorescence intensity was higher with 6C11-3A11 than with 6G7-E1, suggesting that 6C11-3A11 is an antibody with higher affinity.

2.2 Comparison of the Detection Sensitivities of Both Antibodies in PD-L1 Expression Analysis of Various Canine Tumors (Immunohistochemical Staining)

Using samples of canine skin squamous cell carcinoma (n=5), nasal adenocarcinoma (n=5), transitional cell carcinoma (n=5), anal sac gland carcinoma (n=5), soft tissue sarcoma (n=5) and osteosarcoma (n=5), immunohistochemical staining with rat anti-bovine PD-L1 antibody 6C11-3A11 was performed according to the method described in 2.6 of Example 1. With rat anti-bovine PD-L1 antibody 6G7-E1, immunohistochemical staining was performed in the same manner using sections derived from the same analytes. The final concentration of 6G7-E1 used on this occasion was 10 μg/ml, and biotin-labeled goal anti-rat IgM antibody (Jackson ImmunoResearch Laboratories) was used as a secondary antibody.

Figure 12:
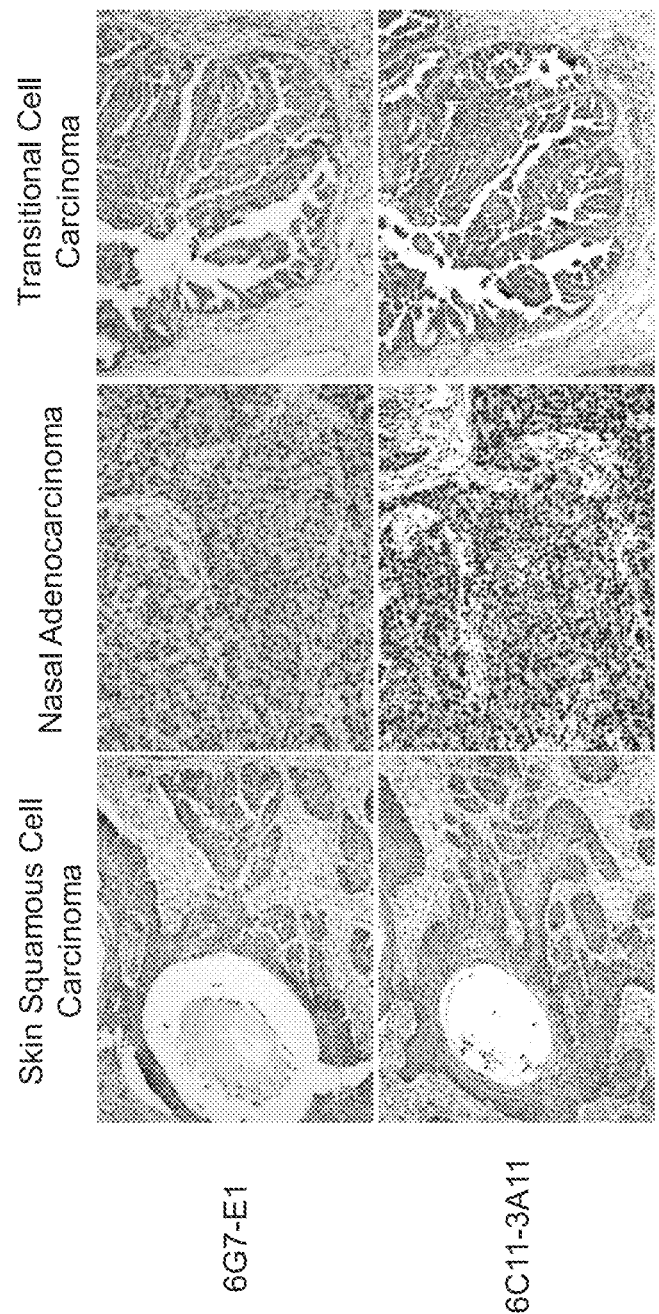
FIG. 12 Immunohistochemical staining images of skin squamous carcinoma, nasal adenocarcinoma and transitional cell carcinoma in dogs. No specific signals were detected with 6G7-E1. Tumor cells were stained 6C11-3A11.
Figure 13:
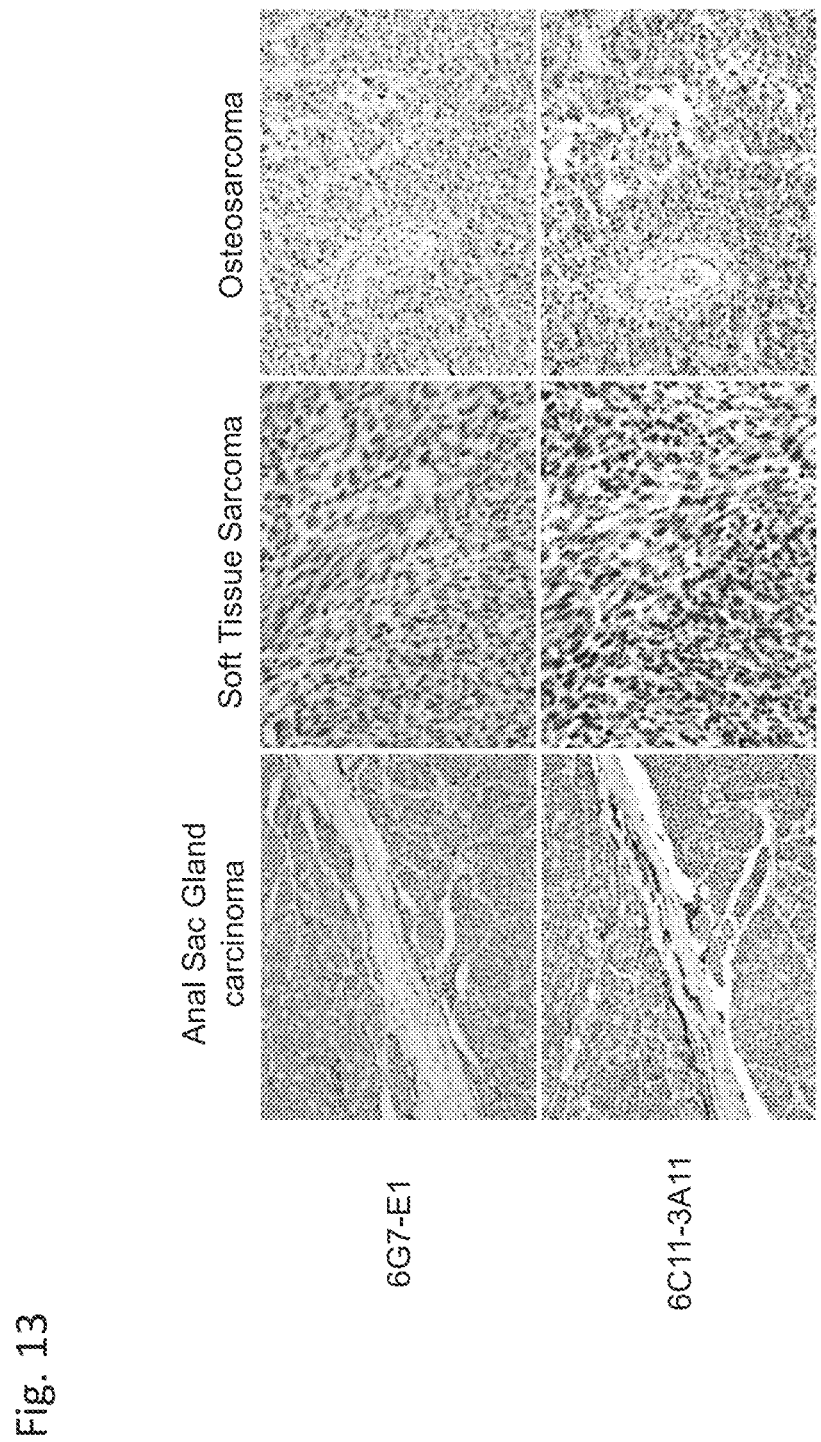
FIG. 13 Immunohistochemical staining images of anal sac gland carcinoma, soft tissue sarcoma and osteosarcoma in dogs. In anal sac gland carcinoma and soft tissue sarcoma, no specific signals were detected with 6G7-E1, but tumor cells were stained with 6C11-3A11. In osteosarcoma, both antibodies stained tumor cells, but stronger signals were obtained with 6C11-3A11.

The results are shown in FIGS. 12 and 13. While specific signals were not observed in squamous cell carcinoma, nasal adenocarcinoma, transitional cell carcinoma, anal sac gland carcinoma and soft tissue sarcoma upon staining with 6G7-E1, satisfactory positive reactions were obtained upon staining with 6C11-3A11. On the other hand, specific signals were also obtained with 6G7-E1 in osteosarcoma but staining with 6C11-3A11 provided higher signal intensities. The PD-L1 positive rate of these tumors obtained by 6C11-3A11 staining was 100% (5 out of 5 cases) in all of the above-listed tumor species excepting soft tissue sarcoma which turned out to be PD-L1 positive at a rate of 80% (4 out of 5 cases).

Subsequently, samples of oral malignant melanoma (n=17), mammary adenocarcinoma (n=10), histiocytic sarcoma (n=10), diffuse large B-cell lymphoma (n=10) and transmissible venereal tumor (n=4) were immunohistochemically stained with 6C11-3A11 to analyze PD-L1 expression therein.

Figure 14:
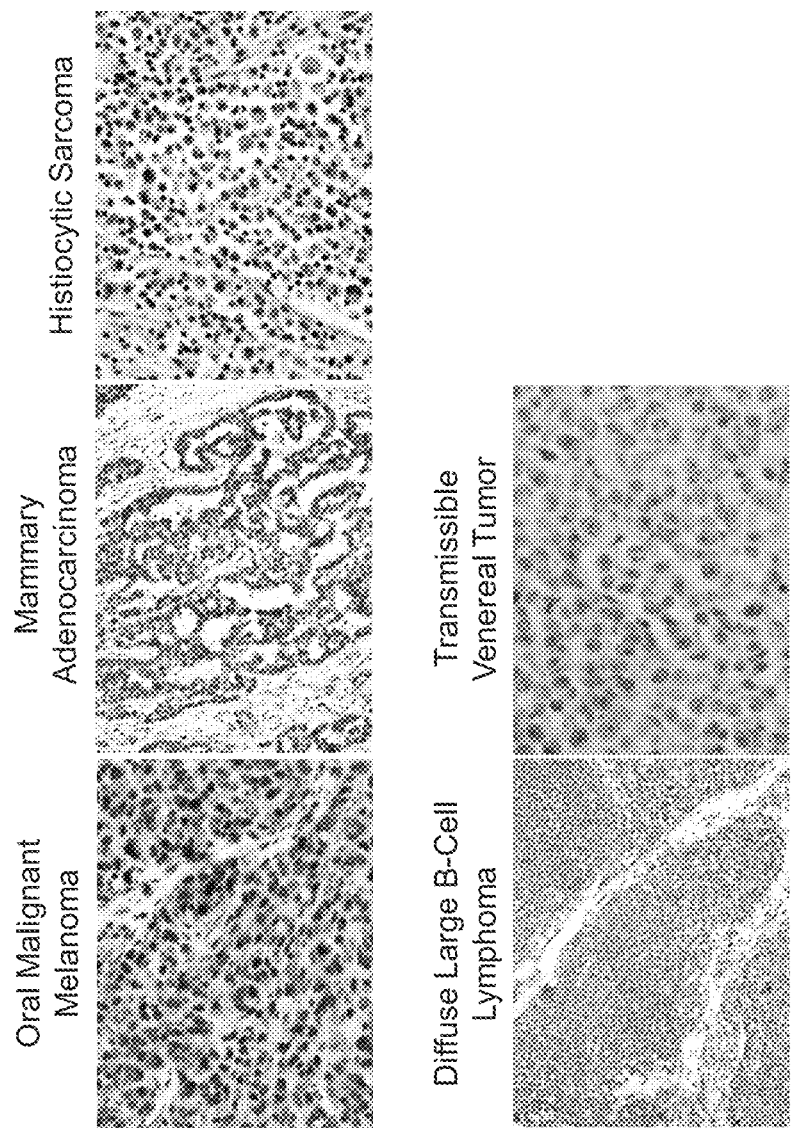
FIG. 14 Immunohistochemical staining images of oral malignant melanoma, mammary adenocarcinoma histiocytic sarcoma, diffuse large B-cell lymphoma and transmissible venereal tumor in dogs using 6C11-3A11. In the tumor species other than transmissible venereal tumor, PD-L1 on tumor cells was stained.

The results are shown in FIG. 14. The PD-L1 positive rate was 100% in oral malignant melanoma (17 out of 17 cases), 100% in mammary adenocarcinoma (10 out of 10 cases), 20% in histiocytic sarcoma (2 out of 10 cases), 20% in diffuse large B-cell lymphoma (2 out of 10 cases) and 0% in transmissible venereal tumor (0 out of 4 cases).

The above-described results revealed that 6C11-3A11 is superior to the existing anti-PD-L1 antibody 6G7-E1 in the detection of canine PD-L1.

Example 5

1. Introduction

Johne's disease is a bovine chronic infection caused by *Mycobacterium avium* subsp. *paratuberculosis*. In cattle affected with Johne's disease, PD-L1 expression has been confirmed in *M. avium* subsp. *paratuberculosis*-infected cells in ileal lesions which are a localized site of infection with this bacterium (Okagawa T, Konnai S, Nishimori A, Ikebuchi R, Mizorogi S, Nagata R, Kawaji S, Tanaka S, Kagawa Y, Murata S, Mori Y and Ohashi K. Infect Immun, 84:77-89, 2016). In the subject Example, immunohistochemical staining of ileal lesions of cattle with Johne's disease was performed in order to examine whether rat anti-bovine PD-L1 antibody 6C11-3A11 could be used for detecting bovine PD-L1 or not.

2. Materials and Methods 2.1. Construction of Bovine PD-L1 Expressing Cells

The nucleotide sequence of the full-length cDNA of bovine PD-L1 gene (GenBank accession number AB510902; Ikebuchi R, Konnai S, Shirai T, Sunden Y, Murata S, Onuma M, Ohashi K, Vet. Res, 2011 September 26;42:103) was determined. Based on the resultant nucleotide sequence, bovine PD-L1 membrane expressing cells were prepared. First, for preparing a bovine PD-L1 expressing plasmid, PCR was performed using a synthesized bovine PBMC-derived cDNA as a template and primers having NheI and XhoI recognition sites added on the 5' side (boPD-L1-EGFP F and R). The PCR products were digested with NheI (Takara) and XhoI (Takara), purified with Fast-Gene Gel/PCR Extraction Kit (NIPPON Genetics) and cloned into pEGFP-N2 vector (Clontech) that had been subjected to similar restriction enzyme treatments. The resultant expression plasmid of interest was extracted with QIAGEN Plasmid Midi kit (Qiagen) and stored at −30° C. until use in experiments. Hereinafter, the thus prepared expression plasmid is designated as pEGFP-N2-boPD-L1.

```
Primer (boPD-L1-EGFP F):
                                (SEQ ID NO: 124)
CTAGCTAGCACCATGAGGATATATAGTGTCTTAAC Primer (boPD-L1-EGFP R):
                                (SEQ ID NO: 125)
CAATCTCGAGTTACAGACAGAAGATGACTGC
```

Bovine PD-L1 membrane expressing cells were prepared by the procedures described below. First, 2.5 μg of pEGFP-N2-boPD-L1 or pEGFP-N2 (negative control) was introduced into 4×10$^6$ CHO-DG44 cells using Lipofectannne LTX (Invitrogen). Forty-eight hours later, the medium was exchanged with CD DG44 medium (Life Technologies) containing G418 (Enzo Life Science) 800 μg/ml, GlutaMAX supplement (Life Technologies) 20 ml/L, and 10% Pluronic F-68 (Life Technologies) 18 ml/L; thereafter, selection was performed simultaneously with cloning by limiting dilution (bovine PD-L1 expressing cell and EGFP expressing cell). In order to confirm the expression of bovine PD-L1 in the thus prepared bovine PD-L1 expressing cell, intracellular localization of EGFP was visualized with an inverted confocal laser microscope LSM700 (ZEISS).

2.2. Binding Specificity of Rat Anti-Bovine PD-L1 Antibody 6C11-3A11 to Bovine PD-L1

It was confirmed by flow cytometry that rat anti-bovine PD-L1 antibody 6C11-3A11 specifically binds to the bovine PD-L1 expressing cell (described above). First, rat anti-bovine PD-L1 antibody 6C11-3A11 or rat IgG2a (κ) isotype control (BD Biosciences) as a negative control was reacted with the bovine PD-L1 expressing cell or the EGFP expressing cell (negative control) at room temperature for 30 min. After washing, APC-labeled anti-rat Ig goat antibody (Southern Biotech) was reacted at room temperature for 30 min. After washing, antibodies bound to cell surfaces were detected by FACS Verse (BD Biosciences). For every washing operation and dilution of antibody, PBS supplemented with 1% bovine serum albumin (Sigma-Aldrich) was used.

Figure 15:
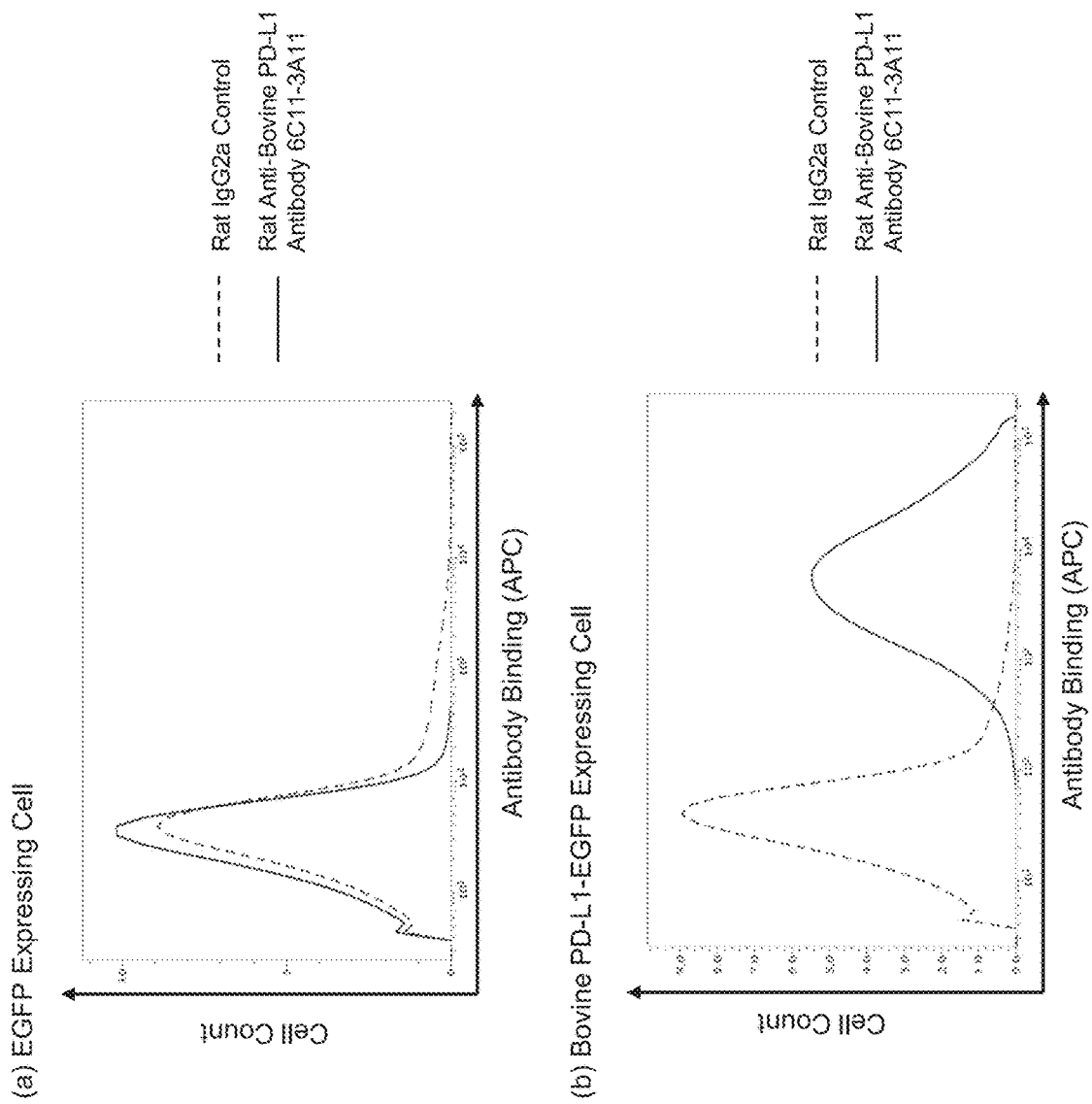
FIG. 15 Binding of rat anti-bovine PD-L1 antibody 6C11-3A11 to bovine PD-L1-EGFP expressing cells. 6C11-3A11 specifically bound to bovine PD-L1-EGFP expressing cells.

The results are shown in FIG. 15. It was revealed that rat anti-bovine PD-L1 antibody 6C11-3A11 binds specifically to the bovine PD-L1 expressing cell.

2.3. Immunohistochemical Staining Using Tissue Samples from Infected Cattle

In order to confirm that rat anti-bovine PD-L1 antibody 6C11-3A11 is applicable to PD-L1 immunohistochemical staining of bovine tissues, immunohistochemical staining was performed with formalin-fixed, paraffin-embedded bovine tissue samples. Briefly, ilium tissue blocks from cattle which naturally developed Johne's disease (#1, presenting clinical symptoms of Johne's disease such as diarrhea and severe emaciation), cattle experimentally infected with *M. avium* subsp. *paratuberculosis* (#65, clinical symptoms such as shedding of *M. avium* subsp. *paratuberculosis* and diarrhea were observed; Okagawa T, Konnai S, Nishimori A, Ikebuchi R, Mizorogi S, Nagata R, Kawaji S, Tanaka S, Kagavva Y, Murata S, Mori Y and Ohashi K. Infect Immun. 84:77-89, 2016) and uninfected control cattle (C #6) (the blocks kindly provided by Dr. Yasuyuki Mori, National Institute of Animal Health, National Agriculture and Food Research Organization) were used for staining. According to conventional methods, the stained samples were deparaffinized and then subjected to microwave treatment (5 min, twice) in citrate buffer. Subsequently, the samples were reacted with rat anti-bovine PD-L1 antibody 6C11-3A11 (400-fold dilution) for 30 min and then with Simple Stain Mouse MAX-PO (Rat) (Nichirei Bioscience) for 30 min. Finally, the samples were reacted with diaminobenzidine (DAB) for 10 min for coloring, followed by observation with an optical microscope.

The results are shown in FIG. 16. Rat anti-bovine PD-L1 antibody 6C11-3A11 detected expression of PD-L1 in *M. avium* subsp. *paratuberculosis*-infected cells (confirmed by Ziehl-Neelsen staining) in ileal lesions of cattle #1 that naturally developed Johne's disease and experimentally infected cattle #65 (FIG. 16*a, b*). On the other hand, PD-L1 was not expressed in the ileum of uninfected cattle (C #6), so reaction of rat anti-bovine PD-L1 antibody 6C11-3A11 (non-specific reaction) was not recognized (FIG. 16*a*).

As described above, it was shown that rat anti-bovine PD-L1 antibody 6C11-3A11 can be used for detecting PD-L1 in bovine tissues by immunohistochemical staining.

All publications, patents and patent applications cited herein are incorporated herein by reference in their entirety.

INDUSTRIAL APPLICABILITY

The anti-PD-L1 antibody of the present invention is applicable to diagnosis of cancers and/or infections. Further, the anti-PD-L1 antibody of the present invention is also applicable to selection of subject animals suitable for therapy with anti-PD-L1 antibodies.

```
SEQUENCE LISTING FREE TEXT

<SEQ ID NO: 1>
SEQ ID NO: 1 shows the amino acid sequence of CDR1 of the
light chain variable region (VL) of anti-PD-L1 antibody
6C11-3A11 (IgG2a).
KSISKY <SEQ ID NO: 2>
SEQ ID NO: 2 shows the amino acid sequence of CDR3 of the
VL of anti-PD-L1 antibody 6C11-3A11 (IgG2a).
QQHNEYPLT <SEQ ID NO: 3>
SEQ ID NO: 3 shows the amino acid sequence of CDR1 of the
heavy chain variable region (VH) of anti-PD-LI antibody
6C11-3A11 (IgG2a).
GYTFIDYI <SEQ ID NO: 4>
SEQ ID NO: 4 shows the amino acid sequence of CDR2 of the
VH of anti-PD-L1 antibody 6C11-3A11 (IgG2a).
INPDSGGN <SEQ ID NO: 5>
SEQ ID NO: 4 shows the amino acid sequence of CDR2 of the
VH of anti-PD-L1 antibody 6C11-3A11 (IgG2a).
INPDSGGN <SEQ ID NO: 6>
SEQ ID NO: 6 shows the amino acid sequence of the VL of
anti-PD-L1 antibody 6C11-3A11 (IgG2a).
MRVQIQFWGLLLLWTSGIQCDVQMTQSPSNLAASPGESVSINCKASKSISKYLAWYQ
QKPGKANKLLIYSGSTLQSGTPSRFSGSGSGTDFTLTIRNLEPEDFGLYYCQQHNEY
PLTFGSGTKLEIK <SEQ ID NO: 7>
SEQ ID NO: 7 shows the amino acid sequence of the VH of
anti-PD-L1 antibody 6C11-3A11(IgG2a).
MGWICIIFLVAIATGAHSQVKLLQSGAALVKPGDSVKMSCKASGYTFTDYIIHWVKQ
SHGKSLEWIGYINPDSGGNNYNEKFKSKATLTVDKSSSTAYMEFSRLTSEDSAIYYC
ARGITMMVVISHWKFDFWGPGTMVTVSS
```

SEQUENCE LISTING FREE TEXT

<SEQ ID NO: 8>
SEQ ID NO: 8 shows the amino acid sequence of the light chain (kappa chain) constant region of anti-PD-L1 antibody 6C11-3A11 (IgG2a).
RADAAPTVSIFPPSTEQLATGGASVVCLMNNFYPRDISVKWKIDGTERRDGVLDSVTDQDS
KDSTYSMSSTLSLTKADYESHNLYTCEVVHKTSSSPVVKSFNRNEC*

<SEQ ID NO: 9>
SEQ ID NO: 9 shows the amino acid sequence of the heavy chain constant region (CH) of anti-PD-L1 antibody 6C11-3A11 IgG2a).
AETTAPSVYPLAPGTALKSNSMVTLGCLVKGYFPEPVTVTWNSGALSSGVHTFPAVLQSGL
YTLTSSVTVPSSTWSSQAVTCNVAHPASSTKVDKKIVPRECNPCGCTGSEVSSVFIFPPKT
KDVLTITLTPKVTCVVVDISQNDPEVRFSWFIDDVEVHTAQTHAPEKQSNSTLRSVSELPI
VHRDWLNGKTFKCKVNSGAFPAPIEKSISKPEGTPRGPQVYTMAPPKEEMTQSQVSITCMV
KGFYPPDIYTEWKMNGQPQENYKNTPPTMDTDGSYFLYSKLNVKKETWQQGNTFTCSVLHE
GLHNHHTEKSLSHSPGK*

<SEQ ID NO: 10>
SEQ ID NO: 10 shows the amino acid sequence (GenBank: #V01241.1) of the light chain (kappa chain) constant region of a rat antibody (IgG2a).
ADAAPTVSIFPPSTEQLATGGASVVCLMNNFYPRDISVKWKIDGTERRDGVLDSVTDQDSK
DSTYSMSSTLSLTKADYESHNLYTCEVVHKTSSSPVVKSFNRNEC*

<SEQ ID NO: 11>
SEQ ID NO: 11 shows the amino acid sequence (GenBank: #X16129.1) of the light chain(kappa chain) constant region of a rat antibody (IgG2a).
RADAAPTVSIFPPSTEQLATGGASVVCLMNNFYPRDISVKWKIDGTERRDGVLDSVTDQDS
KDSTYSMSSTLSLSKADYESHNLYTCEVVHKTSSSPVVKSFNRNEC <SEQ ID NO: 12>
SEQ ID NO: 12 shows the amino acid sequence (GenBank: #DQ402417.1) of the light chain (kappa chain) constant region of a rat antibody (IgG2a).
AAPTVSIFPPSMEQLTSGGATVVCFVNNFYPRDISVKWKIDGSEQRDGVLDSVTDQDSKDS
TYSMSSTLSLTKVEYERHNLYTCEVVHKTSSSPVVKSFNRNEC*

<SEQ ID NO: 13>
SEQ ID NO: 13 shows the amino acid sequence (GenBank: #DQ402472.1) of the CH of a rat antibody (IgG2a).
APSVYPLAPGTALKSNSMVTLGCLVKGYFPEPVTVTWNSGALSSGVHTFPAVLQSGLYTLT
SSVTVPSSTWSSQAVTCNVAHPASSTKVDKKIVPRECNPCGCTGSEVSSVFIFPPKTKDVL
TITLTPKVTCVVVDISQNDPEVRFSWFIDDVEVHTAQTHAPEKQSNSTLRSVSELPIHRDW
LNGKTFKCKVNSGAFPAPIEKSISKPEGTPRGPQVYTMAPPKEEMTQSQVSITCMVKGFYP
PDIYTEWKMNGQPQENYKNTPPTMDTDGSYFLYSKLNVKKETWQQGNTFTCSVLHEGLHNH
HTEKSLSHSPGK*

<SEQ ID NO: 14>
SEQ ID NO: 14 shows the nucleotide sequence of the VL of anti-PD-L1 antibody 6C11-3A11(IgG2a).
ATGAGGGTCCAGATTCAGTTTTGGGGGCTTCTTCTGCTCTGGACATCAGGTATACAGTGTG
ATGTCCAGATGACCCAGTCTCCATCTAATCTTGCTGCCTCTCCTGGAGAAAGTGTTTCCAT
CAATTGCAAGGCAAGTAAGAGCATTAGCAAGTATTTAGCCTGGTATCAACAGAAACCTGGG
AAAGCAAATAAGCTTCTTATCTACTCTGGGTCAACTTTGCAATCTGGAACTCCATCGAGGT
TCAGTGGCAGTGGATCTGGTACAGATTTCACTCTCACCATCAGAAACCTGGAGCCTGAAGA
TTTTGGACTCTATTACTGTCAACAGCATAATGAATACCCGCTCACGTTCGGTTCTGGGACC
AAGCTGGAGATCAAA <SEQ ID NO: 15>
SEQ ID NO: 15 shows the nucleotide sequence of the VH of anti-PD-L1 antibody 6C11-3A11 (IgG2a).
ATGGGATGGATCTGTATCATCTTTCTTGTGGCAATAGCTACAGGTGCCCACTCCCAGGTCA
AGCTGCTGCAGTCTGGGGCTGCACTGGTGAAGCCTGGGGACTCTGTGAAGATGTCTTGCAA
AGCTTCTGGTTATACATTCACTGACTACATTATACACTGGGTGAAGCAGAGTCATGGAAAA
AGCCTTGAGTGGATTGGTTATATTAATCCTGACAGTGGTGGTAATAACTACAATGAAAAGT
TCAAGAGCAAGGCCACATTGACTGTAGACAAATCCAGCAGCACAGCCTATATGGAGTTTAG
CAGATTGACATCTGAGGATTCTGCAATCTACTACTGTGCAAGAGGGATTACCATGATGGTA
GTTATTAGCCACTGGAAGTTTGACTTCTGGGGCCCAGGAACCATGGTCACCGTGTCCTCA

SEQUENCE LISTING FREE TEXT

<SEQ ID NO: 16>
SEQ ID NO: 16 shows the nucleotide sequence of the light
chain (kappa chain) constant region of anti-PD-L1 antibody
6C11-3A11 (IgG2a).
CGGGCTGATGCTGCACCAACTGTATCTATCTTCCCACCATCCACGGAACAGTTAGCAACTG
GAGGTGCCTCAGTCGTGTGCCTCATGAACAACTTCTATCCCAGAGACATCAGTGTCAAGTG
GAAGATTGATGGCACTGAACGACGAGATGGTGTCCTGGACAGTGTTACTGATCAGGACAGC
AAAGACAGCACGTACAGCATGAGCAGCACCCTCTCGTTGACCAAGGCTGACTATGAAAGTC
ATAACCTCTATACCTGTGAGGTTGTTCATAAGACATCATCCTCACCCGTCGTCAAGAGCTT
CAACAGGAATGAGTGTTAG <SEQ ID NO: 17>
SEQ ID NO: 17 shows the nucleotide sequence of the CH of
anti-PD-L1 antibody 6C11-3A11 (IgG2a).
GCTGAAACAACAGCCCCATCTGTCTATCCACTGGCTCCTGGAACTGCTCTCAAAAGTAACT
CCATGGTGACCCTGGGATGCCTGGTCAAGGGCTATTTCCCTGAGCCAGTCACCGTGACCTG
GAACTCTGGAGCCCTGTCCAGCGGTGTGCACACCTTCCCAGCTGTCCTGCAGTCTGGACTC
TACACTCTCACCAGCTCAGTGACTGTACCCTCCAGCACCTGGTCCAGCCAGGCCGTCACCT
GCAACGTAGCCCACCCGGCCAGCAGCACCAAGGTGGACAAGAAAATTGTGCCAAGGGAATG
CAATCCTTGTGGATGTACAGGCTCAGAAGTATCATCTGTCTTCATCTTCCCCCCAAGACC
AAAGATGTGCTCACCATCACTCTGACTCCTAAGGTCACGTGTGTTGTGGTAGACATTAGCC
AGAATGATCCCGAGGTCCGGTTCAGCTGGTTTATAGATGACGTGGAAGTCCACACAGCTCA
GACTCATGCCCCGGAGAAGCAGTCCAACAGCACTTTACGCTCAGTCAGTGAACTCCCCATC
GTGCACCGGGACTGGCTCAATGGCAAGACGTTCAAATGCAAAGTCAACAGTGGAGCATTCC
CTGCCCCCATCGAGAAAAGCATCTCCAAACCCGAAGGCACACCACGAGGTCCACAGGTATA
CACCATGGCGCCTCCCAAGGAAGAGATGACCCAGAGTCAAGTCAGTATCACCTGCATGGTA
AAAGGCTTCTATCCCCCAGACATTTATACGGAGTGGAAGATGAACGGGCAGCCACAGGAAA
ACTACAAGAACACTCCACCTACGATGGACACAGATGGGAGTTACTTCCTCTACAGCAAGCT
CAATGTAAAGAAAGAAACATGGCAGCAGGGAAACACTTTCACGTGTTCTGTGCTGCATGAG
GGCCTGCACAACCACCATACTGAGAAGAGTCTCTCCCACTCTCCTGGTAAATGA <SEQ ID NO: 18>
SEQ ID NO: 18 shows the nucleotide sequence (GenBank:
V01241.1) of the light chain (kappa chain) constant region
of a rat antibody (IgG2a).
GGGCTGATGCTGCACCAACTGTATCTATCTTCCCACCATCCACGGAACAGTTAGCAACTGG
AGGTGCCTCAGTCGTGTGCCTCATGAACAACTTCTATCCCAGAGACATCAGTGTCAAGTGG
AAGATTGATGGCACTGAACGACGAGATGGTGTCCTGGACAGTGTTACTGATCAGGACAGCA
AAGACAGCACGTACAGCATGAGCAGCACCCTCTCGTTGACCAAGGCTGACTATGAAAGTCA
TAACCTCTATACCTGTGAGGTTGTTCATAAGACATCATCCTCACCCGTCGTCAAGAGCTTC
AACAGGAATGAGTGTTAG <SEQ ID NO: 19>
SEQ ID NO: 19 shows the nucleotide sequence (GenBank:
X16129.1) of the light chain (kappa chain) constant region
of a rat antibody (IgG2a).
CGGGCTGATGCTGCACCAACTGTATCTATCTTCCCACCATCCACGGAACAGTTAGCAACTG
GAGGTGCCTCAGTCGTGTCCTCATGAACAACTTCTATCCCAGAGACATCAGTGTCAAGTGG
AAGATTGATGGCACTGAACGACGAGATGGTGTCCTGGACAGTGTTACTGATCAGGACAGCA
AAGACAGCACGTACAGCATGAGCAGCACCCTCTCGTTGTCCAAGGCTGACTATGAAAGTCA
TAACCTCTATACCTGTGAGGTTGTTCATAAGACATCATCCTCACCCGTCGTCAAGAGCTTC
AACAGGAATGAGTGTTAG <SEQ ID NO: 20>
SEQ ID NO: 20 shows the nucleotide sequence (GenBank:
DQ402471.1) of the light chain (kappa chain) constant region
of a rat antibody (IgG2a).
GCCGCACCAACTGTATCCATCTTCCCACCATCCATGGAACAGTTAACATCTGGAGGTGCCA
CAGTCGTGTGCTTCGTGAACAACTTCTATCCCAGAGACATCAGTGTCAAGTGGAAGATTGA
TGGCAGTGAACAACGAGATGGTGTCCTGGACAGTGTTACTGATCAGGACAGCAAAGACAGC
ACGTACAGCATGAGCAGCACCCTCTCGTTGACCAAGGTTGAATATGAAAGGCATAACCTCT
ATACCTGTGAGGTTGTTCATAAGACATCATCCTCACCCGTCGTCAAGAGCTTCAACAGGAA
TGAGTGTTAG <SEQ ID NO: 21>
SEQ ID NO: 21 shows the nucleotide sequence (GenBank:
DQ402472.1) of the CH of a rat antibody (IgG2a).
CAGCCCCCTCTGTCTATCCACTGGCTCCTGGAACTGCTCTCAAAAGTAACTCCATGGTGAC
CCTGGGATGCCTGGTCAAGGGCTATTTCCCTGAGCCAGTCACCGTGACCTGGAACTCTGGA
GCCCTGTCCAGCGGTGTGCACACCTTCCCAGCTGTCCTGCAGTCTGGACTCTACACTCTCA
CCAGCTCAGTGACTGTACCCTCCAGCACCTGGTCCAGCCAGGCCGTCACCTGCAACGTAGC
CCACCCGGCCAGCAGCACCAAGGTGGACAAGAAAATTGTGCCAAGGGAATGCAATCCTTGT
GGATGTACAGGCTCAGAAGTATCATCTGTCTTCATCTTCCCCCCAAAGACCAAAGATGTGC
TCACCATCACTCTGACTCCTAAGGTCACGTGTGTTGTGGTAGACATTAGCCAGAATGATCC
CGAGGTCCGGTTCAGCTGGTTTATAGATGACGTGGAAGTCCACACAGCTCAGACTCATGCC
CCGGAGAAGCAGTCCAACAGCACTTTACGCTCAGTCAGTGAACTCCCCATCGTGCACCGGG
ACTGGCTCAATGGCAAGACGTTCAAATGCAAAGTCAACAGTGGAGCATTCCCTGCCCCCAT

SEQUENCE LISTING FREE TEXT

```
CGAGAAAAGCATCTCCAAACCCGAAGGCACACCACGAGGTCCACAGGTATACACCATGGCG
CCTCCCAAGGAAGAGATGACCCAGAGTCAAGTCAGTATCACCTGCATGGTAAAAGGCTTCT
ATCCCCCAGACATTTATACGGAGTGGAAGATGAACGGGCAGCCACAGGAAAACTACAAGAA
CACTCCACCTACGATGGACACAGATGGGAGTTACTTCCTCTACAGCAAGCTCAATGTAAAG
AAAGAAACATGGCAGCAGGGAAACACTTTCACGTGTTCTGTGCTGCATGAGGGCCTGCACA
ACCACCATACTGAGAAGAGTCTCTCCCACTCTCCTGGTAAATGA
```

<SEQ ID NOS: 22 to 27>
SEQ ID NOS: 22 to 27 show the nucleotide sequences of primers cPD-L1 inner F, cPD-L1 inner R, cPD-L1 5'GSP, cPD-L1 3'GSP, cPD-L1-EGFP F and cPD-L1-EGFP R, in this order.

<SEQ ID NO: 28>
SEQ ID NO: 28 shows the amino acid sequence of the light chain (kappa chain) constant region of a human antibody.

<SEQ ID NO: 29>
SEQ ID NO: 29 shows the nucleotide sequence of the light chain (kappa chain) constant region of a human antibody.

<SEQ ID NO: 30>
SEQ ID NO: 30 shows the amino acid sequence of the CH (CH1—CH3) of a human antibody (IgG4 variant 1).

<SEQ ID NO: 31>
SEQ ID NO: 31 shows the nucleotide sequence of the CH (CH1—CH3) of a human antibody (IgG4 variant 1).

<SEQ ID NO: 32>
SEQ ID NO: 32 shows the amino acid sequence of the CH (CH1—CH3) of a human antibody (IgG4 variant 2).

<SEQ ID NO: 33>
SEQ ID NO: 33 shows the nucleotide sequence of the CH (CH1—CH3) of a human antibody (IgG4 variant 2).

<SEQ ID NO: 34>
SEQ ID NO: 34 shows the amino acid sequence of the CH (CH1—CH3) of a human antibody (IgG4 variant 3).

<SEQ ID NO: 35>
SEQ ID NO: 35 shows the nucleotide sequence of the CH (CH1—CH3) of a human antibody (IgG4 variant 3).

<SEQ ID NO: 36>
SEQ ID NO: 36 shows the amino acid sequence of the light chain (kappa chain) constant region of a mouse antibody.

<SEQ ID NO: 37>
SEQ ID NO: 37 shows the nucleotide sequence of the light chain (kappa chain) constant region of a mouse antibody.

<SEQ ID NO: 38>
SEQ ID NO: 38 shows the amino acid sequence of the light chain (kappa chain) constant region of a mouse antibody.

<SEQ ID NO: 39>
SEQ ID NO: 39 shows the nucleotide sequence of the light chain (kappa chain) constant region of a mouse antibody.

<SEQ ID NO: 40>
SEQ ID NO: 40 shows the amino acid sequence of the light chain (kappa chain) constant region of a mouse antibody.

<SEQ ID NO: 41>
SEQ ID NO: 41 shows the nucleotide sequence of the light chain (kappa chain) constant region of a mouse antibody.

<SEQ ID NO: 42>
SEQ ID NO: 42 shows the amino acid sequence of the light chain (kappa chain) constant region of a mouse antibody, <SEQ ID NO: 43>
SEQ ID NO: 43 shows the nucleotide sequence of the light chain (kappa chain) constant region of a mouse antibody.

SEQUENCE LISTING FREE TEXT

<SEQ ID NO: 44>
SEQ ID NO: 44 shows the amino acid sequence of the CH
(CH1-CH3) of a mouse antibody (IgG1 variant 1).

<SEQ ID NO: 45>
SEQ ID NO: 45 shows the nucleotide sequence of the CH
(CH1-CH3) of a mouse antibody (IgG1 variant 1).

<SEQ ID NO: 46>
SEQ ID NO: 46 shows the amino acid sequence of the CH
(CH1-CH3) of a mouse antibody (IgG1 variant 2).

<SEQ ID NO: 47>
SEQ ID NO: 47 shows the nucleotide sequence of the CH
(CH1-CH3) of a mouse antibody (IgG1 variant 2).

<SEQ ID NO: 48>
SEQ ID NO: 48 shows the amino acid sequence of the CH
(CH1-CH3) of a mouse antibody (IgG2a variant 1).

<SEQ ID NO: 49>
SEQ ID NO: 49 shows the nucleotide sequence of the CH
(CH1-CH3) of a mouse antibody (IgG2a variant 1).

<SEQ ID NO: 50>
SEQ ID NO: 50 shows the amino acid sequence of the CH
(CH1-CH3) of a mouse antibody (IgG2a variant 2).

<SEQ ID NO: 51>
SEQ ID NO: 51 shows the nucleotide sequence of the CH
(CH1-CH3) of a mouse antibody (IgG2a variant 2).

<SEQ ID NO: 52>
SEQ ID NO: 52 shows the amino acid sequence of the CH
(CH1-CH3) of a mouse antibody (IgG2b variant 1).

<SEQ ID NO: 53>
SEQ ID NO: 53 shows the nucleotide sequence of the CH
(CH1-CH3) of a mouse antibody (IgG2b variant 1).

<SEQ ID NO: 54>
SEQ ID NO: 54 shows the amino acid sequence of the CH
(CH1-CH3) of a mouse antibody (IgG2b variant 2).

<SEQ ID NO: 55>
SEQ ID NO: 55 shows the nucleotide sequence of the CH
(CH1-CH3) of a mouse antibody (IgG2b variant 2).

<SEQ ID NO: 56>
SEQ ID NO: 56 shows the amino acid sequence of the CH
(CH1-CH3) of a mouse antibody (IgG2c variant 1).

<SEQ ID NO: 57>
SEQ ID NO: 57 shows the nucleotide sequence of the CH
(CH1-CH3) of a mouse antibody (IgG2c variant 1).

<SEQ ID NO: 58>
SEQ ID NO: 58 shows the amino acid sequence of the CH
(CH1-CH3) of a mouse antibody (IgG2c variant 2).

<SEQ ID NO: 59>
SEQ ID NO: 59 shows the nucleotide sequence of the CH
(CH1-CH3) of a mouse antibody (IgG2c variant 2).

<SEQ ID NO: 60>
SEQ ID NO: 60 shows the amino acid sequence of the CH
(CH1-CH3) of a mouse antibody (IgG2c variant 3).

<SEQ ID NO: 61>
SEQ ID NO: 61 shows the nucleotide sequence of the CH
(CH1-CH3) of a mouse antibody (IgG2c variant 3).

<SEQ ID NO: 62>
SEQ ID NO: 62 shows the amino acid sequence of the CH
(CH1-CH3) of a mouse antibody (IgG3).

SEQUENCE LISTING FREE TEXT

<SEQ ID NO: 63>
SEQ ID NO: 63 shows the nucleotide sequence of the CH (CH1—CH3) of a mouse antibody (IgG3).

<SEQ ID NO: 64>
SEQ ID NO: 64 shows the amino acid sequence of the light chain (lambda chain) constant region of a bovine antibody.

<SEQ ID NO: 65>
SEQ ID NO: 65 shows the nucleotide sequence of the light chain (lambda chain) constant region of a bovine antibody.

<SEQ ID NO: 66>
SEQ ID NO: 66 shows the amino acid sequence of the CH (CH1—CH3) of a bovine antibody (IgG1 variant 1).

<SEQ ID NO: 67>
SEQ ID NO: 67 shows the nucleotide sequence of the CH (CH1—CH3) of a bovine antibody (IgG1 variant 1).

<SEQ ID NO: 68>
SEQ ID NO: 68 shows the amino acid sequence of the CH (CH1—CH3) of a bovine antibody (IgG1 variant 2).

<SEQ ID NO: 69>
SEQ ID NO: 69 shows the nucleotide sequence of the CH (CH1—CH3) of a bovine antibody (IgG1 variant 2).

<SEQ ID NO: 70>
SEQ ID NO: 70 shows the amino acid sequence of the CH (CH1—CH3) of a bovine antibody (IgG1 variant 3).

<SEQ ID NO: 71>
SEQ ID NO: 71 shows the nucleotide sequence of the CH (CH1—CH3) of a bovine antibody (IgG4 variant 3).

<SEQ ID NO: 72>
SEQ ID NO: 72 shows the amino acid sequence of the CH (CH1—CH3) of a bovine antibody (IgG2 variant 1).

<SEQ ID NO: 73>
SEQ ID NO: 73 shows the nucleotide sequence of the CH (CH1—CH3) of a bovine antibody (IgG2 variant 1).

<SEQ ID NO: 74>
SEQ ID NO: 74 shows the amino acid sequence of the CH (CH1—CH3) of a bovine antibody (IgG2 variant 2).

<SEQ ID NO: 75>
SEQ ID NO: 75 shows the nucleotide sequence of the CH (CH1—CH3) of a bovine antibody (IgG2 variant 2).

<SEQ ID NO: 76>
SEQ ID NO: 76 shows the amino acid sequence of the CH (CH1-CH3) of a bovine antibody (IgG2 variant 3).

<SEQ ID NO: 77>
SEQ ID NO: 77 shows the nucleotide sequence of the CH (CH1—CH3) of a bovine antibody (IgG2 variant 3).

<SEQ ID NO: 78>
SEQ ID NO: 78 shows the amino acid sequence of the CH (CH1—CH3) of a bovine antibody (IgG3 variant 1).

<SEQ ID NO: 79>
SEQ ID NO: 79 shows the nucleotide sequence of the CH (CH1—CH3) of a bovine antibody (IgG3 variant 1).

<SEQ ID NO: 80>
SEQ ID NO: 80 shows the amino acid sequence of the CH (CH1—CH3) of a bovine antibody (IgG3 variant 2).

<SEQ ID NO: 81>
SEQ ID NO: 81 shows the nucleotide sequence of the CH (CH1—CH3) of a bovine antibody (IgG3 variant 2).

SEQUENCE LISTING FREE TEXT

<SEQ ID NO: 82>
SEQ ID NO: 82 shows the amino acid sequence of the light chain (lambda chain) constant region of a canine antibody.

<SEQ ID NO: 83>
SEQ ID NO; 83 shows the nucleotide sequence of the light chain (lambda chain) constant region of a canine antibody.

<SEQ ID NO: 84>
SEQ ID NO: 84 shows the amino acid sequence of the CH (CH1–CH3) of a canine antibody (IgG-D).

<SEQ ID NO: 85>
SEQ ID NO: 85 shows the nucleotide sequence of the CH (CH1–CH3) of a canine antibody (IgG-D).

<SEQ ID NO: 86>
SEQ ID NO: 86 shows the amino acid sequence of the light chain (kappa chain) constant region of an ovine antibody.

<SEQ ID NO: 87>
SEQ ID NO: 87 shows the nucleotide sequence of the light chain (kappa chain) constant region of an ovine antibody.

<SEQ ID NO: 88>
SEQ ID NO: 88 shows the amino acid sequence of the light chain (lambda chain) constant region of an ovine antibody.

<SEQ ID NO: 89>
SEQ ID NO: 89 shows the nucleotide sequence of the light chain (lambda chain) constant region of an ovine antibody.

<SEQ ID NO: 90>
SEQ ID NO: 90 shows the amino acid sequence of the CH (CH1–CH3) of an ovine antibody (IgG1).

<SEQ ID NO: 91>
SEQ ID NO: 91 shows the nucleotide sequence of the CH (CH1–CH3) of an ovine antibody (IgG1).

<SEQ ID NO: 92>
SEQ ID NO: 92 shows the amino acid sequence of the CH (CH1–CH3) of an ovine antibody (IgG2).

<SEQ ID NO: 93>
SEQ ID NO: 93 shows the nucleotide sequence of the CH (CH1–CH3) of an ovine antibody (IgG2).

<SEQ ID NO: 94>
SEQ ID NO: 94 shows the amino acid sequence of the CH (CH1–CH3) of a porcine antibody (IgG1$^a$).

<SEQ ID NO: 95>
SEQ ID NO: 95 shows the nucleotide sequence of the CH (CH1–CH3) of a porcine antibody (IgG1$^a$).

<SEQ ID NO: 96>
SEQ ID NO: 96 shows the amino acid sequence of the CH (CH1–CH3) of a porcine antibody (IgG1$^b$).

<SEQ ID NO: 97>
SEQ ID NO: 97 shows the nucleotide sequence of the CH (CH1–CH3) of a porcine antibody (IgG1$^b$).

<SEQ ID NO: 98>
SEQ ID NO: 98 shows the amino acid sequence of the CH (CH1–CH3) of a porcine antibody (IgG2$^a$).

<SEQ ID NO: 99>
SEQ ID NO: 99 shows the nucleotide sequence of the CH (CH1–CH3) of a porcine antibody (IgG2$^a$).

<SEQ ID NO: 100>
SEQ ID NO: 100 shows the amino acid sequence of the CH (CH1–CH3) of a porcine antibody (IgG2$^b$).

SEQUENCE LISTING FREE TEXT

<SEQ ID NO: 101>
SEQ ID NO: 101 shows the nucleotide sequence of the CH (CH1-CH3) of a porcine antibody (IgG2$^b$).

<SEQ ID NO: 102>
SEQ ID NO: 102 shows the amino acid sequence of the CH (CH1-CH3) of a porcine antibody (IgG3).

<SEQ ID NO: 103>
SEQ ID NO: 103 shows the nucleotide sequence of the CH (CH1-CH3) of a porcine antibody (IgG3).

<SEQ ID NO: 104>
SEQ ID NO: 104 shows the amino acid sequence of the CH (CH1-CH3) of a porcine antibody (IgG4$^a$).

<SEQ ID NO: 105>
SEQ ID NO: 105 shows the nucleotide sequence of the CH (CH1-CH3) of a porcine antibody (IgG4$^a$).

<SEQ ID NO: 106>
SEQ ID NO: 106 shows the amino acid sequence of the CH (CH1-CH3) of a porcine antibody (IgG4$^b$).

<SEQ ID NO: 107>
SEQ ID NO: 107 shows the nucleotide sequence of the CH (CH1-CH3) of a porcine antibody (IgG4$^b$).

<SEQ ID NO: 108>
SEQ ID NO: 108 shows the amino acid sequence of the CH (CH1-CH3) of a porcine antibody (IgG5$^a$).

<SEQ ID NO: 109>
SEQ ID NO: 109 shows the nucleotide sequence of the CH (CH1-CH3) of a porcine antibody (IgG5$^a$).

<SEQ ID NO: 110>
SEQ ID NO: 110 shows the amino acid sequence of the CH (CH1-CH3) of a porcine antibody (IgG5$^b$).

<SEQ ID NO: 111>
SEQ ID NO: 111 shows the nucleotide sequence of the CH (CH1-CH3) of a porcine antibody (IgG5b).

<SEQ ID NO: 112>
SEQ ID NO: 112 shows the amino acid sequence of the CH (CH1-CH3) of a porcine antibody (IgG6$^a$).

<SEQ ID NO: 113>
SEQ ID NO: 113 shows the nucleotide sequence of the CH (CH1-CH3) of a porcine antibody (IgG6$^a$).

<SEQ ID NO: 114>
SEQ ID NO: 114 shows the amino acid sequence of the CH (CH1-CH3) of a porcine antibody (IgG6$^b$).

<SEQ ID NO: 115>
SEQ ID NO: 115 shows the nucleotide sequence of the CH (CH1-CH3) of a porcine antibody (IgG6$^b$).

<SEQ ID NO: 116>
SEQ ID NO: 116 shows the amino acid sequence of the light chain (estimated to be Ig lambda) constant region (CL) of a water buffalo antibody.

<SEQ ID NO: 117>
SEQ ID NO: 117 shows the nucleotide sequence of the light chain (estimated to be Ig lambda) constant region (CL) of a water buffalo antibody.

<SEQ ID NO: 118>
SEQ IlD NO: 118 shows the amino acid sequence of the CH (CH1-CH3) of a water buffalo antibody (estimated to be IgG1).

SEQUENCE LISTING FREE TEXT

<SEQ ID NO: 119>
SEQ ID NO: 119 shows the nucleotide sequence of the CH (CH1-CH3) of a water buffalo antibody (estimated to be IgG1).

<SEQ ID NO: 120>
SEQ ID NO: 120 shows the amino acid sequence of the CH (CH1-CH3) of a water buffalo antibody (estimated to be IgG2).

<SEQ ID NO: 121>
SEQ ID NO: 121 shows the nucleotide sequence of the CH (CH1-CH3) of a water buffalo antibody (estimated to be IgG2).

<SEQ ID NO: 122>
SEQ ID NO: 122 shows the amino acid sequence of the CH (CH1-CH3) of a water buffalo antibody (estimated to be IgG3).

<SEQ ID NO: 123>
SEQ ID NO: 123 shows the nucleotide sequence of the CH (CH1-CH3) of a water buffalo antibody (estimated to be IgG3).

<SEQ ID NO: 124>
SEQ ID NO: 124 shows the nucleotide sequence of prime boPD-L1-EGFP F.

<SEQ ID NO: 125>
SEQ ID NO: 125 shows the nucleotide sequence of primer boPD-L1-EGFP R.

The invention claimed is:

1. A method to diagnose cancer and/or infection comprising contacting in vitro one or more cells from a subject with an antibody; and determining if said antibody binds to said one or more cells, wherein increased binding to said cells as compared to a control is indicative of cancer and/or infection, wherein the cancer is a cancer where cancer cells express PD-L1, wherein the infection is an infection where infected cells express PD-L1, and wherein said antibody is an anti-PD-L1 antibody comprising
  (a) a light chain comprising CDR1 having the amino acid sequence of KSISKY (SEQ ID NO: 1), CDR2 having the amino acid sequence of SGS and CDR3 having the amino acid sequence of QQHNEYPLT (SEQ ID NO: 2) and
  (b) a heavy chain comprising CDR1 having the amino acid sequence of GYTFTDYI (SEQ ID NO: 3), CDR2 having the amino acid sequence of INPDSGGN (SEQ ID NO: 4) and CDR3 having the amino acid sequence of ARGITMMVVISHWKFDF (SEQ ID NO: 5),
wherein said antibody binds ovine, bovine, porcine or canine PD-L1 proteins, and
wherein the cancer is not malignant melanoma.

2. The method of claim 1, further comprising selecting the subject as a candidate for an anti-PD-L1 antibody therapy.

3. The method of claim 1, further comprising administering an anti-PD-L1 antibody therapy to the subject.

4. The method of claim 1, wherein the subject is selected from the group consisting of canine, ovine, porcine and bovine.

5. The method of claim 1, wherein the antibody is derived from rat.

6. The method of claim 5, wherein the antibody is a rat anti-bovine PD-L1 antibody.

7. The method of claim 6, wherein the light chain variable region of the antibody has the amino acid sequence as shown in SEQ ID NO. 6 and the heavy chain variable region of the antibody has the amino acid sequence as shown in SEQ ID NO: 7.

8. The method of claim 1, wherein the light chain constant region of the antibody has the amino acid sequence of the constant region of kappa chain.

9. The method of claim 1, wherein the heavy chain constant region of the antibody has the amino acid sequence of the constant region of IgG2a.

10. The method of claim 8, wherein the light chain constant region of the antibody has the amino acid sequence set forth in any one of SEQ ID NOs: 8, 10 to 12 and the heavy chain constant region of the antibody has the amino acid sequence set forth in SEQ ID NO: 9 or 13.

11. The method of claim 1, wherein the antibody has a four-chain structure comprising two light chains and two heavy chains.

12. The method of claim 1, wherein the cancer and/or infection is a neoplastic disease, leukemia, Johne's disease, anaplasmosis, bacterial mastitis, mycotic mastitis, a mycoplasma infection, tuberculosis, *Theileria orientalis* infection, cryptosporidiosis, coccidiosis, trypanosomiasis or leishmaniasis.

13. The method of claim 12, wherein the mycoplasma infection is mycoplasma mastitis or mycoplasma pneumonia.

* * * * *

SEQUENCE LISTING

<160> NUMBER OF SEQ ID NOS: 125

<210> SEQ ID NO 1
<211> LENGTH: 6
<212> TYPE: PRT
<213> ORGANISM: Bubalus arnee

<400> SEQUENCE: 1

Lys Ser Ile Ser Lys Tyr
1               5

<210> SEQ ID NO 2
<211> LENGTH: 9
<212> TYPE: PRT
<213> ORGANISM: Bubalus arnee

<400> SEQUENCE: 2

Gln Gln His Asn Glu Tyr Pro Leu Thr
1               5

<210> SEQ ID NO 3
<211> LENGTH: 8
<212> TYPE: PRT
<213> ORGANISM: Bubalus arnee

<400> SEQUENCE: 3

Gly Tyr Thr Phe Thr Asp Tyr Ile
1               5

<210> SEQ ID NO 4
<211> LENGTH: 8
<212> TYPE: PRT
<213> ORGANISM: Bubalus arnee

```
<400> SEQUENCE: 4

Ile Asn Pro Asp Ser Gly Gly Asn
1               5

<210> SEQ ID NO 5
<211> LENGTH: 17
<212> TYPE: PRT
<213> ORGANISM: Bubalus arnee

<400> SEQUENCE: 5

Ala Arg Gly Ile Thr Met Met Val Val Ile Ser His Trp Lys Phe Asp
1               5                   10                  15

Phe

<210> SEQ ID NO 6
<211> LENGTH: 127
<212> TYPE: PRT
<213> ORGANISM: Bubalus arnee

<400> SEQUENCE: 6

Met Arg Val Gln Ile Gln Phe Trp Gly Leu Leu Leu Trp Thr Ser
1               5                   10                  15

Gly Ile Gln Cys Asp Val Gln Met Thr Gln Ser Pro Ser Asn Leu Ala
                20                  25                  30

Ala Ser Pro Gly Glu Ser Val Ser Ile Asn Cys Lys Ala Ser Lys Ser
            35                  40                  45

Ile Ser Lys Tyr Leu Ala Trp Tyr Gln Gln Lys Pro Gly Lys Ala Asn
        50                  55                  60

Lys Leu Leu Ile Tyr Ser Gly Ser Thr Leu Gln Ser Gly Thr Pro Ser
65                  70                  75                  80

Arg Phe Ser Gly Ser Gly Ser Gly Thr Asp Phe Thr Leu Thr Ile Arg
                85                  90                  95

Asn Leu Glu Pro Glu Asp Phe Gly Leu Tyr Tyr Cys Gln Gln His Asn
            100                 105                 110

Glu Tyr Pro Leu Thr Phe Gly Ser Gly Thr Lys Leu Glu Ile Lys
        115                 120                 125

<210> SEQ ID NO 7
<211> LENGTH: 142
<212> TYPE: PRT
<213> ORGANISM: Bubalus arnee

<400> SEQUENCE: 7

Met Gly Trp Ile Cys Ile Ile Phe Leu Val Ala Ile Ala Thr Gly Ala
1               5                   10                  15

His Ser Gln Val Lys Leu Leu Gln Ser Gly Ala Ala Leu Val Lys Pro
                20                  25                  30

Gly Asp Ser Val Lys Met Ser Cys Lys Ala Ser Gly Tyr Thr Phe Thr
            35                  40                  45

Asp Tyr Ile Ile His Trp Val Lys Gln Ser His Gly Lys Ser Leu Glu
        50                  55                  60

Trp Ile Gly Tyr Ile Asn Pro Asp Ser Gly Gly Asn Asn Tyr Asn Glu
65                  70                  75                  80

Lys Phe Lys Ser Lys Ala Thr Leu Thr Val Asp Lys Ser Ser Ser Thr
                85                  90                  95

Ala Tyr Met Glu Phe Ser Arg Leu Thr Ser Glu Asp Ser Ala Ile Tyr
            100                 105                 110
```

```
Tyr Cys Ala Arg Gly Ile Thr Met Met Val Val Ile Ser His Trp Lys
            115                 120                 125

Phe Asp Phe Trp Gly Pro Gly Thr Met Val Thr Val Ser Ser
            130                 135                 140

<210> SEQ ID NO 8
<211> LENGTH: 107
<212> TYPE: PRT
<213> ORGANISM: Bubalus arnee

<400> SEQUENCE: 8

Arg Ala Asp Ala Ala Pro Thr Val Ser Ile Phe Pro Pro Ser Thr Glu
1               5                   10                  15

Gln Leu Ala Thr Gly Gly Ala Ser Val Val Cys Leu Met Asn Asn Phe
            20                  25                  30

Tyr Pro Arg Asp Ile Ser Val Lys Trp Lys Ile Asp Gly Thr Glu Arg
        35                  40                  45

Arg Asp Gly Val Leu Asp Ser Val Thr Asp Gln Asp Ser Lys Asp Ser
    50                  55                  60

Thr Tyr Ser Met Ser Ser Thr Leu Ser Leu Thr Lys Ala Asp Tyr Glu
65                  70                  75                  80

Ser His Asn Leu Tyr Thr Cys Glu Val Val His Lys Thr Ser Ser Ser
                85                  90                  95

Pro Val Val Lys Ser Phe Asn Arg Asn Glu Cys
            100                 105

<210> SEQ ID NO 9
<211> LENGTH: 322
<212> TYPE: PRT
<213> ORGANISM: Bubalus arnee

<400> SEQUENCE: 9

Ala Glu Thr Thr Ala Pro Ser Val Tyr Pro Leu Ala Pro Gly Thr Ala
1               5                   10                  15

Leu Lys Ser Asn Ser Met Val Thr Leu Gly Cys Leu Val Lys Gly Tyr
            20                  25                  30

Phe Pro Glu Pro Val Thr Val Thr Trp Asn Ser Gly Ala Leu Ser Ser
        35                  40                  45

Gly Val His Thr Phe Pro Ala Val Leu Gln Ser Gly Leu Tyr Thr Leu
    50                  55                  60

Thr Ser Ser Val Thr Val Pro Ser Ser Thr Trp Ser Ser Gln Ala Val
65                  70                  75                  80

Thr Cys Asn Val Ala His Pro Ala Ser Ser Thr Lys Val Asp Lys Lys
                85                  90                  95

Ile Val Pro Arg Glu Cys Asn Pro Cys Gly Cys Thr Gly Ser Glu Val
            100                 105                 110

Ser Ser Val Phe Ile Phe Pro Pro Lys Thr Lys Asp Val Leu Thr Ile
            115                 120                 125

Thr Leu Thr Pro Lys Val Thr Cys Val Val Val Asp Ile Ser Gln Asn
            130                 135                 140

Asp Pro Glu Val Arg Phe Ser Trp Phe Ile Asp Asp Val Glu Val His
145                 150                 155                 160

Thr Ala Gln Thr His Ala Pro Glu Lys Gln Ser Asn Ser Thr Leu Arg
                165                 170                 175

Ser Val Ser Glu Leu Pro Ile Val His Arg Asp Trp Leu Asn Gly Lys
            180                 185                 190
```

-continued

```
Thr Phe Lys Cys Lys Val Asn Ser Gly Ala Phe Pro Ala Pro Ile Glu
            195                 200                 205

Lys Ser Ile Ser Lys Pro Glu Gly Thr Pro Arg Gly Pro Gln Val Tyr
        210                 215                 220

Thr Met Ala Pro Pro Lys Glu Glu Met Thr Gln Ser Gln Val Ser Ile
225                 230                 235                 240

Thr Cys Met Val Lys Gly Phe Tyr Pro Pro Asp Ile Tyr Thr Glu Trp
                245                 250                 255

Lys Met Asn Gly Gln Pro Gln Glu Asn Tyr Lys Asn Thr Pro Pro Thr
            260                 265                 270

Met Asp Thr Asp Gly Ser Tyr Phe Leu Tyr Ser Lys Leu Asn Val Lys
        275                 280                 285

Lys Glu Thr Trp Gln Gln Gly Asn Thr Phe Thr Cys Ser Val Leu His
290                 295                 300

Glu Gly Leu His Asn His His Thr Gly Lys Ser Leu Ser His Ser Pro
305                 310                 315                 320

Gly Lys

<210> SEQ ID NO 10
<211> LENGTH: 106
<212> TYPE: PRT
<213> ORGANISM: Bubalus arnee

<400> SEQUENCE: 10

Ala Asp Ala Ala Pro Thr Val Ser Ile Phe Pro Pro Ser Thr Glu Gln
1               5                   10                  15

Leu Ala Thr Gly Gly Ala Ser Val Val Cys Leu Met Asn Asn Phe Tyr
            20                  25                  30

Pro Arg Asp Ile Ser Val Lys Trp Lys Ile Asp Gly Thr Glu Arg Arg
        35                  40                  45

Asp Gly Val Leu Asp Ser Val Thr Asp Gln Asp Ser Lys Asp Ser Thr
    50                  55                  60

Tyr Ser Met Ser Ser Thr Leu Ser Leu Thr Lys Ala Asp Tyr Glu Ser
65                  70                  75                  80

His Asn Leu Tyr Thr Cys Glu Val Val His Lys Thr Ser Ser Ser Pro
                85                  90                  95

Val Val Lys Ser Phe Asn Arg Asn Glu Cys
            100                 105

<210> SEQ ID NO 11
<211> LENGTH: 107
<212> TYPE: PRT
<213> ORGANISM: Bubalus arnee

<400> SEQUENCE: 11

Arg Ala Asp Ala Ala Pro Thr Val Ser Ile Phe Pro Pro Ser Thr Glu
1               5                   10                  15

Gln Leu Ala Thr Gly Gly Ala Ser Val Val Cys Leu Met Asn Asn Phe
            20                  25                  30

Tyr Pro Arg Asp Ile Ser Val Lys Trp Lys Ile Asp Gly Thr Glu Arg
        35                  40                  45

Arg Asp Gly Val Leu Asp Ser Val Thr Asp Gln Asp Ser Lys Asp Ser
    50                  55                  60

Thr Tyr Ser Met Ser Ser Thr Leu Ser Leu Ser Lys Ala Asp Tyr Glu
65                  70                  75                  80
```

```
Ser His Asn Leu Tyr Thr Cys Glu Val Val His Lys Thr Ser Ser Ser
                85                  90                  95

Pro Val Val Lys Ser Phe Asn Arg Asn Glu Cys
            100                 105

<210> SEQ ID NO 12
<211> LENGTH: 104
<212> TYPE: PRT
<213> ORGANISM: Bubalus arnee

<400> SEQUENCE: 12

Ala Ala Pro Thr Val Ser Ile Phe Pro Pro Ser Met Glu Gln Leu Thr
1               5                   10                  15

Ser Gly Gly Ala Thr Val Val Cys Phe Val Asn Asn Phe Tyr Pro Arg
            20                  25                  30

Asp Ile Ser Val Lys Trp Lys Ile Asp Gly Ser Glu Gln Arg Asp Gly
        35                  40                  45

Val Leu Asp Ser Val Thr Asp Gln Asp Ser Lys Asp Ser Thr Tyr Ser
    50                  55                  60

Met Ser Ser Thr Leu Ser Leu Thr Lys Val Glu Tyr Glu Arg His Asn
65                  70                  75                  80

Leu Tyr Thr Cys Glu Val Val His Lys Thr Ser Ser Pro Val Val
                85                  90                  95

Lys Ser Phe Asn Arg Asn Glu Cys
            100

<210> SEQ ID NO 13
<211> LENGTH: 318
<212> TYPE: PRT
<213> ORGANISM: Bubalus arnee

<400> SEQUENCE: 13

Ala Pro Ser Val Tyr Pro Leu Ala Pro Gly Thr Ala Leu Lys Ser Asn
1               5                   10                  15

Ser Met Val Thr Leu Gly Cys Leu Val Lys Gly Tyr Phe Pro Glu Pro
            20                  25                  30

Val Thr Val Thr Trp Asn Ser Gly Ala Leu Ser Ser Gly Val His Thr
        35                  40                  45

Phe Pro Ala Val Leu Gln Ser Gly Leu Tyr Thr Leu Thr Ser Ser Val
    50                  55                  60

Thr Val Pro Ser Ser Thr Trp Ser Ser Gln Ala Val Thr Cys Asn Val
65                  70                  75                  80

Ala His Pro Ala Ser Thr Lys Val Asp Lys Lys Ile Val Pro Arg
                85                  90                  95

Glu Cys Asn Pro Cys Gly Cys Thr Gly Ser Glu Val Ser Val Phe
            100                 105                 110

Ile Phe Pro Pro Lys Thr Lys Asp Val Leu Thr Ile Thr Leu Thr Pro
    115                 120                 125

Lys Val Thr Cys Val Val Asp Ile Ser Gln Asn Asp Pro Glu Val
    130                 135                 140

Arg Phe Ser Trp Phe Ile Asp Asp Val Glu Val His Thr Ala Gln Thr
145                 150                 155                 160

His Ala Pro Glu Lys Gln Ser Asn Ser Thr Leu Arg Ser Val Ser Glu
                165                 170                 175

Leu Pro Ile Val His Arg Asp Trp Leu Asn Gly Lys Thr Phe Lys Cys
            180                 185                 190
```

```
Lys Val Asn Ser Gly Ala Phe Pro Ala Pro Ile Glu Lys Ser Ile Ser
        195                 200                 205

Lys Pro Glu Gly Thr Pro Arg Gly Pro Gln Val Tyr Thr Met Ala Pro
    210                 215                 220

Pro Lys Glu Glu Met Thr Gln Ser Gln Val Ser Ile Thr Cys Met Val
225                 230                 235                 240

Lys Gly Phe Tyr Pro Pro Asp Ile Tyr Thr Glu Trp Lys Met Asn Gly
                245                 250                 255

Gln Pro Gln Glu Asn Tyr Lys Asn Pro Pro Thr Met Asp Thr Asp
        260                 265                 270

Gly Ser Tyr Phe Leu Tyr Ser Lys Leu Asn Val Lys Lys Glu Thr Trp
        275                 280                 285

Gln Gln Gly Asn Thr Phe Thr Cys Ser Val Leu His Glu Gly Leu His
        290                 295                 300

Asn His His Thr Glu Lys Ser Leu Ser His Ser Pro Gly Lys
305                 310                 315

<210> SEQ ID NO 14
<211> LENGTH: 381
<212> TYPE: DNA
<213> ORGANISM: Bubalus arnee

<400> SEQUENCE: 14
atgagggtcc agattcagtt ttgggggctt cttctgctct ggacatcagg tatacagtgt      60
gatgtccaga tgacccagtc tccatctaat cttgctgcct ctcctggaga aagtgtttcc     120
atcaattgca aggcaagtaa gagcattagc aagtatttag cctggtatca acagaaacct     180
gggaaagcaa ataagcttct tatctactct gggtcaactt gcaatctgg aactccatcg     240 aggttcagtg gcagtggatc tggtacagat ttcactctca ccatcagaaa cctggagcct     300
gaagattttg gactctatta ctgtcaacag cataatgaat acccgctcac gttcggttct     360
gggaccaagc tggagatcaa a                                                381

<210> SEQ ID NO 15
<211> LENGTH: 426
<212> TYPE: DNA
<213> ORGANISM: Bubalus arnee

<400> SEQUENCE: 15
atgggatgga tctgtatcat ctttcttgtg caatagcta caggtgccca ctcccaggtc       60
aagctgctgc agtctggggc tgcactggtg aagcctgggg actctgtgaa gatgtcttgc    120
aaagcttctg gttatacatt cactgactac attatacact gggtgaagca gagtcatgga    180
aaaagccttg agtggattgg ttatattaat cctgacagtg gtggtaataa ctacaatgaa    240
aagttcaaga gcaaggccac attgactgta gacaaatcca gcagcacagc ctatatggag    300
tttagcagat tgacatctga ggattctgca atctactact gtgcaagagg gattaccatg    360
atggtagtta ttagccactg gaagtttgac ttctggggcc aggaaccatg gtcaccgtg     420 tcctca                                                                426

<210> SEQ ID NO 16
<211> LENGTH: 324
<212> TYPE: DNA
<213> ORGANISM: Bubalus arnee

<400> SEQUENCE: 16
cgggctgatg ctgcaccaac tgtatctatc ttcccaccat ccacggaaca gttagcaact      60
```

```
ggaggtgcct cagtcgtgtg cctcatgaac aacttctatc ccagagacat cagtgtcaag    120
tggaagattg atggcactga acgacgagat ggtgtcctgg acagtgttac tgatcaggac    180
agcaaagaca gcacgtacag catgagcagc accctctcgt tgaccaaggc tgactatgaa    240
agtcataacc tctatacctg tgaggttgtt cataagacat catcctcacc cgtcgtcaag    300
agcttcaaca ggaatgagtg ttag                                          324
```

<210> SEQ ID NO 17
<211> LENGTH: 969
<212> TYPE: DNA
<213> ORGANISM: Bubalus arnee

<400> SEQUENCE: 17

```
gctgaaacaa cagccccatc tgtctatcca ctggctcctg gaactgctct caaaagtaac     60
tccatggtga ccctgggatg cctggtcaag ggctatttcc ctgagccagt caccgtgacc    120
tggaactctg gagccctgtc cagcggtgtg cacaccttcc cagctgtcct gcagtctgga    180
ctctacactc tcaccagctc agtgactgta ccctccagca cctggtccag ccaggccgtc    240
acctgcaacg tagcccaccc ggccagcagc accaaggtgg acaagaaaat tgtgccaagg    300
gaatgcaatc cttgtggatg tacaggctca gaagtatcat ctgtcttcat cttcccccca    360
aagaccaaag atgtgctcac catcactctg actcctaagg tcacgtgtgt tgtggtagac    420
attagccaga atgatcccga ggtccggttc agctggttta tagatgacgt ggaagtccac    480
acagctcaga ctcatgcccc ggagaagcag tccaacagca ctttacgctc agtcagtgaa    540
ctccccatcg tgcaccggga ctggctcaat ggcaagacgt tcaaatgcaa agtcaacagt    600
ggagcattcc ctgcccccat cgagaaaagc atctccaaac ccgaaggcac accacgaggt    660
ccacaggtat acaccatggc gcctcccaag gaagagatga cccagagtca agtcagtatc    720
acctgcatgg taaaaggctt ctatccccca gacatttata cggagtggaa gatgaacggg    780
cagccacagg aaaactacaa gaacactcca cctacgatgg acacagatgg gagttacttc    840
ctctacagca agctcaatgt aaagaaagaa acatggcagc agggaaacac tttcacgtgt    900
tctgtgctgc atgagggcct gcacaaccac catactgaga agagtctctc ccactctcct    960
ggtaaatga                                                           969
```

<210> SEQ ID NO 18
<211> LENGTH: 323
<212> TYPE: DNA
<213> ORGANISM: Bubalus arnee

<400> SEQUENCE: 18

```
gggctgatgc tgcaccaact gtatctatct tcccaccatc cacggaacag ttagcaactg     60
gaggtgcctc agtcgtgtgc ctcatgaaca acttctatcc cagagacatc agtgtcaagt    120
ggaagattga tggcactgaa cgacgagatg gtgtcctgga cagtgttact gatcaggaca    180
gcaaagacag cacgtacagc atgagcagca ccctctcgtt gaccaaggct gactatgaaa    240
gtcataacct ctatacctgt gaggttgttc ataagacatc atcctcaccc gtcgtcaaga    300
gcttcaacag gaatgagtgt tag                                           323
```

<210> SEQ ID NO 19
<211> LENGTH: 324
<212> TYPE: DNA
<213> ORGANISM: Bubalus arnee

<400> SEQUENCE: 19

```
cgggctgatg ctgcaccaac tgtatctatc ttcccaccat ccacggaaca gttagcaact    60
ggaggtgcct cagtcgtgtg cctcatgaac aacttctatc ccagagacat cagtgtcaag   120
tggaagattg atggcactga acgacgagat ggtgtcctgg acagtgttac tgatcaggac   180
agcaaagaca gcacgtacag catgagcagc accctctcgt tgtccaaggc tgactatgaa   240
agtcataacc tctatacctg tgaggttgtt cataagacat catcctcacc cgtcgtcaag   300
agcttcaaca ggaatgagtg ttag                                          324
```

<210> SEQ ID NO 20
<211> LENGTH: 315
<212> TYPE: DNA
<213> ORGANISM: Bubalus arnee

<400> SEQUENCE: 20

```
gccgcaccaa ctgtatccat cttcccacca tccatggaac agttaacatc tggaggtgcc    60
acagtcgtgt gcttcgtgaa caacttctat cccagagaca tcagtgtcaa gtggaagatt   120
gatggcagtg aacaacgaga tggtgtcctg gacagtgtta ctgatcagga cagcaaagac   180
agcacgtaca gcatgagcag caccctctcg ttgaccaagg ttgaatatga aaggcataac   240
ctctatacct gtgaggttgt tcataagaca tcatcctcac ccgtcgtcaa gagcttcaac   300
aggaatgagt gttag                                                    315
```

<210> SEQ ID NO 21
<211> LENGTH: 959
<212> TYPE: DNA
<213> ORGANISM: Bubalus arnee

<400> SEQUENCE: 21

```
cagccccctc tgtctatcca ctggctcctg gaactgctct caaaagtaac tccatggtga    60
ccctgggatg cctggtcaag ggctatttcc ctgagccagt caccgtgacc tggaactctg   120
gagccctgtc cagcggtgtg cacaccttcc cagctgtcct gcagtctgga ctctacactc   180
tcaccagctc agtgactgta ccctccagca cctggtccag ccaggccgtc acctgcaacg   240
tagcccaccc ggccagcagc accaaggtgg acaagaaaat tgtgccaagg gaatgcaatc   300
cttgtggatg tacaggctca gaagtatcat ctgtcttcat cttcccccca agaccaaag   360 atgtgctcac catcactctg actcctaagg tcacgtgtgt tgtggtagac attagccaga   420
atgatcccga ggtccggttc agctggttta tagatgacgt ggaagtccac acagctcaga   480
ctcatgcccc ggagaagcag tccaacagca ctttacgctc agtcagtgaa ctccccatcg   540
tgcaccggga ctggctcaat ggcaagacgt tcaaatgcaa agtcaacagt ggagcattcc   600
ctgcccccat cgagaaaagc atctccaaac ccgaaggcac accacgaggt ccacaggtat   660
acaccatggc cctcccaagg aagagatga cccagagtca agtcagtatc acctgcatgg   720
taaaaggctt ctatccccca gacatttata cggagtggaa gatgaacggg cagccacagg   780
aaaactacaa gaacactcca cctacgatgg acacagatgg gagttacttc ctctacagca   840
agctcaatgt aaagaaagaa acatggcagc agggaaacac tttcacgtgt tctgtgctgc   900
atgagggcct gcacaaccac catactgaga gagtctctc ccactctcct ggtaaatga    959
```

<210> SEQ ID NO 22
<211> LENGTH: 20
<212> TYPE: DNA
<213> ORGANISM: Bubalus arnee

<400> SEQUENCE: 22
atgagaatgt ttagtgtctt                                              20

<210> SEQ ID NO 23
<211> LENGTH: 24
<212> TYPE: DNA
<213> ORGANISM: Bubalus arnee

<400> SEQUENCE: 23
ttatgtctct tcaaattgta tatc                                         24

<210> SEQ ID NO 24
<211> LENGTH: 17
<212> TYPE: DNA
<213> ORGANISM: Bubalus arnee

<400> SEQUENCE: 24
ttttagacag aaagtga                                                 17

<210> SEQ ID NO 25
<211> LENGTH: 20
<212> TYPE: DNA
<213> ORGANISM: Bubalus arnee

<400> SEQUENCE: 25
gaccagctct tcttggggaa                                              20

<210> SEQ ID NO 26
<211> LENGTH: 26
<212> TYPE: DNA
<213> ORGANISM: Bubalus arnee

<400> SEQUENCE: 26
gaagatctat gagaatgttt agtgtc                                       26

<210> SEQ ID NO 27
<211> LENGTH: 28
<212> TYPE: DNA
<213> ORGANISM: Bubalus arnee

<400> SEQUENCE: 27
ggaattctgt ctcttcaaat tgtatatc                                     28

<210> SEQ ID NO 28
<211> LENGTH: 106
<212> TYPE: PRT
<213> ORGANISM: Bubalus arnee

<400> SEQUENCE: 28

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro

```
                         85                  90                  95

Val Thr Lys Ser Phe Asn Arg Gly Glu Cys
                100                 105

<210> SEQ ID NO 29
<211> LENGTH: 321
<212> TYPE: DNA
<213> ORGANISM: Bubalus arnee

<400> SEQUENCE: 29
actgtggctg caccatctgt cttcatcttc ccgccatctg atgagcagtt gaaatctgga       60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgcccgt cacaaagagc     300
ttcaacaggg gagagtgtta g                                                321

<210> SEQ ID NO 30
<211> LENGTH: 229
<212> TYPE: PRT
<213> ORGANISM: Bubalus arnee

<400> SEQUENCE: 30

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
        210                 215                 220

Leu Ser Leu Gly Lys
225
```

```
<210> SEQ ID NO 31
<211> LENGTH: 690
<212> TYPE: DNA
<213> ORGANISM: Bubalus arnee

<400> SEQUENCE: 31
gagtccaaat atggtccccc atgcccatca tgcccagcac ctgagttcct ggggggacca      60
tcagtcttcc tgttcccccc aaaacccaag gacactctca tgatctcccg gaccoctgag     120 gtcacgtgcg tggtggtgga cgtgagccag gaagaccccg aggtccagtt caactggtac     180
gtggatggcg tggaggtgca taatgccaag acaaagccgc gggaggagca gttcaacagc     240
acgtaccgtg tggtcagcgt cctcaccgtc ctgcaccagg actggctgaa cggcaaggag     300
tacaagtgca aggtctccaa caaaggcctc ccgtcctcca tcgagaaaac catctccaaa     360
gccaaagggc agccccgaga gccacaggtg tacaccctgc ccccatccca ggaggagatg     420
accaagaacc aggtcagcct gacctgcctg gtcaaaggct tctacccag cgacatcgcc      480 gtggagtggg agagcaatgg gcagccggag aacaactaca agaccacgcc tcccgtgctg     540
gactccgacg gctccttctt cctctacagc aggctaaccg tggacaagag caggtggcag     600
gaggggaatg tcttctcatg ctccgtgatg catgaggctc tgcacaacca ctacacacag     660
aagagcctct ccctgtctct gggtaaatga                                     690

<210> SEQ ID NO 32
<211> LENGTH: 229
<212> TYPE: PRT
<213> ORGANISM: Bubalus arnee

<400> SEQUENCE: 32

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Val His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
```

Leu Ser Leu Gly Lys
225

<210> SEQ ID NO 33
<211> LENGTH: 690
<212> TYPE: DNA
<213> ORGANISM: Bubalus arnee

<400> SEQUENCE: 33

```
gagtccaaat atggtccccc gtgcccatca tgcccagcac ctgagttcct ggggggacca     60
tcagtcttcc tgttcccccc aaacccaag gacactctca tgatctcccg gaccctgag    120
gtcacgtgcg tggtggtgga cgtgagccag gaagaccccg aggtccagtt caactggtac   180
gtggatggcg tggaggtgca taatgccaag acaaagccgc gggaggagca gttcaacagc   240
acgtaccgtg tggtcagcgt cctcaccgtc gtgcaccagg actggctgaa cggcaaggag   300
tacaagtgca aggtctccaa caaaggcctc ccgtcctcca tcgagaaaac catctccaaa   360
gccaaagggc agccccgaga gccacaggtg tacaccctgc ccccatccca ggaggagatg   420
accaagaacc aggtcagcct gacctgcctg gtcaaaggct tctacccag cgacatcgcc   480
gtggagtggg agagcaatgg gcagccggag aacaactaca agaccacgcc tcccgtgctg   540
gactccgacg gctccttctt cctctacagc aggctaaccg tggacaagag caggtggcag   600
gaggggaatg tcttctcatg ctccgtgatg catgaggctc tgcacaacca ctacacgcag   660
aagagcctct ccctgtctct gggtaaatga                                    690
```

<210> SEQ ID NO 34
<211> LENGTH: 217
<212> TYPE: PRT
<213> ORGANISM: Bubalus arnee

<400> SEQUENCE: 34

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Glu Gly Asn Val

```
                180               185               190
Phe Ser Cys Ser Val Met His Glu Ala Leu His Asn His Tyr Thr Gln
            195               200               205

Lys Ser Leu Ser Leu Ser Leu Gly Lys
    210               215
```

<210> SEQ ID NO 35
<211> LENGTH: 654
<212> TYPE: DNA
<213> ORGANISM: Bubalus arnee

<400> SEQUENCE: 35

```
gcacctgagt tcctgggggg accatcagtc ttcctgttcc ccccaaaacc caaggacact    60
ctcatgatct cccggacccc tgaggtcacg tgcgtggtgg tggacgtgag ccaggaagac   120
cccgaggtcc agttcaactg gtacgtggat ggcgtggagg tgcataatgc caagacaaag   180
ccgcgggagg agcagttcaa cagcacgtac cgtgtggtca gcgtcctcac cgtcctgcac   240
caggactggc tgaacggcaa ggagtacaag tgcaaggtct ccaacaaagg cctcccgtcc   300
tccatcgaga aaccatctc caaagccaaa gggcagcccc gagagccaca ggtgtacacc    360
ctgccccat cccaggagga gatgaccaag aaccaggtca gcctgacctg cctggtcaaa     420
ggcttctacc ccagcgacat cgccgtggag tgggagagca atgggcagcc ggagaacaac   480
tacaagacca cgcctcccgt gctggactcc gacggctcct tcttcctcta cagcaagctc   540
accgtggaca gagcaggtg gcaggagggg aacgtcttct catgctccgt gatgcatgag    600
gctctgcaca accactacac gcagaagagc ctctccctgt ctctgggtaa atga         654
```

<210> SEQ ID NO 36
<211> LENGTH: 106
<212> TYPE: PRT
<213> ORGANISM: Bubalus arnee

<400> SEQUENCE: 36

```
Ala Asp Ala Ala Pro Thr Val Ser Ile Phe Pro Pro Ser Ser Glu Gln
1               5                  10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105
```

<210> SEQ ID NO 37
<211> LENGTH: 321
<212> TYPE: DNA
<213> ORGANISM: Bubalus arnee

<400> SEQUENCE: 37

```
gctgatgctg caccaactgt atccatcttc ccaccatcca gtgagcagtt aacatctgga    60
ggtgcctcag tcgtgtgctt cttgaacaac ttctacccca agacatcaa tgtcaagtgg   120
```

```
aagattgatg gcagtgaacg acaaaatggc gtcctgaaca gttggactga tcaggacagc       180
aaagacagca cctacagcat gagcagcacc ctcacgttga ccaaggacga gtatgaacga       240
cataacagct atacctgtga ggccactcac aagacatcaa cttcacccat tgtcaagagc       300
ttcaacagga atgagtgtta g                                                 321
```

<210> SEQ ID NO 38
<211> LENGTH: 106
<212> TYPE: PRT
<213> ORGANISM: Bubalus arnee

<400> SEQUENCE: 38

```
Gly Gln Pro Lys Ser Ser Pro Ser Val Thr Leu Phe Pro Pro Ser Ser
1               5                   10                  15

Glu Glu Leu Glu Thr Asn Lys Ala Thr Leu Val Cys Thr Ile Thr Asp
            20                  25                  30

Phe Tyr Pro Gly Val Val Thr Val Asp Trp Lys Val Asp Gly Thr Pro
        35                  40                  45

Val Thr Gln Gly Met Glu Thr Thr Gln Pro Ser Lys Gln Ser Asn Asn
    50                  55                  60

Lys Tyr Met Ala Ser Ser Tyr Leu Thr Leu Thr Ala Arg Ala Trp Glu
65                  70                  75                  80

Arg His Ser Ser Tyr Ser Cys Gln Val Thr His Glu Gly His Thr Val
                85                  90                  95

Glu Lys Ser Leu Ser Arg Ala Asp Cys Ser
            100                 105
```

<210> SEQ ID NO 39
<211> LENGTH: 321
<212> TYPE: DNA
<213> ORGANISM: Bubalus arnee

<400> SEQUENCE: 39

```
ggccagccca agtcttcgcc atcagtcacc ctgtttccac cttcctctga agagctcgag       60
actaacaagg ccacactggt gtgtacgatc actgatttct acccaggtgt ggtgacagtg       120
gactggaagg tagatggtac ccctgtcact cagggtatgg agacaaccca gccttccaaa       180
cagagcaaca acaagtacat ggctagcagc tacctgaccc tgacagcaag agcatgggaa       240
aggcatagca gttacagctg ccaggtcact catgaaggtc acactgtgga aaagagtttg       300
tcccgtgctg actgttccta g                                                 321
```

<210> SEQ ID NO 40
<211> LENGTH: 105
<212> TYPE: PRT
<213> ORGANISM: Bubalus arnee

<400> SEQUENCE: 40

```
Gly Gln Pro Lys Ser Thr Pro Thr Leu Thr Val Phe Pro Pro Ser Ser
1               5                   10                  15

Glu Glu Leu Lys Glu Asn Lys Ala Thr Leu Val Cys Leu Ile Ser Asn
            20                  25                  30

Phe Ser Pro Ser Gly Val Thr Val Ala Trp Lys Ala Asn Gly Thr Pro
        35                  40                  45

Ile Thr Gln Gly Val Asp Thr Ser Asn Pro Thr Lys Glu Gly Asn Lys
    50                  55                  60

Phe Met Ala Ser Ser Phe Leu His Leu Thr Ser Asp Gln Trp Arg Ser
65                  70                  75                  80
```

His Asn Ser Phe Thr Cys Gln Val Thr His Glu Gly Asp Thr Val Glu
                85                  90                  95

Lys Ser Leu Ser Pro Ala Glu Cys Leu
            100                 105

<210> SEQ ID NO 41
<211> LENGTH: 318
<212> TYPE: DNA
<213> ORGANISM: Bubalus arnee

<400> SEQUENCE: 41
ggtcagccca agtccactcc cactctcacc gtgtttccac cttcctctga ggagctcaag      60
gaaaacaaag ccacactggt gtgtctgatt ccaactttt ccccgagtgg tgtgacagtg     120
gcctggaagg caaatggtac acctatcacc agggtgtgg acacttcaaa tcccaccaaa     180
gagggcaaca agttcatggc cagcagcttc ctacatttga catcggacca gtggagatct     240
cacaacagtt ttacctgtca agttacacat gaaggggaca ctgtggagaa gagtctgtct     300
cctgcagaat gtctctaa                                                   318

<210> SEQ ID NO 42
<211> LENGTH: 105
<212> TYPE: PRT
<213> ORGANISM: Bubalus arnee

<400> SEQUENCE: 42

Gly Gln Pro Lys Ser Thr Pro Thr Leu Thr Met Phe Pro Pro Ser Pro
1               5                   10                  15

Glu Glu Leu Gln Glu Asn Lys Ala Thr Leu Val Cys Leu Ile Ser Asn
            20                  25                  30

Phe Ser Pro Ser Gly Val Thr Val Ala Trp Lys Ala Asn Gly Thr Pro
        35                  40                  45

Ile Thr Gln Gly Val Asp Thr Ser Asn Pro Lys Glu Asp Asn Lys
    50                  55                  60

Tyr Met Ala Ser Ser Phe Leu His Leu Thr Ser Asp Gln Trp Arg Ser
65                  70                  75                  80

His Asn Ser Phe Thr Cys Gln Val Thr His Glu Gly Asp Thr Val Glu
                85                  90                  95

Lys Ser Leu Ser Pro Ala Glu Cys Leu
            100                 105

<210> SEQ ID NO 43
<211> LENGTH: 318
<212> TYPE: DNA
<213> ORGANISM: Bubalus arnee

<400> SEQUENCE: 43
ggtcagccca agtccactcc cacactcacc atgtttccac cttcccctga ggagctccag      60
gaaaacaaag ccacactcgt gtgtctgatt ccaattttt ccccaagtgg tgtgacagtg     120
gcctggaagg caaatggtac acctatcacc agggtgtgg acacttcaaa tcccaccaaa     180
gaggacaaca agtacatggc cagcagcttc ttacatttga catcggacca gtggagatct     240
cacaacagtt ttacctgcca agttacacat gaaggggaca ctgtggagaa gagtctgtct     300
cctgcagaat gtctctaa                                                   318

<210> SEQ ID NO 44
<211> LENGTH: 324

```
<212> TYPE: PRT
<213> ORGANISM: Bubalus arnee

<400> SEQUENCE: 44

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Glu Ser Asp Leu Tyr Thr Leu
    50                  55                  60

Ser Ser Ser Val Thr Val Pro Ser Ser Pro Arg Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asn Thr Asn Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 45
<211> LENGTH: 975
<212> TYPE: DNA
<213> ORGANISM: Bubalus arnee

<400> SEQUENCE: 45
gccaaaacga caccccatc tgtctatcca ctggcccctg gatctgctgc ccaaactaac    60
tccatggtga ccctgggatg cctggtcaag ggctatttcc ctgagccagt gacagtgacc   120
```

-continued

```
tggaactctg gatccctgtc cagcggtgtg cacaccttcc cagctgtcct ggagtctgac       180
ctctacactc tgagcagctc agtgactgtc ccctccagcc ctcggcccag cgagaccgtc       240
acctgcaacg ttgcccaccc ggccagcagc accaaggtgg acaagaaaat tgtgcccagg       300
gattgtggtt gtaagccttg catatgtaca gtcccagaag tatcatctgt cttcatcttc       360
cccccaaagc ccaaggatgt gctcaccatt actctgactc taaggtcac gtgtgttgtg        420 gtagacatca gcaaggatga tcccgaggtc cagttcagct ggtttgtaga tgatgtggag       480
gtgcacacag ctcagacgca accccgggag gagcagttca acagcacttt ccgctcagtc       540
agtgaacttc ccatcatgca ccaggactgg ctcaatggca aggagttcaa atgcagggtc       600
aacagtgcag ctttccctgc ccccatcgag aaaaccatct ccaaaccaa aggcagaccg        660 aaggctccac aggtgtacac cattccacct cccaaggagc agatggccaa ggataaagtc       720
agtctgacct gcatgataac agacttcttc cctgaagaca ttactgtgga gtggcagtgg      780
aatgggcagc cagcggagaa ctacaagaac actcagccca tcatgaacac gaatggctct      840
tacttcgtct acagcaagct caatgtgcag aagagcaact gggaggcagg aaatactttc       900
acctgctctg tgttacatga gggcctgcac aaccaccata ctgagaagag cctctcccac       960
tctcctggta aatga                                                       975
```

<210> SEQ ID NO 46
<211> LENGTH: 324
<212> TYPE: PRT
<213> ORGANISM: Bubalus arnee

<400> SEQUENCE: 46

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Gln Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Lys Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220
```

| Val | Tyr | Thr | Ile | Pro | Pro | Lys | Glu | Gln | Met | Ala | Lys | Asp | Lys | Val |
| 225 | | | | 230 | | | | | 235 | | | | | 240 |

Ser Leu Thr Cys Met Ile Thr Asn Phe Phe Pro Glu Asp Ile Thr Val
    245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305             310                 315                 320

Ser Pro Gly Lys

<210> SEQ ID NO 47
<211> LENGTH: 975
<212> TYPE: DNA
<213> ORGANISM: Bubalus arnee

<400> SEQUENCE: 47

```
gccaaaacga caccccatc tgtctatcca ctggcccctg gatctgctgc ccaaactaac      60
tccatggtga ccctgggatg cctggtcaag ggctatttcc ctgagccagt gacagtgacc     120
tggaactctg gatccctgtc cagcggtgtg cacaccttcc cagctgtcct gcagtctgac     180
ctctacactc tgagcagctc agtgactgtc ccctccagca cctggcccag ccagaccgtc     240
acctgcaacg ttgcccaccc ggccagcagc accaaggtgg acaagaaaat tgtgcccagg     300
gattgtggtt gtaagccttg catatgtaca gtcccagaag tatcatctgt cttcatcttc     360
cccccaaagc ccaaggatgt gctcaccatt actctgactc ctaaggtcac gtgtgttgtg     420
gtagacatca gcaaggatga tcccgaggtc cagttcagct ggtttgtaga tgatgtggag     480
gtgcacacag ctcagacgaa accccgggag gagcagatca cagcactttt ccgttcagtc     540
agtgaacttc ccatcatgca ccaggactgg ctcaatggca aggagttcaa atgcagggtc     600
aacagtgcag ctttccctgc ccccatcgag aaaaccatct ccaaaaccaa aggcagaccg     660
aaggctccac aggtgtacac cattccacct cccaaggagc agatggccaa ggataaagtc     720
agtctgacct gcatgataac aaacttcttc cctgaagaca ttactgtgga gtggcagtgg     780
aatgggcagc cagcggagaa ctacaagaac actcagccca tcatggacac agatggctct     840
tacttcgtct acagcaagct caatgtgcag aagagcaact gggaggcagg aaatactttc     900
acctgctctg tgttacatga gggcctgcac aaccaccata ctgagaagag cctctcccac     960
tctcctggta aatga                                                     975
```

<210> SEQ ID NO 48
<211> LENGTH: 330
<212> TYPE: PRT
<213> ORGANISM: Bubalus arnee

<400> SEQUENCE: 48

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
            115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
            195                 200                 205

Lys Asp Leu Pro Ala Pro Ile Glu Arg Thr Ile Ser Lys Pro Lys Gly
210                 215                 220

Ser Val Arg Ala Pro Gln Val Tyr Val Leu Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
            275                 280                 285

Met Tyr Ser Lys Leu Arg Val Glu Lys Lys Asn Trp Val Glu Arg Asn
290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 49
<211> LENGTH: 993
<212> TYPE: DNA
<213> ORGANISM: Bubalus arnee

<400> SEQUENCE: 49
gccaaaacaa cagccccatc ggtctatcca ctggcccctg tgtgtggaga tacaactggc     60
tcctcggtga ctctaggatg cctggtcaag ggttatttcc ctgagccagt gaccttgacc    120
tggaactctg gatccctgtc cagtggtgtg cacaccttcc agctgtcct gcagtctgac     180 ctctacaccc tcagcagctc agtgactgta acctcgagca cctggcccag ccagtccatc    240
acctgcaatg tggcccaccc ggcaagcagc accaaggtgg acaagaaaat tgagcccaga    300
gggcccacaa tcaagccctg tcctccatgc aaatgcccag cacctaacct cttgggtgga    360
ccatccgtct tcatcttccc tccaaagatc aaggatgtac tcatgatctc cctgagcccc    420
atagtcacat gtgtggtggt ggatgtgagc gaggatgacc cagatgtcca gatcagctgg    480

-continued

```
tttgtgaaca acgtggaagt acacacagct cagacacaaa cccatagaga ggattacaac      540
agtactctcc gggtggtcag tgccctcccc atccagcacc aggactggat gagtggcaag      600
gagttcaaat gcaaggtcaa caacaaagac ctcccagcgc ccatcgagag aaccatctca      660
aaacccaaag ggtcagtaag agctccacag gtatatgtct tgcctccacc agaagaagag      720
atgactaaga acaggtcac tctgacctgc atggtcacag acttcatgcc tgaagacatt       780
tacgtggagt ggaccaacaa cgggaaaaca gagctaaact acaagaacac tgaaccagtc      840
ctggactctg atggttctta cttcatgtac agcaagctga gagtggaaaa gaagaactgg      900
gtggaaagaa atagctactc ctgttcagtg gtccacgagg gtctgcacaa tcaccacacg      960
actaagagct tctcccggac tccgggtaaa tga                                   993
```

<210> SEQ ID NO 50
<211> LENGTH: 330
<212> TYPE: PRT
<213> ORGANISM: Bubalus arnee

<400> SEQUENCE: 50

```
Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Met Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val Leu Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Ala Leu Pro Ala Pro Ile Glu Arg Thr Ile Ser Lys Pro Lys Gly
        210                 215                 220

Ser Val Arg Ala Pro Gln Val Tyr Val Leu Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285
```

Met Tyr Ser Lys Leu Arg Val Glu Lys Lys Asn Trp Val Glu Arg Asn
          290                 295                 300

Ser Tyr Ser Cys Ser Val His Glu Gly Leu His Asn His His Thr
305                 310                 315                 320

Thr Lys Ser Phe Ser Arg Thr Pro Gly Lys
                325                 330

<210> SEQ ID NO 51
<211> LENGTH: 993
<212> TYPE: DNA
<213> ORGANISM: Bubalus arnee

<400> SEQUENCE: 51

| | | | | | |
|---|---|---|---|---|---|
| gccaaaacaa | cagccccatc | ggtctatcca | ctggcccctg | tgtgtggaga | tacaactggc | 60 |
| tcctcggtga | ctctaggatg | cctggtcaag | ggttatttcc | ctgagccagt | gaccttgacc | 120 |
| tggaactctg | gatccctgtc | cagtggtgtg | cacaccttcc | cagctgtcct | gcagtctgac | 180 |
| ctctacaccc | tcagcagctc | agtgactgta | acctcgagca | cctggcccag | ccagtccatc | 240 |
| acctgcaatg | tggcccaccc | ggcaagcagc | accaaggtgg | acaagaaaat | tgagcccaga | 300 |
| gggcccacaa | tcaagccctg | tcctccatgc | aaatgcccag | cacctaacct | cttgggtgga | 360 |
| ccatccgtct | tcatcttccc | tccaaagatc | aaggatgtac | tcatgatctc | cctgagtccc | 420 |
| atggtcacat | gtgtggtggt | ggatgtgagc | gaggatgacc | cagatgtcca | gatcagctgg | 480 |
| ttcgtgaaca | acgtggaagt | actcacagct | cagacacaaa | cccatagaga | ggattacaac | 540 |
| agtactctcc | gggtggtcag | tgccctcccc | atccagcacc | aggactggat | gagtggcaag | 600 |
| gagttcaaat | gcaaggtcaa | caacaaagcc | ctcccagcgc | ccatcgagag | aaccatctca | 660 |
| aaacccaaag | ggtcagtaag | agctccacag | gtatatgtct | tgcctccacc | agaagaagag | 720 |
| atgactaaga | acaggtcac | tctgacctgc | atggtcacag | acttcatgcc | tgaagacatt | 780 |
| tacgtggagt | ggaccaacaa | cgggaaaaca | gagctaaact | acaagaacac | tgaaccagtc | 840 |
| ctggactctg | atggttctta | cttcatgtac | agcaagctga | gagtggaaaa | gaagaactgg | 900 |
| gtggaaagaa | atagctactc | ctgttcagtg | gtccacgagg | gtctgcacaa | tcaccacacg | 960 |
| actaagagct | tctcccggac | tccgggtaaa | tga | | | 993 |

<210> SEQ ID NO 52
<211> LENGTH: 336
<212> TYPE: PRT
<213> ORGANISM: Bubalus arnee

<400> SEQUENCE: 52

Ala Lys Thr Thr Pro Pro Ser Val Tyr Pro Leu Ala Pro Gly Cys Gly
1               5                   10                  15

Asp Thr Thr Gly Ser Ser Val Thr Leu Gly Cys Leu Val Lys Gly Tyr
            20                  25                  30

Phe Pro Glu Ser Val Thr Val Trp Asn Ser Gly Ser Leu Ser Ser
        35                  40                  45

Ser Val His Thr Phe Pro Ala Leu Leu Gln Ser Gly Leu Tyr Thr Met
    50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
                85                  90                  95

Leu Glu Pro Ser Gly Pro Ile Ser Thr Ile Asn Pro Cys Pro Pro Cys

|  | 100 |  |  |  | 105 |  |  |  | 110 |  |  |
|---|---|---|---|---|---|---|---|---|---|---|---|

Lys Glu Cys His Lys Cys Pro Ala Pro Asn Leu Glu Gly Gly Pro Ser
   115       120      125

Val Phe Ile Phe Pro Asn Ile Lys Asp Val Leu Met Ile Ser Leu
130       135      140

Thr Pro Lys Val Thr Cys Val Val Asp Val Ser Glu Asp Asp Pro
145      150      155      160

Asp Val Gln Ile Ser Trp Phe Val Asn Asn Val Glu Val His Thr Ala
     165      170      175

Gln Thr Gln Thr His Arg Glu Asp Tyr Asn Ser Thr Ile Arg Val Val
     180      185      190

Ser Thr Leu Pro Ile Gln His Gln Asp Trp Met Ser Gly Lys Glu Phe
    195      200      205

Lys Cys Lys Val Asn Asn Lys Asp Leu Pro Ser Pro Ile Glu Arg Thr
    210      215      220

Ile Ser Lys Ile Lys Gly Leu Val Arg Ala Pro Gln Val Tyr Ile Leu
225      230      235      240

Pro Pro Pro Ala Glu Gln Leu Ser Arg Lys Asp Val Ser Leu Thr Cys
     245      250      255

Leu Val Val Gly Phe Asn Pro Gly Asp Ile Ser Val Glu Trp Thr Ser
     260      265      270

Asn Gly His Thr Glu Glu Asn Tyr Lys Asp Thr Ala Pro Val Leu Asp
    275      280      285

Ser Asp Gly Ser Tyr Phe Ile Tyr Ser Lys Leu Asn Met Lys Thr Ser
    290      295      300

Lys Trp Glu Lys Thr Asp Ser Phe Ser Cys Asn Val Arg His Glu Gly
305      310      315      320

Leu Lys Asn Tyr Tyr Leu Lys Lys Thr Ile Ser Arg Ser Pro Gly Lys
    325      330      335

<210> SEQ ID NO 53
<211> LENGTH: 1011
<212> TYPE: DNA
<213> ORGANISM: Bubalus arnee

<400> SEQUENCE: 53

| | | | | | |
|---|---|---|---|---|---|
| gccaaaacaa | cacccccatc | agtctatcca | ctggcccctg | ggtgtggaga | tacaactggt | 60 |
| tcctccgtga | ctctgggatg | cctggtcaag | ggctacttcc | ctgagtcagt | gactgtgact | 120 |
| tggaactctg | gatccctgtc | cagcagtgtg | cacaccttcc | cagctctcct | gcagtctgga | 180 |
| ctctacacta | tgagcagctc | agtgactgtc | ccctccagca | cttggccaag | tcagaccgtc | 240 |
| acctgcagcg | ttgctcaccc | agccagcagc | accacggtgg | acaaaaaact | tgagcccagc | 300 |
| gggcccattt | caacaatcaa | ccctgtcct | ccatgcaagg | agtgtcacaa | atgcccagct | 360 |
| cctaacctcg | agggtggacc | atccgtcttc | atcttccctc | caaatatcaa | ggatgtactc | 420 |
| atgatctccc | tgacacccaa | ggtcacgtgt | gtggtggtgg | atgtgagcga | ggatgaccca | 480 |
| gacgtccaga | tcagctggtt | tgtgaacaac | gtggaagtac | acacagctca | gacacaaacc | 540 |
| catagagagg | attacaacag | tactatccgg | gtggtcagca | ccctccccat | ccagcaccag | 600 |
| gactggatga | gtggcaagga | gttcaaatgc | aaggtcaaca | acaaagacct | cccatcaccc | 660 |
| atcgagagaa | ccatctcaaa | aattaaaggg | ctagtcagag | ctccacaagt | atacatcttg | 720 |
| ccgccaccag | cagagcagtt | gtccaggaaa | gatgtcagtc | tcacttgcct | ggtcgtgggc | 780 |
| ttcaaccctg | gagacatcag | tgtggagtgg | accagcaatg | ggcatacaga | ggagaactac | 840 |

```
aaggacaccg caccagtcct agactctgac ggttcttact tcatatatag caagctcaat    900
atgaaaacaa gcaagtggga gaaaacagat tccttctcat gcaacgtgag acacgagggt    960
ctgaaaaatt actacctgaa gaagaccatc tcccggtctc cgggtaaatg a             1011
```

<210> SEQ ID NO 54
<211> LENGTH: 336
<212> TYPE: PRT
<213> ORGANISM: Bubalus arnee

<400> SEQUENCE: 54

```
Ala Lys Thr Thr Pro Pro Ser Val Tyr Pro Leu Ala Pro Gly Cys Gly
1               5                   10                  15

Asp Thr Thr Gly Ser Ser Val Thr Ser Gly Cys Leu Val Lys Gly Tyr
            20                  25                  30

Phe Pro Glu Pro Val Thr Val Thr Trp Asn Ser Gly Ser Leu Ser Ser
        35                  40                  45

Ser Val His Thr Phe Pro Ala Leu Leu Gln Ser Gly Leu Tyr Thr Met
    50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
                85                  90                  95

Leu Glu Pro Ser Gly Pro Ile Ser Thr Ile Asn Pro Cys Pro Pro Cys
            100                 105                 110

Lys Glu Cys His Lys Cys Pro Ala Pro Asn Leu Glu Gly Gly Pro Ser
        115                 120                 125

Val Phe Ile Phe Pro Pro Asn Ile Lys Asp Val Leu Met Ile Ser Leu
    130                 135                 140

Thr Pro Lys Val Thr Cys Val Val Val Asp Val Ser Glu Asp Asp Pro
145                 150                 155                 160

Asp Val Gln Ile Ser Trp Phe Val Asn Asn Val Glu Val His Thr Ala
                165                 170                 175

Gln Thr Gln Thr His Arg Glu Asp Tyr Asn Ser Thr Ile Arg Val Val
            180                 185                 190

Ser Thr Leu Pro Ile Gln His Gln Asp Trp Met Ser Gly Lys Glu Phe
        195                 200                 205

Lys Cys Lys Val Asn Asn Lys Asp Leu Pro Ser Pro Ile Glu Arg Thr
    210                 215                 220

Ile Ser Lys Ile Lys Gly Leu Val Arg Ala Pro Gln Val Tyr Thr Leu
225                 230                 235                 240

Pro Pro Pro Ala Glu Gln Leu Ser Arg Lys Asp Val Ser Leu Thr Cys
                245                 250                 255

Leu Val Val Gly Phe Asn Pro Gly Asp Ile Ser Val Glu Trp Thr Ser
            260                 265                 270

Asn Gly His Thr Glu Glu Asn Tyr Lys Asp Thr Ala Pro Val Leu Asp
        275                 280                 285

Ser Asp Gly Ser Tyr Phe Ile Tyr Ser Lys Leu Asn Met Lys Thr Ser
    290                 295                 300

Lys Trp Glu Lys Thr Asp Ser Phe Ser Cys Asn Val Arg His Glu Gly
305                 310                 315                 320

Leu Lys Asn Tyr Tyr Leu Lys Lys Thr Ile Ser Arg Ser Pro Gly Lys
                325                 330                 335
```

<210> SEQ ID NO 55
<211> LENGTH: 1011
<212> TYPE: DNA
<213> ORGANISM: Bubalus arnee

<400> SEQUENCE: 55

```
gccaaaacaa cacccccatc agtctatcca ctggcccctg ggtgtggaga tacaactggt      60
tcctccgtga cctctgggtg cctggtcaag gggtacttcc ctgagccagt gactgtgact     120
tggaactctg gatccctgtc cagcagtgtg cacaccttcc cagctctcct gcagtctgga     180
ctctacacta tgagcagctc agtgactgtc ccctccagca cctggccaag tcagaccgtc     240
acctgcagcg ttgctcaccc agccagcagc accacggtgg acaaaaaact tgagcccagc     300
gggcccattt caacaatcaa cccctgtcct ccatgcaagg agtgtcacaa atgcccagct     360
cctaacctcg agggtggacc atccgtcttc atcttccctc caaatatcaa ggatgtactc     420
atgatctccc tgacacccaa ggtcacgtgt gtggtggtgg atgtgagcga ggatgaccca     480
gacgtccaga tcagctggtt tgtgaacaac gtggaagtac acacagctca gacacaaacc     540
catagagagg attacaacag tactatccgg gtggtcagca ccctccccat ccagcaccag     600
gactggatga gtggcaagga gttcaaatgc aaggtgaaca acaaagacct cccatcaccc     660
atcgagagaa ccatctcaaa aattaaaggg ctagtcagag ctccacaagt atacactttg     720
ccgccaccag cagagcagtt gtccaggaaa gatgtcagtc tcacttgcct ggtcgtgggc     780
ttcaaccctg agacatcag tgtggagtgg accagcaatg ggcatacaga ggagaactac     840
aaggacaccg caccagttct tgactctgac ggttcttact tcatatatag caagctcaat     900
atgaaaacaa gcaagtggga gaaaacagat tccttctcat gcaacgtgag acacgagggt     960
ctgaaaaatt actacctgaa gaagaccatc tcccggtctc cgggtaaatg a             1011
```

<210> SEQ ID NO 56
<211> LENGTH: 335
<212> TYPE: PRT
<213> ORGANISM: Bubalus arnee

<400> SEQUENCE: 56

```
Ala Lys Thr Thr Ala Pro Ser Val Tyr Pro Leu Ala Pro Val Cys Gly
1               5                   10                  15

Gly Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Leu Leu Gln Ser Gly Leu Tyr Thr Leu
    50                  55                  60

Ser Ser Ser Val Thr Val Thr Ser Asn Thr Trp Pro Ser Gln Thr Ile
65                  70                  75                  80

Thr Cys Asn Val Ala His Pro Ala Ser Ser Thr Lys Val Asp Lys Lys
                85                  90                  95

Ile Glu Pro Arg Val Pro Ile Thr Gln Asn Pro Cys Pro Pro Leu Lys
            100                 105                 110

Glu Cys Pro Pro Cys Ala Ala Pro Asp Leu Leu Gly Gly Pro Ser Val
        115                 120                 125

Phe Ile Phe Pro Pro Lys Ile Lys Asp Val Leu Met Ile Ser Leu Ser
    130                 135                 140

Pro Met Val Thr Cys Val Val Val Asp Val Ser Glu Asp Asp Pro Asp
145                 150                 155                 160
```

```
Val Gln Ile Ser Trp Phe Val Asn Asn Val Glu His Thr Ala Gln
            165                 170                 175

Thr Gln Thr His Arg Glu Asp Tyr Asn Ser Thr Leu Arg Val Val Ser
        180                 185                 190

Ala Leu Pro Ile Gln His Gln Asp Trp Met Ser Gly Lys Glu Phe Lys
            195                 200                 205

Cys Lys Val Asn Asn Arg Ala Leu Pro Ser Pro Ile Glu Lys Thr Ile
        210                 215                 220

Ser Lys Pro Arg Gly Pro Val Arg Ala Pro Gln Val Tyr Val Leu Pro
225                 230                 235                 240

Pro Pro Ala Glu Glu Met Thr Lys Lys Glu Phe Ser Leu Thr Cys Met
                245                 250                 255

Ile Thr Gly Phe Leu Pro Ala Glu Ile Ala Val Asp Trp Thr Ser Asn
            260                 265                 270

Gly Arg Thr Glu Gln Asn Tyr Lys Asn Thr Ala Thr Val Leu Asp Ser
        275                 280                 285

Asp Gly Ser Tyr Phe Met Tyr Ser Lys Leu Arg Val Gln Lys Ser Thr
    290                 295                 300

Trp Glu Arg Gly Ser Leu Phe Ala Cys Ser Val Val His Glu Val Leu
305                 310                 315                 320

His Asn His Leu Thr Thr Lys Thr Ile Ser Arg Ser Leu Gly Lys
                325                 330                 335

<210> SEQ ID NO 57
<211> LENGTH: 1008
<212> TYPE: DNA
<213> ORGANISM: Bubalus arnee

<400> SEQUENCE: 57
gccaaaacaa cagccccatc ggtctatcca ctggcccctg tgtgtggagg tacaactggc      60
tcctcggtga ctctaggatg cctggtcaag ggttatttcc ctgagccagt gaccttgacc     120
tggaactctg gatccctgtc cagtggtgtg cacaccttcc cagctctcct gcagtctggc     180
ctctacaccc tcagcagctc agtgactgta acctcgaaca cctggcccag ccagaccatc     240
acctgcaatg tggcccaccc ggcaagcagc accaaagtgg acaagaaaat tgagcccaga     300
gtgcccataa cacagaaccc ctgtcctcca ctcaaagagt gtcccccatg cgcagctcca     360
gacctcttgg gtgaccatc cgtcttcatc ttccctccaa agatcaagga tgtactcatg     420
atctccctga gccccatggt cacatgtgtg gtggtggatg tgagcgagga tgacccagac     480
gtccagatca gctggtttgt gaacaacgtg aagtacacac agctcagac acaaacccat     540 agagaggatt acaacagtac tctccgggtg gtcagtgccc tccccatcca gcaccaggac     600
tggatgagtg gcaaggagtt caaatgcaag gtcaacaaca gagccctccc atccccatc      660 gagaaaacca tctcaaaacc cagagggcca gtaagagctc cacaggtata tgtcttgcct     720
ccaccagcag aagagatgac taagaaagag ttcagtctga cctgcatgat cacaggcttc     780
ttacctgccg aaattgctgt ggactggacc agcaatgggc gtacagagca aaactacaag     840
aacaccgcaa cagtcctgga ctctgatggt tcttacttca gtacagcaa gctcagagta      900 caaaagagca cttgggaaag aggaagtctt ttcgcctgct cagtggtcca cgaggtgctg     960
cacaatcacc ttacgactaa gaccatctcc cggtctctgg gtaaatga               1008

<210> SEQ ID NO 58
<211> LENGTH: 335
<212> TYPE: PRT
```

<213> ORGANISM: Bubalus arnee

<400> SEQUENCE: 58

```
Ala Lys Thr Thr Ala Pro Ser Val Tyr Pro Leu Ala Pro Val Cys Gly
1               5                   10                  15
Gly Thr Thr Gly Ser Ser Val Thr Leu Gly Cys Leu Val Lys Gly Tyr
            20                  25                  30
Phe Pro Glu Pro Val Thr Leu Thr Trp Asn Ser Gly Ser Leu Ser Ser
        35                  40                  45
Gly Val His Thr Phe Pro Ala Leu Leu Gln Ser Gly Leu Tyr Thr Leu
    50                  55                  60
Ser Ser Ser Val Thr Val Thr Ser Asn Thr Trp Pro Ser Gln Thr Ile
65                  70                  75                  80
Thr Cys Asn Val Ala His Pro Ala Ser Ser Thr Lys Val Asp Lys Lys
                85                  90                  95
Ile Glu Ser Arg Arg Pro Ile Pro Pro Asn Ser Cys Pro Pro Cys Lys
            100                 105                 110
Glu Cys Ser Ile Phe Pro Ala Pro Asp Leu Leu Gly Gly Pro Ser Val
        115                 120                 125
Phe Ile Phe Pro Pro Lys Ile Lys Asp Val Leu Met Ile Ser Leu Ser
    130                 135                 140
Pro Ile Val Thr Cys Val Val Asp Val Ser Glu Asp Asp Pro Asp
145                 150                 155                 160
Val Gln Ile Ser Trp Phe Val Asn Asn Val Glu Val His Thr Ala Gln
                165                 170                 175
Thr Gln Thr His Arg Glu Asp Tyr Asn Ser Thr Leu Arg Val Val Ser
            180                 185                 190
Ala Leu Pro Ile Gln His Gln Asp Trp Met Ser Gly Lys Glu Phe Lys
        195                 200                 205
Cys Lys Val Asn Asn Arg Ala Leu Pro Ser Pro Ile Glu Lys Thr Ile
    210                 215                 220
Ser Lys Pro Arg Gly Pro Val Arg Ala Pro Gln Val Tyr Val Leu Pro
225                 230                 235                 240
Pro Pro Ala Glu Glu Met Thr Lys Lys Glu Phe Ser Leu Thr Cys Met
                245                 250                 255
Ile Thr Asp Phe Leu Pro Ala Glu Ile Ala Val Asp Trp Thr Ser Asn
            260                 265                 270
Gly His Lys Glu Leu Asn Tyr Lys Asn Thr Ala Pro Val Leu Asp Thr
        275                 280                 285
Asp Gly Ser Tyr Phe Met Tyr Ser Lys Leu Arg Val Gln Lys Ser Thr
    290                 295                 300
Trp Glu Lys Gly Ser Leu Phe Ala Cys Ser Val Val His Glu Gly Leu
305                 310                 315                 320
His Asn His His Thr Thr Lys Thr Ile Ser Arg Ser Leu Gly Lys
                325                 330                 335
```

<210> SEQ ID NO 59
<211> LENGTH: 1008
<212> TYPE: DNA
<213> ORGANISM: Bubalus arnee

<400> SEQUENCE: 59

```
gccaaaacaa cagccccatc ggtctatcca ctggcccctg tgtgtggagg tacaactggc    60
tcctcggtga ctctaggatg cctggtcaag ggttatttcc ctgagccagt gaccttgacc   120
```

```
tggaactctg gatccctgtc cagtggtgtg cacaccttcc cagctctcct gcagtctggc      180
ctctacaccc tcagcagctc agtgactgta acctcgaaca cctggcccag ccagaccatc      240
acctgcaatg tggcccaccc ggcaagcagc accaaagtgg acaagaaaat tgaatccaga      300
aggcccatac cacccaactc ctgtcctcca tgcaaagagt gttccatatt cccagctcct      360
gacctcttgg gtggaccatc cgtcttcatc ttccctccaa agatcaagga tgtactcatg      420
atctccctga gccccatagt cacatgtgtg gtggtggatg tgagcgagga tgacccagat      480
gtccagatca gctggtttgt gaacaacgtg gaagtacaca cagctcagac acaaacccat      540
agagaggatt acaacagtac tctccgggtg gtcagtgccc tccccatcca gcaccaggac      600
tggatgagtg gcaaggagtt caaatgcaag gtcaacaaca gagccctccc atcccccatc      660
gagaaaacca tctcaaaacc cagagggcca gtaagagctc acaggtata tgtcttgcct       720 ccaccagcag aagagatgac taagaaagag ttcagtctga cctgcatgat cacagacttc      780
ttacctgccg aaattgctgt ggactggacc agcaatgggc ataaagagct gaactacaag      840
aacaccgcac cagtcctgga cactgatggt tcttacttca tgtacagcaa gctcagagtg      900
caaaagagca cttgggaaaa aggaagtctt ttcgcctgct cagtggtcca cgagggtctg      960
cacaatcacc atacgactaa gaccatctcc cggtctctgg gtaaatga                    1008
```

<210> SEQ ID NO 60
<211> LENGTH: 335
<212> TYPE: PRT
<213> ORGANISM: Bubalus arnee

<400> SEQUENCE: 60

```
Ala Lys Thr Thr Ala Pro Ser Val Tyr Pro Leu Ala Pro Val Cys Gly
1               5                   10                  15

Gly Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Leu Leu Gln Ser Gly Leu Tyr Thr Leu
    50                  55                  60

Ser Ser Ser Val Thr Val Thr Ser Asn Thr Trp Pro Ser Gln Thr Ile
65                  70                  75                  80

Thr Cys Asn Val Ala His Pro Ala Ser Ser Thr Lys Val Asp Lys Lys
                85                  90                  95

Ile Glu Pro Arg Val Pro Ile Thr Gln Asn Pro Cys Pro Pro Leu Lys
            100                 105                 110

Glu Cys Pro Pro Cys Ala Ala Pro Asp Leu Leu Gly Gly Pro Ser Val
        115                 120                 125

Phe Ile Phe Pro Pro Lys Ile Lys Asp Val Leu Met Ile Ser Leu Ser
    130                 135                 140

Pro Met Val Thr Cys Val Val Val Asp Val Ser Glu Asp Asp Pro Asp
145                 150                 155                 160

Val Gln Ile Ser Trp Phe Val Asn Asn Val Glu Val His Thr Ala Gln
                165                 170                 175

Thr Gln Thr His Arg Glu Asp Tyr Asn Ser Thr Leu Arg Val Val Ser
            180                 185                 190

Ala Leu Pro Ile Gln His Gln Asp Trp Met Ser Gly Lys Glu Phe Lys
        195                 200                 205

Cys Lys Val Asn Asn Arg Ala Leu Pro Ser Pro Ile Glu Lys Thr Ile
    210                 215                 220
```

Ser Lys Pro Arg Gly Pro Val Arg Ala Pro Gln Val Tyr Val Leu Pro
225                 230                 235                 240

Pro Pro Ala Glu Glu Met Thr Lys Lys Glu Phe Ser Leu Thr Cys Met
            245                 250                 255

Ile Thr Gly Phe Leu Pro Ala Glu Ile Ala Val Asp Trp Thr Ser Asn
        260                 265                 270

Gly Arg Thr Glu Gln Asn Tyr Lys Asn Thr Ala Thr Val Leu Asp Ser
    275                 280                 285

Asp Gly Ser Tyr Phe Met Tyr Ser Lys Leu Arg Val Gln Lys Ser Thr
290                 295                 300

Trp Glu Arg Gly Ser Leu Phe Ala Cys Ser Val Val His Glu Gly Leu
305                 310                 315                 320

His Asn His Leu Thr Thr Lys Thr Ile Ser Arg Ser Leu Gly Lys
                325                 330                 335

<210> SEQ ID NO 61
<211> LENGTH: 1008
<212> TYPE: DNA
<213> ORGANISM: Bubalus arnee

<400> SEQUENCE: 61
gccaaaacaa cagccccatc ggtctatcca ctggcccctg tgtgtggagg tacaactggc    60
tcctcggtga ctctaggatg cctggtcaag ggttatttcc ctgagccagt gaccttgacc   120
tggaactctg gatccctgtc cagtggtgtg cacaccttcc cagctctcct gcagtctggc   180
ctctacaccc tcagcagctc agtgactgta acctcgaaca cctggcccag ccagaccatc   240
acctgcaatg tggcccaccc ggcaagcagc accaaagtgg acaagaaaat tgagcccaga   300
gtgcccataa cacagaaccc ctgtcctcca ctcaaagagt gtcccccatg cgcagctcca   360
gacctcttgg gtggaccatc cgtcttcatc ttccctccaa agatcaagga tgtactcatg   420
atctccctga gccccatggt cacatgtgtg gtggtggatg tgagcgagga tgacccagac   480
gtccagatca gctggtttgt gaacaacgtg gaagtacaca cagctcagac acaaacccat   540
agagaggatt acaacagtac tctccgggtg gtcagtgccc tccccatcca gcaccaggac   600
tggatgagtg gcaaggagtt caaatgcaag gtcaacaaca gagccctccc atccccatc    660
gagaaaacca tctcaaaacc cagagggcca gtaagagctc cacaggtata tgtcttgcct   720
ccaccagcag aagagatgac taagaaagag ttcagtctga cctgcatgat cacaggcttc   780
ttacctgccg aaattgctgt ggactggacc agcaatgggc gtacagagca aaactacaag   840
aacaccgcaa cagtcctgga ctctgatggt tcttacttca tgtacagcaa gctcagagta   900
caaaagagca cttgggaaag aggaagtctt ttcgcctgct cagtggtcca cgagggtctg   960
cacaatcacc ttacgactaa gaccatctcc cggtctctgg gtaaatga             1008

<210> SEQ ID NO 62
<211> LENGTH: 330
<212> TYPE: PRT
<213> ORGANISM: Bubalus arnee

<400> SEQUENCE: 62

Ala Thr Thr Thr Ala Pro Ser Val Tyr Pro Leu Val Pro Gly Cys Ser
1               5                   10                  15

Asp Thr Ser Gly Ser Ser Val Thr Leu Gly Cys Leu Val Lys Gly Tyr
            20                  25                  30

Phe Pro Glu Pro Val Thr Val Lys Trp Asn Tyr Gly Ala Leu Ser Ser

```
                35                  40                  45
Gly Val Arg Thr Val Ser Ser Val Leu Gln Ser Gly Phe Tyr Ser Leu
 50                  55                  60

Ser Ser Leu Val Thr Val Pro Ser Ser Thr Trp Pro Ser Gln Thr Val
 65                  70                  75                  80

Ile Cys Asn Val Ala His Pro Ala Ser Lys Thr Glu Leu Ile Lys Arg
                 85                  90                  95

Ile Glu Pro Arg Ile Pro Lys Pro Ser Thr Pro Pro Gly Ser Ser Cys
                100                 105                 110

Pro Pro Gly Asn Ile Leu Gly Gly Pro Ser Val Phe Ile Phe Pro Pro
            115                 120                 125

Lys Pro Lys Asp Ala Leu Met Ile Ser Leu Thr Pro Lys Val Thr Cys
130                 135                 140

Val Val Val Asp Val Ser Glu Asp Pro Asp Val His Val Ser Trp
145                 150                 155                 160

Phe Val Asp Asn Lys Glu Val His Thr Ala Trp Thr Gln Pro Arg Glu
                165                 170                 175

Ala Gln Tyr Asn Ser Thr Phe Arg Val Val Ser Ala Leu Pro Ile Gln
            180                 185                 190

His Gln Asp Trp Met Arg Gly Lys Glu Phe Lys Cys Lys Val Asn Asn
        195                 200                 205

Lys Ala Leu Pro Ala Pro Ile Glu Arg Thr Ile Ser Lys Pro Lys Gly
210                 215                 220

Arg Ala Gln Thr Pro Gln Val Tyr Thr Ile Pro Pro Pro Arg Glu Gln
225                 230                 235                 240

Met Ser Lys Lys Lys Val Ser Leu Thr Cys Leu Val Thr Asn Phe Phe
                245                 250                 255

Ser Glu Ala Ile Ser Val Glu Trp Glu Arg Asn Gly Glu Leu Glu Gln
            260                 265                 270

Asp Tyr Lys Asn Thr Pro Pro Ile Leu Asp Ser Asp Gly Thr Tyr Phe
        275                 280                 285

Leu Tyr Ser Lys Leu Thr Val Asp Thr Asp Ser Trp Leu Gln Gly Glu
290                 295                 300

Ile Phe Thr Cys Ser Val Val His Glu Ala Leu His Asn His His Thr
305                 310                 315                 320

Gln Lys Asn Leu Ser Arg Ser Pro Gly Lys
                325                 330

<210> SEQ ID NO 63
<211> LENGTH: 993
<212> TYPE: DNA
<213> ORGANISM: Bubalus arnee

<400> SEQUENCE: 63
gctacaacaa cagccccatc tgtctatccc ttggtccctg gctgcagtga cacatctgga      60
tcctcggtga cactgggatg ccttgtcaaa ggctacttcc ctgagccggt aactgtaaaa     120
tggaactatg gagccctgtc cagcggtgtg cgcacagtct catctgtcct gcagtctggg     180
ttctattccc tcagcagctt ggtgactgta ccctccagca cctggcccag ccagactgtc     240
atctgcaacg tagcccaccc agccagcaag actgagttga tcaagagaat cgagcctaga     300
atacccaagc ccagtacccc cccaggttct tcatgcccac tggtaacatc ttgggtgga     360 ccatccgtct tcatcttccc cccaaagccc aaggatgcac tcatgatctc cctaaccccc     420
aaggttacgt gtgtggtggt ggatgtgagc gaggatgacc cagatgtcca tgtcagctgg     480
```

```
tttgtggaca acaaagaagt acacacagcc tggacacagc cccgtgaagc tcagtacaac    540
agtaccttcc gagtggtcag tgccctcccc atccagcacc aggactggat gaggggcaag    600
gagttcaaat gcaaggtcaa caacaaagcc ctcccagccc ccatcgagag aaccatctca    660
aaacccaaag aagagcccca gacacctcaa gtatacacca taccccccacc tcgtgaacaa    720 atgtccaaga agaaggttag tctgacctgc ctggtcacca acttcttctc tgaagccatc    780
agtgtggagt gggaaaggaa cggagaactg gagcaggatt acaagaacac tccacccatc    840
ctggactcag atgggaccta cttcctctac agcaagctca ctgtggatac agacagttgg    900
ttgcaaggag aaatttttac ctgctccgtg gtgcatgagg ctctccataa ccaccacaca    960
cagaagaacc tgtctcgctc ccctggtaaa tga                                 993
```

<210> SEQ ID NO 64
<211> LENGTH: 105
<212> TYPE: PRT
<213> ORGANISM: Bubalus arnee

<400> SEQUENCE: 64

```
Gln Pro Lys Ser Pro Pro Ser Val Thr Leu Phe Pro Pro Ser Thr Glu
1               5                   10                  15

Glu Leu Asn Gly Asn Lys Ala Thr Leu Val Cys Leu Ile Ser Asp Phe
            20                  25                  30

Tyr Pro Gly Ser Val Thr Val Val Trp Lys Ala Asp Gly Ser Thr Ile
        35                  40                  45

Thr Arg Asn Val Glu Thr Thr Arg Ala Ser Lys Gln Ser Asn Ser Lys
    50                  55                  60

Tyr Ala Ala Ser Ser Tyr Leu Ser Leu Thr Ser Ser Asp Trp Lys Ser
65                  70                  75                  80

Lys Gly Ser Tyr Ser Cys Glu Val Thr His Glu Gly Ser Thr Val Thr
                85                  90                  95

Lys Thr Val Lys Pro Ser Glu Cys Ser
            100                 105
```

<210> SEQ ID NO 65
<211> LENGTH: 318
<212> TYPE: DNA
<213> ORGANISM: Bubalus arnee

<400> SEQUENCE: 65

```
cagcccaagt ccccaccctc ggtcaccctg ttcccgccct ccacggagga gctcaacggc     60
aacaaggcca ccctggtgtg tctcatcagc gacttctacc cgggtagcgt gaccgtggtc    120
tggaaggcag acggcagcac catcacccgc aacgtggaga ccaccggggc tccaaacag    180 agcaacagca agtacgcggc cagcagctac ctgagcctga cgagcagcga ctggaaatcg    240
aaaggcagtt acagctgcga ggtcacgcac gaggggagca ccgtgacgaa gacagtgaag    300 cccctcagagt gttcttag                                                 318
```

<210> SEQ ID NO 66
<211> LENGTH: 329
<212> TYPE: PRT
<213> ORGANISM: Bubalus arnee

<400> SEQUENCE: 66

```
Ala Ser Thr Thr Ala Pro Lys Val Tyr Pro Leu Ser Ser Cys Cys Gly
1               5                   10                  15
```

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Gly Ser Thr Ser Gly Gln Thr Phe
65                  70                  75                  80

Thr Cys Asn Val Ala His Pro Ala Ser Ser Thr Lys Val Asp Lys Ala
                85                  90                  95

Val Asp Pro Thr Cys Lys Pro Ser Pro Cys Asp Cys Cys Pro Pro Pro
            100                 105                 110

Glu Leu Pro Gly Gly Pro Ser Val Phe Ile Phe Pro Pro Lys Pro Lys
        115                 120                 125

Asp Thr Leu Thr Ile Ser Gly Thr Pro Glu Val Thr Cys Val Val Val
    130                 135                 140

Asp Val Gly His Asp Asp Pro Glu Val Lys Phe Ser Trp Phe Val Asp
145                 150                 155                 160

Asp Val Glu Val Asn Thr Ala Thr Thr Lys Pro Arg Glu Glu Gln Phe
                165                 170                 175

Asn Ser Thr Tyr Arg Val Val Ser Ala Leu Arg Ile Gln His Gln Asp
            180                 185                 190

Trp Thr Gly Gly Lys Glu Phe Lys Cys Lys Val His Asn Glu Gly Leu
        195                 200                 205

Pro Ala Pro Ile Val Arg Thr Ile Ser Arg Thr Lys Gly Pro Ala Arg
    210                 215                 220

Glu Pro Gln Val Tyr Val Leu Ala Pro Pro Gln Glu Glu Leu Ser Lys
225                 230                 235                 240

Ser Thr Val Ser Leu Thr Cys Met Val Thr Ser Phe Tyr Pro Asp Tyr
                245                 250                 255

Ile Ala Val Glu Trp Gln Arg Asn Gly Gln Pro Glu Ser Glu Asp Lys
            260                 265                 270

Tyr Gly Thr Thr Pro Pro Gln Leu Asp Ala Asp Ser Ser Tyr Phe Leu
        275                 280                 285

Tyr Ser Lys Leu Arg Val Asp Arg Asn Ser Trp Gln Glu Gly Asp Thr
    290                 295                 300

Tyr Thr Cys Val Val Met His Glu Ala Leu His Asn His Tyr Thr Gln
305                 310                 315                 320

Lys Ser Thr Ser Lys Ser Ala Gly Lys
                325

<210> SEQ ID NO 67
<211> LENGTH: 990
<212> TYPE: DNA
<213> ORGANISM: Bubalus arnee

<400> SEQUENCE: 67
gcctccacca cagccccgaa agtctaccct ctgagttctt gctgcgggga caagtccagc      60
tccaccgtga ccctgggctg cctggtctcc agctacatgc ccgagccggt gaccgtgacc     120
tggaactcgg gtgccctgaa gagcggcgtg cacaccttcc cggctgtcct tcagtcctcc     180
gggctgtact ctctcagcag catggtgacc gtgcccggca gcacctcagg acagaccttc     240
acctgcaacg tagcccaccc ggccagcagc accaaggtgg acaaggctgt tgatcccaca     300
tgcaaaccat caccctgtga ctgttgccca cccccctgagc tccccggagg accctctgtc     360

```
ttcatcttcc caccgaaacc caaggacacc ctcacaatct cgggaacgcc cgaggtcacg      420
tgtgtggtgg tggacgtggg ccacgatgac cccgaggtga agttctcctg gttcgtggac      480
gacgtggagg taaacacagc cacgacgaag ccgagagagg agcagttcaa cagcacctac      540
cgcgtggtca gcgccctgcg catccagcac caggactgga ctggaggaaa ggagttcaag      600
tgcaaggtcc acaacgaagg cctcccggcc ccatcgtga ggaccatctc caggaccaaa       660
gggccggccc gggagccgca ggtgtatgtc ctggccccac cccaggaaga gctcagcaaa      720
agcacggtca gcctcaccctg catggtcacc agcttctacc cagactacat cgccgtggag     780
tggcagagaa acgggcagcc tgagtcggag gacaagtacg cacgacccc gccccagctg       840 gacgccgaca gctcctactt cctgtacagc aagctcaggg tggacaggaa cagctggcag      900
gaaggagaca cctacacgtg tgtggtgatg cacgaggccc tgcacaatca ctacacgcag      960
aagtccacct ctaagtctgc gggtaaatga                                       990
```

<210> SEQ ID NO 68
<211> LENGTH: 329
<212> TYPE: PRT
<213> ORGANISM: Bubalus arnee

<400> SEQUENCE: 68

```
Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
                20                  25                  30

Met Pro Glu Pro Val Thr Val Thr Trp Asn Ser Gly Ala Leu Lys Ser
            35                  40                  45

Gly Val His Thr Phe Pro Ala Val Leu Gln Ser Ser Gly Leu Tyr Ser
        50                  55                  60

Leu Ser Ser Met Val Thr Val Pro Gly Ser Thr Ser Gly Gln Thr Phe
65                  70                  75                  80

Thr Cys Asn Val Ala His Pro Ala Ser Ser Thr Lys Val Asp Lys Ala
                85                  90                  95

Val Asp Pro Thr Cys Lys Pro Ser Pro Cys Asp Cys Pro Pro
                100                 105                 110

Glu Leu Pro Gly Gly Pro Ser Val Phe Ile Phe Pro Pro Lys Pro Lys
            115                 120                 125

Asp Thr Leu Thr Ile Ser Gly Thr Pro Glu Val Thr Cys Val Val Val
        130                 135                 140

Asp Val Gly His Asp Asp Pro Glu Val Lys Phe Ser Trp Phe Val Asp
145                 150                 155                 160

Asp Val Glu Val Asn Thr Ala Thr Thr Lys Pro Arg Glu Glu Gln Phe
                165                 170                 175

Asn Ser Thr Tyr Arg Val Val Ser Ala Leu Arg Ile Gln His Gln Asp
            180                 185                 190

Trp Thr Gly Gly Lys Glu Phe Lys Cys Lys Val His Asn Glu Gly Leu
        195                 200                 205

Pro Ala Pro Ile Val Arg Thr Ile Ser Arg Thr Lys Gly Pro Ala Arg
    210                 215                 220

Glu Pro Gln Val Tyr Val Leu Ala Pro Pro Gln Glu Glu Leu Ser Lys
225                 230                 235                 240

Ser Thr Val Ser Leu Thr Cys Met Val Thr Ser Phe Tyr Pro Asp Tyr
                245                 250                 255
```

```
Ile Ala Val Glu Trp Gln Arg Asn Gly Gln Pro Glu Ser Glu Asp Lys
            260                 265                 270

Tyr Gly Thr Thr Pro Pro Gln Leu Asp Ala Asp Ser Ser Tyr Phe Leu
        275                 280                 285

Tyr Ser Lys Leu Arg Val Asp Arg Asn Ser Trp Gln Glu Gly Asp Thr
    290                 295                 300

Tyr Thr Cys Val Val Met His Glu Ala Leu His Asn His Tyr Thr Gln
305                 310                 315                 320

Lys Ser Thr Ser Lys Ser Ala Gly Lys
                325
```

<210> SEQ ID NO 69
<211> LENGTH: 990
<212> TYPE: DNA
<213> ORGANISM: Bubalus arnee

<400> SEQUENCE: 69

```
gcctccacca cagccccgaa agtctaccct ctgagttctt gctgcgggga caagtccagc    60
tccaccgtga ccctgggctg cctggtctcc agctacatgc ccgagccggt gaccgtgacc   120
tggaactcgg gtgccctgaa gagcggcgtg cacaccttcc cggccgtcct tcagtcctcc   180
gggctgtact ctctcagcag catggtgacc gtgcccggca gcacctcagg acagaccttc   240
acctgcaacg tagcccaccc ggccagcagc accaaggtgg acaaggctgt tgatcccaca   300
tgcaaaccat cccctgtga ctgttgccca ccccctgagc tccccggagg accctctgtc   360
ttcatcttcc caccgaaacc caaggacacc ctcacaatct cgggaacgcc cgaggtcacg   420
tgtgtggtgg tggacgtggg ccacgatgac cccgaggtga agttctcctg gttcgtggac   480
gacgtggagg taaacacagc cacgacgaag ccgagagagg agcagttcaa cagcacctac   540
cgcgtggtca gcgccctgcg catccagcac caggactgga ctggaggaaa ggagttcaag   600
tgcaaggtcc acaacgaagg cctcccggcc ccatcgtga ggaccatctc caggaccaaa   660
gggccggccc gggagccgca ggtgtatgtc ctggccccac cccaggaaga gctcagcaaa   720
agcacggtca gcctcacctg catggtcacc agcttctacc cagactacat cgccgtggag   780
tggcagagaa acgggcagcc tgagtcggag acaagtacg gcacgacccc gccccagctg   840
gacgccgaca gctcctactt cctgtacagc aagctcaggg tggacaggaa cagctggcag   900
gaaggagaca cctacacgtg tgtggtgatg cacgaggccc tgcacaatca ctacacgcag   960
aagtccacct ctaagtctgc gggtaaatga                                    990
```

<210> SEQ ID NO 70
<211> LENGTH: 329
<212> TYPE: PRT
<213> ORGANISM: Bubalus arnee

<400> SEQUENCE: 70

```
Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Gly Ser Thr Ser Gly Thr Gln Thr
65                  70                  75                  80
```

Phe Thr Cys Asn Val Ala His Pro Ala Ser Ser Thr Lys Val Asp Lys
                 85                  90                  95

Ala Val Asp Pro Arg Cys Lys Thr Thr Cys Asp Cys Cys Pro Pro Pro
            100                 105                 110

Glu Leu Pro Gly Gly Pro Ser Val Phe Ile Phe Pro Pro Lys Pro Lys
        115                 120                 125

Asp Thr Leu Thr Ile Ser Gly Thr Pro Glu Val Thr Cys Val Val Val
    130                 135                 140

Asp Val Gly His Asp Asp Pro Glu Val Lys Phe Ser Trp Phe Val Asp
145                 150                 155                 160

Asp Val Glu Val Asn Thr Ala Thr Thr Lys Pro Arg Glu Glu Gln Phe
                165                 170                 175

Asn Ser Thr Tyr Arg Val Val Ser Ala Leu Arg Ile Gln His Gln Asp
            180                 185                 190

Trp Thr Gly Gly Lys Glu Phe Lys Cys Lys Val His Asn Glu Gly Leu
        195                 200                 205

Pro Ala Pro Ile Val Arg Thr Ile Ser Arg Thr Lys Gly Pro Ala Arg
    210                 215                 220

Glu Pro Gln Val Tyr Val Leu Ala Pro Gln Glu Glu Leu Ser Lys
225                 230                 235                 240

Ser Thr Val Ser Leu Thr Cys Met Val Thr Ser Phe Tyr Pro Asp Tyr
                245                 250                 255

Ile Ala Val Glu Trp Gln Arg Asn Gly Gln Pro Glu Ser Glu Asp Lys
            260                 265                 270

Tyr Gly Thr Thr Pro Pro Gln Leu Asp Ala Asp Gly Ser Tyr Phe Leu
        275                 280                 285

Tyr Ser Arg Leu Arg Val Asp Arg Asn Ser Trp Gln Glu Gly Asp Thr
    290                 295                 300

Tyr Thr Cys Val Val Met His Glu Ala Leu His Asn His Tyr Thr Gln
305                 310                 315                 320

Lys Ser Thr Ser Lys Ser Ala Gly Lys
                325

<210> SEQ ID NO 71
<211> LENGTH: 990
<212> TYPE: DNA
<213> ORGANISM: Bubalus arnee

<400> SEQUENCE: 71

| | | |
|---|---|---|
| gcctccacca cagccccgaa agtctaccct ctgagttctt gctgcgggga caagtccagc | 60 |
| tccaccgtga ccctgggctg cctggtctcc agctacatgc ccgagccggt gaccgtgacc | 120 |
| tggaactcgg gtgccctgaa gagcggcgtg cacaccttcc cggccgtcct tcagtcctcc | 180 |
| gggctctact ctctcagcag catggtgacc gtgcccggca gcacctcagg aacccagacc | 240 |
| ttcacctgca acgtagccca cccggccagc agcaccaagg tggacaaggc tgttgatccc | 300 |
| agatgcaaaa caacctgtga ctgttgccca ccgcctgagc tccctggagg accctctgtc | 360 |
| ttcatcttcc caccgaaacc caaggacacc ctcacaatct cgggaacgcc cgaggtcacg | 420 |
| tgtgtggtgg tggacgtggg ccacgatgac cccgaggtga agttctcctg gttcgtggac | 480 |
| gacgtggagg taaacacagc cacgacgaag ccgagagagg agcagttcaa cagcacctac | 540 |
| cgcgtggtca gcgccctgcg catccagcac caggactgga ctggaggaaa ggagttcaag | 600 |
| tgcaaggtcc acaacgaagg cctcccagcc cccatcgtga ggaccatctc caggaccaaa | 660 |

```
gggccggccc gggagccgca ggtgtatgtc ctggccccac cccaggaaga gctcagcaaa      720
agcacggtca gcctcacctg catggtcacc agcttctacc cagactacat cgccgtggag      780
tggcagagaa atgggcagcc tgagtcagag gacaagtacg gcacgacccc tccccagctg      840
gacgccgacg gctcctactt cctgtacagc aggctcaggg tggacaggaa cagctggcag      900
gaaggagaca cctacacgtg tgtggtgatg cacgaggccc tgcacaatca ctacacgcag      960
aagtccacct ctaagtctgc gggtaaatga                                       990
```

<210> SEQ ID NO 72
<211> LENGTH: 326
<212> TYPE: PRT
<213> ORGANISM: Bubalus arnee
<400> SEQUENCE: 72

```
Ala Ser Thr Thr Ala Pro Lys Val Tyr Pro Leu Ala Ser Ser Cys Gly
1               5                   10                  15

Asp Thr Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Ala Ser Ser Ser Gly Gln Thr Phe
65                  70                  75                  80

Thr Cys Asn Val Ala His Pro Ala Ser Ser Thr Lys Val Asp Lys Ala
                85                  90                  95

Val Gly Val Ser Ile Asp Cys Ser Lys Cys His Asn Gln Pro Cys Val
            100                 105                 110

Arg Glu Pro Ser Val Phe Ile Phe Pro Pro Lys Pro Lys Asp Thr Leu
        115                 120                 125

Met Ile Thr Gly Thr Pro Glu Val Thr Cys Val Val Val Asn Val Gly
    130                 135                 140

His Asp Asn Pro Glu Val Gln Phe Ser Trp Phe Val Asp Asp Val Glu
145                 150                 155                 160

Val His Thr Ala Arg Ser Lys Pro Arg Glu Glu Gln Phe Asn Ser Thr
                165                 170                 175

Tyr Arg Val Val Ser Ala Leu Pro Ile Gln His Gln Asp Trp Thr Gly
            180                 185                 190

Gly Lys Glu Phe Lys Cys Lys Val Asn Asn Lys Gly Leu Ser Ala Pro
        195                 200                 205

Ile Val Arg Ile Ile Ser Arg Ser Lys Gly Pro Ala Arg Glu Pro Gln
    210                 215                 220

Val Tyr Val Leu Asp Pro Pro Lys Glu Glu Leu Ser Lys Ser Thr Leu
225                 230                 235                 240

Ser Val Thr Cys Met Val Thr Gly Phe Tyr Pro Glu Asp Val Ala Val
                245                 250                 255

Glu Trp Gln Arg Asn Arg Gln Thr Glu Ser Glu Asp Lys Tyr Arg Thr
            260                 265                 270

Thr Pro Pro Gln Leu Asp Thr Asp Arg Ser Tyr Phe Leu Tyr Ser Lys
        275                 280                 285

Leu Arg Val Asp Arg Asn Ser Trp Gln Glu Gly Asp Ala Tyr Thr Cys
    290                 295                 300

Val Val Met His Glu Ala Leu His Asn His Tyr Met Gln Lys Ser Thr
305                 310                 315                 320
```

Ser Lys Ser Ala Gly Lys
            325

<210> SEQ ID NO 73
<211> LENGTH: 981
<212> TYPE: DNA
<213> ORGANISM: Bubalus arnee

<400> SEQUENCE: 73

| | | | | |
|---|---|---|---|---|
| gcctccacca cagccccgaa agtctaccct ctggcatcca gctgcggaga cacatccagc | 60 |
| tccaccgtga ccctgggctg cctggtgtcc agctacatgc ccgagccggt gaccgtgacc | 120 |
| tggaactcgg gtgccctgaa gagcggcgtg cacaccttcc cggctgtcct tcagtcctcc | 180 |
| gggctctact ctctcagcag catggtgacc gtgcccgcca gcagctcagg acagaccttc | 240 |
| acctgcaacg tagcccaccc ggccagcagc accaaggtgg acaaggctgt tggggtctcc | 300 |
| attgactgct ccaagtgtca taaccagcct tgcgtgaggg aaccatctgt cttcatcttc | 360 |
| ccaccgaaac ccaaagacac cctgatgatc acaggaacgc ccgaggtcac gtgtgtggtg | 420 |
| gtgaacgtgg ccacgataa ccccgaggtg cagttctcct ggttcgtgga tgacgtggag | 480 |
| gtgcacacgg ccaggtcgaa gccaagagag gagcagttca acagcacgta ccgcgtggtc | 540 |
| agcgccctgc ccatccagca ccaggactgg actggaggaa aggagttcaa gtgcaaggtc | 600 |
| aacaacaaag gcctctcggc ccccatcgtg aggatcatct ccaggagcaa agggccggcc | 660 |
| cgggagccgc aggtgtatgt cctggaccca cccaaggaag agctcagcaa aagcacgctc | 720 |
| agcgtcacct gcatggtcac cggcttctac ccagaagatg tagccgtgga gtggcagaga | 780 |
| aaccggcaga ctgagtcgga ggacaagtac cgcacgaccc cgccccagct ggacaccgac | 840 |
| cgctcctact tcctgtacag caagctcagg gtggacagga acagctggca ggaaggagac | 900 |
| gcctacacgt gtgtggtgat gcacgaggcc ctgcacaatc actacatgca gaagtccacc | 960 |
| tctaagtctg cgggtaaatg a | 981 |

<210> SEQ ID NO 74
<211> LENGTH: 326
<212> TYPE: PRT
<213> ORGANISM: Bubalus arnee

<400> SEQUENCE: 74

Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Gly Ser Thr Ser Gly Gln Thr Phe
65                  70                  75                  80

Thr Cys Asn Val Ala His Pro Ala Ser Ser Thr Lys Val Asp Lys Ala
                85                  90                  95

Val Gly Val Ser Ser Asp Cys Ser Lys Pro Asn Asn Gln His Cys Val
            100                 105                 110

Arg Glu Pro Ser Val Phe Ile Phe Pro Pro Lys Pro Lys Asp Thr Leu
        115                 120                 125

Met Ile Thr Gly Thr Pro Glu Val Thr Cys Val Val Val Asn Val Gly

```
            130                 135                 140
His Asp Asn Pro Glu Val Gln Phe Ser Trp Phe Val Asp Asp Val Glu
145                 150                 155                 160

Val His Thr Ala Arg Thr Lys Pro Arg Glu Glu Gln Phe Asn Ser Thr
                165                 170                 175

Tyr Arg Val Val Ser Ala Leu Pro Ile Gln His Gln Asp Trp Thr Gly
            180                 185                 190

Gly Lys Glu Phe Lys Cys Lys Val Asn Ile Lys Gly Leu Ser Ala Ser
        195                 200                 205

Ile Val Arg Ile Ile Ser Arg Ser Lys Gly Pro Ala Arg Glu Pro Gln
    210                 215                 220

Val Tyr Val Leu Asp Pro Pro Lys Glu Glu Leu Ser Lys Ser Thr Val
225                 230                 235                 240

Ser Val Thr Cys Met Val Ile Gly Phe Tyr Pro Glu Asp Val Asp Val
                245                 250                 255

Glu Trp Gln Arg Asp Arg Gln Thr Glu Ser Glu Asp Lys Tyr Arg Thr
            260                 265                 270

Thr Pro Pro Gln Leu Asp Ala Asp Arg Ser Tyr Phe Leu Tyr Ser Lys
        275                 280                 285

Leu Arg Val Asp Arg Asn Ser Trp Gln Arg Gly Asp Thr Tyr Thr Cys
    290                 295                 300

Val Val Met His Glu Ala Leu His Asn His Tyr Met Gln Lys Ser Thr
305                 310                 315                 320

Ser Lys Ser Ala Gly Lys
                325

<210> SEQ ID NO 75
<211> LENGTH: 981
<212> TYPE: DNA
<213> ORGANISM: Bubalus arnee

<400> SEQUENCE: 75
gcctccacca cagccccgaa agtctaccct ctgagttctt gctgcgggga caagtccagc     60
tccaccgtga ccctgggctg cctggtgtcc agctacatgc ccgagccggt gaccgtgacc    120
tggaactcgg gtgccctgaa gagcggcgtg cacaccttcc cggccgtcct tcagtcctcc    180
gggctctact ctctcagcag catggtgacc gtgcccggca gcacctcagg acagaccttc    240
acctgcaacg tagcccaccc ggccagcagc accaaggtgg acaaggctgt tggggtctcc    300
agtgactgct ccaagcctaa taaccagcat tgcgtgaggg aaccatctgt cttcatcttc    360
ccaccgaaac ccaaagacac cctgatgatc acaggaacgc ccgaggtcac gtgtgtggtg    420
gtgaacgtgg ccacgataa ccccgaggtg cagttctcct ggttcgtgga cgacgtggag    480
gtgcacacgg ccaggacgaa gccgagagag gagcagttca acagcacgta ccgcgtggtc    540
agcgccctgc ccatccagca ccaggactgg actggaggaa aggagttcaa gtgcaaggtc    600
aacatcaaag gcctctcggc tccatcgtg aggatcatct ccaggagcaa agggccggcc    660
cgggagccgc aggtgtatgt cctggaccca cccaaggaag agctcagcaa aagcacggtc    720
agcgtcacct gcatggtcat cggcttctac ccagaagatg tagacgtgga gtggcagaga    780
gaccggcaga ctgagtcgga ggacaagtac cgcacgaccc cgccccagct ggacgccgac    840
cgctcctact cctgtacag caagctcagg gtggacagaa acagctggca gagaggagac    900
acctacacgt gtgtggtgat gcacgaggcc ctgcacaatc actacatgca gaagtccacc    960
tctaagtctg cgggtaaatg a                                              981
```

<210> SEQ ID NO 76
<211> LENGTH: 327
<212> TYPE: PRT
<213> ORGANISM: Bubalus arnee

<400> SEQUENCE: 76

```
Ala Ser Thr Thr Ala Pro Lys Val Tyr Pro Leu Ser Ser Cys Cys Gly
1               5                   10                  15

Asp Lys Ser Ser Ser Gly Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Ala Ser Ser Gly Thr Gln Thr
65                  70                  75                  80

Phe Thr Cys Asn Val Ala His Pro Ala Ser Ser Thr Lys Val Asp Lys
                85                  90                  95

Ala Val Gly Val Ser Ser Asp Cys Ser Lys Pro Asn Asn Gln His Cys
            100                 105                 110

Val Arg Glu Pro Ser Val Phe Ile Phe Pro Pro Lys Pro Lys Asp Thr
        115                 120                 125

Leu Met Ile Thr Gly Thr Pro Glu Val Thr Cys Val Val Val Asn Val
    130                 135                 140

Gly His Asp Asn Pro Glu Val Gln Phe Ser Trp Phe Val Asp Asp Val
145                 150                 155                 160

Glu Val His Thr Ala Arg Thr Lys Pro Arg Glu Glu Gln Phe Asn Ser
                165                 170                 175

Thr Tyr Arg Val Val Ser Ala Leu Pro Ile Gln His Gln Asp Trp Thr
            180                 185                 190

Gly Gly Lys Glu Phe Lys Cys Lys Val Asn Ile Lys Gly Leu Ser Ala
        195                 200                 205

Ser Ile Val Arg Ile Ile Ser Arg Ser Lys Gly Pro Ala Arg Glu Pro
    210                 215                 220

Gln Val Tyr Val Leu Asp Pro Pro Lys Glu Glu Leu Ser Lys Ser Thr
225                 230                 235                 240

Val Ser Leu Thr Cys Met Val Ile Gly Phe Tyr Pro Glu Asp Val Asp
                245                 250                 255

Val Glu Trp Gln Arg Asp Arg Gln Thr Glu Ser Glu Asp Lys Tyr Arg
            260                 265                 270

Thr Thr Pro Pro Gln Leu Asp Ala Asp Arg Ser Tyr Phe Leu Tyr Ser
        275                 280                 285

Lys Leu Arg Val Asp Arg Asn Ser Trp Gln Arg Gly Asp Thr Tyr Thr
    290                 295                 300

Cys Val Val Met His Glu Ala Leu His Asn His Tyr Met Gln Lys Ser
305                 310                 315                 320

Thr Ser Lys Ser Ala Gly Lys
                325
```

<210> SEQ ID NO 77
<211> LENGTH: 984
<212> TYPE: DNA
<213> ORGANISM: Bubalus arnee

<400> SEQUENCE: 77

```
gcctccacca cagccccgaa agtctaccct ctgagttctt gctgcgggga caagtccagc    60 tcggggtga ccctgggctg cctggtctcc agctacatgc ccgagccggt gaccgtgacc    120
tggaactcgg gtgccctgaa gagcggcgtg cacaccttcc cggccgtcct tcagtcctcc    180
gggctctact ctctcagcag catggtgacc gtgcccgcca gcagctcagg aacccagacc    240
ttcacctgca acgtagccca cccggccagc agcaccaagg tggacaaggc tgttggggtc    300
tccagtgact gctccaagcc taataaccag cattgcgtga gggaaccatc tgtcttcatc    360
ttcccaccga aacccaaaga caccctgatg atcacaggaa cgcccgaggt cacgtgtgtg    420
gtggtgaacg tgggccacga taaccccgag gtgcagttct cctggttcgt ggacgacgtg    480
gaggtgcaca cggccaggac gaagccgaga gaggagcagt tcaacagcac gtaccgcgtg    540
gtcagcgccc tgcccatcca gcaccaggac tggactggag aaaggagtt caagtgcaag    600 gtcaacatca aaggcctctc ggcctccatc gtgaggatca tctccaggag caaagggccg    660
gcccgggagc cgcaggtgta tgtcctggac ccacccaagg aagagctcag caaaagcacg    720
gtcagcctca cctgcatggt catcggcttc tacccagaag atgtagacgt ggagtggcag    780
agagaccggc agactgagtc ggaggacaag taccgcacga ccccgcccca gctggacgcc    840
gaccgctcct acttcctgta cagcaagctc agggtggaca ggaacagctg gcagagagga    900
gacacctaca cgtgtgtggt gatgcacgag gccctgcaca atcactacat gcagaagtcc    960
acctctaagt ctgcgggtaa atga                                           984
```

<210> SEQ ID NO 78
<211> LENGTH: 352
<212> TYPE: PRT
<213> ORGANISM: Bubalus arnee

<400> SEQUENCE: 78

```
Ala Ser Thr Thr Ala Pro Lys Val Tyr Pro Leu Ala Ser Ser Cys Gly
1               5                   10                  15

Asp Thr Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Arg Gln Ser Ser Gly Leu Tyr Ser
    50                  55                  60

Leu Ser Ser Met Val Thr Val Pro Ala Ser Ser Ser Glu Thr Gln Thr
65                  70                  75                  80

Phe Thr Cys Asn Val Ala His Pro Ala Ser Ser Thr Lys Val Asp Lys
                85                  90                  95

Ala Val Thr Ala Arg Arg Pro Val Pro Thr Thr Pro Lys Thr Thr Ile
            100                 105                 110

Pro Pro Gly Lys Pro Thr Thr Pro Lys Ser Glu Val Glu Lys Thr Pro
        115                 120                 125

Cys Gln Cys Ser Lys Cys Pro Glu Pro Leu Gly Gly Leu Ser Val Phe
    130                 135                 140

Ile Phe Pro Pro Lys Pro Lys Asp Thr Leu Thr Ile Ser Gly Thr Pro
145                 150                 155                 160

Glu Val Thr Cys Val Val Val Asp Val Gly Gln Asp Asp Pro Glu Val
                165                 170                 175

Gln Phe Ser Trp Phe Val Asp Asp Val Glu Val His Thr Ala Arg Thr
            180                 185                 190
```

Lys Pro Arg Glu Glu Gln Phe Asn Ser Thr Tyr Arg Val Val Ser Ala
            195                 200                 205

Leu Arg Ile Gln His Gln Asp Trp Leu Gln Gly Lys Glu Phe Lys Cys
        210                 215                 220

Lys Val Asn Asn Lys Gly Leu Pro Ala Pro Ile Val Arg Thr Ile Ser
225                 230                 235                 240

Arg Thr Lys Gly Gln Ala Arg Glu Pro Gln Val Tyr Val Leu Ala Pro
                245                 250                 255

Pro Arg Glu Glu Leu Ser Lys Ser Thr Leu Ser Leu Thr Cys Leu Ile
            260                 265                 270

Thr Gly Phe Tyr Pro Glu Glu Ile Asp Val Glu Trp Gln Arg Asn Gly
        275                 280                 285

Gln Pro Glu Ser Glu Asp Lys Tyr His Thr Thr Ala Pro Gln Leu Asp
    290                 295                 300

Ala Asp Gly Ser Tyr Phe Leu Tyr Ser Lys Leu Arg Val Asn Lys Ser
305                 310                 315                 320

Ser Trp Gln Glu Gly Asp His Tyr Thr Cys Ala Val Met His Glu Ala
                325                 330                 335

Leu Arg Asn His Tyr Lys Glu Lys Ser Ile Ser Arg Ser Pro Gly Lys
            340                 345                 350

<210> SEQ ID NO 79
<211> LENGTH: 1059
<212> TYPE: DNA
<213> ORGANISM: Bubalus arnee

<400> SEQUENCE: 79
gcctccacca cagccccgaa agtctaccct ctggcatcca gctgcggaga cacatccagc     60
tccaccgtga ccctgggctg cctggtctcc agctacatgc ccgagccggt gaccgtgacc    120
tggaactcgg gtgccctgaa gagcggcgtg cacaccttcc cggccgtccg gcagtcctct    180
gggctgtact ctctcagcag catggtgact gtgcccgcca gcagctcaga aacccagacc    240
ttcacctgca acgtagccca cccggccagc agcaccaagg tggacaaggc tgtcactgca    300
aggcgtccag tcccgacgac gccaaagaca actatccctc ctggaaaacc cacaacccca    360
aagtctgaag ttgaaaagac ccctgccag tgttccaaat gcccagaacc tctgggagga    420
ctgtctgtct tcatcttccc accgaaaccc aaggacaccc tcacaatctc gggaacgccc    480
gaggtcacgt gtgtggtggt ggacgtgggc caggatgacc ccgaggtgca gttctcctgg    540
ttcgtggacg acgtggaggt gcacacggcc aggacgaagc cgagagagga gcagttcaac    600
agcacctacc gcgtggtcag cgccctgcgc atccagcacc aggactggct gcagggaaag    660
gagttcaagt gcaaggtcaa caacaaaggc ctcccggccc ccattgtgag gaccatctcc    720
aggaccaaag ggcaggcccg ggagccgcag gtgtatgtcc tggccccacc ccgggaagag    780
ctcagcaaaa gcacgctcag cctcacctgc ctgatcaccg gtttctaccc agaagagata    840
gacgtggagt ggcagagaaa tgggcagcct gagtcggagg acaagtacca cacgaccgca    900
ccccagctgg atgctgacgg ctcctacttc ctgtacagca agctcagggt gaacaagagc    960
agctggcagg aaggagacca ctacacgtgt gcagtgatgc acgaagcttt acggaatcac   1020
tacaaagaga agtccatctc gaggtctccg ggtaaatga                          1059

<210> SEQ ID NO 80
<211> LENGTH: 352
<212> TYPE: PRT
<213> ORGANISM: Bubalus arnee

<400> SEQUENCE: 80

```
Ala Ser Thr Thr Ala Pro Lys Val Tyr Pro Leu Ala Ser Arg Cys Gly
1               5                   10                  15

Asp Thr Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Ala Ser Ser Glu Thr Gln Thr
65                  70                  75                  80

Phe Thr Cys Asn Val Ala His Pro Ala Ser Ser Thr Lys Val Asp Lys
                85                  90                  95

Ala Val Thr Ala Arg Arg Pro Val Pro Thr Thr Pro Lys Thr Thr Ile
            100                 105                 110

Pro Pro Gly Lys Pro Thr Thr Gln Glu Ser Glu Val Glu Lys Thr Pro
        115                 120                 125

Cys Gln Cys Ser Lys Cys Pro Glu Pro Leu Gly Gly Leu Ser Val Phe
    130                 135                 140

Ile Phe Pro Pro Lys Pro Lys Asp Thr Leu Thr Ile Ser Gly Thr Pro
145                 150                 155                 160

Glu Val Thr Cys Val Val Val Asp Val Gly Gln Asp Asp Pro Glu Val
                165                 170                 175

Gln Phe Ser Trp Phe Val Asp Asp Val Glu Val His Thr Ala Arg Thr
            180                 185                 190

Lys Pro Arg Glu Glu Gln Phe Asn Ser Thr Tyr Arg Val Val Ser Ala
        195                 200                 205

Leu Arg Ile Gln His Gln Asp Trp Leu Gln Gly Lys Glu Phe Lys Cys
    210                 215                 220

Lys Val Asn Asn Lys Gly Leu Pro Ala Pro Ile Val Arg Thr Ile Ser
225                 230                 235                 240

Arg Thr Lys Gly Gln Ala Arg Glu Pro Gln Val Tyr Val Leu Ala Pro
                245                 250                 255

Pro Arg Glu Glu Leu Ser Lys Ser Thr Leu Ser Leu Thr Cys Leu Ile
            260                 265                 270

Thr Gly Phe Tyr Pro Glu Glu Ile Asp Val Glu Trp Gln Arg Asn Gly
        275                 280                 285

Gln Pro Glu Ser Glu Asp Lys Tyr His Thr Thr Ala Pro Gln Leu Asp
    290                 295                 300

Ala Asp Gly Ser Tyr Phe Leu Tyr Ser Arg Leu Arg Val Asn Lys Ser
305                 310                 315                 320

Ser Trp Gln Glu Gly Asp His Tyr Thr Cys Ala Val Met His Glu Ala
                325                 330                 335

Leu Arg Asn His Tyr Lys Glu Lys Ser Ile Ser Arg Ser Pro Gly Lys
            340                 345                 350
```

<210> SEQ ID NO 81
<211> LENGTH: 1059
<212> TYPE: DNA
<213> ORGANISM: Bubalus arnee

<400> SEQUENCE: 81

```
gcctccacca cagccccgaa agtctaccct ctggcatccc gctgcggaga cacatccagc    60
```

```
tccaccgtga ccctgggctg cctggtctcc agctacatgc ccgagccggt gaccgtgacc      120
tggaactcgg gtgccctgaa gagtggcgtg cacaccttcc cggccgtcct tcagtcctcc      180
gggctgtact ctctcagcag catggtgacc gtgcccgcca gcacctcaga aacccagacc      240
ttcacctgca acgtagccca cccggccagc agcaccaagg tggacaaggc tgtcactgca      300
aggcgtccag tcccgacgac gccaaagaca accatccctc ctggaaaacc cacaacccag      360
gagtctgaag ttgaaaagac accctgccag tgttccaaat gcccagaacc tctgggagga      420
ctgtctgtct tcatcttccc accgaaaccc aaggacaccc tcacaatctc gggaacgccc      480
gaggtcacgt gtgtggtggt ggacgtgggc caggatgacc ccgaggtgca gttctcctgg      540
ttcgtggacg acgtggaggt gcacacggcc aggacgaagc cgagagagga gcagttcaac      600
agcacctacc gcgtggtcag cgccctgcgc atccagcacc aggactggct gcagggaaag      660
gagttcaagt gcaaggtcaa caacaaaggc ctcccggccc ccattgtgag gaccatctcc      720
aggaccaaag gcaggcccg ggagccgcag gtgtatgtcc tggccccacc ccgggaagag      780
ctcagcaaaa gcacgctcag cctcacctgc ctgatcaccg gtttctaccc agaagagata      840
gacgtggagt ggcagagaaa tgggcagcct gagtcggagg acaagtacca cacgaccgca      900
ccccagctgg atgctgacgg ctcctacttc ctgtacagca ggctcagggt gaacaagagc      960
agctggcagg aaggagacca ctacacgtgt gcagtgatgc atgaagcttt acggaatcac     1020
tacaaagaga agtccatctc gaggtctccg ggtaaatga                            1059

<210> SEQ ID NO 82
<211> LENGTH: 105
<212> TYPE: PRT
<213> ORGANISM: Bubalus arnee

<400> SEQUENCE: 82

Gln Pro Lys Ala Ser Pro Ser Val Thr Leu Phe Pro Pro Ser Ser Glu
1               5                   10                  15

Glu Leu Gly Ala Asn Lys Ala Thr Leu Val Cys Leu Ile Ser Asp Phe
            20                  25                  30

Tyr Pro Ser Gly Val Thr Val Ala Trp Lys Ala Ser Gly Ser Pro Val
        35                  40                  45

Thr Gln Gly Val Glu Thr Thr Lys Pro Ser Lys Gln Ser Asn Asn Lys
    50                  55                  60

Tyr Ala Ala Ser Ser Tyr Leu Ser Leu Thr Pro Asp Lys Trp Lys Ser
65                  70                  75                  80

His Ser Ser Phe Ser Cys Leu Val Thr His Glu Gly Ser Thr Val Glu
                85                  90                  95

Lys Lys Val Ala Pro Ala Glu Cys Ser
            100                 105

<210> SEQ ID NO 83
<211> LENGTH: 318
<212> TYPE: DNA
<213> ORGANISM: Bubalus arnee

<400> SEQUENCE: 83
cagcccaagg cctccccctc ggtcacactc ttcccgccct cctctgagga gctcggcgcc       60
aacaaggcca ccctggtgtg cctcatcagc gacttctacc ccagcggcgt gacggtggcc      120
tggaaggcaa gcggcagccc cgtcacccag ggcgtggaga ccaccaagcc ctccaagcag      180
agcaacaaca gtacgcggc cagcagctac ctgagcctga cgcctgacaa gtggaaatct      240
```

```
cacagcagct tcagctgcct ggtcacgcac gaggggagca ccgtggagaa gaaggtggcc    300
cccgcagagt gctcttag                                                  318
```

<210> SEQ ID NO 84
<211> LENGTH: 331
<212> TYPE: PRT
<213> ORGANISM: Bubalus arnee

<400> SEQUENCE: 84

```
Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Thr Val Thr Val Pro Ser Ser Arg Trp Pro Ser Glu Thr
65                  70                  75                  80

Phe Thr Cys Asn Val Val His Pro Ala Ser Asn Thr Lys Val Asp Lys
                85                  90                  95

Pro Val Pro Lys Glu Ser Thr Cys Lys Cys Ile Ser Pro Cys Pro Val
            100                 105                 110

Pro Glu Ser Leu Gly Gly Pro Ser Val Phe Ile Phe Pro Pro Lys Pro
        115                 120                 125

Lys Asp Ile Leu Arg Ile Thr Arg Thr Pro Glu Ile Thr Cys Val Val
130                 135                 140

Leu Asp Leu Gly Arg Glu Asp Pro Glu Val Gln Ile Ser Trp Phe Val
145                 150                 155                 160

Asp Gly Lys Glu Val His Thr Ala Lys Thr Gln Pro Arg Glu Gln Gln
                165                 170                 175

Phe Asn Ser Thr Tyr Arg Val Val Ser Val Leu Pro Ile Glu His Gln
            180                 185                 190

Asp Trp Leu Thr Gly Lys Glu Phe Lys Cys Arg Val Asn His Ile Gly
        195                 200                 205

Leu Pro Ser Pro Ile Glu Arg Thr Ile Ser Lys Ala Arg Gly Gln Ala
    210                 215                 220

His Gln Pro Ser Val Tyr Val Leu Pro Pro Ser Pro Lys Glu Leu Ser
225                 230                 235                 240

Ser Ser Asp Thr Val Thr Leu Thr Cys Leu Ile Lys Asp Phe Phe Pro
                245                 250                 255

Pro Glu Ile Asp Val Glu Trp Gln Ser Asn Gly Gln Pro Glu Pro Glu
            260                 265                 270

Ser Lys Tyr His Thr Thr Ala Pro Gln Leu Asp Glu Asp Gly Ser Tyr
        275                 280                 285

Phe Leu Tyr Ser Lys Leu Ser Val Asp Lys Ser Arg Trp Gln Gln Gly
    290                 295                 300

Asp Thr Phe Thr Cys Ala Val Met His Glu Ala Leu Gln Asn His Tyr
305                 310                 315                 320

Thr Asp Leu Ser Leu Ser His Ser Pro Gly Lys
                325                 330
```

<210> SEQ ID NO 85
<211> LENGTH: 996
<212> TYPE: DNA

<213> ORGANISM: Bubalus arnee

<400> SEQUENCE: 85

| | |
|---|---|
| gcctccacca cggcccctc ggttttccca ctggccccca gctgcgggtc cacttccggc | 60 |
| tccacggtgg ccctggcctg cctggtgtca ggctacttcc ccgagcctgt aactgtgtcc | 120 |
| tggaattccg gctccttgac cagcggtgtg cacaccttcc cgtccgtcct gcagtcctca | 180 |
| gggctctact ccctcagcag cacggtgaca gtgccctcca gcaggtggcc cagcgagacc | 240 |
| ttcacctgca acgtggtcca cccggccagc aacactaaag tagacaagcc agtgcccaaa | 300 |
| gagtccacct gcaagtgtat atccccatgc ccagtccctg aatcactggg agggccttcg | 360 |
| gtcttcatct ttccccgaa acccaaggac atcctcagga ttacccgaac acccgagatc | 420 |
| acctgtgtgg tgttagatct gggccgtgag accctgagg tgcagatcag ctggttcgtg | 480 |
| gatggtaagg aggtgcacac agccaagacg cagcctcgtg agcagcagtt caacagcacc | 540 |
| taccgtgtgg tcagcgtcct ccccattgag caccaggact ggctcaccgg aaaggagttc | 600 |
| aagtgcagag tcaaccacat aggcctcccg tcccccatcg agaggactat ctccaaagcc | 660 |
| agagggcaag cccatcagcc cagtgtgtat gtcctgccac catccccaaa ggagttgtca | 720 |
| tccagtgaca cggtcaccct gacctgcctg atcaaagact tcttcccacc tgagattgat | 780 |
| gtggagtggc agagcaatgg acagccggag cccgagagca gtaccacac gactgcgccc | 840 |
| cagctggaca aggacgggtc ctacttcctg tacagcaagc tctctgtgga caagagccgc | 900 |
| tggcagcagg agacaccttt cacatgtgcg gtgatgcatg aagctctaca gaaccactac | 960 |
| acagatctat ccctctccca ttctccgggt aaatga | 996 |

<210> SEQ ID NO 86
<211> LENGTH: 102
<212> TYPE: PRT
<213> ORGANISM: Bubalus arnee

<400> SEQUENCE: 86

Pro Ser Val Phe Leu Phe Lys Pro Ser Glu Glu Gln Leu Arg Thr Gly
1               5                   10                  15

Thr Val Ser Val Val Cys Leu Val Asn Asp Phe Tyr Pro Lys Asp Ile
            20                  25                  30

Asn Val Lys Val Lys Val Asp Gly Val Thr Gln Asn Ser Asn Phe Gln
        35                  40                  45

Asn Ser Phe Thr Asp Gln Asp Ser Lys Lys Ser Thr Tyr Ser Leu Ser
    50                  55                  60

Ser Thr Leu Thr Leu Ser Ser Ser Glu Tyr Gln Ser His Asn Ala Tyr
65                  70                  75                  80

Ala Cys Glu Val Ser His Lys Ser Leu Pro Thr Ala Leu Val Lys Ser
                85                  90                  95

Phe Asn Lys Asn Glu Cys
            100

<210> SEQ ID NO 87
<211> LENGTH: 309
<212> TYPE: DNA
<213> ORGANISM: Bubalus arnee

<400> SEQUENCE: 87

| | |
|---|---|
| ccatccgtct tcctcttcaa accatctgag gaacagctga ggaccggaac tgtctctgtc | 60 |
| gtgtgcttgg tgaatgattt ctaccccaaa gatatcaatg tcaaggtgaa agtggatggg | 120 |

```
gttacccaga acagcaactt ccagaacagc ttcacagacc aggacagcaa gaaaagcacc      180
tacagcctca gcagcaccct gacactgtcc agctcagagt accagagcca taacgcctat      240
gcgtgtgagg tcagccacaa gagcctgccc accgccctcg tcaagagctt caataagaat      300
gaatgttag                                                              309
```

<210> SEQ ID NO 88
<211> LENGTH: 106
<212> TYPE: PRT
<213> ORGANISM: Bubalus arnee

<400> SEQUENCE: 88

```
Gly Gln Pro Lys Ser Ala Pro Ser Val Thr Leu Phe Pro Pro Ser Thr
1               5                   10                  15

Glu Glu Leu Ser Thr Asn Lys Ala Thr Val Val Cys Leu Ile Asn Asp
            20                  25                  30

Phe Tyr Pro Gly Ser Val Asn Val Val Trp Lys Ala Asp Gly Ser Thr
        35                  40                  45

Ile Asn Gln Asn Val Lys Thr Thr Gln Ala Ser Lys Gln Ser Asn Ser
    50                  55                  60

Lys Tyr Ala Ala Ser Ser Tyr Leu Thr Leu Thr Gly Ser Glu Trp Lys
65                  70                  75                  80

Ser Lys Ser Ser Tyr Thr Cys Glu Val Thr His Glu Gly Ser Thr Val
                85                  90                  95

Thr Lys Thr Val Lys Pro Ser Glu Cys Ser
            100                 105
```

<210> SEQ ID NO 89
<211> LENGTH: 321
<212> TYPE: DNA
<213> ORGANISM: Bubalus arnee

<400> SEQUENCE: 89

```
ggtcagccca agtccgcacc ctcggtcacc ctgttcccgc cttccacgga ggagctcagt      60
accaacaagg ccaccgtggt gtgtctcatc aacgacttct acccgggtag cgtgaacgtg     120
gtctggaagg cagatggcag caccatcaat cagaacgtga agaccaccca ggcctccaaa     180
cagagcaaca gcaagtacgc ggccagcagc tacctgaccc tgacgggcag cgagtggaag     240
tctaagagca gttacacctg cgaggtcacg cacgagggga gcaccgtgac gaagacagtg     300
aagccctcag agtgttctta g                                               321
```

<210> SEQ ID NO 90
<211> LENGTH: 331
<212> TYPE: PRT
<213> ORGANISM: Bubalus arnee

<400> SEQUENCE: 90

```
Ala Ser Thr Thr Pro Pro Lys Val Tyr Pro Leu Thr Ser Cys Cys Gly
1               5                   10                  15

Asp Thr Ser Ser Ser Ile Val Thr Leu Gly Cys Leu Val Ser Ser Tyr
            20                  25                  30

Met Pro Glu Pro Val Thr Val Thr Trp Asn Ser Gly Ala Leu Thr Ser
        35                  40                  45

Gly Val His Thr Phe Pro Ala Ile Leu Gln Ser Ser Gly Leu Tyr Ser
    50                  55                  60

Leu Ser Ser Val Val Thr Val Pro Ala Ser Thr Ser Gly Ala Gln Thr
65                  70                  75                  80
```

Phe Ile Cys Asn Val Ala His Pro Ala Ser Ser Thr Lys Val Asp Lys
                85                  90                  95

Arg Val Glu Pro Gly Cys Pro Asp Pro Cys Lys His Cys Arg Cys Pro
            100                 105                 110

Pro Pro Glu Leu Pro Gly Gly Pro Ser Val Phe Ile Phe Pro Pro Lys
        115                 120                 125

Pro Lys Asp Thr Leu Thr Ile Ser Gly Thr Pro Glu Val Thr Cys Val
130                 135                 140

Val Val Asp Val Gly Gln Asp Pro Glu Val Gln Phe Ser Trp Phe
145                 150                 155                 160

Val Asp Asn Val Glu Val Arg Thr Ala Arg Thr Lys Pro Arg Glu Glu
                165                 170                 175

Gln Phe Asn Ser Thr Phe Arg Val Val Ser Ala Leu Pro Ile Gln His
            180                 185                 190

Gln Asp Trp Thr Gly Gly Lys Glu Phe Lys Cys Lys Val His Asn Glu
        195                 200                 205

Ala Leu Pro Ala Pro Ile Val Arg Thr Ile Ser Arg Thr Lys Gly Gln
210                 215                 220

Ala Arg Glu Pro Gln Val Tyr Val Leu Ala Pro Pro Gln Glu Glu Leu
225                 230                 235                 240

Ser Lys Ser Thr Leu Ser Val Thr Cys Leu Val Thr Gly Phe Tyr Pro
                245                 250                 255

Asp Tyr Ile Ala Val Glu Trp Gln Lys Asn Gly Gln Pro Glu Ser Glu
            260                 265                 270

Asp Lys Tyr Gly Thr Thr Thr Ser Gln Leu Asp Ala Asp Gly Ser Tyr
        275                 280                 285

Phe Leu Tyr Ser Arg Leu Arg Val Asp Lys Asn Ser Trp Gln Glu Gly
290                 295                 300

Asp Thr Tyr Ala Cys Val Val Met His Glu Ala Leu His Asn His Tyr
305                 310                 315                 320

Thr Gln Lys Ser Ile Ser Lys Pro Pro Gly Lys
                325                 330

<210> SEQ ID NO 91
<211> LENGTH: 996
<212> TYPE: DNA
<213> ORGANISM: Bubalus arnee

<400> SEQUENCE: 91
gcctcaacaa cacccccgaa agtctaccct ctgacttctt gctgcgggga cacgtccagc      60
tccatcgtga ccctgggctg cctggtctcc agctatatgc ccgagccggt gaccgtgacc     120
tggaactctg gtgccctgac cagcggcgtg cacaccttcc cggccatcct gcagtcctcc     180
gggctctact ctctcagcag cgtggtgacc gtgccggcca gcacctcagg agcccagacc     240
ttcatctgca acgtagccca cccggccagc agcaccaagg tggacaagcg tgttgagccc     300
ggatgcccgg acccatgcaa acattgccga tgcccacccc ctgagctccc cggaggaccg     360
tctgtcttca tcttcccacc gaaacccaag gacaccctta caatctctgg aacgcccgag     420
gtcacgtgtg tggtggtgga cgtgggccag gatgaccccg aggtgcagtt ctcctggttc     480
gtggacaacg tggaggtgcg cacggccagg acaaagccga gaggagca gttcaacagc     540 accttccgcg tggtcagcgc cctgcccatc cagcaccaag actggactgg aggaaaggag     600
ttcaagtgca aggtccacaa cgaagccctc ccggccccca tcgtgaggac catctccagg     660

```
accaaagggc aggcccggga gccgcaggtg tacgtcctgg ccccacccca ggaagagctc    720
agcaaaagca cgctcagcgt cacctgcctg gtcaccggct tctacccaga ctacatcgcc    780
gtggagtggc agaaaaatgg gcagcctgag tcggaggaca gtacggcac gaccacatcc     840 cagctggacg ccgacggctc ctacttcctg tacagcaggc tcagggtgga caagaacagc    900
tggcaagaag gagacaccta cgcgtgtgtg gtgatgcacg aggctctgca caaccactac    960
acacagaagt cgatctctaa gcctccgggt aaatga                              996
```

```
<210> SEQ ID NO 92
<211> LENGTH: 329
<212> TYPE: PRT
<213> ORGANISM: Bubalus arnee

<400> SEQUENCE: 92
```

```
Ala Ser Thr Thr Ala Pro Lys Val Tyr Pro Leu Thr Ser Cys Cys Gly
1               5                   10                  15

Asp Thr Ser Ser Ser Ser Ile Val Thr Leu Gly Cys Leu Val Ser
            20                  25                  30

Ser Tyr Met Pro Glu Pro Val Thr Val Thr Trp Asn Ser Gly Ala Leu
        35                  40                  45

Thr Ser Gly Val His Thr Phe Pro Ala Ile Leu Gln Ser Ser Gly Leu
    50                  55                  60

Tyr Ser Leu Ser Ser Val Val Thr Val Pro Ala Ser Thr Ser Gly Ala
65                  70                  75                  80

Gln Thr Phe Ile Cys Asn Val Ala His Pro Ala Ser Ser Ala Lys Val
                85                  90                  95

Asp Lys Arg Val Gly Ile Ser Ser Asp Tyr Ser Lys Cys Ser Lys Pro
            100                 105                 110

Pro Cys Val Ser Arg Pro Ser Val Phe Ile Phe Pro Pro Lys Pro Lys
        115                 120                 125

Asp Ser Leu Met Ile Thr Gly Thr Pro Glu Val Thr Cys Val Val Val
    130                 135                 140

Asp Val Gly Gln Gly Asp Pro Glu Val Gln Phe Ser Trp Phe Val Asp
145                 150                 155                 160

Asn Val Glu Val Arg Thr Ala Arg Thr Lys Pro Arg Glu Glu Gln Phe
                165                 170                 175

Asn Ser Thr Phe Arg Val Val Ser Ala Leu Pro Ile Gln His Asp His
            180                 185                 190

Trp Thr Gly Gly Lys Glu Phe Lys Cys Lys Val His Ser Lys Gly Leu
        195                 200                 205

Pro Ala Pro Ile Val Arg Thr Ile Ser Arg Ala Lys Gly Gln Ala Arg
    210                 215                 220

Glu Pro Gln Val Tyr Val Leu Ala Pro Pro Gln Glu Glu Leu Ser Lys
225                 230                 235                 240

Ser Thr Leu Ser Val Thr Cys Leu Val Thr Gly Phe Tyr Pro Asp Tyr
                245                 250                 255

Ile Ala Val Glu Trp Gln Arg Ala Arg Gln Pro Glu Ser Glu Asp Lys
            260                 265                 270

Tyr Gly Thr Thr Thr Ser Gln Leu Asp Ala Asp Gly Ser Tyr Phe Leu
        275                 280                 285

Tyr Ser Arg Leu Arg Val Asp Lys Ser Ser Trp Gln Arg Gly Asp Thr
    290                 295                 300

Tyr Ala Cys Val Val Met His Glu Ala Leu His Asn His Tyr Thr Gln
305                 310                 315                 320
```

Lys Ser Ile Ser Lys Pro Pro Gly Lys
                325

<210> SEQ ID NO 93
<211> LENGTH: 990
<212> TYPE: DNA
<213> ORGANISM: Bubalus arnee

<400> SEQUENCE: 93
gcctccacca cagccccgaa agtctaccct ctgacttctt gctgcgggga cacgtccagc        60
tccagctcca tcgtgaccct gggctgcctg gtctccagct atatgcccga gccggtgacc       120
gtgacctgga actctggtgc cctgaccagc ggcgtgcaca ccttcccggc catcctgcag       180
tcctccgggc tctactctct cagcagcgtg gtgaccgtgc cggccagcac ctcaggagcc       240
cagaccttca tctgcaacgt agcccacccg gccagcagcg ccaaggtgga caagcgtgtt       300
gggatctcca gtgactactc caagtgttct aaaccgcctt gcgtgagccg accgtctgtc       360
ttcatcttcc ccccgaaacc caaggacagc ctcatgatca caggaacgcc cgaggtcacg       420
tgtgtggtgg tggacgtggg ccagggtgac cccgaggtgc agttctcctg gttcgtggac       480
aacgtggagt gcgcacggc caggacaaag ccgagagagg agcagttcaa cagcaccttc       540
cgcgtggtca gcgccctgcc catccagcac gaccactgga ctggaggaaa ggagttcaag       600
tgcaaggtcc acagcaaagg cctcccggcc ccatcgtga ggaccatctc cagggccaaa       660
gggcaggccc gggagccgca ggtgtacgtc ctggccccac cccaggaaga gctcagcaaa       720
agcacgctca cgtcacctg cctggtcacc ggcttctacc cagactacat cgccgtggag       780
tggcagagag cgcggcagcc tgagtcggag gacaagtacg gcacgaccac atcccagctg       840
gacgccgacg gctcctactt cctgtacagc aggctcaggg tggacaagag cagctggcaa       900
agaggagaca cctacgcgtg tgtggtgatg cacgaggctc tgcacaacca ctacacacag       960
aagtcgatct ctaagcctcc gggtaaatga                                        990

<210> SEQ ID NO 94
<211> LENGTH: 328
<212> TYPE: PRT
<213> ORGANISM: Bubalus arnee

<400> SEQUENCE: 94

Ala Pro Lys Thr Ala Pro Ser Val Tyr Pro Leu Ala Pro Cys Gly Arg
1               5                   10                  15

Asp Thr Ser Gly Pro Asn Val Ala Leu Gly Cys Leu Ala Ser Ser Tyr
            20                  25                  30

Phe Pro Glu Pro Val Thr Met Thr Trp Asn Ser Gly Ala Leu Thr Ser
        35                  40                  45

Gly Val His Thr Phe Pro Ser Val Leu Gln Pro Ser Gly Leu Tyr Ser
    50                  55                  60

Leu Ser Ser Met Val Thr Val Pro Ala Ser Ser Leu Ser Lys Ser
65                  70                  75                  80

Tyr Thr Cys Asn Val Asn His Pro Ala Thr Thr Lys Val Asp Lys
                85                  90                  95

Arg Val Gly Thr Lys Thr Lys Pro Pro Cys Pro Ile Cys Pro Gly Cys
            100                 105                 110

Glu Val Ala Gly Pro Ser Val Phe Ile Phe Pro Pro Lys Pro Lys Asp
        115                 120                 125

Thr Leu Met Ile Ser Gln Thr Pro Glu Val Thr Cys Val Val Val Asp

```
                130                 135                 140
Val Ser Lys Glu His Ala Glu Val Gln Phe Ser Trp Tyr Val Asp Gly
145                 150                 155                 160

Val Glu Val His Thr Ala Glu Thr Arg Pro Lys Glu Glu Gln Phe Asn
                165                 170                 175

Ser Thr Tyr Arg Val Val Ser Val Leu Pro Ile Gln His Gln Asp Trp
                180                 185                 190

Leu Lys Gly Lys Glu Phe Lys Cys Lys Val Asn Asn Val Asp Leu Pro
                195                 200                 205

Ala Pro Ile Thr Arg Thr Ile Ser Lys Ala Ile Gly Gln Ser Arg Glu
                210                 215                 220

Pro Gln Val Tyr Thr Leu Pro Pro Pro Ala Glu Glu Leu Ser Arg Ser
225                 230                 235                 240

Lys Val Thr Val Thr Cys Leu Val Ile Gly Phe Tyr Pro Pro Asp Ile
                245                 250                 255

His Val Glu Trp Lys Ser Asn Gly Gln Pro Glu Pro Glu Gly Asn Tyr
                260                 265                 270

Arg Thr Thr Pro Pro Gln Gln Asp Val Asp Gly Thr Phe Phe Leu Tyr
                275                 280                 285

Ser Lys Leu Ala Val Asp Lys Ala Arg Trp Asp His Gly Glu Thr Phe
                290                 295                 300

Glu Cys Ala Val Met His Glu Ala Leu His Asn His Tyr Thr Gln Lys
305                 310                 315                 320

Ser Ile Ser Lys Thr Gln Gly Lys
                325
```

<210> SEQ ID NO 95
<211> LENGTH: 987
<212> TYPE: DNA
<213> ORGANISM: Bubalus arnee

<400> SEQUENCE: 95

```
gcccccaaga cggccccatc ggtctaccct ctggcccect gcggcaggga cacgtctggc    60
cctaacgtgg ccttgggctg cctggcctca agctacttcc ccgagccagt gaccatgacc   120
tggaactcgg gcgccctgac cagtggcgtg cataccttcc catccgtcct gcagccgtca   180
gggctctact ccctcagcag catggtgacc gtgccggcca gcagcctgtc agcaagagc    240
tacacctgca atgtcaacca cccggccacc accaccaagg tggacaagcg tgttggaaca   300
aagaccaaac caccatgtcc catatgccca ggctgtgaag tggccgggcc ctcggtcttc   360
atcttccctc caaaacccaa ggacaccctc atgatctccc agaccccga ggtcacgtgc    420
gtggtggtgg acgtcagcaa ggagcacgcc gaggtccagt tctcctggta cgtggacggc   480
gtagaggtgc acacggccga cgagacca aaggaggagc agttcaacag cacctaccgt     540
gtggtcagcg tcctgcccat ccagcaccag gactggctga aggggaagga gttcaagtgc   600
aaggtcaaca acgtagacct cccagccccc atcacgagga ccatctccaa ggctataggg   660
cagagccggg agccgcaggt gtacaccctg cccccacccg ccgaggagct gtccaggagc   720
aaagtcaccg taacctgcct ggtcattggc ttctacccac ctgacatcca tgttgagtgg   780
aagagcaacg gacagccgga gccagagggc aattaccgca ccacccgcc ccagcaggac   840
gtggacggga ccttcttcct gtacagcaag ctcgcggtgg acaaggcaag atgggaccat   900
ggagaaacat tgagtgtgc ggtgatgcac gaggctctgc acaaccacta cacccagaag    960
tccatctcca agactcaggg taaatga                                       987
```

<210> SEQ ID NO 96
<211> LENGTH: 328
<212> TYPE: PRT
<213> ORGANISM: Bubalus arnee

<400> SEQUENCE: 96

Ala Pro Lys Thr Ala Pro Ser Val Tyr Pro Leu Ala Pro Cys Gly Arg
1               5                   10                  15

Asp Val Ser Gly Pro Asn Val Ala Leu Gly Cys Leu Ala Ser Ser Tyr
            20                  25                  30

Phe Pro Glu Pro Val Thr Val Thr Trp Asn Ser Gly Ala Leu Thr Ser
        35                  40                  45

Gly Val His Thr Phe Pro Ser Val Leu Gln Pro Ser Gly Leu Tyr Ser
50                  55                  60

Leu Ser Ser Met Val Thr Val Pro Ala Ser Ser Leu Ser Ser Lys Ser
65                  70                  75                  80

Tyr Thr Cys Asn Val Asn His Pro Ala Thr Thr Thr Lys Val Asp Lys
                85                  90                  95

Arg Val Gly Ile His Gln Pro Gln Thr Cys Pro Ile Cys Pro Gly Cys
            100                 105                 110

Glu Val Ala Gly Pro Ser Val Phe Ile Phe Pro Pro Lys Pro Lys Asp
        115                 120                 125

Thr Leu Met Ile Ser Gln Thr Pro Glu Val Thr Cys Val Val Val Asp
    130                 135                 140

Val Ser Lys Glu His Ala Glu Val Gln Phe Ser Trp Tyr Val Asp Gly
145                 150                 155                 160

Val Glu Val His Thr Ala Glu Thr Arg Pro Lys Glu Glu Gln Phe Asn
                165                 170                 175

Ser Thr Tyr Arg Val Val Ser Val Leu Pro Ile Gln His Gln Asp Trp
            180                 185                 190

Leu Lys Gly Lys Glu Phe Lys Cys Lys Val Asn Asn Val Asp Leu Pro
        195                 200                 205

Ala Pro Ile Thr Arg Thr Ile Ser Lys Ala Ile Gly Gln Ser Arg Glu
    210                 215                 220

Pro Gln Val Tyr Thr Leu Pro Pro Pro Ala Glu Glu Leu Ser Arg Ser
225                 230                 235                 240

Lys Val Thr Leu Thr Cys Leu Val Ile Gly Phe Tyr Pro Pro Asp Ile
                245                 250                 255

His Val Glu Trp Lys Ser Asn Gly Gln Pro Glu Pro Gln Asn Thr Tyr
            260                 265                 270

Arg Thr Thr Pro Pro Gln Gln Asp Val Asp Gly Thr Phe Phe Leu Tyr
        275                 280                 285

Ser Lys Leu Ala Val Asp Lys Ala Arg Trp Asp His Gly Asp Lys Phe
    290                 295                 300

Glu Cys Ala Val Met His Glu Ala Leu His Asn His Tyr Thr Gln Lys
305                 310                 315                 320

Ser Ile Ser Lys Thr Gln Gly Lys
                325

<210> SEQ ID NO 97
<211> LENGTH: 987
<212> TYPE: DNA
<213> ORGANISM: Bubalus arnee

<400> SEQUENCE: 97

```
gccccccaaga cggccccatc ggtctaccct ctggcccccct gcggcaggga cgtgtctggc    60
cctaacgtgg ccttgggctg cctggcctca agctacttcc ccgagccagt gaccgtgacc   120
tggaactcgg gcgccctgac cagtggcgtg cacaccttcc catccgtcct gcagccgtca   180
gggctctact ccctcagcag catggtgacc gtgccggcca gcagcctgtc cagcaagagc   240
tacacctgca atgtcaacca cccggccacc accaccaagg tggacaagcg tgttggaata   300
caccagccgc aaacatgtcc catatgccca ggctgtgaag tggccgggcc ctcggtcttc   360
atcttccctc caaaacccaa ggacaccctc atgatctccc agaccccga ggtcacgtgc   420 gtggtggtgg acgtcagcaa ggagcacgcc gaggtccagt tctcctggta cgtggacggc   480
gtagaggtgc acacggccga gacgagacca aggaggagc agttcaacag cacctaccgt   540
gtggtcagcg tcctgcccat ccagcaccag gactggctga aggggaagga gttcaagtgc   600
aaggtcaaca acgtagacct cccagccccc atcacgagga ccatctccaa ggctataggg   660
cagagccggg agccgcaggt gtacaccctg cccccacccg ccgaggagct gtccaggagc   720
aaagtcacgc taacctgcct ggtcattggc ttctacccac ctgacatcca tgttgagtgg   780
aagagcaacg gacagccgga gccagagaac ataccgca ccaccccgcc ccagcaggac   840
gtggacggga ccttcttcct gtacagcaaa ctcgcggtgg acaaggcaag atgggaccat   900
ggagacaaat ttgagtgtgc ggtgatgcac gaggctctgc acaaccacta cacccagaag   960
tccatctcca agactcaggg taaatga                                        987

<210> SEQ ID NO 98
<211> LENGTH: 328
<212> TYPE: PRT
<213> ORGANISM: Bubalus arnee

<400> SEQUENCE: 98

Ala Pro Lys Thr Ala Pro Ser Val Tyr Pro Leu Ala Pro Cys Ser Arg
1               5                   10                  15

Asp Thr Ser Gly Pro Asn Val Ala Leu Gly Cys Leu Ala Ser Ser Tyr
            20                  25                  30

Phe Pro Glu Pro Val Thr Val Thr Trp Asn Ser Gly Ala Leu Ser Ser
        35                  40                  45

Gly Val His Thr Phe Pro Ser Val Leu Gln Pro Ser Gly Leu Tyr Ser
    50                  55                  60

Leu Ser Ser Met Val Thr Val Pro Ala Ser Ser Leu Ser Ser Lys Ser
65                  70                  75                  80

Tyr Thr Cys Asn Val Asn His Pro Ala Thr Thr Thr Lys Val Asp Lys
                85                  90                  95

Arg Val Gly Thr Lys Thr Lys Pro Pro Cys Pro Ile Cys Pro Ala Cys
            100                 105                 110

Glu Ser Pro Gly Pro Ser Val Phe Ile Phe Pro Pro Lys Pro Lys Asp
        115                 120                 125

Thr Leu Met Ile Ser Arg Thr Pro Gln Val Thr Cys Val Val Val Asp
    130                 135                 140

Val Ser Gln Glu Asn Pro Glu Val Gln Phe Ser Trp Tyr Val Asp Gly
145                 150                 155                 160

Val Glu Val His Thr Ala Gln Thr Arg Pro Lys Glu Glu Gln Phe Asn
                165                 170                 175

Ser Thr Tyr Arg Val Val Ser Val Leu Pro Ile Gln His Gln Asp Trp
            180                 185                 190
```

```
Leu Asn Gly Lys Glu Phe Lys Cys Lys Val Asn Asn Lys Asp Leu Pro
            195                 200                 205

Ala Pro Ile Thr Arg Ile Ile Ser Lys Ala Lys Gly Gln Thr Arg Glu
    210                 215                 220

Pro Gln Val Tyr Thr Leu Pro Pro His Ala Glu Glu Leu Ser Arg Ser
225                 230                 235                 240

Lys Val Ser Ile Thr Cys Leu Val Ile Gly Phe Tyr Pro Pro Asp Ile
                245                 250                 255

Asp Val Glu Trp Gln Arg Asn Gly Gln Pro Glu Pro Glu Gly Asn Tyr
            260                 265                 270

Arg Thr Thr Pro Pro Gln Gln Asp Val Asp Gly Thr Tyr Phe Leu Tyr
        275                 280                 285

Ser Lys Phe Ser Val Asp Lys Ala Ser Trp Gln Gly Gly Gly Ile Phe
            290                 295                 300

Gln Cys Ala Val Met His Glu Ala Leu His Asn His Tyr Thr Gln Lys
305                 310                 315                 320

Ser Ile Ser Lys Thr Pro Gly Lys
                325
```

<210> SEQ ID NO 99
<211> LENGTH: 987
<212> TYPE: DNA
<213> ORGANISM: Bubalus arnee

<400> SEQUENCE: 99

```
gcccccaaga cggccccatc ggtctaccct ctggccccct gcagcaggga cacgtctggc    60
cctaacgtgg ccttgggctg cctggcctca agctacttcc ccgagccagt gaccgtgacc   120
tggaactcgg gcgccctgtc cagtggcgtg cataccttcc catccgtcct gcagccgtca   180
gggctctact ccctcagcag catggtgacc gtgccggcca gcagcctgtc cagcaagagc   240
tacacctgca atgtcaacca cccggccacc accaccaagg tggacaagcg tgttggaaca   300
aagaccaaac caccatgtcc catatgccca gcctgtgaat caccagggcc ctcggtcttc   360
atcttccctc caaaacccaa ggacaccctc atgatctccc ggacacccca ggtcacgtgc   420
gtggtggttg atgtgagcca ggagaacccg gaggtccagt tctcctggta cgtggacggc   480
gtagaggtgc acacggccca gacgaggcca aggaggagc agttcaacag cacctaccgc   540
gtggtcagcg tcctacccat ccagcaccag gactggctga acgggaagga gttcaagtgc   600
aaggtcaaca acaaagacct cccagccccc atcacaagga tcatctccaa ggccaagggg   660
cagacccggg agccgcaggt gtacaccctg cccccacacg ccgaggagct gtccaggagc   720
aaagtcagca taacctgcct ggtcattggc ttctacccac ctgacatcga tgtcgagtgg   780
caaagaaacg gacagccgga gccagagggc aattaccgca ccaccccgcc ccagcaggac   840
gtggacggga cctacttcct gtacagcaag ttctcggtgg acaaggccag ctggcagggt   900
ggaggcatat tccagtgtgc ggtgatgcac gaggctctgc acaaccacta cacccagaag   960
tctatctcca agactccggg taaatga                                      987
```

<210> SEQ ID NO 100
<211> LENGTH: 328
<212> TYPE: PRT
<213> ORGANISM: Bubalus arnee

<400> SEQUENCE: 100

```
Ala Pro Lys Thr Ala Pro Leu Val Tyr Pro Leu Ala Pro Cys Gly Arg
1               5                   10                  15
```

```
Asp Thr Ser Gly Pro Asn Val Ala Leu Gly Cys Leu Ala Ser Ser Tyr
             20                  25                  30
Phe Pro Glu Pro Val Thr Val Thr Trp Asn Ser Gly Ala Leu Thr Ser
         35                  40                  45
Gly Val His Thr Phe Pro Ser Val Leu Gln Pro Ser Gly Leu Tyr Ser
     50                  55                  60
Leu Ser Ser Met Val Thr Val Pro Ala Ser Ser Leu Ser Ser Lys Ser
 65                  70                  75                  80
Tyr Thr Cys Asn Val Asn His Pro Ala Thr Thr Lys Val Asp Lys
                 85                  90                  95
Arg Val Gly Thr Lys Thr Lys Pro Pro Cys Pro Ile Cys Pro Ala Cys
                100                 105                 110
Glu Ser Pro Gly Pro Ser Val Phe Ile Phe Pro Pro Lys Pro Lys Asp
            115                 120                 125
Thr Leu Met Ile Ser Arg Thr Pro Gln Val Thr Cys Val Val Asp
    130                 135                 140
Val Ser Gln Glu Asn Pro Glu Val Gln Phe Ser Trp Tyr Val Asp Gly
145                 150                 155                 160
Val Glu Val His Thr Ala Gln Thr Arg Pro Lys Glu Glu Gln Phe Asn
                165                 170                 175
Ser Thr Tyr Arg Val Val Ser Val Leu Pro Ile Gln His Gln Asp Trp
            180                 185                 190
Leu Asn Gly Lys Glu Phe Lys Cys Lys Val Asn Asn Lys Asp Leu Pro
        195                 200                 205
Ala Pro Ile Thr Arg Ile Ile Ser Lys Ala Lys Gly Gln Thr Arg Glu
    210                 215                 220
Pro Gln Val Tyr Thr Leu Pro Pro His Ala Glu Glu Leu Ser Arg Ser
225                 230                 235                 240
Lys Val Ser Ile Thr Cys Leu Val Ile Gly Phe Tyr Pro Pro Asp Ile
                245                 250                 255
Asp Val Glu Trp Gln Arg Asn Gly Gln Pro Glu Pro Glu Gly Asn Tyr
            260                 265                 270
Arg Thr Thr Pro Pro Gln Gln Asp Val Asp Gly Thr Tyr Phe Leu Tyr
        275                 280                 285
Ser Lys Phe Ser Val Asp Lys Ala Ser Trp Gln Gly Gly Ile Phe
    290                 295                 300
Gln Cys Ala Val Met His Glu Ala Leu His Asn His Tyr Thr Gln Lys
305                 310                 315                 320
Ser Ile Ser Lys Thr Pro Gly Lys
                325

<210> SEQ ID NO 101
<211> LENGTH: 987
<212> TYPE: DNA
<213> ORGANISM: Bubalus arnee

<400> SEQUENCE: 101
gcccccaaga cggccccatt ggtctaccct ctggccccct gcggcaggga cacgtctggc      60
cctaacgtgg ccttgggctg cctggcctca agctacttcc ccgagccagt gaccgtgacc    120
tggaactcgg gcgccctgac cagtggcgtg cataccttcc catccgtcct gcagccgtca    180
gggctctact ccctcagcag catggtgacc gtgccggcca gcagcctgtc cagcaagagc    240
tacacctgca atgtcaacca cccggccacc accaccaagg tggacaagcg tgttggaaca    300
```

```
aagaccaaac caccatgtcc catatgccca gcctgtgaat cgccagggcc ctcggtcttc    360
atcttccctc caaacccaa ggacaccctc atgatctccc ggacacccca ggtcacgtgc     420
gtggtagttg atgtgagcca ggagaacccg gaggtccagt tctcctggta cgtggacggc    480
gtagaggtgc acacggccca gacgaggcca aggaggagc agttcaacag cacctaccgc     540
gtggtcagcg tcctgcccat ccagcaccag gactggctga acgggaagga gttcaagtgc    600
aaggtcaaca acaaagacct cccagccccc atcacaagga tcatctccaa ggccaaaggg    660
cagacccggg agccgcaggt gtacaccctg cccccacacg ccgaggagct gtccaggagc    720
aaagtcagca taacctgcct ggtcattggc ttctacccac ctgacatcga tgtcgagtgg    780
caaagaaacg gacagccgga gccagagggc aattaccgca ccacccccgcc ccagcaggac   840
gtggacggga cctacttcct gtacagcaag ttctcggtgg acaaggccag ctggcagggt    900
ggaggcatat tccagtgtgc ggtgatgcac gaggctctgc acaaccacta cacccagaag    960
tctatctcca agactccggg taaatga                                         987
```

<210> SEQ ID NO 102
<211> LENGTH: 333
<212> TYPE: PRT
<213> ORGANISM: Bubalus arnee

<400> SEQUENCE: 102

```
Ala Tyr Asn Thr Ala Pro Ser Val Tyr Pro Leu Ala Pro Cys Gly Arg
1               5                   10                  15

Asp Val Ser Asp His Asn Val Ala Leu Gly Cys Leu Val Ser Ser Tyr
            20                  25                  30

Phe Pro Glu Pro Val Thr Val Thr Trp Asn Ser Gly Ala Leu Ser Arg
        35                  40                  45

Val Val His Thr Phe Pro Ser Val Leu Gln Pro Ser Gly Leu Tyr Ser
    50                  55                  60

Leu Ser Ser Met Val Ile Val Ala Ala Ser Ser Leu Ser Thr Leu Ser
65                  70                  75                  80

Tyr Thr Cys Asn Val Tyr His Pro Ala Thr Asn Thr Lys Val Asp Lys
                85                  90                  95

Arg Val Asp Ile Glu Pro Pro Thr Pro Ile Cys Pro Glu Ile Cys Ser
            100                 105                 110

Cys Pro Ala Ala Glu Val Leu Gly Ala Pro Ser Val Phe Leu Phe Pro
        115                 120                 125

Pro Lys Pro Lys Asp Ile Leu Met Ile Ser Arg Thr Pro Lys Val Thr
    130                 135                 140

Cys Val Val Val Asp Val Ser Gln Glu Glu Ala Glu Val Gln Phe Ser
145                 150                 155                 160

Trp Tyr Val Asp Gly Val Gln Leu Tyr Thr Ala Gln Thr Arg Pro Met
                165                 170                 175

Glu Glu Gln Phe Asn Ser Thr Tyr Arg Val Val Ser Val Leu Pro Ile
            180                 185                 190

Gln His Gln Asp Trp Leu Lys Gly Lys Glu Phe Lys Cys Lys Val Asn
        195                 200                 205

Asn Lys Asp Leu Leu Ser Pro Ile Thr Arg Thr Ile Ser Lys Ala Thr
    210                 215                 220

Gly Pro Ser Arg Val Pro Gln Val Tyr Thr Leu Pro Pro Ala Trp Glu
225                 230                 235                 240

Glu Leu Ser Lys Ser Lys Val Ser Ile Thr Cys Leu Val Thr Gly Phe
                245                 250                 255
```

Tyr Pro Pro Asp Ile Asp Val Glu Trp Gln Ser Asn Gly Gln Gln Glu
            260                 265                 270

Pro Glu Gly Asn Tyr Arg Thr Thr Pro Pro Gln Gln Asp Val Asp Gly
        275                 280                 285

Thr Tyr Phe Leu Tyr Ser Lys Leu Ala Val Asp Lys Val Arg Trp Gln
290                 295                 300

Arg Gly Asp Leu Phe Gln Cys Ala Val Met His Glu Ala Leu His Asn
305                 310                 315                 320

His Tyr Thr Gln Lys Ser Ile Ser Lys Thr Gln Gly Lys
                325                 330

<210> SEQ ID NO 103
<211> LENGTH: 1002
<212> TYPE: DNA
<213> ORGANISM: Bubalus arnee

<400> SEQUENCE: 103

```
gcctacaaca cagctccatc ggtctaccct ctggccccct gtggcaggga cgtgtctgat      60
cataacgtgg ccttgggctg ccttgtctca agctacttcc ccgagccagt gaccgtgacc     120
tggaactcgg gtgccctgtc cagagtcgtg catccttcc catccgtcct gcagccgtca     180
gggctctact ccctcagcag catggtgatc gtggcggcca gcagcctgtc caccctgagc    240
tacacgtgca acgtctacca ccggccacc aacaccaagg tggacaagcg tgttgacatc     300
gaacccccca cacccatctg tcccgaaatt tgctcatgcc agctgcaga ggtcctggga    360
gcaccgtcgg tcttcctctt ccctccaaaa cccaaggaca tcctcatgat ctcccggaca    420
cccaaggtca cgtgcgtggt ggtggacgtg agccaggagg aggctgaagt ccagttctcc    480
tggtacgtgg acggcgtaca gttgtacacg gcccagacga ggccaatgga ggagcagttc    540
aacagcacct accgcgtggt cagcgtcctg cccatccagc accaggactg gctgaagggg    600
aaggagttca gtgcaaggt caacaacaaa gactcctttt ccccatcac gaggaccatc    660
tccaaggcta cagggccgag ccgggtgccg caggtgtaca ccctgccccc agcctgggaa    720
gagctgtcca gagcaaagt cagcataacc tgcctggtca ctggcttcta cccacctgac    780
atcgatgtcg agtggcagag caacggacaa caagagccag agggcaatta ccgcaccacc    840
ccgcccagc aggacgtgga tgggacctac ttcctgtaca gcaagctcgc ggtggacaag    900
gtcaggtggc agcgtggaga cctattccag tgtgcggtga tgcacgaggc tctgcacaac    960
cactacaccc agaagtccat ctccaagact cagggtaaat ga                      1002
```

<210> SEQ ID NO 104
<211> LENGTH: 277
<212> TYPE: PRT
<213> ORGANISM: Bubalus arnee

<400> SEQUENCE: 104

Thr Phe Pro Ser Val Leu Gln Pro Ser Gly Leu Tyr Ser Leu Ser Ser
1               5                   10                  15

Met Val Thr Val Pro Ala Ser Ser Leu Ser Ser Lys Ser Tyr Thr Cys
            20                  25                  30

Asn Val Asn His Pro Ala Thr Thr Lys Val Asp Lys Arg Val Gly
        35                  40                  45

Thr Lys Thr Lys Pro Pro Cys Pro Ile Cys Pro Ala Cys Glu Gly Pro
    50                  55                  60

Gly Pro Ser Ala Phe Ile Phe Pro Pro Lys Pro Lys Asp Thr Leu Met

```
            65                  70                  75                  80
Ile Ser Arg Thr Pro Lys Val Thr Cys Val Val Asp Val Ser Gln
                85                  90                  95
Glu Asn Pro Glu Val Gln Phe Ser Trp Tyr Val Asp Gly Val Glu Val
            100                 105                 110
His Thr Ala Gln Thr Arg Pro Lys Glu Glu Gln Phe Asn Ser Thr Tyr
            115                 120                 125
Arg Val Val Ser Val Leu Pro Ile Gln His Gln Asp Trp Leu Asn Gly
            130                 135                 140
Lys Glu Phe Lys Cys Lys Val Asn Asn Lys Asp Leu Pro Ala Pro Ile
145                 150                 155                 160
Thr Arg Ile Ile Ser Lys Ala Lys Gly Gln Thr Arg Glu Pro Gln Val
                165                 170                 175
Tyr Thr Leu Pro Pro Thr Glu Glu Leu Ser Arg Ser Lys Val Thr
            180                 185                 190
Leu Thr Cys Leu Val Thr Gly Phe Tyr Pro Pro Asp Ile Asp Val Glu
            195                 200                 205
Trp Gln Arg Asn Gly Gln Pro Glu Pro Glu Gly Asn Tyr Arg Thr Thr
210                 215                 220
Pro Pro Gln Gln Asp Val Asp Gly Thr Tyr Phe Leu Tyr Ser Lys Leu
225                 230                 235                 240
Ala Val Asp Lys Ala Ser Trp Gln Arg Gly Asp Thr Phe Gln Cys Ala
                245                 250                 255
Val Met His Glu Ala Leu His Asn His Tyr Thr Gln Lys Ser Ile Phe
                260                 265                 270
Lys Thr Pro Gly Lys
        275

<210> SEQ ID NO 105
<211> LENGTH: 834
<212> TYPE: DNA
<213> ORGANISM: Bubalus arnee

<400> SEQUENCE: 105
accttcccat ccgtcctgca gccgtcaggg ctctactccc tcagcagcat ggtgaccgtg      60
ccggccagca gcctgtccag caagagctac acctgcaatg tcaaccaccc ggccaccacc     120
accaaggtgg acaagcgtgt tggaacaaag accaaaccac catgtcccat atgcccagcc     180
tgtgaagggc ccgggccctc ggccttcatc ttccctccaa acccaaggga caccctcatg     240
atctcccgga cccccaaggt cacgtgcgtg gtggtagatg tgagccagga gaacccggag     300
gtccagttct cctggtacgt ggacggcgta gaggtgcaca cggcccagac gaggccaaag     360
gaggagcagt tcaacagcac ctaccgcgtg gtcagcgtcc tgcccatcca gcaccaggac     420
tggctgaacg gaaggagtt caagtgcaag gtcaacaaca agacctccc agccccatc      480 acaaggatca tctccaaggc caagggcag acccgggagc cgcaggtgta cccctgccc     540 ccacccaccg aggagctgtc caggagcaaa gtcacgctaa cctgcctggt cactggcttc     600
tacccacctg acatcgatgt cgagtggcaa agaaacggac agccggagcc agagggcaat     660
taccgcacca ccccgcccca gcaggacgtg gacgggacct acttcctgta cagcaagctc     720
gcggtggaca aggccagctg gcagcgtgga gacacattcc agtgtgcggt gatgcacgag     780
gctctgcaca accactacac ccagaagtcc atcttcaaga ctccgggtaa atga          834

<210> SEQ ID NO 106
```

```
<211> LENGTH: 318
<212> TYPE: PRT
<213> ORGANISM: Bubalus arnee

<400> SEQUENCE: 106
```

| | | | | | | | | | | | | | | |
|---|---|---|---|---|---|---|---|---|---|---|---|---|---|---|
|Ala|Pro|Lys|Thr|Ala|Pro|Ser|Val|Tyr|Pro|Leu|Ala|Pro|Cys|Gly|Arg|
|1| | | |5| | | | |10| | | | |15|

Asp Val Ser Gly Pro Asn Val Ala Leu Gly Cys Leu Ala Ser Ser Tyr
              20                  25                  30

Phe Pro Glu Pro Val Thr Val Thr Trp Asn Ser Gly Ala Leu Thr Ser
             35                  40                  45

Gly Val His Thr Phe Pro Ser Val Leu Gln Pro Ser Gly Leu Tyr Ser
         50                  55                  60

Leu Ser Ser Met Val Thr Val Pro Ala Ser Ser Leu Ser Ser Lys Ser
65                  70                  75                  80

Tyr Thr Cys Asn Val Asn His Pro Ala Thr Thr Lys Val Asp Lys
                 85                  90                  95

Arg Val Gly Ile His Gln Pro Gln Thr Cys Pro Ile Cys Pro Ala Cys
                100                 105                 110

Glu Gly Pro Gly Pro Ser Ala Phe Ile Phe Pro Pro Lys Pro Lys Asp
            115                 120                 125

Thr Leu Met Ile Ser Arg Thr Pro Lys Val Thr Cys Val Val Val Asp
130                 135                 140

Val Ser Gln Glu Asn Pro Glu Val Gln Phe Ser Trp Tyr Val Asp Gly
145                 150                 155                 160

Val Glu Val His Thr Ala Gln Thr Arg Pro Lys Glu Glu Gln Phe Asn
                165                 170                 175

Ser Thr Tyr Arg Val Val Ser Val Leu Leu Ile Gln His Gln Asp Trp
            180                 185                 190

Leu Asn Gly Lys Glu Phe Lys Cys Lys Val Asn Asn Lys Asp Leu Pro
        195                 200                 205

Ala Pro Ile Thr Arg Ile Ile Ser Lys Ala Lys Gly Gln Thr Arg Glu
210                 215                 220

Pro Gln Val Tyr Thr Leu Pro Pro Thr Glu Glu Leu Ser Arg Ser
225                 230                 235                 240

Lys Val Thr Leu Thr Cys Leu Val Thr Gly Phe Tyr Pro Pro Asp Ile
                245                 250                 255

Asp Val Glu Trp Gln Arg Asn Gly Gln Pro Glu Pro Glu Gly Asn Tyr
            260                 265                 270

Arg Thr Thr Pro Pro Gln Gln Asp Val Asp Gly Thr Tyr Phe Leu Tyr
        275                 280                 285

Ser Lys Leu Ala Val Asp Lys Ala Ser Trp Gln Arg Gly Asp Thr Phe
290                 295                 300

Gln Cys Ala Val Met His Glu Ala Leu His Asn His Tyr Thr
305                 310                 315

```
<210> SEQ ID NO 107
<211> LENGTH: 955
<212> TYPE: DNA
<213> ORGANISM: Bubalus arnee

<400> SEQUENCE: 107
gcccccaaga cggccccatc ggtctaccct ctggccccct gcggcaggga cgtgtctggc      60
cctaacgtgg ccttgggctg cctggcctca agctacttcc ccgagccagt gaccgtgacc     120
tggaactcgg gcgccctgac cagtggcgtg cacaccttcc catccgtcct gcagccgtca     180
```

-continued

```
gggctctact ccctcagcag catggtgacc gtgccggcca gcagcctgtc cagcaagagc      240
tacacctgca atgtcaacca cccggccacc accaccaagg tggacaagcg tgttggaata      300
caccagccgc aaacatgtcc catatgccca gcctgtgaag ggcccgggcc ctcggccttc      360
atcttccctc caaacccaa  ggacaccctc atgatctccc ggaccccaa  ggtcacgtgc      420 gtggtggttg atgtgagcca ggagaacccg gaggtccagt tctcctggta cgtggacggc      480
gtagaggtgc acacggccca gacgaggcca aggaggagc  agttcaacag cacctaccgc      540
gtggtcagcg tcctgctcat ccagcaccag gactggctga acgggaagga gttcaagtgc      600
aaggtcaaca acaaagacct cccagccccc atcacaagga tcatctccaa ggccaaaggg      660
cagacccggg agccgcaggt gtacaccctg cccccaccca ccgaggagct gtccaggagc      720
aaagtcacgc taacctgcct ggtcactggc ttctacccac tgacatcga  tgtcgagtgg      780 caaagaaacg gacagccgga gccagagggc aattaccgca ccaccccgcc ccagcaggac      840
gtggacggga cctacttcct gtacagcaag ctcgcggtgg acaaggccag ctggcagcgt      900
ggagacacat tccagtgtgc ggtgatgcac gaggctctgc acaaccacta caccc          955
```

<210> SEQ ID NO 108
<211> LENGTH: 323
<212> TYPE: PRT
<213> ORGANISM: Bubalus arnee

<400> SEQUENCE: 108

```
Ala Pro Lys Thr Ala Pro Ser Val Tyr Pro Leu Ala Pro Cys Ser Arg
1               5                   10                  15

Asp Thr Ser Gly Pro Asn Val Ala Leu Gly Cys Leu Val Ser Ser Tyr
            20                  25                  30

Phe Pro Glu Pro Val Thr Val Thr Trp Asn Ser Gly Ala Leu Thr Ser
        35                  40                  45

Gly Val His Thr Phe Pro Ser Val Leu Gln Pro Ser Gly Leu Tyr Ser
    50                  55                  60

Leu Ser Ser Met Val Thr Val Pro Ala His Ser Leu Ser Ser Lys Arg
65                  70                  75                  80

Tyr Thr Cys Asn Val Asn His Pro Ala Thr Lys Thr Lys Val Asp Leu
                85                  90                  95

Cys Val Gly Arg Pro Cys Pro Ile Cys Pro Gly Cys Glu Val Ala Gly
            100                 105                 110

Pro Ser Val Phe Ile Phe Pro Pro Lys Pro Lys Asp Ile Leu Met Ile
        115                 120                 125

Ser Arg Thr Pro Glu Val Thr Cys Val Val Val Asp Val Ser Lys Glu
    130                 135                 140

His Ala Glu Val Gln Phe Ser Trp Tyr Val Asp Gly Glu Glu Val His
145                 150                 155                 160

Thr Ala Glu Thr Arg Pro Lys Glu Glu Gln Phe Asn Ser Thr Tyr Arg
                165                 170                 175

Val Val Ser Val Leu Pro Ile Gln His Glu Asp Trp Leu Lys Gly Lys
            180                 185                 190

Glu Phe Glu Cys Lys Val Asn Asn Glu Asp Leu Pro Gly Pro Ile Thr
        195                 200                 205

Arg Thr Ile Ser Lys Ala Lys Gly Val Val Arg Ser Pro Glu Val Tyr
    210                 215                 220

Thr Leu Pro Pro Pro Ala Glu Glu Leu Ser Lys Ser Ile Val Thr Leu
225                 230                 235                 240
```

```
Thr Cys Leu Val Lys Ser Ile Phe Pro Phe Ile His Val Glu Trp Lys
                245                 250                 255

Ile Asn Gly Lys Pro Glu Pro Glu Asn Ala Tyr Arg Thr Thr Pro Pro
            260                 265                 270

Gln Glu Asp Glu Asp Arg Thr Tyr Phe Leu Tyr Ser Lys Leu Ala Val
        275                 280                 285

Asp Lys Ala Arg Trp Asp His Gly Glu Thr Phe Glu Cys Ala Val Met
    290                 295                 300

His Glu Ala Leu His Asn His Tyr Thr Gln Lys Ser Ile Ser Lys Thr
305                 310                 315                 320

Gln Gly Lys

<210> SEQ ID NO 109
<211> LENGTH: 975
<212> TYPE: DNA
<213> ORGANISM: Bubalus arnee
<220> FEATURE:
<221> NAME/KEY: misc_feature
<222> LOCATION: (748)..(748)
<223> OTHER INFORMATION: n is a, c, g, or t

<400> SEQUENCE: 109
gcccccaaga cggccccatc ggtctaccct ctggccccct gcagcaggga cacgtctggc    60
cctaacgtgg ccttgggctg cctggtctca agctacttcc ccgagccagt gaccgtgacc   120
tggaactcgg gcgccctgac cagtggcgtg cacaccttcc catccgtcct gcagccgtca   180
gggctctact ccctcagcag catggtgacc gtgccggccc acagcttgtc cagcaagcgc   240
tatacgtgca atgtcaacca cccagccacc aaaaccaagg tggacctgtg tgttggacga   300
ccatgtccca tatgcccagg ctgtgaagtg gccgggcccc cggtcttcat cttccctcca   360
aaacccaagg acatcctcat gatctcccgg accccgagg tcacgtgcgt ggtggtggac   420
gtcagcaagg agcacgccga ggtccagttc tcctggtacg tggacggcga agaggtgcac   480
acggccgaga cgaggccaaa ggaggagcag ttcaacagca cctaccgcgt ggtcagcgtc   540
ctgcccatcc agcacgagga ctggctgaag gggaaggagt cgagtgcaa ggtcaacaac   600
gaagacctcc caggccccat cacgaggacc atctccaagg ccaagggggt ggtacggagc   660
ccggaggtgt acaccctgcc cccacccgcc gaggagctgt ccaagagcat agtcacgcta   720
acctgcctgg tcaaaagcat cttcccgnct ttcatccatg ttgagtggaa aatcaacgga   780
aaaccagagc cagagaacgc atatcgcacc accccgcctc aggaggacga ggacaggacc   840
tacttcctgt acagcaagct cgcggtggac aaggcaagat gggaccatgg agaaacattt   900
gagtgtgcgg tgatgcacga ggctctgcac aaccactaca cccagaagtc catctccaag   960
actcagggta aatga                                                   975

<210> SEQ ID NO 110
<211> LENGTH: 317
<212> TYPE: PRT
<213> ORGANISM: Bubalus arnee

<400> SEQUENCE: 110

Ala Tyr Asn Thr Ala Pro Ser Val Tyr Pro Leu Ala Pro Cys Gly Arg
1               5                   10                  15

Asp Val Ser Asp His Asn Val Ala Leu Gly Cys Leu Val Ser Ser Tyr
            20                  25                  30

Phe Pro Glu Pro Val Thr Val Thr Trp Asn Trp Gly Ala Gln Thr Ser
```

```
            35                  40                  45
Gly Val His Thr Phe Pro Ser Val Leu Gln Pro Ser Gly Leu Tyr Ser
        50                  55                  60

Leu Ser Ser Thr Val Thr Val Pro Ala His Ser Leu Ser Ser Lys Cys
 65                  70                  75                  80

Phe Thr Cys Asn Val Asn His Pro Ala Thr Thr Lys Val Asp Leu
                85                  90                  95

Cys Val Gly Lys Lys Thr Lys Pro Arg Cys Pro Ile Cys Pro Gly Cys
                100                 105                 110

Glu Val Ala Gly Pro Ser Val Phe Ile Phe Pro Pro Lys Pro Lys Asp
            115                 120                 125

Ile Leu Met Ile Ser Arg Thr Pro Glu Val Thr Cys Val Val Val Asp
        130                 135                 140

Val Ser Lys Glu His Ala Glu Val Gln Phe Ser Trp Tyr Val Asp Gly
145                 150                 155                 160

Glu Glu Val His Thr Ala Glu Thr Arg Pro Lys Glu Glu Gln Phe Asn
                165                 170                 175

Ser Thr Tyr Arg Val Val Ser Val Leu Pro Ile Gln His Glu Asp Trp
                180                 185                 190

Leu Lys Gly Lys Glu Phe Glu Cys Lys Val Asn Asn Glu Asp Leu Pro
            195                 200                 205

Gly Pro Ile Thr Arg Thr Ile Ser Lys Ala Lys Gly Val Val Arg Ser
        210                 215                 220

Pro Glu Val Tyr Thr Leu Pro Pro Pro Ala Glu Glu Leu Ser Lys Ser
225                 230                 235                 240

Ile Val Thr Leu Thr Cys Leu Val Lys Ser Phe Phe Pro Pro Phe Ile
                245                 250                 255

His Val Glu Trp Lys Ile Asn Gly Lys Pro Glu Pro Glu Asn Ala Tyr
                260                 265                 270

Arg Thr Thr Pro Pro Gln Glu Asp Glu Asp Gly Thr Tyr Phe Leu Tyr
            275                 280                 285

Ser Lys Phe Ser Val Glu Lys Phe Arg Trp His Ser Gly Gly Ile His
        290                 295                 300

Cys Ala Val Met His Glu Ala Leu His Asn His Tyr Thr
305                 310                 315
```

<210> SEQ ID NO 111
<211> LENGTH: 952
<212> TYPE: DNA
<213> ORGANISM: Bubalus arnee

<400> SEQUENCE: 111

```
gcctacaaca cagctccatc ggtctaccct ctggccccct gtggcaggga cgtgtctgat      60
cataacgtgg ccttgggctg cctggtctca agctacttcc ccgagccagt gaccgtgacc     120
tggaactggg gcgcccagac cagtggcgtg cacaccttcc catccgtcct gcagccgtca     180
gggctctact ccctcagcag cacggtgacc gtgccggccc acagcttgtc cagcaagtgc     240
ttcacgtgca atgtcaacca cccggccacc accaccaagg tggacctgtg tgttggaaaa     300
aagaccaagc ctcgatgtcc catatgccca ggctgtgaag tggccgggcc ctcggtcttc     360
atcttccctc caaaacccaa ggacatcctc atgatctccc ggaccccga  ggtcacgtgc     420
gtggtggtgg acgtcagcaa ggagcacgcc gaggtccagt tctcctggta cgtggacggc     480
gaagaggtgc acacggccga gacgagacca aggaggagc agttcaacag cacttaccgc     540
```

```
gtggtcagcg tcctgcccat ccagcacgag gactggctga aggggaagga gttcgagtgc    600
aaggtcaaca acgaagacct cccaggcccc atcacgagga ccatctccaa ggccaaaggg    660
gtggtacgga gcccggaggt gtacaccctg cccccacccg ccgaggagct gtccaagagc    720
atagtcacgc taacctgcct ggtcaaaagc ttcttcccgc ctttcatcca tgttgagtgg    780
aaaatcaacg gaaaaccaga gccagagaac gcataccgca ccaccccgcc ccaggaggac    840
gaggacggga cctacttcct gtacagcaag ttctcggtgg aaaagttcag gtggcacagt    900
ggaggcatcc actgtgcggt gatgcacgag gctctgcaca accactacac cc            952
```

```
<210> SEQ ID NO 112
<211> LENGTH: 314
<212> TYPE: PRT
<213> ORGANISM: Bubalus arnee

<400> SEQUENCE: 112
```

Ala Pro Lys Thr Ala Pro Ser Val Tyr Pro Leu Ala Pro Cys Gly Arg
1               5                   10                  15

Asp Thr Ser Gly Pro Asn Val Ala Leu Gly Cys Leu Ala Ser Ser Tyr
            20                  25                  30

Phe Pro Glu Pro Val Thr Leu Thr Trp Asn Ser Gly Ala Leu Thr Ser
        35                  40                  45

Gly Val His Thr Phe Pro Ser Val Leu Gln Pro Ser Gly Leu Tyr Ser
    50                  55                  60

Leu Ser Ser Met Val Thr Val Pro Ala Ser Ser Leu Ser Ser Lys Ser
65                  70                  75                  80

Tyr Thr Cys Asn Val Asn His Pro Ala Thr Thr Thr Lys Val Asp Leu
                85                  90                  95

Cys Val Gly Arg Pro Cys Pro Ile Cys Pro Ala Cys Glu Gly Pro Gly
            100                 105                 110

Pro Ser Val Phe Ile Phe Pro Pro Lys Pro Lys Asp Thr Leu Met Ile
        115                 120                 125

Ser Arg Thr Pro Gln Val Thr Cys Val Val Val Asp Val Ser Gln Glu
    130                 135                 140

Asn Pro Glu Val Gln Phe Ser Trp Tyr Val Asp Gly Val Glu Val His
145                 150                 155                 160

Thr Ala Gln Thr Arg Pro Lys Glu Ala Gln Phe Asn Ser Thr Tyr Arg
                165                 170                 175

Val Val Ser Val Leu Pro Ile Gln His Glu Asp Trp Leu Lys Gly Lys
            180                 185                 190

Glu Phe Glu Cys Lys Val Asn Asn Lys Asp Leu Pro Ala Pro Ile Thr
        195                 200                 205

Arg Ile Ile Ser Lys Ala Lys Gly Pro Ser Arg Glu Pro Gln Val Tyr
    210                 215                 220

Thr Leu Ser Pro Ser Ala Glu Glu Leu Ser Arg Ser Lys Val Ser Ile
225                 230                 235                 240

Thr Cys Leu Val Thr Gly Phe Tyr Pro Pro Asp Ile Asp Val Glu Trp
                245                 250                 255

Lys Ser Asn Gly Gln Pro Glu Pro Glu Gly Asn Tyr Arg Thr Thr Pro
            260                 265                 270

Pro Gln Gln Asp Val Asp Gly Thr Tyr Phe Leu Tyr Ser Lys Leu Ala
        275                 280                 285

Val Asp Lys Ala Ser Trp Gln Arg Gly Asp Pro Phe Gln Cys Ala Val
    290                 295                 300

Met His Glu Ala Leu His Asn His Tyr Thr
305                 310

<210> SEQ ID NO 113
<211> LENGTH: 943
<212> TYPE: DNA
<213> ORGANISM: Bubalus arnee

<400> SEQUENCE: 113

| | | | | | |
|---|---|---|---|---|---|
| gcccccaaga | cggccccatc | ggtctaccct | ctggccccct | gcggcaggga | cacgtctggc | 60 |
| cctaacgtgg | ccttgggctg | cctggcctca | agctacttcc | ccgagccagt | gaccctgacc | 120 |
| tggaactcgg | gcgccctgac | cagtggcgtg | catacctttcc | catccgtcct | gcagccgtca | 180 |
| gggctctact | ccctcagcag | catggtgacc | gtgccggcca | gcagcctgtc | cagcaagagc | 240 |
| tacacctgca | atgtcaacca | cccggccacc | accaccaagg | tggacctgtg | tgttggacga | 300 |
| ccatgtccca | tatgcccagc | ctgtgaaggg | cccgggccct | cggtcttcat | cttccctcca | 360 |
| aaacccaagg | acaccctcat | gatctcccgg | acacccagg | tcacgtgcgt | ggtggtagat | 420 |
| gtgagccagg | aaaacccgga | ggtccagttc | tcctggtatg | tggacggtgt | agaggtgcac | 480 |
| acggcccaga | cgaggccaaa | ggaggcgcag | ttcaacagca | cctaccgtgt | ggtcagcgtc | 540 |
| ctgcccatcc | agcacgagga | ctggctgaag | gggaaggagt | tcgagtgcaa | ggtcaacaac | 600 |
| aaagacctcc | cagcccccat | cacaaggatc | atctccaagg | ccaaagggcc | gagccgggag | 660 |
| ccgcaggtgt | acaccctgtc | cccatccgcc | gaggagctgt | ccaggagcaa | agtcagcata | 720 |
| acctgcctgg | tcactggctt | ctacccacct | gacatcgatg | tcgagtggaa | gagcaacgga | 780 |
| cagccggagc | cagagggcaa | ttaccgcacc | accccgcccc | agcaggacgt | ggacgggacc | 840 |
| tacttcctgt | acagcaagct | cgcggtggac | aaggccagct | ggcagcgtgg | agacccattc | 900 |
| cagtgtgcgg | tgatgcacga | ggctctgcac | aaccactaca | ccc | | 943 |

<210> SEQ ID NO 114
<211> LENGTH: 320
<212> TYPE: PRT
<213> ORGANISM: Bubalus arnee

<400> SEQUENCE: 114

Ala Pro Lys Thr Ala Pro Ser Val Tyr Pro Leu Ala Pro Cys Gly Arg
1               5                   10                  15

Asp Thr Ser Gly Pro Asn Val Ala Leu Gly Cys Leu Ala Ser Ser Tyr
            20                  25                  30

Phe Pro Glu Pro Val Thr Val Thr Trp Asn Ser Gly Ala Leu Thr Ser
        35                  40                  45

Gly Val His Thr Phe Pro Ser Val Leu Gln Pro Ser Gly Leu Tyr Ser
    50                  55                  60

Leu Ser Ser Thr Val Thr Val Pro Ala Arg Ser Ser Arg Lys Cys
65                  70                  75                  80

Phe Thr Cys Asn Val Asn His Pro Ala Thr Thr Thr Lys Val Asp Leu
                85                  90                  95

Cys Val Gly Arg Pro Cys Pro Ile Cys Pro Ala Cys Glu Gly Asn Gly
            100                 105                 110

Pro Ser Val Phe Ile Phe Pro Pro Lys Pro Lys Asp Thr Leu Met Ile
        115                 120                 125

Ser Arg Thr Pro Glu Val Thr Cys Val Val Val Asp Val Ser Gln Glu
    130                 135                 140

Asn Pro Glu Val Gln Phe Ser Trp Tyr Val Asp Gly Glu Glu Val His

```
                145                 150                 155                 160
Thr Ala Glu Thr Arg Pro Lys Glu Gln Phe Asn Ser Thr Tyr Arg
                165                 170                 175
Val Val Ser Val Leu Pro Ile Gln His Gln Asp Trp Leu Lys Gly Lys
                180                 185                 190
Glu Phe Glu Cys Lys Val Asn Asn Lys Asp Leu Pro Ala Pro Ile Thr
                195                 200                 205
Arg Ile Ile Ser Lys Ala Lys Gly Pro Ser Arg Glu Pro Gln Val Tyr
    210                 215                 220
Thr Leu Ser Pro Ser Ala Glu Glu Leu Ser Arg Ser Lys Val Ser Ile
225                 230                 235                 240
Thr Cys Leu Val Thr Gly Phe Tyr Pro Pro Asp Ile Asp Val Glu Trp
                245                 250                 255
Lys Ser Asn Gly Gln Pro Glu Pro Glu Gly Asn Tyr Arg Ser Thr Pro
                260                 265                 270
Pro Gln Glu Asp Glu Asp Gly Thr Tyr Phe Leu Tyr Ser Lys Leu Ala
                275                 280                 285
Val Asp Lys Ala Arg Leu Gln Ser Gly Gly Ile His Cys Ala Val Met
                290                 295                 300
His Glu Ala Leu His Asn His Tyr Thr Gln Lys Ser Ile Ser Lys Thr
305                 310                 315                 320
```

<210> SEQ ID NO 115
<211> LENGTH: 960
<212> TYPE: DNA
<213> ORGANISM: Bubalus arnee

<400> SEQUENCE: 115

```
gcccccaaga cggcccccatc ggtctaccct ctggccccct gcggcaggga cacgtctggc     60
cctaacgtgg ccttgggctg cctggcctca agctacttcc ccgagccagt gaccgtgacc    120
tggaactcgg gcgccctgac cagtggcgtg cacaccttcc catccgtcct gcagccgtca    180
gggctctact ccctcagcag cacggtgacc gtgccggcca ggagctcgtc cagaaagtgc    240
ttcacgtgca atgtcaacca cccggccacc accaccaagg tggacctgtg tgttggacga    300
ccatgtccca tatgcccagc ctgtgaaggg aacgggccct cggtcttcat cttccctcca    360
aaacccaagg acaccctcat gatctcccgg acccccgagg tcacgtgcgt ggtggtagat    420
gtgagccagg aaaacccgga ggtccagttc tcctggtacg tggacggcga agaggtgcac    480
acggccgaga cgaggccaaa ggaggagcag ttcaacagca cctaccgtgt ggtcagcgtc    540
ctgcccatcc agcaccagga ctggctgaag ggaaaggagt tcgagtgcaa ggtcaacaac    600
aaagacctcc cagcccccat cacaaggatc atctccaagg ccaagggcc gagccgggag    660
ccgcaggtgt acaccctgtc ccatccgcc gaggagctgt ccaggagcaa agtcagcata    720
acctgcctgg tcactggctt ctacccacct gacatcgatg tcgagtggaa gagcaacgga    780
cagccggagc cagagggcaa ttaccgctcc accccgcccc aggaggacga ggacgggacc    840
tacttcctgt acagcaaact cgcggtggac aaggcgaggt tgcagagtgg aggcatccac    900
tgtgcggtga tgcacgaggc tctgcacaac cactacaccc agaagtccat ctccaagact    960
```

<210> SEQ ID NO 116
<211> LENGTH: 105
<212> TYPE: PRT
<213> ORGANISM: Bubalus arnee

<400> SEQUENCE: 116

Gln Pro Lys Ser Ala Pro Ser Val Thr Leu Phe Pro Pro Ser Thr Glu
1               5                   10                  15

Glu Leu Ser Ala Asn Lys Ala Thr Leu Val Cys Leu Ile Ser Asp Phe
            20                  25                  30

Tyr Pro Gly Ser Met Thr Val Ala Arg Lys Ala Asp Gly Ser Thr Ile
        35                  40                  45

Thr Arg Asn Val Glu Thr Thr Arg Ala Ser Lys Gln Ser Asn Ser Lys
    50                  55                  60

Tyr Ala Ala Ser Ser Tyr Leu Ser Leu Thr Gly Ser Glu Trp Lys Ser
65              70                  75                  80

Lys Gly Ser Tyr Ser Cys Glu Val Thr His Glu Gly Ser Thr Val Thr
                85                  90                  95

Lys Thr Val Lys Pro Ser Glu Cys Ser
            100                 105

<210> SEQ ID NO 117
<211> LENGTH: 318
<212> TYPE: DNA
<213> ORGANISM: Bubalus arnee

<400> SEQUENCE: 117
cagcccaagt ccgcaccctc agtcaccctg ttcccaccct ccacggagga gctcagcgcc      60
aacaaggcca ccctggtgtg tctcatcagc gacttctacc cgggtagcat gaccgtggcc     120
aggaaggcag acggcagcac catcacccgg aacgtggaga ccacccgggc ctccaaacag     180
agcaacagca gtacgcggc cagcagctac ctgagcctga cgggcagcga gtggaaatcg     240
aaaggcagtt acagctgcga ggtcacgcac gaggggagca ccgtgacaaa gacagtgaag     300
ccctcagagt gttcttag                                                   318

<210> SEQ ID NO 118
<211> LENGTH: 266
<212> TYPE: PRT
<213> ORGANISM: Bubalus arnee

<400> SEQUENCE: 118

Ser Gly Val His Thr Phe Pro Ala Val Leu Gln Ser Ser Gly Leu Tyr
1               5                   10                  15

Ser Leu Ser Ser Val Thr Ala Pro Ala Ser Ala Thr Lys Ser Gln
            20                  25                  30

Thr Phe Thr Cys Asn Val Ala His Pro Ala Ser Ser Thr Lys Val Asp
        35                  40                  45

Lys Ala Val Val Pro Pro Cys Arg Pro Lys Pro Cys Asp Cys Cys Pro
    50                  55                  60

Pro Pro Glu Leu Pro Gly Gly Pro Ser Val Phe Ile Phe Pro Pro Lys
65              70                  75                  80

Pro Lys Asp Thr Leu Thr Ile Ser Gly Thr Pro Glu Val Thr Cys Val
                85                  90                  95

Val Val Asp Val Gly His Asp Asp Pro Glu Val Lys Phe Ser Trp Phe
            100                 105                 110

Val Asp Asp Val Glu Val Asn Thr Ala Arg Thr Lys Pro Arg Glu Glu
        115                 120                 125

Gln Phe Asn Ser Thr Tyr Arg Val Val Ser Ala Leu Pro Ile Gln His
    130                 135                 140

Asn Asp Trp Thr Gly Gly Lys Glu Phe Lys Cys Lys Val Tyr Asn Glu
145             150                 155                 160

```
Gly Leu Pro Ala Pro Ile Val Arg Thr Ile Ser Arg Thr Lys Gly Gln
            165                 170                 175

Ala Arg Glu Pro Gln Val Tyr Val Leu Ala Pro Pro Gln Asp Glu Leu
        180                 185                 190

Ser Lys Ser Thr Val Ser Ile Cys Met Val Thr Gly Phe Tyr Pro
            195                 200                 205

Asp Tyr Ile Ala Val Glu Trp Gln Lys Asp Gly Gln Pro Glu Ser Glu
        210                 215                 220

Asp Lys Tyr Gly Thr Thr Pro Pro Gln Leu Asp Ser Asp Gly Ser Tyr
225                 230                 235                 240

Phe Leu Tyr Ser Arg Leu Arg Val Asn Lys Asn Ser Trp Gln Glu Gly
            245                 250                 255

Gly Ala Tyr Thr Cys Val Val Met His Glu
            260                 265
```

<210> SEQ ID NO 119
<211> LENGTH: 801
<212> TYPE: DNA
<213> ORGANISM: Bubalus arnee

<400> SEQUENCE: 119

```
gagcggcgtg cacaccttcc cggccgtcct tcagtcctcc gggctctact ctctcagcag    60
cacggtgacc gcgcccgcca gcgccacaaa agccagacc ttcacctgca cgtagccca    120
cccggccagc agcaccaagg tggacaaggc tgttgttccc ccatgcagac cgaaaccctg    180
tgattgctgc ccacccctg agctccccgg aggaccctct gtcttcatct tcccaccaaa    240
acccaaggac accctcacaa tctctggaac tcctgaggtc acgtgtgtgg tggtggacgt    300
gggccacgat gaccccgagg tgaagttctc ctggttcgtg gacgatgtgg aggtaaacac    360
agccaggacg aagccaagag aggagcagtt caacagcacc taccgcgtgg tcagcgccct    420
gcccatccag cacaacgact ggactggagg aaaggagttc aagtgcaagg tctacaatga    480
aggcctccca gcccccatcg tgaggaccat ctccaggacc aaagggcagg cccgggagcc    540
gcaggtgtac gtcctggccc caccccagga cgagctcagc aaaagcacgg tcagcatcac    600
ttgcatggtc actggcttct acccagacta catcgccgta gagtggcaga agatgggca    660
gcctgagtca gaggacaaat atggcacgac cccgccccag ctggacagcg atggctccta    720
cttcctgtac agcaggctca gggtgaacaa gaacagctgg caagaaggag cgcctacac    780
gtgtgtagtg atgcatgagg c                                              801
```

<210> SEQ ID NO 120
<211> LENGTH: 309
<212> TYPE: PRT
<213> ORGANISM: Bubalus arnee

<400> SEQUENCE: 120

```
Ala Ser Ile Thr Ala Pro Lys Val Tyr Pro Leu Thr Ser Cys Arg Gly
1               5                   10                  15

Glu Thr Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Thr Val Thr Ala Pro Ala Ser Ala Thr Lys Ser Gln Thr
```

```
            65                  70                  75                  80
    Phe Thr Cys Asn Val Ala His Pro Ala Ser Ser Thr Lys Val Asp Thr
                     85                  90                  95
    Ala Val Gly Phe Ser Ser Asp Cys Cys Lys Phe Pro Lys Pro Cys Val
                    100                 105                 110
    Arg Gly Pro Ser Val Phe Ile Phe Pro Pro Lys Pro Lys Asp Thr Leu
                    115                 120                 125
    Met Ile Thr Gly Asn Pro Glu Val Thr Cys Val Val Asp Val Gly
                130                 135                 140
    Arg Asp Asn Pro Glu Val Gln Phe Ser Trp Phe Val Gly Asp Val Glu
    145                 150                 155                 160
    Val His Thr Gly Arg Ser Lys Pro Arg Glu Glu Gln Phe Asn Ser Thr
                    165                 170                 175
    Tyr Arg Val Val Ser Thr Leu Pro Ile Gln His Asn Asp Trp Thr Gly
                    180                 185                 190
    Gly Lys Glu Phe Lys Cys Lys Val Asn Asn Lys Gly Leu Pro Ala Pro
                    195                 200                 205
    Ile Val Arg Thr Ile Ser Arg Thr Lys Gly Gln Ala Arg Glu Pro Gln
                    210                 215                 220
    Val Tyr Val Leu Ala Pro Pro Gln Glu Glu Leu Ser Lys Ser Thr Val
    225                 230                 235                 240
    Ser Val Thr Cys Met Val Thr Gly Phe Tyr Pro Asp Tyr Ile Ala Val
                    245                 250                 255
    Glu Trp His Arg Asp Arg Gln Ala Glu Ser Glu Asp Lys Tyr Arg Thr
                    260                 265                 270
    Thr Pro Pro Gln Leu Asp Ser Asp Gly Ser Tyr Phe Leu Tyr Ser Arg
                    275                 280                 285
    Leu Lys Val Asn Lys Asn Ser Trp Gln Glu Gly Gly Ala Tyr Thr Cys
                    290                 295                 300
    Val Val Met His Glu
    305

<210> SEQ ID NO 121
<211> LENGTH: 929
<212> TYPE: DNA
<213> ORGANISM: Bubalus arnee

<400> SEQUENCE: 121
gcctccatca cagccccgaa agtctaccct ctgacttctt gccgcgggga aacgtccagc      60
tccaccgtga ccctgggctg cctggtctcc agctacatgc cgagccggt gaccgtgacc     120 tggaactcgg gtgccctgaa gagcggcgtg cacaccttcc cggccgtcct tcagtcctct    180
gggctctact ctctcagcag cacggtgacc gcgcccgcca gcgccacaaa aagccagacc    240
ttcacctgca acgtagccca cccggccagc agcaccaagg tggacacggc tgttgggttc    300
tccagtgact gctgcaagtt tcctaagcct tgtgtgaggg gaccatctgt cttcatcttc    360
ccgccgaaac ccaaagacac cctgatgatc acaggaaatc ccgaggtcac atgtgtggtg    420
gtggacgtgg gccgggataa ccccgaggtg cagttctcct ggttcgtggg tgatgtggag    480
gtgcacacgg gcaggtcgaa gccgagagag gagcagttca acagcaccta ccgcgtggtc    540
agcaccctgc ccatccagca caatgactgg actggaggaa aggagttcaa gtgcaaggtc    600
aacaacaaag gcctcccagc ccccatcgtg aggaccatct ccaggaccaa agggcaggcc    660
cgggagccgc aggtgtacgt cctggcccca ccccaggaag agctcagcaa aagcacggtc    720
```

```
agcgtcactt gcatggtcac tggcttctac ccagactaca tcgccgtaga gtggcataga    780
gaccggcagg ctgagtcgga ggacaagtac cgcacgaccc cgccccagct ggacagcgat    840
ggctcctact tcctgtacag caggctcaag gtgaacaaga acagctggca agaaggaggc    900
gcctacacgt gtgtagtgat gcatgaggc                                      929
```

```
<210> SEQ ID NO 122
<211> LENGTH: 352
<212> TYPE: PRT
<213> ORGANISM: Bubalus arnee

<400> SEQUENCE: 122
```

| Ala | Ser | Thr | Thr | Ala | Pro | Lys | Val | Tyr | Pro | Leu | Ala | Ser | Ser | Cys | Gly |
|---|---|---|---|---|---|---|---|---|---|---|---|---|---|---|---|
| 1 | | | | 5 | | | | | 10 | | | | | 15 | |

Asp Thr Ser Ser Ser Thr Val Thr Leu Gly Cys Leu Val Ser Ser Tyr
                20                  25                  30

Met Pro Glu Pro Val Thr Val Thr Trp Asn Ser Gly Ala Leu Lys Asn
            35                  40                  45

Gly Val His Thr Phe Pro Ala Val Arg Gln Ser Ser Gly Leu Tyr Ser
50                  55                  60

Leu Ser Ser Met Val Thr Met Pro Thr Ser Thr Ala Gly Thr Gln Thr
65                  70                  75                  80

Phe Thr Cys Asn Val Ala His Pro Ala Ser Ser Thr Lys Val Asp Thr
                85                  90                  95

Ala Val Thr Ala Arg His Pro Val Pro Lys Thr Pro Glu Thr Pro Ile
            100                 105                 110

His Pro Val Lys Pro Pro Thr Gln Glu Pro Arg Asp Glu Lys Thr Pro
        115                 120                 125

Cys Gln Cys Pro Lys Cys Pro Glu Pro Leu Gly Gly Leu Ser Val Phe
130                 135                 140

Ile Phe Pro Pro Lys Pro Lys Asp Thr Leu Thr Ile Ser Gly Thr Pro
145                 150                 155                 160

Glu Val Thr Cys Val Val Asp Val Gly Gln Asp Pro Glu Val
                165                 170                 175

Gln Phe Ser Trp Phe Val Asp Asp Val Glu Val His Thr Ala Arg Met
            180                 185                 190

Lys Pro Arg Glu Glu Gln Phe Asn Ser Thr Tyr Arg Val Val Ser Ala
        195                 200                 205

Leu Pro Ile Gln His Gln Asp Trp Leu Arg Glu Lys Glu Phe Lys Cys
210                 215                 220

Lys Val Asn Asn Lys Gly Leu Pro Ala Pro Ile Val Arg Thr Ile Ser
225                 230                 235                 240

Arg Thr Lys Gly Gln Ala Arg Glu Pro Gln Val Tyr Val Leu Ala Pro
                245                 250                 255

Pro Arg Glu Glu Leu Ser Lys Ser Thr Leu Ser Leu Thr Cys Leu Ile
            260                 265                 270

Thr Gly Phe Tyr Pro Glu Glu Val Asp Val Glu Trp Gln Arg Asn Gly
        275                 280                 285

Gln Pro Glu Ser Glu Asp Lys Tyr His Thr Thr Pro Pro Gln Leu Asp
290                 295                 300

Ala Asp Gly Ser Tyr Phe Leu Tyr Ser Arg Leu Arg Val Asn Arg Ser
305                 310                 315                 320

Ser Trp Gln Glu Gly Asp His Tyr Thr Cys Ala Val Met His Glu Ala
                325                 330                 335

```
Leu Arg Asn His Tyr Lys Glu Lys Pro Ile Ser Arg Ser Pro Gly Lys
        340                 345                 350

<210> SEQ ID NO 123
<211> LENGTH: 1059
<212> TYPE: DNA
<213> ORGANISM: Bubalus bubalis

<400> SEQUENCE: 123
gcctccacca cagccccgaa agtctaccct ctggcatcca gctgcgggga cacgtccagc        60
tccaccgtga ccctgggctg cctggtctcc agctacatgc ccgagccggt gaccgtgacc       120
tggaactcgg gtgccctgaa gaacggcgtg cacaccttcc cggccgtccg gcagtcctcc       180
gggctctact ctctcagcag catggtgacc atgcccacca gcaccgcagg aacccagacc       240
ttcacctgca acgtagccca cccggccagc agcaccaagg tggacacggc tgtcactgca       300
aggcatccgg tcccgaagac accagagaca cctatccatc ctgtaaaacc cccaacccag       360
gagcccagag atgaaaagac ccctgccag tgtcccaaat gcccagaacc tctgggagga       420
ctgtctgtct tcatcttccc accgaaaccc aaggacaccc tcacaatctc tggaacgccc       480
gaggtcacgt gtgtggtggt ggacgtgggc caggatgacc ccgaagtgca gttctcctgg       540
ttcgtggatg acgtggaggt gcacacagcc aggatgaagc caagagagga gcagttcaac       600
agcacctacc gcgtggtcag cgccctgccc atccagcacc aggactggct gcgggaaaag       660
gagttcaagt gcaaggtcaa caacaaaggc ctcccggccc ccatcgtgag gaccatctcc       720
aggaccaaag ggcaggcccg ggagccacag gtgtatgtcc tggccccacc ccgggaagag       780
ctcagcaaaa gcacgctcag cctcacctgc ctaatcaccg gcttctaccc agaagaggta       840
gacgtggagt ggcagagaaa tgggcagcct gagtcagagg acaagtacca cacgacccca       900
ccccagctgg acgctgacgg ctcctacttc ctgtacagca ggctcagggt gaacaggagc       960
agctggcagg aaggagacca ctacacgtgt gcagtgatgc atgaagcttt acggaatcac      1020
tacaaagaga agcccatctc gaggtctccg ggtaaatga                             1059

<210> SEQ ID NO 124
<211> LENGTH: 35
<212> TYPE: DNA
<213> ORGANISM: Artificial Sequence
<220> FEATURE:
<223> OTHER INFORMATION: A synthetic primer

<400> SEQUENCE: 124
ctagctagca ccatgaggat atatagtgtc ttaac                                   35

<210> SEQ ID NO 125
<211> LENGTH: 31
<212> TYPE: DNA
<213> ORGANISM: Artificial Sequence
<220> FEATURE:
<223> OTHER INFORMATION: A synthetic primer

<400> SEQUENCE: 125
caatctcgag ttacagacag aagatgactg c                                       31
```